United States Patent [19]

MacDonald et al.

[11] Patent Number: 5,686,288
[45] Date of Patent: Nov. 11, 1997

[54] HUNTINGTIN DNA, PROTEIN AND USES THEREOF

[75] Inventors: Marcy E. MacDonald, Lexington; Christine M. Ambrose, Charlestown; Mabel P. Duyao, Cambridge; James F. Gusella, Framingham, all of Mass.

[73] Assignee: The General Hospital Corporation, Boston, Mass.

[21] Appl. No.: 246,982

[22] Filed: May 20, 1994

Related U.S. Application Data

[63] Continuation-in-part of Ser. No. 85,000, Jul. 1, 1993, abandoned, which is a continuation-in-part of Ser. No. 27,498, Mar. 5, 1993, abandoned.

[51] Int. Cl.$^6$ .......................... C12N 5/00; C12N 15/12; C07H 17/00; C07K 14/00
[52] U.S. Cl. .................................. 435/240.1; 435/320.1; 435/69.1; 536/23.5; 530/350
[58] Field of Search ................. 435/6, 69.1, 240.2, 435/320.1, 252.3, 254.11; 530/350; 536/22.1, 23.1, 23.4, 23.5

[56] References Cited

PUBLICATIONS

Allitto, B.A. et al., "Increased recombination adjacent to the Huntington disease–linked D4S10 marker," *Genomics* 9:104–112 (1991).

Altherr, M.R. et al., "Radiation hybrid map spanning the Huntington disease gene region of chromosome 4," *Genomics* 13:1040–1046 (1992).

Altschul, S.F. et al., "Basic local alignment search tool," *J. Mol. Biol.* 215:403–410 (1990).

Ambrose, C. et al., "A novel G protein–coupled receptor kinase gene cloned from 4p16.3," *Hum. Mol. Genet.* 1(9):697–703 (1992).

Anderson M.A. and Gusella, J.F., "Use of cyclosporin A in establishing Epstein–Barr virus–transformed human lymphoblastoid cell lines," *In Vitro* 20(11):856–858 (Nov. 1984).

Andrew S.E. et al., "The relationship between trinucleotide (CAG) repeat length and clinical features of Huntington's disease," *Nature Genet.* 4:398–403 (Aug. 1993).

Ashizawa, T. and Epstein, H.F., "Ethnic distribution of myotonic dystrophy" *Lancet* 338:642–643 (Sep. 7, 1991).

Aslanidis, C. et al., "Cloning of the essential myotonic dystrophy region and mapping of the putative defect," *Nature* 355:548–551 (Feb. 6, 1992).

Bates, G.P. et al., "Characterization of a yeast artificial chromosome contig spanning the Huntington's disease gene candidate region," *Nature Genet.* 1:180–187 (Jun. 1992).

Bates, G.P. et al., "Defined physical limits of the Huntington disease gene candidate region," *Am. J. Hum. Genet.* 49:7–16 (1991).

Bates, G.P. et al., "A yeast artificial chromosome telomere clone spanning a possible location of the Huntington disease gene," *Am. J. Hum. Genet.* 46:762–775 (1990).

US005686288A

Baxendale, S. et al. "The direct screening of cosmid libraries with YAC clones," *Nucleic Acids Res.* 19(23):6651 (Aug. 20, 1991).

Biancalana, V. et al., "Moderate instability of the trinucleotide repeat in spino bulbar muscular atrophy," *Hum. Mol. Genet.* (4):255–258 (1992).

Brook, J.D. et al., "Molecular basis of myotonic dystrophy: expansion of a trinucleotide (CTG) repeat at the 3' end of a transcript encoding a protein kinase family member," *Cell* 68:799–808 (Feb. 21, 1992).

Brunner, H.G. et al., "Brief report: reverse mutation in myotonic dystrophy," *New Engl. J. Med.* 328(7):476–480 (Feb. 18, 1993).

Bucan, M. et al., "Physical maps of 4p16.3, the area expected to contain the Huntington disease mutation," *Genomics* 6:1–15 (1990).

Buckler, A.J. et al., "Exon amplification: a strategy to isolate mammalian genes based on RNA splicing," *Proc. Natl. Acad. Sci. USA* 88:4005–4009 (May 1991).

Buxton, J. et al., "Detection of an unstable fragment of DNA specific to individuals with myotonic dystrophy," *Nature* 355:547–548 (Feb. 6, 1992).

Cheng, S.V. et al., "Synteny on Mouse Chromosome 5 of Homologs for human DNA Loci Linked to the Huntington Disease Gene," *Genomics* 4:419–426 (1989).

Conneally, P.M. et al., "Huntington disease: no evidence for locus heterogeneity," *Genomics* 5:304–308 (1989).

Daly, C.B., "Genetic cause is identified for Huntington's disease," *The Washington Post*, Mar. 24, 1993.

DeBoulle, K. et al., "A point mutation in the FMR–1 gene associated with fragile X mental retardation," *Nature Genet.* 3:31–35 (Jan. 1993).

Doucette–Stamm, L.A. et al., "Generation and characterization of irradiation hybrids of human chromosome 4," *Somat. Cell Mol. Genet.* 17(5):471–480 (1991).

Duyao, M. et al., "Trinucleotide repeat length instability and age of onset in Huntington's disease," *Nature Genet.* 4:387–392 (Aug. 1993).

Fu Y.H. et al., "An unstable triplet repeat in a gene related to myotonic muscular dystrophy," *Science* 255:1256–1258 (Mar. 6, 1992).

Fu, Y.H. et al., "Variation of the CGG repeat at the fragile X site results in genetic instability: resolution of the Sherman paradox," *Cell* 67:1047–1058 (Dec. 20, 1991).

Goldberg, Y.P. et al., "Identification of an Alu retrotransposition event in close proximity to a strong candidate gene for Huntington's disease," *Nature* 362:370–373 (Mar. 25, 1993).

(List continued on next page.)

*Primary Examiner*—Vasu S. Jagannathan
*Assistant Examiner*—K. Cochrane Carlson
*Attorney, Agent, or Firm*—Sterne, Kessler, Goldstein, Fox P.L.L.C.

[57] ABSTRACT

A novel gene, huntingtin, is described, encoding huntingtin protein, recombinant vectors and hosts capable of expressing huntingtin. Methods for the diagnosis and treatment of Huntington's disease are also provided.

7 Claims, 50 Drawing Sheets

PUBLICATIONS

Goodfellow, P.N., "Planting alfalfa and cloning the Huntington's disease gene," *Cell* 72:817–818 (Mar. 26, 1993).

Gusella, J.F. "Chapter 3—Huntington's disease," *Adv. Hum. Genet.* 20:125–151 (1991).

Gusella, J.F., "Location cloning strategy for characterizing genetic defects in Huntington's disease and Alzheimer's disease," *FASEB J.* 3:2036–2041 (Jul. 1989).

Gusella, J.F. et al. "DNA markers for nervous system diseases," *Science* 225:1320–1326 (Sep. 21, 1984).

Gusella, J.F. et al., "A polymorphic DNA marker genetically linked to Huntington's disease," *Nature* 306:234–238 (Nov. 17, 1983).

Gusella, J.F. et al., "Precise localization of human β–globin gene complex on chromosome 11," *Proc. Natl. Acad. Sci. USA* 76(10):5239–5243 (Oct. 1979).

Gusella, J.F. and Macdonald, M.E., "Hunting for Huntington's Disease," In: *Molecular Genetic Medicine*, vol. III, Ed. Friedmann, Academic Press (San Diego), pp. 139–158 (1993).

Harley, H.G. et al., "Unstable DNA sequence in myotonic dystrophy," *Lancet* 339:1125–1128 (May 9, 1992).

Harley, H.G. et al., "Expansion of an unstable DNA region and phenotypic variation in myotonic dystrophy," *Nature* 355:545–546 (Feb. 6, 1992).

Harley, H.G. et al., "Detection of linkage disequilibrium between the myotonic dystrophy locus and a new polymorphic DNA marker," *Am. J. Hum. Genet.* 49:68–75 (1991).

Harper, P.S., "The epidemiology of Huntington's disease," *Hum. Genet.* 89:365–376 (1992).

Hoogeveen, A.T. et al., "Characterization and localization of the Huntington disease gene product," *Hum. Mol. Genet.* 2(12):2069–2073 (1993).

Jerome, R., "Huntington's cornered," *The Sciences*, p. 7 (May/Jun. 1993).

Kremer, E.J. et al., "Mapping of DNA instability at the fragile X to a trinucleotide repeat sequence p(CCG)n," *Science* 252:1711–1714 (Jun. 21, 1991).

LaSpada, A.R. et al., "Androgen receptor gene mutations in X–linked spinal and bulbar muscular atrophy," *Nature* 352:77–79 (Jul. 4, 1991).

Lin, B. et al., "Sequence of the murine Huntington disease gene: evidence for conservation, and polymorphism in a triplet (CCG) repeat alternate splicing," *Hum. Mol. Genet.* 3(1):85–92 (1994).

Lin, B. et al., "Differential 3' polyadenylation of the Huntington disease gene results in two mRNA species with variable tissue expression," *Hum. Mol. Genet.* 2(10):1541–1545 (1993).

Lin, C.S. et al., "New DNA markers in the Huntington's disease gene candidate region," *Somat. Cell Mol. Genet.* 17(5):481–488 (1991).

Little, P., "The end of the beginning," *Nature* 362:408–409 (Apr. 1, 1993).

MacDonald, M.E. et al. "A novel gene containing a trinucleotide repeat that is expanded and unstable on Huntington's disease chromosomes," *Cell* 72:971–983 (Mar. 26, 1993).

MacDonald, M.E. et al., "Gametic but not somatic instability of CAG repeat length in Huntington's disease," *J. Med. Genet.* 30:982–986 (1993).

MacDonald, M.E. et al., "The Huntington's disease candidate region exhibits many different haplotypes," *Nature Genet.* 1:99–103 (May 1992).

MacDonald M.E. et al., "Complex patterns of linkage disequilibrium in the Huntington disease region," *Am. J. Hum. Genet.* 49:723–734 (1991).

MacDonald, M.E. et al., "Clustering of multiallele DNA markers near the Huntington's disease gene," *J. Clin. Invest.* 84:1013–1016 (Sep. 1989).

MacDonald, M.E. et al., "Recombination events suggest potential sites for the Huntington's disease gene," *Neuron* 3:183–190 (Aug. 1989).

Mahadevan, M. et al., "Myotonic dystrophy mutation: an unstable CTG repeat in the 3' untranslated region of the gene," *Science* 255:1253–1255 (Mar. 6, 1992).

Martin, J.B. and Gusella, J.F., "Huntington's disease: pathogenesis and management," *New Engl. J. Med.* 315(20):1267–1276 (Nov. 13, 1986).

McClatchey, A.I. et al., "The genomic structure of the human skeletal muscle sodium channel gene," *Hum. Mol. Genet.* 1(7):521–527 (1992).

Merritt, A.D. et al., "Juvenile Huntington's chorea," *Excerpta Medica*, Amsterdam, pp. 645–650 (1969).

Morell, V., "Huntington's gene finally found," *Science* 260:28–30 (Apr. 2, 1993).

Myers, R.H. et al., "Homozygote for Huntington disease," *Am. J. Hum. Genet.* 45:615–618 (1989).

Oudet C. et al., "Linkage disequilibrium between the fragile X mutation and two closely linked CA repeats suggests that fragile X chromosomes are derived from a small number of founder chromosomes," *Am. J. Hum. Genet.* 52:297–304 (1993).

Pieretti, M. et al., "Absence of expression of the FMR-1 gene in fragile X syndrome," *Cell* 66:817–822 (Aug. 23, 1991).

Pohl, T.M. et al., "Construction of a NotI linking library and isolation of new markers close to the Huntington's disease gene," *Nucleic Acids Res.* 16(19):9185–9198 (1988).

Pritchard, C. et al., "Recombination of 4p16 DNA markers in an unusual family with Huntington disease," *Am. J. Hum. Genet.* 50:1218–1230 (1992).

Richards, R.I. et al., "Evidence of founder chromosomes in fragile X syndrome," *Nature Genet.* 1:257–260 (Jul. 1992).

Rubinsztein, D.C. et al., "Site of (CCG) polymorphism in the HD gene," *Nature Genet.* 5:214–215 (Nov. 1993).

Sanger, F. et al., "DNA sequencing with chain-terminating inhibitors," *Proc. Natl. Acad. Sci. USA* 74(12):5463–5467 (Dec. 1977).

Snell, R.G. et al., "Relationship between trinucleotide, repeat expansion and phenotypic variation in Huntington's disease," *Nature Genet.* 4:393–397 (Aug. 1993).

Snell, R.G. et al., "A recombination event that redefines the Huntington disease region," *Am. J. Hum. Genet.* 51:357–362 (1992).

Snell, R.G. et al. "Linkage disequilibrium in Huntington's disease: an improved localisation for the gene," *J. Med. Genet.* 26:673–675 (1989).

Suthers, G.K. et al., "Instability versus predictability: the molecular diagnosis of myotonic dystrophy," *J. Med. Genet.* 29:761–765 (1992).

Taylor, S.A.M. et al., "Cloning of the α–adducin gene from the Huntington's disease candidate region of chromosome 4 by exon amplification," *Nature Genet.* 2:223–227 (Nov. 1992).

Theilmann, J. et al., "Non–random association between alleles detected at D4S95 and D4S98 and the Huntington's disease gene," *J. Med. Genet.* 26:676–681 (1989).

Thompson, L.M. et al., "A gene encoding a fibroblast growth factor receptor isolated from the Huntington disease gene region of human chromosome 4," *Genomics* 11:1133–1142 (1991).

Tsilfidis, C. et al., "Correlation between CTG trinucleotide repeat length and frequency of severe congenital myotonic dystrophy," *Nature Genet.* 1:192–195 (Jun. 1992).

Verkerk, A.J.M.H. et al., "Identification of a gene (FMR–1) containing a CGG repeat coincident with a breakpoint cluster region exhibiting length variation in fragile X syndrome," *Cell* 65:905–914 (May 31, 1991).

Wexler, N.S. et al "Homozygotes for Huntington's disease," *Nature* 326:194–197 (Mar. 12, 1987).

Whaley, W.L. et al., "Mapping of cosmid clones in Huntington's disease region of chromosome 4," *Somat. Cell Mol. Genet.* 17(1):83–91 (1991).

Wolff, G. et al., "New mutation to Huntington's disease" *J. Med. Genet.* 26:18–27 (1989).

Youngman, S. et al., "The telomeric 60 kb of chromosome arm 4p is homologous to telomeric regions on 13p, 15p, 21p and 22p," *Genomics* 14:350 356 (1992).

Yu, S. et al., "Fragile–X syndrome: unique genetics of the heritable unstable element," *Am. J. Hum. Genet.* 50:968–980 (1992).

| | |
|---|---:|
| TTGCTGTGTG AGGCAGAACC TGCGGGGGCA GGGGCGGGCT GGTTCCCTGG CCAGCCATTG | 60 |
| GCAGAGTCCG CAGGCTAGGG CTGTCAATCA TGCTGGCCGG CGTGGCCCCG CCTCCGCCGG | 120 |
| CGCGGCCCCG CCTCCGCCGG CGGACGTCTG GGACGCAAGG CGCCGTGGGG GCTGCCGGGA | 180 |
| CGGGTCCAAG ATGGACGGCC GCTCAGGTTC TGCTTTTACC TGCGGCCCAG AGCCCCATTC | 240 |
| ATTGCCCCGG TGCTGAGCGG CGCCGCGAGT CGGCCCGAGG CCTCCGGGGA CTGCCGTGCC | 300 |

```
GGGCGGGAGA CCGCC ATG GCG ACC CTG GAA AAG CTG ATG AAG GCC TTC GAG        351
           Met Ala Thr Leu Glu Lys Leu Met Lys Ala Phe Glu
            1               5                  10

TCC CTC AAG TCC TTC CAG CAG CAG CAG CAG CAG CAG CAG CAG CAG CAG        399
Ser Leu Lys Ser Phe Gln Gln Gln Gln Gln Gln Gln Gln Gln Gln Gln
         15              20                  25

CAG CAG CAG CAG CAG CAG CAG CAG CAG CAG CAA CAG CCG CCA CCG CCG        447
Gln Gln Gln Gln Gln Gln Gln Gln Gln Gln Gln Gln Pro Pro Pro Pro
     30                  35                  40

CCG CCG CCG CCG CCG CCT CCT CAG CTT CCT CAG CCG CCG CCG CAG GCA        495
Pro Pro Pro Pro Pro Pro Pro Gln Leu Pro Gln Pro Pro Pro Gln Ala
 45                  50                  55                  60

CAG CCG CTG CTG CCT CAG CCG CAG CCC CCG CCG CCG CCC CCG CCG            543
Gln Pro Leu Leu Pro Gln Pro Gln Pro Pro Pro Pro Pro Pro Pro
                 65                  70                  75

CCA CCC GGC CCG GCT GTG GCT GAG GAG CCG CTG CAC CGA CCA AAG AAA        591
Pro Pro Gly Pro Ala Val Ala Glu Glu Pro Leu His Arg Pro Lys Lys
             80                  85                  90

GAA CTT TCA GCT ACC AAG AAA GAC CGT GTG AAT CAT TGT CTG ACA ATA        639
Glu Leu Ser Ala Thr Lys Lys Asp Arg Val Asn His Cys Leu Thr Ile
             95                  100                 105

TGT GAA AAC ATA GTG GCA CAG TCT GTC AGA AAT TCT CCA GAA TTT CAG        687
Cys Glu Asn Ile Val Ala Gln Ser Val Arg Asn Ser Pro Glu Phe Gln
 110                 115                 120
```

FIG.4A

| | |
|---|---|
| AAA CTT CTG GGC ATC GCT ATG GAA CTT TTT CTG CTG TGC AGT GAT GAC<br>Lys Leu Leu Gly Ile Ala Met Glu Leu Phe Leu Leu Cys Ser Asp Asp<br>125               130               135             140 | 735 |
| GCA GAG TCA GAT GTC AGG ATG GTG GCT GAC GAA TGC CTC AAC AAA GTT<br>Ala Glu Ser Asp Val Arg Met Val Ala Asp Glu Cys Leu Asn Lys Val<br>            145               150             155 | 783 |
| ATC AAA GCT TTG ATG GAT TCT AAT CTT CCA AGG TTA CAG CTC GAG CTC<br>Ile Lys Ala Leu Met Asp Ser Asn Leu Pro Arg Leu Gln Leu Glu Leu<br>      160             165             170 | 831 |
| TAT AAG GAA ATT AAA AAG AAT GGT GCC CCT CGG AGT TTG CGT GCT GCC<br>Tyr Lys Glu Ile Lys Lys Asn Gly Ala Pro Arg Ser Leu Arg Ala Ala<br>175               180              185 | 879 |
| CTG TGG AGG TTT GCT GAG CTG GCT CAC CTG GTT CGG CCT CAG AAA TGC<br>Leu Trp Arg Phe Ala Glu Leu Ala His Leu Val Arg Pro Gln Lys Cys<br>      190             195             200 | 927 |
| AGG CCT TAC CTG GTG AAC CTT CTG CCG TGC CTG ACT CGA ACA AGC AAG<br>Arg Pro Tyr Leu Val Asn Leu Leu Pro Cys Leu Thr Arg Thr Ser Lys<br>205               210              215            220 | 975 |
| AGA CCC GAA GAA TCA GTC CAG GAG ACC TTG GCT GCA GCT GTT CCC AAA<br>Arg Pro Glu Glu Ser Val Gln Glu Thr Leu Ala Ala Ala Val Pro Lys<br>            225               230             235 | 1023 |
| ATT ATG GCT TCT TTT GGC AAT TTT GCA AAT GAC AAT GAA ATT AAG GTT<br>Ile Met Ala Ser Phe Gly Asn Phe Ala Asn Asp Asn Glu Ile Lys Val<br>      240             245             250 | 1071 |
| TTG TTA AAG GCC TTC ATA GCG AAC CTG AAG TCA AGC TCC CCC ACC ATT<br>Leu Leu Lys Ala Phe Ile Ala Asn Leu Lys Ser Ser Ser Pro Thr Ile<br>            255               260             265 | 1119 |
| CGG CGG ACA GCG GCT GGA TCA GCA GTG AGC ATC TGC CAG CAC TCA AGA<br>Arg Arg Thr Ala Ala Gly Ser Ala Val Ser Ile Cys Gln His Ser Arg<br>270               275              280 | 1167 |

FIG.4B

```
AGG ACA CAA TAT TTC TAT AGT TGG CTA CTA AAT GTG CTC TTA GGC TTA    1215
Arg Thr Gln Tyr Phe Tyr Ser Trp Leu Leu Asn Val Leu Leu Gly Leu
285                 290                 295                 300

CTC GTT CCT GTC GAG GAT GAA CAC TCC ACT CTG CTG ATT CTT GGC GTG    1263
Leu Val Pro Val Glu Asp Glu His Ser Thr Leu Leu Ile Leu Gly Val
                    305                 310                 315

CTG CTC ACC CTG AGG TAT TTG GTG CCC TTG CTG CAG CAG CAG GTC AAG    1311
Leu Leu Thr Leu Arg Tyr Leu Val Pro Leu Leu Gln Gln Gln Val Lys
                320                 325                 330

GAC ACA AGC CTG AAA GGC AGC TTC GGA GTG ACA AGG AAA GAA ATG GAA    1359
Asp Thr Ser Leu Lys Gly Ser Phe Gly Val Thr Arg Lys Glu Met Glu
            335                 340                 345

GTC TCT CCT TCT GCA GAG CAG CTT GTC CAG GTT TAT GAA CTG ACG TTA    1407
Val Ser Pro Ser Ala Glu Gln Leu Val Gln Val Tyr Glu Leu Thr Leu
350                 355                 360

CAT CAT ACA CAG CAC CAA GAC CAC AAT GTT GTG ACC GGA GCC CTG GAG    1455
His His Thr Gln His Gln Asp His Asn Val Val Thr Gly Ala Leu Glu
365                 370                 375                 380

CTG TTG CAG CAG CTC TTC AGA ACG CCT CCA CCC GAG CTT CTG CAA ACC    1503
Leu Leu Gln Gln Leu Phe Arg Thr Pro Pro Pro Glu Leu Leu Gln Thr
                385                 390                 395

CTG ACC GCA GTC GGG GGC ATT GGG CAG CTC ACC GCT GCT AAG GAG GAG    1551
Leu Thr Ala Val Gly Gly Ile Gly Gln Leu Thr Ala Ala Lys Glu Glu
                400                 405                 410

TCT GGT GGC CGA AGC CGT AGT GGG AGT ATT GTG GAA CTT ATA GCT GGA    1599
Ser Gly Gly Arg Ser Arg Ser Gly Ser Ile Val Glu Leu Ile Ala Gly
                415                 420                 425

GGG GGT TCC TCA TGC AGC CCT GTC CTT TCA AGA AAA CAA AAA GGC AAA    1647
Gly Gly Ser Ser Cys Ser Pro Val Leu Ser Arg Lys Gln Lys Gly Lys
            430                 435                 440
```

FIG.4C

```
GTG CTC TTA GGA GAA GAA GAA GCC TTG GAG GAT GAC TCT GAA TCG AGA        1695
Val Leu Leu Gly Glu Glu Glu Ala Leu Glu Asp Asp Ser Glu Ser Arg
445             450                 455                 460

TCG GAT GTC AGC AGC TCT GCC TTA ACA GCC TCA GTG AAG GAT GAG ATC        1743
Ser Asp Val Ser Ser Ser Ala Leu Thr Ala Ser Val Lys Asp Glu Ile
                465                 470                 475

AGT GGA GAG CTG GCT GCT TCT TCA GGG GTT TCC ACT CCA GGG TCA GCA        1791
Ser Gly Glu Leu Ala Ala Ser Ser Gly Val Ser Thr Pro Gly Ser Ala
            480                 485                 490

GGT CAT GAC ATC ATC ACA GAA CAG CCA CGG TCA CAG CAC ACA CTG CAG        1839
Gly His Asp Ile Ile Thr Glu Gln Pro Arg Ser Gln His Thr Leu Gln
                495                 500                 505

GCG GAC TCA CTG GAT CTG GCC AGC TGT GAC TTG ACA AGC TCT GCC ACT        1887
Ala Asp Ser Leu Asp Leu Ala Ser Cys Asp Leu Thr Ser Ser Ala Thr
            510                 515                 520

GAT GGG GAT GAG GAG GAT ATC TTG AGC CAC AGC TCC AGC CAG GTC AGC        1935
Asp Gly Asp Glu Glu Asp Ile Leu Ser His Ser Ser Ser Gln Val Ser
525             530                 535                 540

GCC GTC CCA TCT GAC CCT GCC ATG GAC CTG AAT GAT GGG ACC CAG GCC        1983
Ala Val Pro Ser Asp Pro Ala Met Asp Leu Asn Asp Gly Thr Gln Ala
                545                 550                 555

TCG TCG CCC ATC AGC GAC AGC TCC CAG ACC ACC ACC GAA GGG CCT GAT        2031
Ser Ser Pro Ile Ser Asp Ser Ser Gln Thr Thr Thr Glu Gly Pro Asp
                560                 565                 570

TCA GCT GTT ACC CCT TCA GAC AGT TCT GAA ATT GTG TTA GAC GGT ACC        2079
Ser Ala Val Thr Pro Ser Asp Ser Ser Glu Ile Val Leu Asp Gly Thr
                575                 580                 585

GAC AAC CAG TAT TTG GCC CTG CAG ATT GGA CAC CCC CAG GAT GAA GAT        2127
Asp Asn Gln Tyr Leu Gly Leu Gln Ile Gly Gln Pro Gln Asp Glu Asp
            590                 595                 600
```

FIG.4D

```
GAG GAA GCC ACA GGT ATT CTT CCT GAT GAA GCC TCG GAG GCC TTC AGG      2175
Glu Glu Ala Thr Gly Ile Leu Pro Asp Glu Ala Ser Glu Ala Phe Arg
605                 610                 615                 620

AAC TCT TCC ATG GCC CTT CAA CAG GCA CAT TTA TTG AAA AAC ATG AGT      2223
Asn Ser Ser Met Ala Leu Gln Gln Ala His Leu Leu Lys Asn Met Ser
                625                 630                 635

CAC TGC AGG CAG CCT TCT GAC AGC AGT GTT GAT AAA TTT GTG TTG AGA      2271
His Cys Arg Gln Pro Ser Asp Ser Ser Val Asp Lys Phe Val Leu Arg
                640                 645                 650

GAT GAA GCT ACT GAA CCG GGT GAT CAA GAA AAC AAG CCT TGC CGC ATC      2319
Asp Glu Ala Thr Glu Pro Gly Asp Gln Glu Asn Lys Pro Cys Arg Ile
                655                 660                 665

AAA GGT GAC ATT GGA CAG TCC ACT GAT GAT GAC TCT GCA CCT CTT GTC      2367
Lys Gly Asp Ile Gly Gln Ser Thr Asp Asp Asp Ser Ala Pro Leu Val
                670                 675                 680

CAT TCT GTC CGC CTT TTA TCT GCT TCG TTT TTG CTA ACA GGG GGA AAA      2415
His Ser Val Arg Leu Leu Ser Ala Ser Phe Leu Leu Thr Gly Gly Lys
685                 690                 695                 700

AAT GTG CTG GTT CCG GAC AGG GAT GTG AGG GTC AGC GTG AAG GCC CTG      2463
Asn Val Leu Val Pro Asp Arg Asp Val Arg Val Ser Val Lys Ala Leu
                705                 710                 715

GCC CTC AGC TGT GTG GGA GCA GCT GTG GCC CTC CAC CCG GAA TCT TTC      2511
Ala Leu Ser Cys Val Gly Ala Ala Val Ala Leu His Pro Glu Ser Phe
                720                 725                 730

TTC AGC AAA CTC TAT AAA GTT CCT CTT GAC ACC ACG GAA TAC CCT GAG      2559
Phe Ser Lys Leu Tyr Lys Val Pro Leu Asp Thr Thr Glu Tyr Pro Glu
                735                 740                 745
```

FIG.4E

```
GAA CAG TAT GTC TCA GAC ATC TTG AAC TAC ATC GAT CAT GGA GAC CCA      2607
Glu Gln Tyr Val Ser Asp Ile Leu Asn Tyr Ile Asp His Gly Asp Pro
    750             755             760

CAG GTT CGA GGA GCC ACT GCC ATT CTC TGT GGG ACC CTC ATC TGC TCC      2655
Gln Val Arg Gly Ala Thr Ala Ile Leu Cys Gly Thr Leu Ile Cys Ser
765             770             775             780

ATC CTC AGC AGG TCC CGC TTC CAC GTG GGA GAT TGG ATG GGC ACC ATT      2703
Ile Leu Ser Arg Ser Arg Phe His Val Gly Asp Trp Met Gly Thr Ile
            785             790             795

AGA ACC CTC ACA GGA AAT ACA TTT TCT TTG GCC GAT TGC ATT CCT TTG      2751
Arg Thr Leu Thr Gly Asn Thr Phe Ser Leu Ala Asp Cys Ile Pro Leu
        800             805             810

CTG CGG AAA ACA CTG AAG GAT GAG TCT TCT GTT ACT TGC AAG TTA GCT      2799
Leu Arg Lys Thr Leu Lys Asp Glu Ser Ser Val Thr Cys Lys Leu Ala
        815             820             825

TGT ACA GCT GTG AGG AAC TGT GTC ATG AGT CTC TGC AGC AGC AGC TAC      2847
Cys Thr Ala Val Arg Asn Cys Val Met Ser Leu Cys Ser Ser Ser Tyr
    830             835             840

AGT GAG TTA GGA CTG CAG CTG ATC ATC GAT GTG CTG ACT CTG AGG AAC      2895
Ser Glu Leu Gly Leu Gln Leu Ile Ile Asp Val Leu Thr Leu Arg Asn
845             850             855             860

AGT TCC TAT TGG CTG GTG AGG ACA GAG CTT CTG GAA ACC CTT GCA GAG      2943
Ser Ser Tyr Trp Leu Val Arg Thr Glu Leu Leu Glu Thr Leu Ala Glu
            865             870             875

ATT GAC TTC AGG CTG GTG AGC TTT TTG GAG GCA AAA GCA GAA AAC TTA      2991
Ile Asp Phe Arg Leu Val Ser Phe Leu Glu Ala Lys Ala Glu Asn Leu
        880             885             890

CAC AGA GGG GCT CAT CAT TAT ACA GGG CTT TTA AAA CTG CAA GAA CGA      3039
His Arg Gly Ala His His Tyr Thr Gly Leu Leu Lys Leu Gln Glu Arg
    895             900             905
```

FIG.4F

```
GTG CTC AAT AAT GTT GTC ATC CAT TTG CTT GGA GAT GAA GAC CCC AGG        3087
Val Leu Asn Asn Val Val Ile His Leu Leu Gly Asp Glu Asp Pro Arg
    910             915             920

GTG CGA CAT GTT GCC GCA GCA TCA CTA ATT AGG CTT GTC CCA AAG CTG        3135
Val Arg His Val Ala Ala Ala Ser Leu Ile Arg Leu Val Pro Lys Leu
925             930             935             940

TTT TAT AAA TGT GAC CAA GGA CAA GCT GAT CCA GTA GTG GCC GTG GCA        3183
Phe Tyr Lys Cys Asp Gln Gly Gln Ala Asp Pro Val Val Ala Val Ala
                945             950             955

AGA GAT CAA AGC AGT GTT TAC CTG AAA CTT CTC ATG CAT GAG ACG CAG        3231
Arg Asp Gln Ser Ser Val Tyr Leu Lys Leu Leu Met His Glu Thr Gln
            960             965             970

CCT CCA TCT CAT TTC TCC GTC AGC ACA ATA ACC AGA ATA TAT AGA GGC        3279
Pro Pro Ser His Phe Ser Val Ser Thr Ile Thr Arg Ile Tyr Arg Gly
        975             980             985

TAT AAC CTA CTA CCA AGC ATA ACA GAC GTC ACT ATG GAA AAT AAC CTT        3327
Tyr Asn Leu Leu Pro Ser Ile Thr Asp Val Thr Met Glu Asn Asn Leu
    990             995             1000

TCA AGA GTT ATT GCA GCA GTT TCT CAT GAA CTA ATC ACA TCA ACC ACC        3375
Ser Arg Val Ile Ala Ala Val Ser His Glu Leu Ile Thr Ser Thr Thr
1005            1010            1015            1020

AGA GCA CTC ACA TTT GGA TGC TGT GAA GCT TTG TGT CTT CTT TCC ACT        3423
Arg Ala Leu Thr Phe Gly Cys Cys Glu Ala Leu Cys Leu Leu Ser Thr
            1025            1030            1035

GCC TTC CCA GTT TGC ATT TGG AGT TTA GGT TGG CAC TGT GGA GTG CCT        3471
Ala Phe Pro Val Cys Ile Trp Ser Leu Gly Trp His Cys Gly Val Pro
        1040            1045            1050

CCA CTG AGT GCC TCA GAT GAG TCT AGG AAG AGC TGT ACC GTT GGG ATG        3519
Pro Leu Ser Ala Ser Asp Glu Ser Arg Lys Ser Cys Thr Val Gly Met
    1055            1060            1065
```

FIG.4G

```
GCC ACA ATG ATT CTG ACC CTG CTC TCG TCA GCT TGG TTC CCA TTG GAT        3567
Ala Thr Met Ile Leu Thr Leu Leu Ser Ser Ala Trp Phe Pro Leu Asp
    1070            1075            1080

CTC TCA GCC CAT CAA GAT GCT TTG ATT TTG GCC GGA AAC TTG CTT GCA        3615
Leu Ser Ala His Gln Asp Ala Leu Ile Leu Ala Gly Asn Leu Leu Ala
1085            1090            1095            1100

GCC AGT GCT CCC AAA TCT CTG AGA AGT TCA TGG GCC TCT GAA GAA GAA        3663
Ala Ser Ala Pro Lys Ser Leu Arg Ser Ser Trp Ala Ser Glu Glu Glu
        1105            1110            1115

GCC AAC CCA GCA GCC ACC AAG CAA GAG GAG GTC TGG CCA GCC CTG GGC        3711
Ala Asn Pro Ala Ala Thr Lys Gln Glu Glu Val Trp Pro Ala Leu Gly
        1120            1125            1130

GAC CGG GCC CTG GTG CCC ATG GTG GAG CAG CTC TTC TCT CAC CTG CTG        3759
Asp Arg Ala Leu Val Pro Met Val Glu Gln Leu Phe Ser His Leu Leu
        1135            1140            1145

AAG GTG ATT AAC ATT TGT GCC CAC GTC CTG GAT GAC GTG GCT CCT GGA        3807
Lys Val Ile Asn Ile Cys Ala His Val Leu Asp Asp Val Ala Pro Gly
    1150            1155            1160

CCC GCA ATA AAG GCA GCC TTG CCT TCT CTA ACA AAC CCC CCT TCT CTA        3855
Pro Ala Ile Lys Ala Ala Leu Pro Ser Leu Thr Asn Pro Pro Ser Leu
1165            1170            1175            1180

AGT CCC ATC CGA CGA AAG GGG AAG GAG AAA GAA CCA GGA GAA CAA GCA        3903
Ser Pro Ile Arg Arg Lys Gly Lys Glu Lys Glu Pro Gly Glu Gln Ala
        1185            1190            1195

TCT GTA CCG TTG AGT CCC AAG AAA GGC AGT GAG GCC AGT GCA GCT TCT        3951
Ser Val Pro Leu Ser Pro Lys Lys Gly Ser Glu Ala Ser Ala Ala Ser
    1200            1205            1210

AGA CAA TCT GAT ACC TCA GGT CCT GTT ACA ACA AGT AAA TCC TCA TCA        3999
Arg Gln Ser Asp Thr Ser Gly Pro Val Thr Thr Ser Lys Ser Ser Ser
    1215            1220            1225
```

FIG.4H

```
CTG GGG AGT TTC TAT CAT CTT CCT TCA TAC CTC AGA CTG CAT GAT GTC        4047
Leu Gly Ser Phe Tyr His Leu Pro Ser Tyr Leu Arg Leu His Asp Val
    1230            1235            1240

CTG AAA GCT ACA CAC GCT AAC TAC AAG GTC ACG CTG GAT CTT CAG AAC        4095
Leu Lys Ala Thr His Ala Asn Tyr Lys Val Thr Leu Asp Leu Gln Asn
1245            1250            1255            1260

AGC ACG GAA AAG TTT GGA GGG TTT CTC CGC TCA GCC TTG GAT GTT CTT        4143
Ser Thr Glu Lys Phe Gly Gly Phe Leu Arg Ser Ala Leu Asp Val Leu
            1265            1270            1275

TCT CAG ATA CTA GAG CTG GCC ACA CTG CAG GAC ATT GGG AAG TGT GTT        4191
Ser Gln Ile Leu Glu Leu Ala Thr Leu Gln Asp Ile Gly Lys Cys Val
        1280            1285            1290

GAA GAG ATC CTA GGA TAC CTG AAA TCC TGC TTT AGT CGA GAA CCA ATG        4239
Glu Glu Ile Leu Gly Tyr Leu Lys Ser Cys Phe Ser Arg Glu Pro Met
    1295            1300            1305

ATG GCA ACT GTT TGT GTT CAA CAA TTG TTG AAG ACT CTC TTT GGC ACA        4287
Met Ala Thr Val Cys Val Gln Gln Leu Leu Lys Thr Leu Phe Gly Thr
    1310            1315            1320

AAC TTG GCC TCC CAG TTT GAT GGC TTA TCT TCC AAC CCC AGC AAG TCA        4335
Asn Leu Ala Ser Gln Phe Asp Gly Leu Ser Ser Asn Pro Ser Lys Ser
1325            1330            1335            1340

CAA GGC CGA GCA CAG CGC CTT GGC TCC TCC AGT GTG AGG CCA GGC TTG        4383
Gln Gly Arg Ala Gln Arg Leu Gly Ser Ser Ser Val Arg Pro Gly Leu
            1345            1350            1355

TAC CAC TAC TGC TTC ATG GCC CCG TAC ACC CAC TTC ACC CAG GCC CTC        4431
Tyr His Tyr Cys Phe Met Ala Pro Tyr Thr His Phe Thr Gln Ala Leu
        1360            1365            1370

GCT GAC GCC AGC CTG AGG AAC ATG GTG CAG GCG GAG CAG GAG AAC GAC        4479
Ala Asp Ala Ser Leu Arg Asn Met Val Gln Ala Glu Gln Glu Asn Asp
    1375            1380            1385
```

FIG. 41

```
ACC TCG GGA TGG TTT GAT GTC CTC CAG AAA GTG TCT ACC CAG TTG AAG         4527
Thr Ser Gly Trp Phe Asp Val Leu Gln Lys Val Ser Thr Gln Leu Lys
        1390            1395            1400

ACA AAC CTC ACG AGT GTC ACA AAG AAC CGT GCA GAT AAG AAT GCT ATT         4575
Thr Asn Leu Thr Ser Val Thr Lys Asn Arg Ala Asp Lys Asn Ala Ile
1405            1410            1415            1420

CAT AAT CAC ATT CGT TTG TTT GAA CCT CTT GTT ATA AAA GCT TTA AAA         4623
His Asn His Ile Arg Leu Phe Glu Pro Leu Val Ile Lys Ala Leu Lys
                1425            1430            1435

CAG TAC ACG ACT ACA ACA TGT GTG CAG TTA CAG AAG CAG GTT TTA GAT         4671
Gln Tyr Thr Thr Thr Thr Cys Val Gln Leu Gln Lys Gln Val Leu Asp
                1440            1445            1450

TTG CTG GCG CAG CTG GTT CAG TTA CGG GTT AAT TAC TGT CTT CTG GAT         4719
Leu Leu Ala Gln Leu Val Gln Leu Arg Val Asn Tyr Cys Leu Leu Asp
        1455            1460            1465

TCA GAT CAG GTG TTT ATT GGC TTT GTA TTG AAA CAG TTT GAA TAC ATT         4767
Ser Asp Gln Val Phe Ile Gly Phe Val Leu Lys Gln Phe Glu Tyr Ile
        1470            1475            1480

GAA GTG GGC CAG TTC AGG GAA TCA GAG GCA ATC ATT CCA AAC ATC TTT         4815
Glu Val Gly Gln Phe Arg Glu Ser Glu Ala Ile Ile Pro Asn Ile Phe
1485            1490            1495            1500

TTC TTC TTG GTA TTA CTA TCT TAT GAA CGC TAT CAT TCA AAA CAG ATC         4863
Phe Phe Leu Val Leu Leu Ser Tyr Glu Arg Tyr His Ser Lys Gln Ile
                1505            1510            1515

ATT GGA ATT CCT AAA ATC ATT CAG CTC TGT GAT GGC ATC ATG GCC AGT         4911
Ile Gly Ile Pro Lys Ile Ile Gln Leu Cys Asp Gly Ile Met Ala Ser
                1520            1525            1530

GGA AGG AAG GCT GTG ACA CAT GCC ATA CCG GCT CTG CAG CCC ATA GTC         4959
Gly Arg Lys Ala Val Thr His Ala Ile Pro Ala Leu Gln Pro Ile Val
        1535            1540            1545
```

FIG.4J

| | |
|---|---:|
| CAC GAC CTC TTT GTA TTA AGA GGA ACA AAT AAA GCT GAT GCA GGA AAA<br>His Asp Leu Phe Val Leu Arg Gly Thr Asn Lys Ala Asp Ala Gly Lys<br>1550               1555              1560 | 5007 |
| GAG CTT GAA ACC CAA AAA GAG GTG GTG GTG TCA ATG TTA CTG AGA CTC<br>Glu Leu Glu Thr Gln Lys Glu Val Val Val Ser Met Leu Leu Arg Leu<br>1565            1570           1575           1580 | 5055 |
| ATC CAG TAC CAT CAG GTG TTG GAG ATG TTC ATT CTT GTC CTG CAG CAG<br>Ile Gln Tyr His Gln Val Leu Glu Met Phe Ile Leu Val Leu Gln Gln<br>          1585            1590           1595 | 5103 |
| TGC CAC AAG GAG AAT GAA GAC AAG TGG AAC CGA CTC TCT CGA CAG ATA<br>Cys His Lys Glu Asn Glu Asp Lys Trp Lys Arg Leu Ser Arg Gln Ile<br>          1600            1605           1610 | 5151 |
| GCT GAC ATC ATC CTC CCA ATG TTA GCC AAA CAG CAG ATG CAC ATT GAC<br>Ala Asp Ile Ile Leu Pro Met Leu Ala Lys Gln Gln Met His Ile Asp<br>          1615            1620           1625 | 5199 |
| TCT CAT GAA GCC CTT GGA GTG TTA AAT ACA TTA TTT GAG ATT TTG GCC<br>Ser His Glu Ala Leu Gly Val Leu Asn Thr Leu Phe Glu Ile Leu Ala<br>          1630            1635           1640 | 5247 |
| CCT TCC TCC CTC CGT CCG GTA GAC ATG CTT TTA CGG AGT ATG TTC GTC<br>Pro Ser Ser Leu Arg Pro Val Asp Met Leu Leu Arg Ser Met Phe Val<br>1645            1650           1655           1660 | 5295 |
| ACT CCA AAC ACA ATG GCG TCC GTG AGC ACT GTT CAA CTG TGG ATA TCG<br>Thr Pro Asn Thr Met Ala Ser Val Ser Thr Val Gln Leu Trp Ile Ser<br>          1665            1670           1675 | 5343 |
| GGA ATT CTG GCC ATT TTG AGG GTT CTG ATT TCC CAG TCA ACT GAA GAT<br>Gly Ile Leu Ala Ile Leu Arg Val Leu Ile Ser Gln Ser Thr Glu Asp<br>          1680            1685           1690 | 5391 |
| ATT GTT CTT TCT CGT ATT CAG GAG CTC TCC TTC TCT CCG TAT TTA ATC<br>Ile Val Leu Ser Arg Ile Gln Glu Leu Ser Phe Ser Pro Tyr Leu Ile<br>          1695            1700           1705 | 5439 |

FIG.4K

```
TCC TGT ACA GTA ATT AAT AGG TTA AGA GAT GGG GAC AGT ACT TCA ACG         5487
Ser Cys Thr Val Ile Asn Arg Leu Arg Asp Gly Asp Ser Thr Ser Thr
        1710            1715            1720

CTA GAA GAA CAC AGT GAA GGG AAA CAA ATA AAG AAT TTG CCA GAA GAA         5535
Leu Glu Glu His Ser Glu Gly Lys Gln Ile Lys Asn Leu Pro Glu Glu
1725            1730            1735                1740

ACA TTT TCA AGG TTT CTA TTA CAA CTG GTT GGT ATT CTT TTA GAA GAC         5583
Thr Phe Ser Arg Phe Leu Leu Gln Leu Val Gly Ile Leu Leu Glu Asp
            1745            1750            1755

ATT GTT ACA AAA CAG CTG AAG GTG GAA ATG AGT GAG CAG CAA CAT ACT         5631
Ile Val Thr Lys Gln Leu Lys Val Glu Met Ser Glu Gln Gln His Thr
        1760            1765            1770

TTC TAT TGC CAG GAA CTA GGC ACA CTG CTA ATG TGT CTG ATC CAC ATC         5679
Phe Tyr Cys Gln Glu Leu Gly Thr Leu Leu Met Cys Leu Ile His Ile
        1775            1780            1785

TTC AAG TCT GGA ATG TTC CGG AGA ATC ACA GCA GCT GCC ACT AGG CTG         5727
Phe Lys Ser Gly Met Phe Arg Arg Ile Thr Ala Ala Ala Thr Arg Leu
        1790            1795            1800

TTC CGC AGT GAT GGC TGT GGC GGC AGT TTC TAC ACC CTG GAC AGC TTG         5775
Phe Arg Ser Asp Gly Cys Gly Gly Ser Phe Tyr Thr Leu Asp Ser Leu
1805            1810            1815            1820

AAC TTG CGG GCT CGT TCC ATG ATC ACC ACC CAC CCG GCC CTG GTC CTG         5823
Asn Leu Arg Ala Arg Ser Met Ile Thr Thr His Pro Ala Leu Val Leu
        1825            1830            1835

CTC TGG TGT CAG ATA CTG CTG CTT GTC AAC CAC ACC GAC TAC CGC TGG         5871
Leu Trp Cys Gln Ile Leu Leu Leu Val Asn His Thr Asp Tyr Arg Trp
            1840            1845            1850
```

FIG.4L

```
TGG GCA GAA GTG CAG CAG ACC CCG AAA AGA CAC AGT CTG TCC AGC ACA           5919
Trp Ala Glu Val Gln Gln Thr Pro Lys Arg His Ser Leu Ser Ser Thr
     1855                1860                1865

AAG TTA CTT AGT CCC CAG ATG TCT GGA GAA GAG GAG GAT TCT GAC TTG           5967
Lys Leu Leu Ser Pro Gln Met Ser Gly Glu Glu Glu Asp Ser Asp Leu
     1870                1875                1880

GCA GCC AAA CTT GGA ATG TGC AAT AGA GAA ATA GTA CGA AGA GGG GCT           6015
Ala Ala Lys Leu Gly Met Cys Asn Arg Glu Ile Val Arg Arg Gly Ala
     1885                1890                1895           1900

CTC ATT CTC TTC TGT GAT TAT GTC TGT CAG AAC CTC CAT GAC TCC GAG           6063
Leu Ile Leu Phe Cys Asp Tyr Val Cys Gln Asn Leu His Asp Ser Glu
                    1905                1910                1915

CAC TTA ACG TGG CTC ATT GTA AAT CAC ATT CAA GAT CTG ATC AGC CTT           6111
His Leu Thr Trp Leu Ile Val Asn His Ile Gln Asp Leu Ile Ser Leu
     1920                1925                1930

TCC CAC GAG CCT CCA GTA CAG GAC TTC ATC AGT GCC GTT CAT CGG AAC           6159
Ser His Glu Pro Pro Val Gln Asp Phe Ile Ser Ala Val His Arg Asn
     1935                1940                1945

TCT GCT GCC AGC GGC CTG TTC ATC CAG GCA ATT CAG TCT CGT TGT GAA           6207
Ser Ala Ala Ser Gly Leu Phe Ile Gln Ala Ile Gln Ser Arg Cys Glu
     1950                1955                1960

AAC CTT TCA ACT CCA ACC ATG CTG AAG AAA ACT CTT CAG TGC TTG GAG           6255
Asn Leu Ser Thr Pro Thr Met Leu Lys Lys Thr Leu Gln Cys Leu Glu
     1965                1970                1975           1980

GGG ATC CAT CTC AGC CAG TCG GGA GCT GTG CTC ACG CTG TAT GTG GAC           6303
Gly Ile His Leu Ser Gln Ser Gly Ala Val Leu Thr Leu Tyr Val Asp
                    1985                1990                1995

AGG CTT CTG TGC ACC CCT TTC CGT GTG CTG GCT CGC ATG GTC GAC ATC           6351
Arg Leu Leu Cys Thr Pro Phe Arg Val Leu Ala Arg Met Val Asp Ile
          2000                2005                2010
```

FIG.4M

```
CTT GCT TGT CGC CGG GTA GAA ATG CTT CTG GCT GCA AAT TTA CAG AGC          6399
Leu Ala Cys Arg Arg Val Glu Met Leu Leu Ala Ala Asn Leu Gln Ser
        2015            2020            2025

AGC ATG GCC CAG TTG CCA ATG GAA GAA CTC AAC AGA ATC CAG GAA TAC          6447
Ser Met Ala Gln Leu Pro Met Glu Glu Leu Asn Arg Ile Gln Glu Tyr
        2030            2035            2040

CTT CAG AGC AGC GGG CTC GCT CAG AGA CAC CAA AGG CTC TAT TCC CTG          6495
Leu Gln Ser Ser Gly Leu Ala Gln Arg His Gln Arg Leu Tyr Ser Leu
        2045            2050            2055            2060

CTG GAC AGG TTT CGT CTC TCC ACC ATG CAA GAC TCA CTT AGT CCC TCT          6543
Leu Asp Arg Phe Arg Leu Ser Thr Met Gln Asp Ser Leu Ser Pro Ser
                2065            2070            2075

CCT CCA GTC TCT TCC CAC CCG CTG GAC GGG GAT GGG CAC GTG TCA CTG          6591
Pro Pro Val Ser Ser His Pro Leu Asp Gly Asp Gly His Val Ser Leu
        2080            2085            2090

GAA ACA GTG AGT CCG GAC AAA GAC TGG TAC GTT CAT CTT GTC AAA TCC          6639
Glu Thr Val Ser Pro Asp Lys Asp Trp Tyr Val His Leu Val Lys Ser
        2095            2100            2105

CAG TGT TGG ACC AGG TCA GAT TCT GCA CTG CTG GAA GGT GCA GAG CTG          6687
Gln Cys Trp Thr Arg Ser Asp Ser Ala Leu Leu Glu Gly Ala Glu Leu
        2110            2115            2120

GTG AAT CGG ATT CCT GCT GAA GAT ATG AAT GCC TTC ATG ATG AAC TCG          6735
Val Asn Arg Ile Pro Ala Glu Asp Met Asn Ala Phe Met Met Asn Ser
    2125            2130            2135            2140

GAG TTC AAC CTA AGC CTG CTA GCT CCA TGC TTA AGC CTA GGG ATG AGT          6783
Glu Phe Asn Leu Ser Leu Leu Ala Pro Cys Leu Ser Leu Gly Met Ser
                2145            2150            2155

GAA ATT TCT GGT GGC CAG AAG AGT GCC CTT TTT GAA GCA GCC CGT GAG          6831
Glu Ile Ser Gly Gly Gln Lys Ser Ala Leu Phe Glu Ala Ala Arg Glu
            2160            2165            2170
```

FIG.4N

| | |
|---|---|
| GTC ACT CTG GCC CGT GTG AGC GGC ACC GTG CAG CAG CTC CCT GCT GTC<br>Val Thr Leu Ala Arg Val Ser Gly Thr Val Gln Gln Leu Pro Ala Val<br>           2175                  2180                 2185 | 6879 |
| CAT CAT GTC TTC CAG CCC GAG CTG CCT GCA GAG CCG GCG GCC TAC TGG<br>His His Val Phe Gln Pro Glu Leu Pro Ala Glu Pro Ala Ala Tyr Trp<br>           2190                  2195                 2200 | 6927 |
| AGC AAG TTG AAT GAT CTG TTT GGG GAT GCT GCA CTG TAT CAG TCC CTG<br>Ser Lys Leu Asn Asp Leu Phe Gly Asp Ala Ala Leu Tyr Gln Ser Leu<br>2205               2210               2215               2220 | 6975 |
| CCC ACT CTG GCC CGG GCC CTG GCA CAG TAC CTG GTG GTG GTC TCC AAA<br>Pro Thr Leu Ala Arg Ala Leu Ala Gln Tyr Leu Val Val Val Ser Lys<br>                  2225               2230              2235 | 7023 |
| CTG CCC AGT CAT TTG CAC CTT CCT CCT GAG AAA GAG AAG GAC ATT GTG<br>Leu Pro Ser His Leu His Leu Pro Pro Glu Lys Glu Lys Asp Ile Val<br>             2240               2245                2250 | 7071 |
| AAA TTC GTG GTG GCA ACC CTT GAG GCC CTG TCC TGG CAT TTG ATC CAT<br>Lys Phe Val Val Ala Thr Leu Glu Ala Leu Ser Trp His Leu Ile His<br>           2255                 2260                 2265 | 7119 |
| GAG CAG ATC CCG CTG AGT CTG GAT CTC CAG GCA GGC CTG GAC TGC TGC<br>Glu Gln Ile Pro Leu Ser Leu Asp Leu Gln Ala Gly Leu Asp Cys Cys<br>           2270                 2275                2280 | 7167 |
| TGC CTG GCC CTG CAG CTG CCT GGC CTC TGG AGC GTG GTC TCC TCC ACA<br>Cys Leu Ala Leu Gln Leu Pro Gly Leu Trp Ser Val Val Ser Ser Thr<br>2285               2290               2295               2300 | 7215 |
| GAG TTT GTG ACC CAC GCC TGC TCC CTC ATC TAC TGT GTG CAC TTC ATC<br>Glu Phe Val Thr His Ala Cys Ser Leu Ile Tyr Cys Val His Phe Ile<br>                 2305               2310               2315 | 7263 |
| CTG GAG GCC GTT GCA GTG CAG CCT GGA GAG CAG CTT CTT AGT CCA GAA<br>Leu Glu Ala Val Ala Val Gln Pro Gly Glu Gln Leu Leu Ser Pro Glu<br>           2320                 2325                2330 | 7311 |

FIG.40

```
AGA AGG ACA AAT ACC CCA AAA GCC ATC AGC GAG GAG GAG GAG GAA GTA      7359
Arg Arg Thr Asn Thr Pro Lys Ala Ile Ser Glu Glu Glu Glu Glu Val
        2335            2340                2345

GAT CCA AAC ACA CAG AAT CCT AAG TAT ATC ACT GCA GCC TGT GAG ATG      7407
Asp Pro Asn Thr Gln Asn Pro Lys Tyr Ile Thr Ala Ala Cys Glu Met
        2350            2355                2360

GTG GCA GAA ATG GTG GAG TCT CTG CAG TCG GTG TTG GCC TTG GGT CAT      7455
Val Ala Glu Met Val Glu Ser Leu Gln Ser Val Leu Ala Leu Gly His
        2365            2370                2375            2380

AAA AGG AAT AGC GGC GTG CCG GCG TTT CTC ACC CCA TTG CTC AGG AAC      7503
Lys Arg Asn Ser Gly Val Pro Ala Phe Leu Thr Pro Leu Leu Arg Asn
            2385                2390                2395

ATC ATC ATC AGC CTG GCC CGC CTG CCC CTT GTC AAC AGC TAC ACA CGT      7551
Ile Ile Ile Ser Leu Ala Arg Leu Pro Leu Val Asn Ser Tyr Thr Arg
            2400                2405                2410

GTG CCC CCA CTG GTG TGG AAG CTT GGA TGC TCA CCC AAA CCG GGA GGC      7599
Val Pro Pro Leu Val Trp Lys Leu Gly Trp Ser Pro Lys Pro Gly Gly
            2415                2420                2425

GAT TTT GGC ACA GCA TTC CCT GAG ATC CCC GTG GAG TTC CTC CAG GAA      7647
Asp Phe Gly Thr Ala Phe Pro Glu Ile Pro Val Glu Phe Leu Gln Glu
            2430                2435                2440

AAG GAA GTC TTT AAG GAG TTC ATC TAC CGC ATC AAC ACA CTA GGC TGG      7695
Lys Glu Val Phe Lys Glu Phe Ile Tyr Arg Ile Asn Thr Leu Gly Trp
        2445            2450                2455            2460

ACC AGT CGT ACT CAG TTT GAA GAA ACT TGG GCC ACC CTC CTT GGT GTC      7743
Thr Ser Arg Thr Gln Phe Glu Glu Thr Trp Ala Thr Leu Leu Gly Val
            2465                2470                2475

CTG GTG ACG CAG CCC CTC GTG ATG GAG CAG GAG GAG AGC CCA CCA GAA      7791
Leu Val Thr Gln Pro Leu Val Met Glu Gln Glu Glu Ser Pro Pro Glu
            2480                2485                2490
```

FIG.4P

| | |
|---|---:|
| GAA GAC ACA GAG AGG ACC CAG ATC AAC GTC CTG GCC GTG CAG GCC ATC<br>Glu Asp Thr Glu Arg Thr Gln Ile Asn Val Leu Ala Val Gln Ala Ile<br>            2495                      2500                      2505 | 7839 |
| ACC TCA CTG GTG CTC AGT GCA ATG ACT GTG CCT GTG GCC GGC AAC CCA<br>Thr Ser Leu Val Leu Ser Ala Met Thr Val Pro Val Ala Gly Asn Pro<br>            2510                      2515                      2520 | 7887 |
| GCT GTA AGC TGC TTG GAG CAG CAG CCC CGG AAC AAG CCT CTG AAA GCT<br>Ala Val Ser Cys Leu Glu Gln Gln Pro Arg Asn Lys Pro Leu Lys Ala<br>            2525                      2530                      2535                    2540 | 7935 |
| CTC GAC ACC AGG TTT GGG AGG AAG CTG AGC ATT ATC AGA GGG ATT GTG<br>Leu Asp Thr Arg Phe Gly Arg Lys Leu Ser Ile Ile Arg Gly Ile Val<br>                      2545                      2550                    2555 | 7983 |
| GAG CAA GAG ATT CAA GCA ATG GTT TCA AAG AGA GAG AAT ATT GCC ACC<br>Glu Gln Glu Ile Gln Ala Met Val Ser Lys Arg Glu Asn Ile Ala Thr<br>                      2560                      2565                    2570 | 8031 |
| CAT CAT TTA TAT CAG GCA TGG GAT CCT GTC CCT TCT CTG TCT CCG GCT<br>His His Leu Tyr Gln Ala Trp Asp Pro Val Pro Ser Leu Ser Pro Ala<br>            2575                      2580                      2585 | 8079 |
| ACT ACA GGT GCC CTC ATC AGC CAC GAG AAG CTG CTG CTA CAG ATC AAC<br>Thr Thr Gly Ala Leu Ile Ser His Glu Lys Leu Leu Leu Gln Ile Asn<br>            2590                      2595                    2600 | 8127 |
| CCC GAG CGG GAG CTG GGG AGC ATG AGC TAC AAA CTC GGC CAG GTG TCC<br>Pro Glu Arg Glu Leu Gly Ser Met Ser Tyr Lys Leu Gly Gln Val Ser<br>2605                      2610                      2615                    2620 | 8175 |
| ATA CAC TCC GTG TGG CTG GGC AAC AGC ATC ACA CCC CTG AGG GAG GAG<br>Ile His Ser Val Trp Leu Gly Asn Ser Ile Thr Pro Leu Arg Glu Glu<br>                      2625                      2630                    2635 | 8223 |
| GAA TGG GAC GAG GAA GAG GAG GAG GAG GCC GAC GCC CCT GCA CCT TCG<br>Glu Trp Asp Glu Glu Glu Glu Glu Glu Ala Asp Ala Pro Ala Pro Ser<br>                      2640                      2645                    2650 | 8271 |

FIG.4Q

```
TCA CCA CCC ACG TCT CCA GTC AAC TCC AGG AAA CAC CGG GCT GGA GTT                    8319
Ser Pro Pro Thr Ser Pro Val Asn Ser Arg Lys His Arg Ala Gly Val
        2655            2660               2665

GAC ATC CAC TCC TGT TCG CAG TTT TTG CTT GAG TTG TAC AGC CGC TGG                    8367
Asp Ile His Ser Cys Ser Gln Phe Leu Leu Glu Leu Tyr Ser Arg Trp
        2670            2675               2680

ATC CTG CCG TCC AGC TCA GCC AGG AGG ACC CCG GCC ATC CTG ATC AGT                    8415
Ile Leu Pro Ser Ser Ser Ala Arg Arg Thr Pro Ala Ile Leu Ile Ser
2685            2690            2695                  2700

GAG GTG GTC AGA TCC CTT CTA GTC GTC TCA GAC TTG TTC ACC GAG CGC                    8463
Glu Val Val Arg Ser Leu Leu Val Val Ser Asp Leu Phe Thr Glu Arg
            2705            2710              2715

AAC CAG TTT GAG CTG ATG TAT GTG ACG CTG ACA GAA CTG CGA AGG GTC                    8511
Asn Gln Phe Glu Leu Met Tyr Val Thr Leu Thr Glu Leu Arg Arg Val
        2720            2725               2730

CAC CCT TCA GAA GAC GAG ATC CTC GCT CAG TAC CTG GTG CCT GCC ACC                    8559
His Pro Ser Glu Asp Glu Ile Leu Ala Gln Tyr Leu Val Pro Ala Thr
        2735            2740               2745

TGC AAG GCA GCT GCC GTC CTT GGC ATG GAC AAG GCC GTG GCG GAG CCT                    8607
Cys Lys Ala Ala Ala Val Leu Gly Met Asp Lys Ala Val Ala Glu Pro
        2750            2755               2760

GTC AGC CGC CTG CTG GAG AGC ACG CTC AGG AGC AGC CAC CTG CCC AGC                    8655
Val Ser Arg Leu Leu Glu Ser Thr Leu Arg Ser Ser His Leu Pro Ser
2765            2770            2775                  2780

AGG GTT GGA GCC CTG CAC GGC ATC CTC TAT GTG CTG GAG TGC GAC CTG                    8703
Arg Val Gly Ala Leu His Gly Ile Leu Tyr Val Leu Glu Cys Asp Leu
        2785            2790               2795

CTG GAC GAC ACT GCC AAG CAG CTC ATC CCG GTC ATC AGC GAC TAT CTC                    8751
Leu Asp Asp Thr Ala Lys Gln Leu Ile Pro Val Ile Ser Asp Tyr Leu
        2800            2805               2810
```

FIG.4R

```
CTC TCC AAC CTG AAA GGG ATC GCC CAC TGC GTG AAC ATT CAC AGC CAG    8799
Leu Ser Asn Leu Lys Gly Ile Ala His Cys Val Asn Ile His Ser Gln
        2815            2820            2825

CAG CAC GTA CTG GTC ATG TGT GCC ACT GCG TTT TAC CTC ATT GAG AAC    8847
Gln His Val Leu Val Met Cys Ala Thr Ala Phe Tyr Leu Ile Glu Asn
    2830            2835            2840

TAT CCT CTG GAC GTA GGG CCG GAA TTT TCA GCA TCA ATA ATA CAG ATG    8895
Tyr Pro Leu Asp Val Gly Pro Glu Phe Ser Ala Ser Ile Ile Gln Met
2845            2850            2855            2860

TGT GGG GTG ATG CTG TCT GGA AGT GAG GAG TCC ACC CCC TCC ATC ATT    8943
Cys Gly Val Met Leu Ser Gly Ser Glu Glu Ser Thr Pro Ser Ile Ile
            2865            2870            2875

TAC CAC TGT GCC CTC AGA GGC CTG GAG CGC CTC CTG CTC TCT GAG CAG    8991
Tyr His Cys Ala Leu Arg Gly Leu Glu Arg Leu Leu Leu Ser Glu Gln
        2880            2885            2890

CTC TCC CGC CTG GAT GCA GAA TCC CTG GTC AAG CTG AGT GTG GAC AGA    9039
Leu Ser Arg Leu Asp Ala Glu Ser Leu Val Lys Leu Ser Val Asp Arg
    2895            2900            2905

GTG AAC GTG CAC AGC CCG CAC CGG GCC ATG GCC GCT CTG GGC CTG ATG    9087
Val Asn Val His Ser Pro His Arg Ala Met Ala Ala Leu Gly Leu Met
2910            2915            2920

CTC ACC TGC ATG TAC ACA GGA AAG GAG AAA GTC AGT CCG GGT AGA ACT    9135
Leu Thr Cys Met Tyr Thr Gly Lys Glu Lys Val Ser Pro Gly Arg Thr
2925            2930            2935            2940

TCA GAC CCT AAT CCT GCA GCC CCC GAC AGC GAG TCA GTG ATT GTT GCT    9183
Ser Asp Pro Asn Pro Ala Ala Pro Asp Ser Glu Ser Val Ile Val Ala
            2945            2950            2955

ATG GAG CGG GTA TCT GTT CTT TTT GAT AGG ATC AGG AAA GGC TTT CCT    9231
Met Glu Arg Val Ser Val Leu Phe Asp Arg Ile Arg Lys Gly Phe Pro
        2960            2965            2970
```

FIG.4S

```
TGT GAA GCC AGA GTG GTG GCC AGG ATC CTG CCC CAG TTT CTA GAC GAC       9279
Cys Glu Ala Arg Val Val Ala Arg Ile Leu Pro Gln Phe Leu Asp Asp
        2975                2980                2985

TTC TTC CCA CCC CAG GAC ATC ATG AAC AAA GTC ATC GGA GAG TTT CTG       9327
Phe Phe Pro Pro Gln Asp Ile Met Asn Lys Val Ile Gly Glu Phe Leu
        2990                2995                3000

TCC AAC CAG CAG CCA TAC CCC CAG TTC ATG GCC ACC GTG GTG TAT AAG       9375
Ser Asn Gln Gln Pro Tyr Pro Gln Phe Met Ala Thr Val Val Tyr Lys
3005                3010                3015                3020

GTG TTT CAG ACT CTG CAC AGC ACC GGG CAG TCG TCC ATG GTC CGG GAC       9423
Val Phe Gln Thr Leu His Ser Thr Gly Gln Ser Ser Met Val Arg Asp
            3025                3030                3035

TGG GTC ATG CTG TCC CTC TCC AAC TTC ACG CAG AGG GCC CCG GTC GCC       9471
Trp Val Met Leu Ser Leu Ser Asn Phe Thr Gln Arg Ala Pro Val Ala
            3040                3045                3050

ATG GCC ACG TGG AGC CTC TCC TGC TTC TTT GTC AGC GCG TCC ACC AGC       9519
Met Ala Thr Trp Ser Leu Ser Cys Phe Phe Val Ser Ala Ser Thr Ser
            3055                3060                3065

CCG TGG GTC GCG GCC ATC CTC CCA CAT GTC ATC AGC AGG ATG GGC AAG       9567
Pro Trp Val Ala Ala Ile Leu Pro His Val Ile Ser Arg Met Gly Lys
        3070                3075                3080

CTG GAG CAG GTG GAC GTG AAC CTT TTC TGC CTG GTC GCC ACA GAC TTC       9615
Leu Glu Gln Val Asp Val Asn Leu Phe Cys Leu Val Ala Thr Asp Phe
3085                3090                3095                3100

TAC AGA CAC CAG ATA GAG GAG GAG CTC GAC CGC AGG GCC TTC CAG TCT       9663
Tyr Arg His Gln Ile Glu Glu Glu Leu Asp Arg Arg Ala Phe Gln Ser
            3105                3110                3115
```

FIG.4T

```
GTG CTT GAG GTC GTT GCA GCC CCA GGA AGC CCA TAT CAC CGG CTG CTG      9711
Val Leu Glu Val Val Ala Ala Pro Gly Ser Pro Tyr His Arg Leu Leu
        3120              3125              3130

ACT TGT TTA CGA AAT GTC CAC AAG GTC ACC ACC TGC T GAGCGCCATG         9758
Thr Cys Leu Arg Asn Val His Lys Val Thr Thr Cys
        3135              3140

GTGGGAGAGA CTGTGAGGCG GCAGCTGGGG CCGGAGCCTT TGGAAGTCTG TGCCCTTGTG    9818

CCCTGCCTCC ACCGAGCCAG CTTGGTCCCT ATGGGCTTCC GCACATGCCG CGGGCGGCCA    9878

GGCAACGTGC GTGTCTCTGC CATGTGGCAG AAGTGCTCTT TGTGGCAGTG GCCAGGCAGG    9938

GAGTGTCTGC AGTCCTGGTG GGGCTGAGCC TGAGGCCTTC CAGAAAGCAG GAGCAGCTGT    9998

GCTGCACCCC ATGTGGGTGA CCAGGTCCTT TCTCCTGATA GTCACCTGCT GGTTGTTGCC    10058

AGGTTGCAGC TGCTCTTGCA TCTGGGCCAG AAGTCCTCCC TCCTGCAGGC TGGCTGTTGG    10118

CCCCTCTGCT GTCCTGCAGT AGAAGGTGCC GTGAGCAGGC TTTGGGAACA CTGGCCTGGG    10178

TCTCCCTGGT GGGGTGTGCA TGCCACGCCC CGTGTCTGGA TGCACAGATG CCATGGCCTG    10238

TGCTGGGCCA GTGGCTGGGG GTGCTAGACA CCCGGCACCA TTCTCCCTTC TCTCTTTTCT    10298

TCTCAGGATT TAAAATTTAA TTATATCAGT AAAGAGATTA ATTTTAACGT AAAAAAAAAA    10358

AAAAAAAA                                                             10366
```

FIG.4U

COMPOSITE 
129-1 
PCC4-8 
PCC4-5 
PCC4-3  An
FIG.18

HUNTINGTIN DNA, PROTEIN AND USES THEREOF

CROSS-REFERENCE TO RELATED APPLICATION

This application is a continuation-in-part of U.S. patent application Ser. No. 08/085,000, filed July 1, 1993, now abandoned, which is a continuation-in-part of U.S. patent application Ser. No. 08/027,498, filed Mar. 5, 1993, abandoned, the contents of both of which are incorporated herein by reference.

STATEMENT AS TO RIGHTS TO INVENTIONS MADE UNDER FEDERALLY-SPONSORED RESEARCH AND DEVELOPMENT

Part of the work performed during development of this invention utilized U.S. Government funds; the U.S. Government has certain rights in this invention.

FIELD OF THE INVENTION

The invention is in the field of the detection and treatment of genetic diseases. Specifically, the invention is directed to the huntingtin gene (also called the IT15 gene), huntingtin protein encoded by such gene, and the use of this gene and protein in assays (1) for the detection of a predisposition to develop Huntington's disease, (2) for the diagnosis of Huntington's disease (3) for the treatment of Huntington's disease, and (4) for monitoring the course of treatment of such treatment.

BACKGROUND OF THE INVENTION

Huntington's disease (HD) is a progressive neurodegenerative disorder characterized by motor disturbance, cognitive loss and psychiatric manifestations (Martin and Gusella, N. Engl. J. Med. 315:1267–1276 (1986). It is inherited in an autosomal dominant fashion, and affects about 1/10,000 individuals in most populations of European origin (Harper, P. S. et al., in Huntington's disease, W. B. Saunders, Philadelphia, 1991). The hallmark of HD is a distinctive choreic movement disorder that typically has a subtle, insidious onset in the fourth to fifth decade of life and gradually worsens over a course of 10 to 20 years until death. Occasionally, HD is expressed in juveniles typically manifesting with more severe symptoms including rigidity and a more rapid course. Juvenile onset of HD is associated with a preponderance of paternal transmission of the disease allele. The neuropathology of HD also displays a distinctive pattern, with selective loss of neurons that is most severe in the caudate and putamen regions of the brain. The biochemical basis for neuronal death in HD has not yet been explained, and there is consequently no treatment effective in delaying or preventing the onset and progression of this devastating disorder.

The genetic defect causing HD was assigned to chromosome 4 in 1983 in one of the first successes of linkage analysis using polymorphic DNA markers in man (Gusella et al., Nature 306:234–238 (1983). Since that time, we have pursued a location cloning approach to isolating and characterizing the HD gene based on progressively refining its localization (Gusella, FASEB J. 3:2036–2041 (1989); Guseila, Adv. Hum. Genet. 20:125–151 (1991)). Among other work, this has involved the generation of new genetic markers in the region by a number of techniques (Pohl et al., Nucleic Acids Res. 16:9185–9198 (1988); Whaley et al., Somat. Cell. Mol. Genet. 17:83–91 (1991); MacDonald et al., J. Clin. Inv. 84:1013–1016 (1989)), the establishment of genetic (MacDonald et al., Neuron 3:183–190 (1989); Allitto et al., Genomics 9:104–112 (1991)) and physical maps of the implicated regions (Bucan et al., Genomics 6:1–15 (1990); Bates et al., Nature Genet. 1:180–187 (1992); Doucette-Stamm et al., Somat. Cell Mol. Genet. 17:471–480 (1991); Altherr et al., Genomics 13:1040–1046 (1992)), the cloning of the 4p telomere of an HD chromosome in a YAC clone (Bates et al., Am. J. Hum. Genet. 46:762–775 (1990); Youngman et al., Genomics 14:350–356 (1992)), the establishment of YAC [yeast artificial chromosome] (Bates et al., Nature Genet. 1:180–187 (1992)) and cosmid contigs (a series of overlapping clones which together form a whole sequence) of the candidate region, as well as the analysis and characterization of a number of candidate genes from the region (Thompson et al., Genomics 11:1133–1142 (1991); Taylor et al., Nature Genet. 2:223–227 (1992); Ambrose et al., Hum. Mol. Genet. 1:697–703 (1992)). Analysis of recombination events in HD kindreds has identified a candidate region of 2.2 Mb, between D4S10 and D4S98 in 4p16.3, as the most likely position of the HD gene (MacDonald et al., Neuron 3:183–190 (1989); Bates et al., Am. J. Hum. Genet. 49:7–16 (1991); Snell et al., Am. J. Hum. Genet. 51:357–362 (1992)). Investigations of linkage disequilibrium between HD and DNA markers in 4p16.3 (Snell et al., J. Med. Genet. 26:673–675 (1989); Theilman et al., J. Med. Genet. 26:676–681 (1989)) have suggested that multiple mutations have occurred to cause the disorder (McDonald et al., Am. J. Hum. Genet. 49:723–734 (1991)). However, haplotype analysis using multi-allele markers has indicated that at least ⅓ of HD chromosomes are ancestrally related (MacDonald et al., Nature Genet. 1:99–103 (1992)). The haplotype shared by these HD chromosomes points to a 500 kb segment between D4S180 and D4S182 as the most likely site of the genetic defect.

Targeting this 500 kb region for saturation with gene transcripts, exon amplification has been used as a rapid method for obtaining candidate coding sequences (Buckler et al., Proc. Natl. Acad. Sci. USA 88:4005–4009 (1991)). This strategy has previously identified three genes: the a-adducin gene (ADDA) (Taylor et al., Nature Genet. 2:223–227 (1992)); a putative novel transporter gene (IT10C3) in the distal portion of this segment; and a novel G protein-coupled receptor kinase gene (IT11) in the central portion (Ambrose et al., Hum. Mol. Genet. 1:697–703 (1992)). However, no defects implicating any of these genes as the HD locus have been found.

SUMMARY OF THE INVENTION

A large gene, termed herein "huntingtin" or "IT15," has been identified that spans about 210 kb and encodes a previously undescribed protein of about 348 kDa. The huntingtin reading frame contains a polymorphic (CAG)$_n$ trinucleotide repeat with at least 17 alleles in the normal population, varying from 11 to about 34 CAG copies. On HD chromosomes, the length of the trinucleotide repeat is substantially increased, for example, about 37 to at least 73 copies, and shows an apparent correlation with age of onset, the longest segments are detected in juvenile HD cases. The instability in length of the repeat is reminiscent of similar trinucleotide repeats in the fragile X syndrome and in myotonic dystrophy (Suthers et al., J. Med. Genet. 29:761–765 (1992)). The presence of an unstable, expandable trinucleotide repeat on HD chromosomes in the region of strongest linkage disequilibrium with the disorder suggests that this alteration underlies the dominant phenotype of HD, and that huntingtin encodes the HD gene.

The invention is directed to the protein huntingtin, DNA and RNA encoding this protein, and uses thereof.

Accordingly, in a first embodiment, the invention is directed to purified preparations of the protein huntingtin.

In a further embodiment, the invention is directed to a recombinant construct containing DNA or RNA encoding huntingtin.

In a further embodiment, the invention is directed to a vector containing such huntingtin-encoding nucleic acid.

In a further embodiment, the invention is directed to a host transformed with such vector.

In a further embodiment, the invention is directed to a method for producing huntingtin from such recombinant host.

In a further embodiment, the invention is direct to a method for diagnosing Huntington's disease using such huntingtin DNA, RNA and/or protein.

In a further embodiment, the invention is directed to a method for treating Huntington's disease using such huntingtin DNA, RNA and/or protein.

In a further embodiment, the invention is directed to a method of gene therapy of a symptomatic or presymptomatic patient, such method comprising providing a functional huntingtin gene with a $(CAG)_n$ repeat of the normal range of 11-34 copies to the desired cells of such patient in need of such treatment, in a manner that permits the expression of the huntingtin protein provided by such gene, for a time and in a quantity sufficient to provide the huntingtin function to the cells of such patient.

In a further embodiment, the invention is directed to a method of gene therapy of a symptomatic or presymptomatic patient, such method comprising providing a functional huntingtin antisense gene to the desired cells of such patient in need of such treatment, in a manner that permits the expression of huntingtin antisense RNA provided by such gene, for a time and in a quantity sufficient to inhibit huntingtin mRNA expression in the cells of such patient.

In a further embodiment, the invention is directed to a method of gene therapy of a symptomatic or presymptomatic patient, such method comprising providing a functional huntingtin gene to the cells of such patient in need of such gene; in one embodiment the functional huntingtin gene contains a $(CAG)_n$ repeat size between 11-34 copies.

In a further embodiment, the invention is directed to a method for diagnosing Huntington's disease or a predisposition to develop Huntington's disease in a patient, such method comprising determining the number of $(CAG)_n$ repeats present in the huntingtin gene in such patient and especially in the affected tissue of such patient.

In a further embodiment, the invention is directed to a method for treating Huntington's disease in a patient, such method comprising decreasing the number of huntingtin $(CAG)_n$ repeats in the huntingtin gene in the desired cells of such patient.

The composite sequence was derived as follows. From 22 bases 3' to the putative initiator Met ATG, the sequence was compiled from the cDNA clones and exons shown. There are 9 bases of sequence intervening between the 3' end of IT16B and the 5' end of IT15B. These were by PCR amplification of first strand cDNA and sequencing of the PCR product. At the 5' end of the composite sequence, the cDNA clone IT16C terminates 27 bases upstream of the $(CAG)_n$. However, when IT16C was identified, we had already generated genomic sequence surrounding the $(CAG)_n$ in an attempt to generate new polymorphisms. This sequence matched the IT16C sequence, and extended it 337 bases upstream, including the apparent Met initiation codon.

FIG. 4. Composite sequence of huntingtin (IT15)(SEQ ID NO:5 and SEQ ID NO:6). The composite DNA sequence of huntingtin (IT15) is shown (SEQ ID NO:5). The predicted protein product (SEQ ID NO:6) is shown below the DNA sequence, based on the assumption that translation begins at the first in-frame methionine of the long open reading frame.

Figure 5:
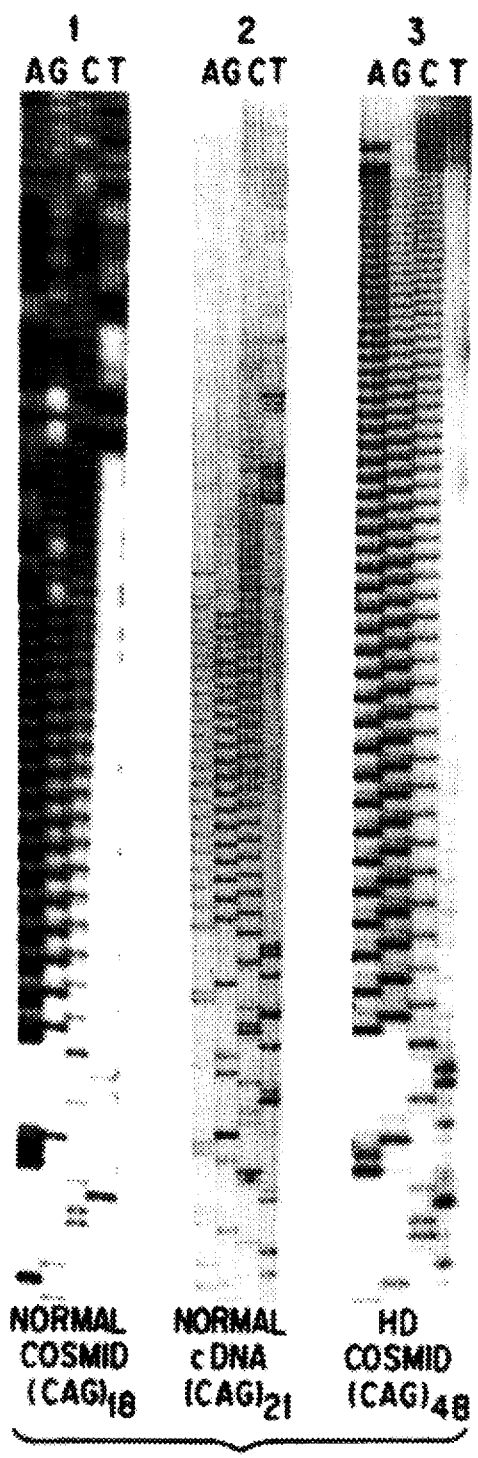

FIG. 5. DNA sequence analysis of the $(CAG)_n$ repeat. DNA sequence shown in panels 1, 2 and 3, demonstrates the variation in the $(CAG)_n$ repeat detected in normal cosmid L191F1 (1), cDNA IT16C (2), and HD cosmid GUS72-2130. Panels 1 and 3 were generated by direct sequencing of cosmid subclones using the following primer (SEQ ID NO:1):

5' GGC GGG AGA CCG CCA TGG CG 3'.

Panel 2 was generated using the pBSKII T7 primer (SEQ ID NO:2):

5' AAT ACG ACT CAC TAT AG 3'.

Figure 6:
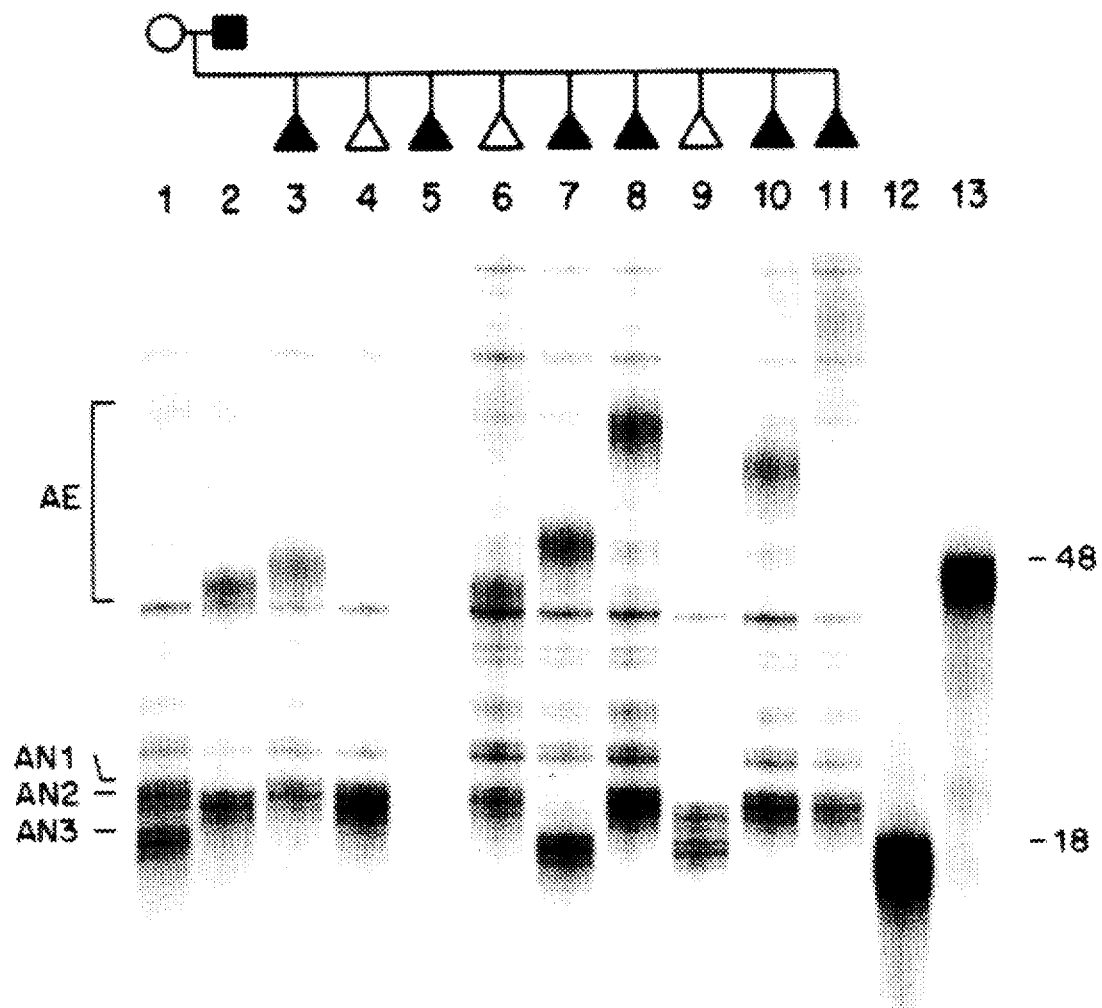

FIG. 6. PCR analysis of the $(CAG)_n$ repeat in a Venezuelan HD sibship with some offspring displaying juvenile onset. Results of PCR analysis of a sibship in the Venezuela HD pedigree are shown. Affected individuals are represented by shaded symbols. Progeny are shown as triangles for confidentiality. AN1, AN2 and AN3 mark the positions of the allelic products from normal chromosomes. AE marks the range of PCR products from the HD chromosome. The intensity of background constant bands, which represent a useful reference for comparison of the above PCR products, varies with slight differences in PCR conditions. The PCR products from cosmids L191F1 and GUS72-2130 are loaded in lanes 12 and 13 and have 18 and 48 CAG repeats, respectively.

Figure 7:
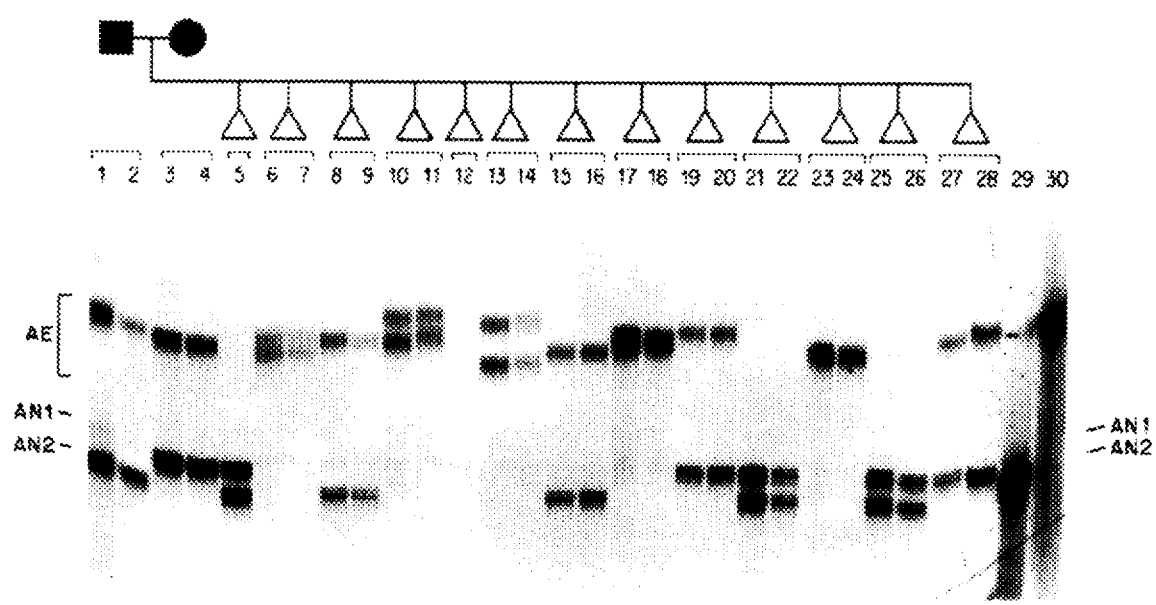

FIG. 7. PCR analysis of the $(CAG)_n$ repeat in a Venezuelan HD sibship with offspring homozygous for the same HD haplotype. Results of PCR analysis of a sibship from the Venezuela HD pedigree in which both parents are affected by HD are shown. Progeny are shown as triangles for confidentiality and no HD diagnostic information is given to preserve the blind status of investigators in the Venezuelan Collaborative Group. AN1 and AN2 mark the positions of the allelic products from normal parental chromosomes. AE marks the range of PCR products from the HD chromosome. The PCR products from cosmids L191F1 and GUS72-2130 are loaded in lanes 29 and 30 and have 18 and 48 CAG repeats, respectively.

Figure 8:
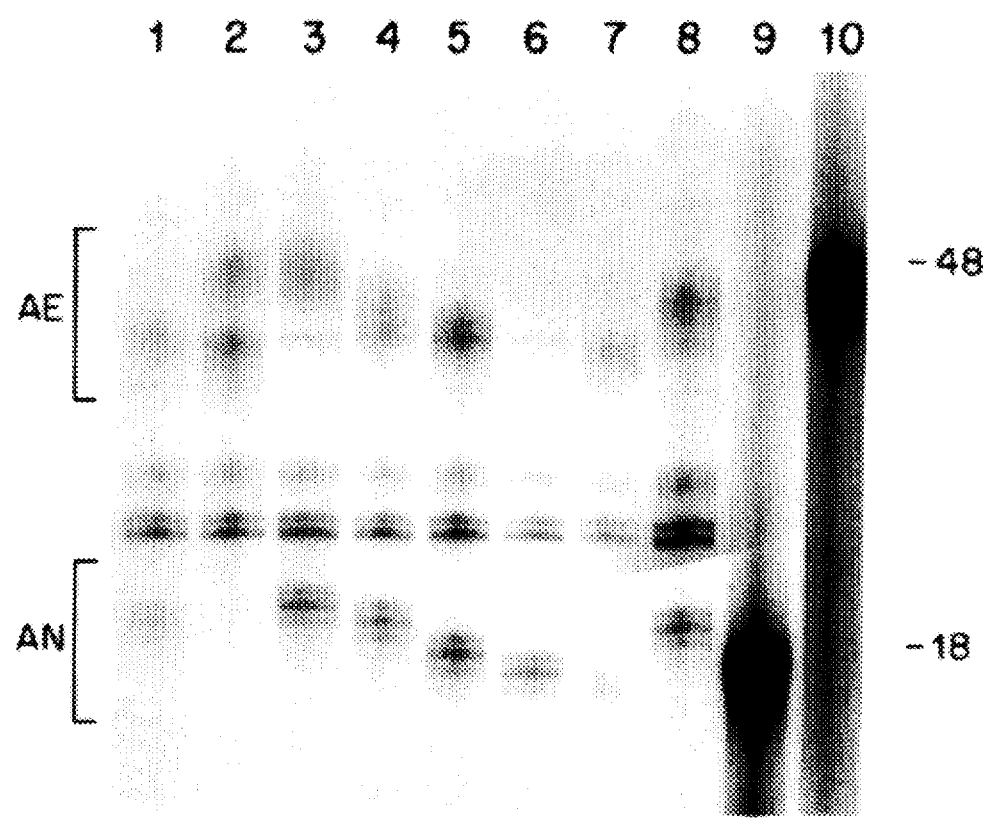

FIG. 8. PCR analysis of the $(CAG)_n$ repeat in members of an American family with an individual homozygous for the major HD haplotype. Results of PCR analysis of members of an American family segregating the major HD haplotype. AN marks the range of normal alleles; AE marks the range of HD alleles. Lanes 1, 3, 4, 5, 7 and 8 represent PCR products from related HD heterozygotes. Lane 2 contains the PCR products from a member of the family homozygous for the same HD chromosome. Lane 6 contains PCR products from a normal individual. Pedigree relationships and affected status are not presented to preserve confidentiality. The PCR products from cosmids L191F1 and GUS72-2130 (which was derived from the individual represented in lane 2) are loaded in lanes 9 and 10 and have 18 and 48 CAG repeats, respectively.

Figure 9:
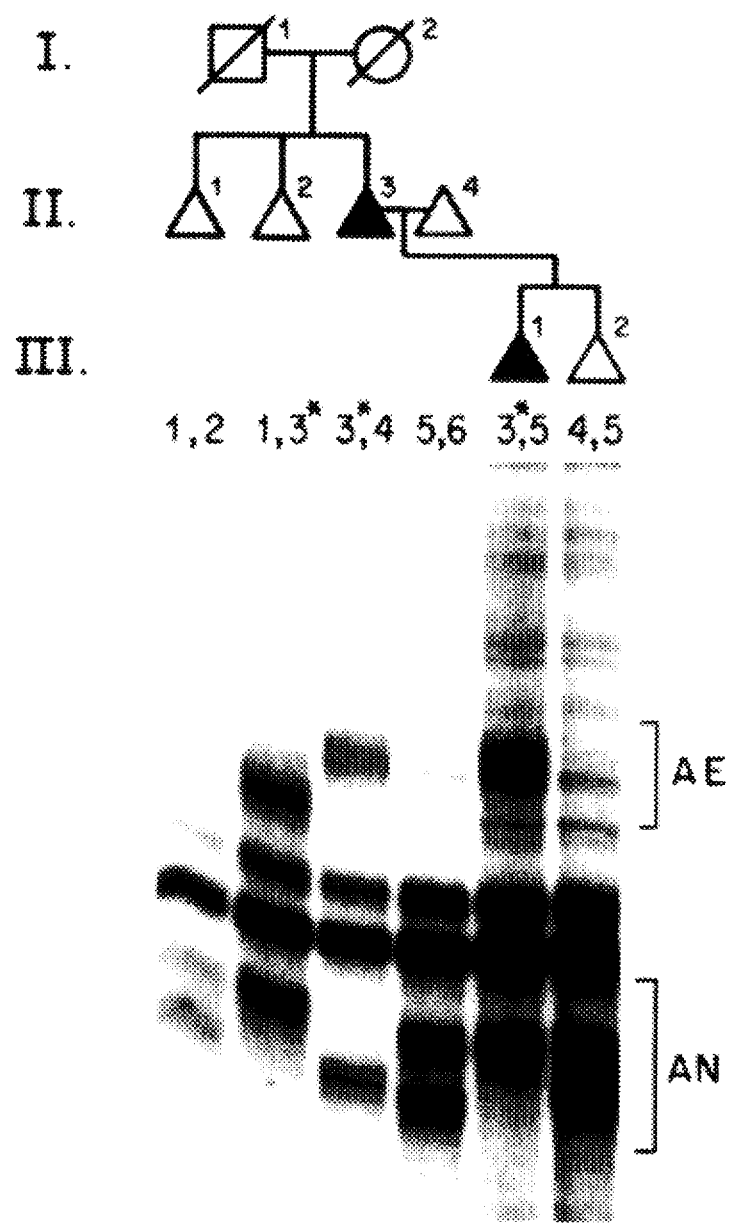
Figure 10:

FIGS. 9 and 10. PCR analysis of the $(CAG)_n$ repeat in two families with supposed new mutation causing HD. Results of PCR analysis of two families in which sporadic HD cases representing putative new mutants are shown. Individuals in each pedigree are numbered by generation (Roman numerals) and order in the pedigree. Triangles are used to protect confidentiality. Filled symbols indicate symptomatic individuals. The different chromosomes segregating in the pedigree have been distinguished by extensive typing with polymorphic markers in 4p16.3 and have been assigned arbitrary numbers shown above the gel lanes. The starred chromosomes (3 in FIG. 9, 1 in FIG. 10) represent the presumed HD chromosome. AN denotes the range of normal alleles; AE denotes the range of alleles present in affected individuals and in their unaffected relatives bearing the same chromosomes.

Figure 11:
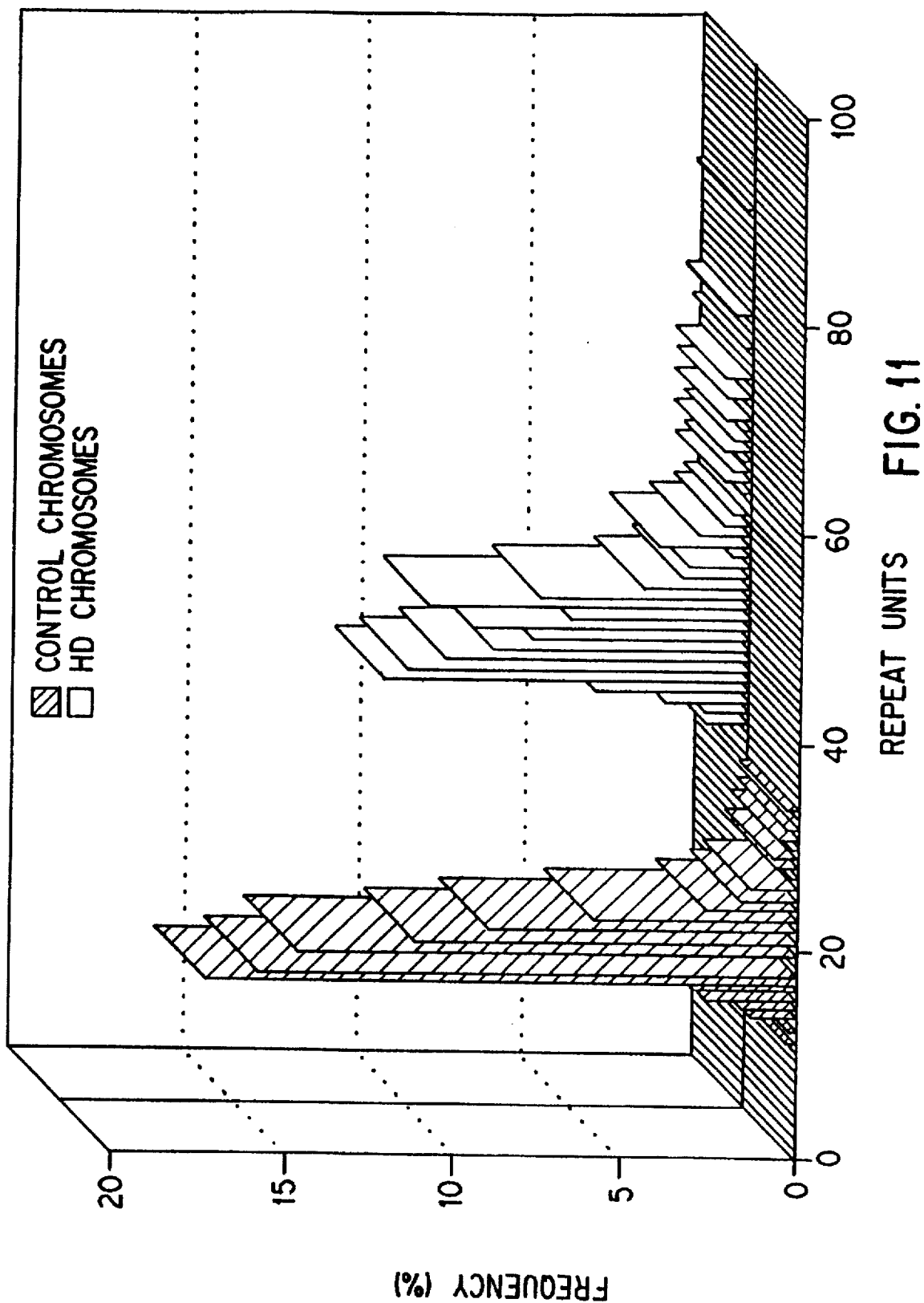

FIG. 11. Comparison of $(CAG)_n$ Repeat Unit Number on Control and HD Chromosomes. Frequency distributions are shown for the number of $(CAG)_n$ repeat units observed on 425 HD chromosomes from 150 independent families, and from 545 control chromosomes.

Figure 12A:
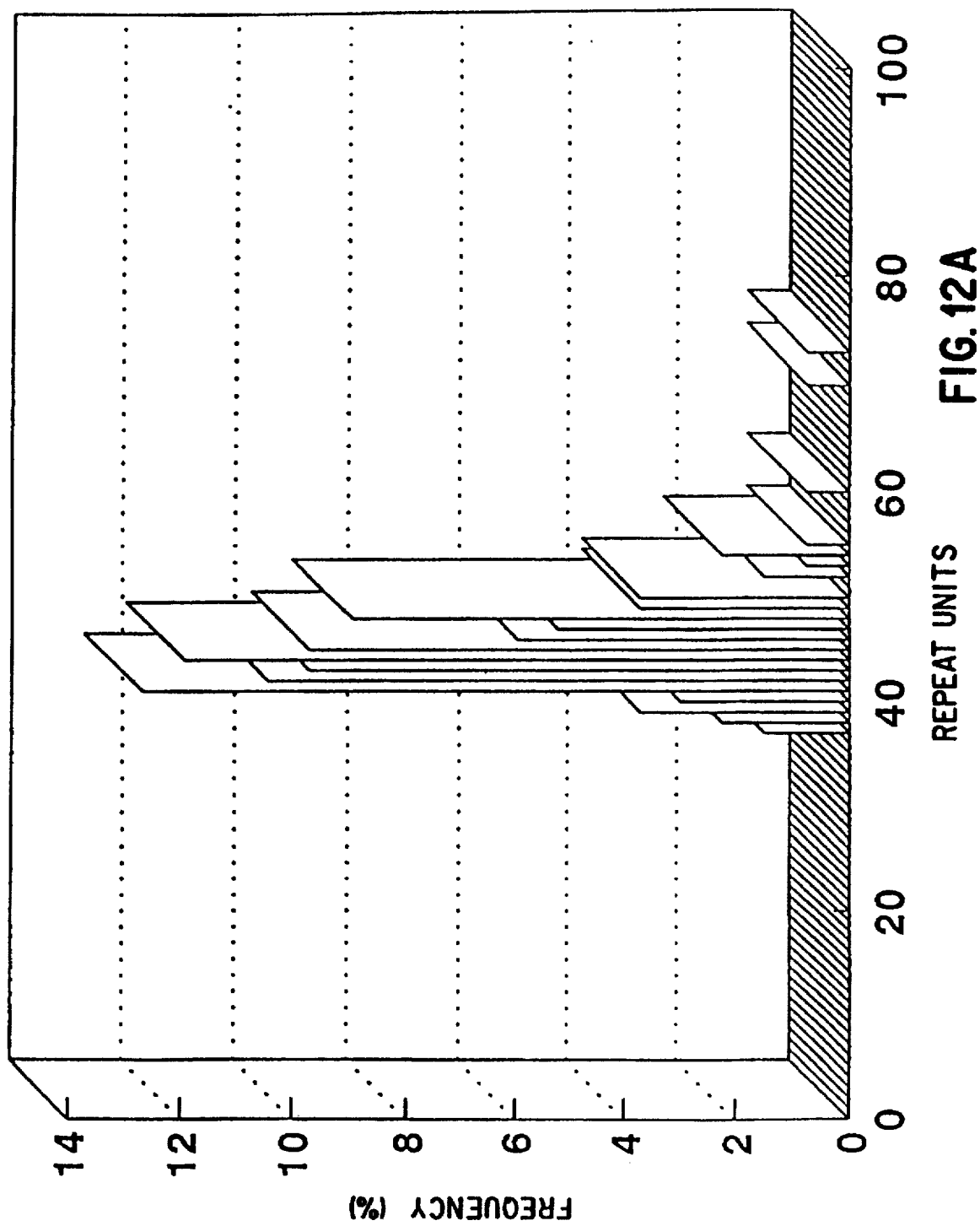
Figure 12B:
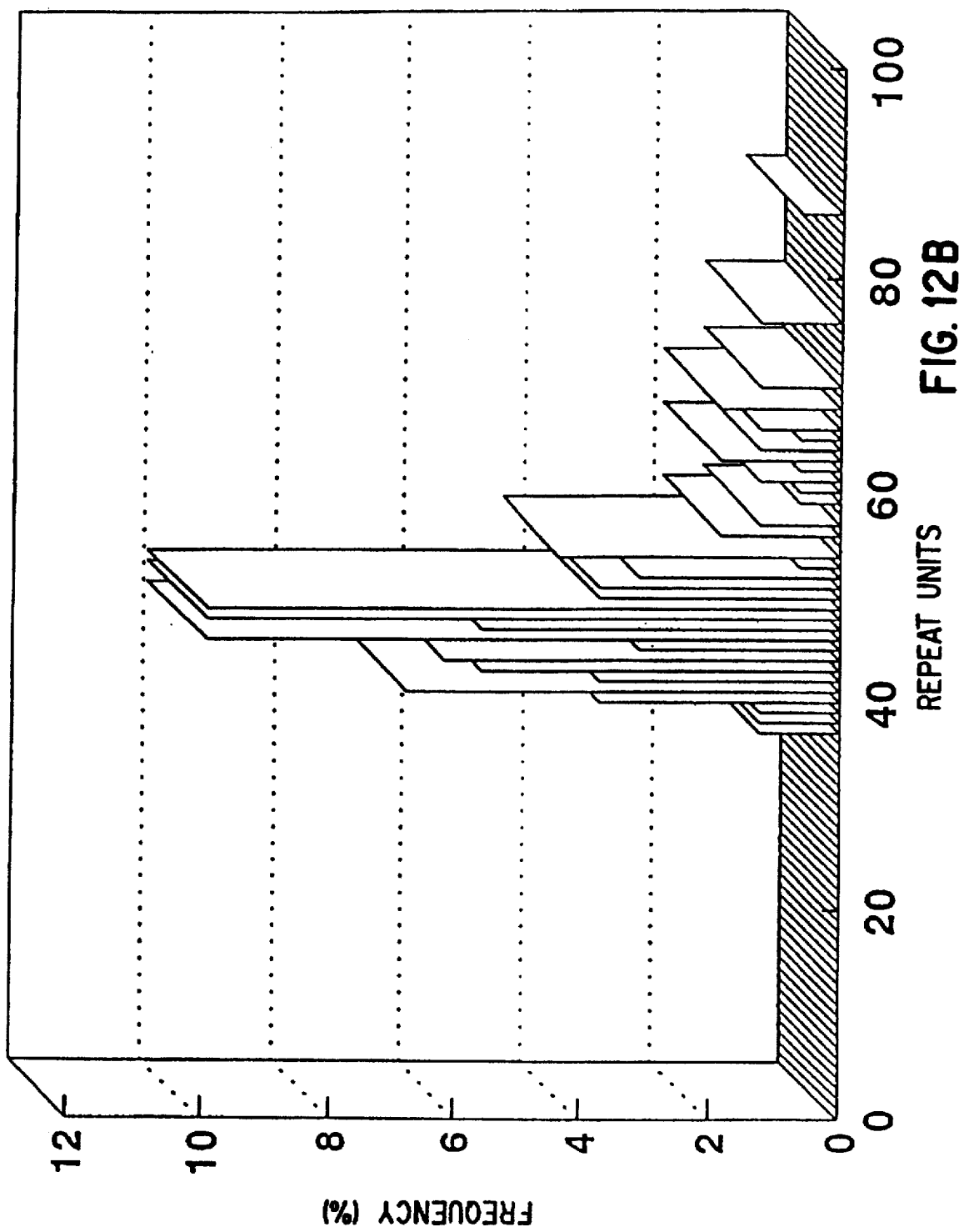

FIGS. 12A–B. Comparison of (CAG)n Repeat Unit Number on Maternally and Paternally Transmitted HD Chromosomes. Frequency distributions are shown for the 134 and 161 HD chromosomes from FIG. 11 known to have been transmitted from the mother (Panel A) and father (Panel B), respectively. The two distributions differ significantly based on a t-test ($t_{272.3}=5.34$, $p<0.0001$).

Figure 13A:
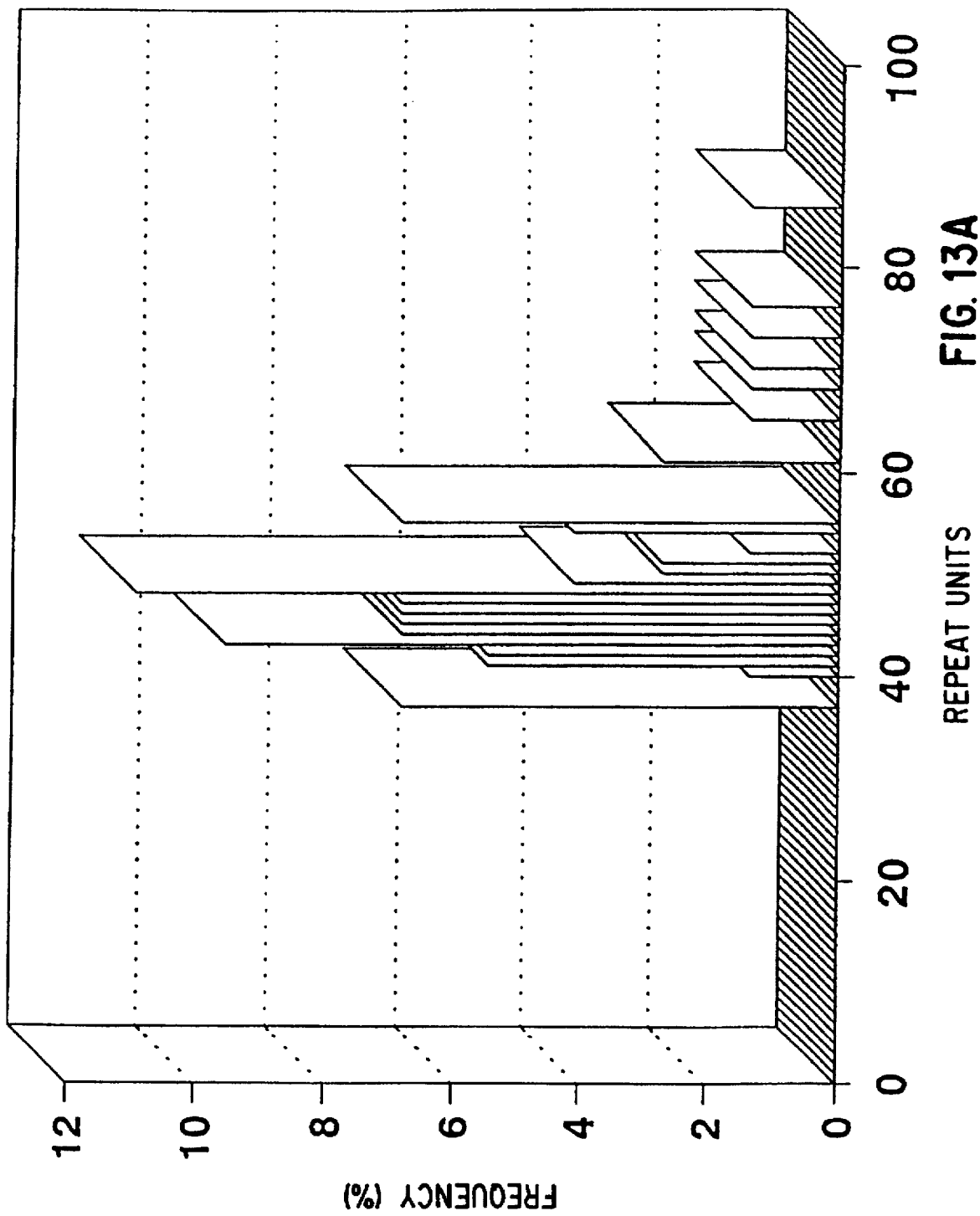
Figure 13B:
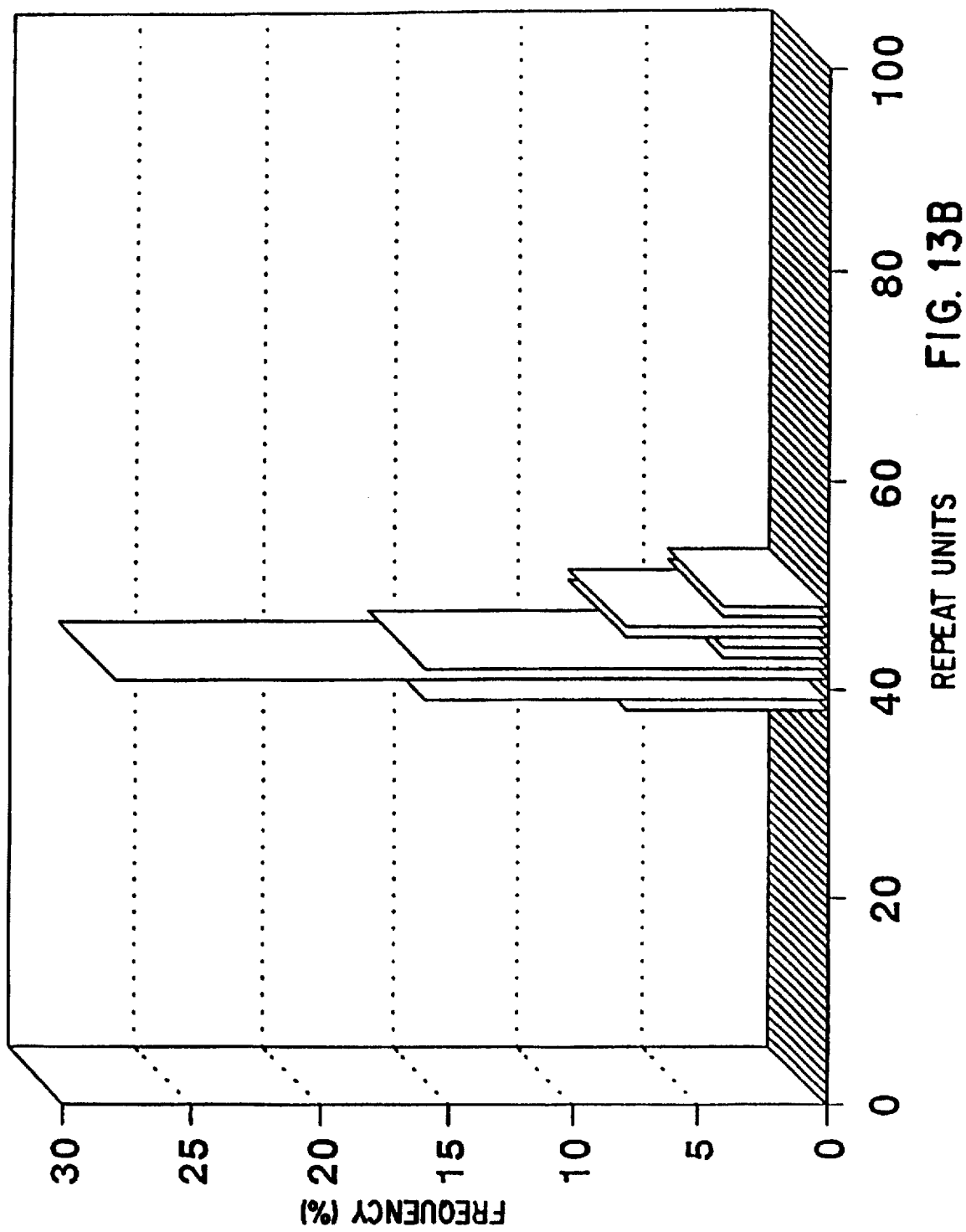

FIGS. 13A–B. Comparison of $(CAG)_n$ Repeat Unit Number on HD Chromosomes from Three Large Families with Different HD Founders. Frequency distributions are shown for 75, 25 and 35 HD chromosomes from the Venezuelan HD family (Panel A) (Gusella, J. F., et al., Nature 306:234–238 (1983); Wexler, N. S., et al., Nature 326:194–197 (1987)), Family Z (Panel B) and Family D (Panel C) (Folstein, S. E., et al., Science 229:776–779 (1985)), respectively. The Venezuelan distribution did not differ from the overall HD chromosome distribution in FIG. 11 ($t_{79.7}=1.58$, $p<0.12$). Both Family Z and Family D did produce distributions significantly different from the overall HD distribution ($t_{42.2}=6.73$, $p<0.0001$ and $t_{458}=2.90$, $p<0.004$, respectively).

Figure 14A:
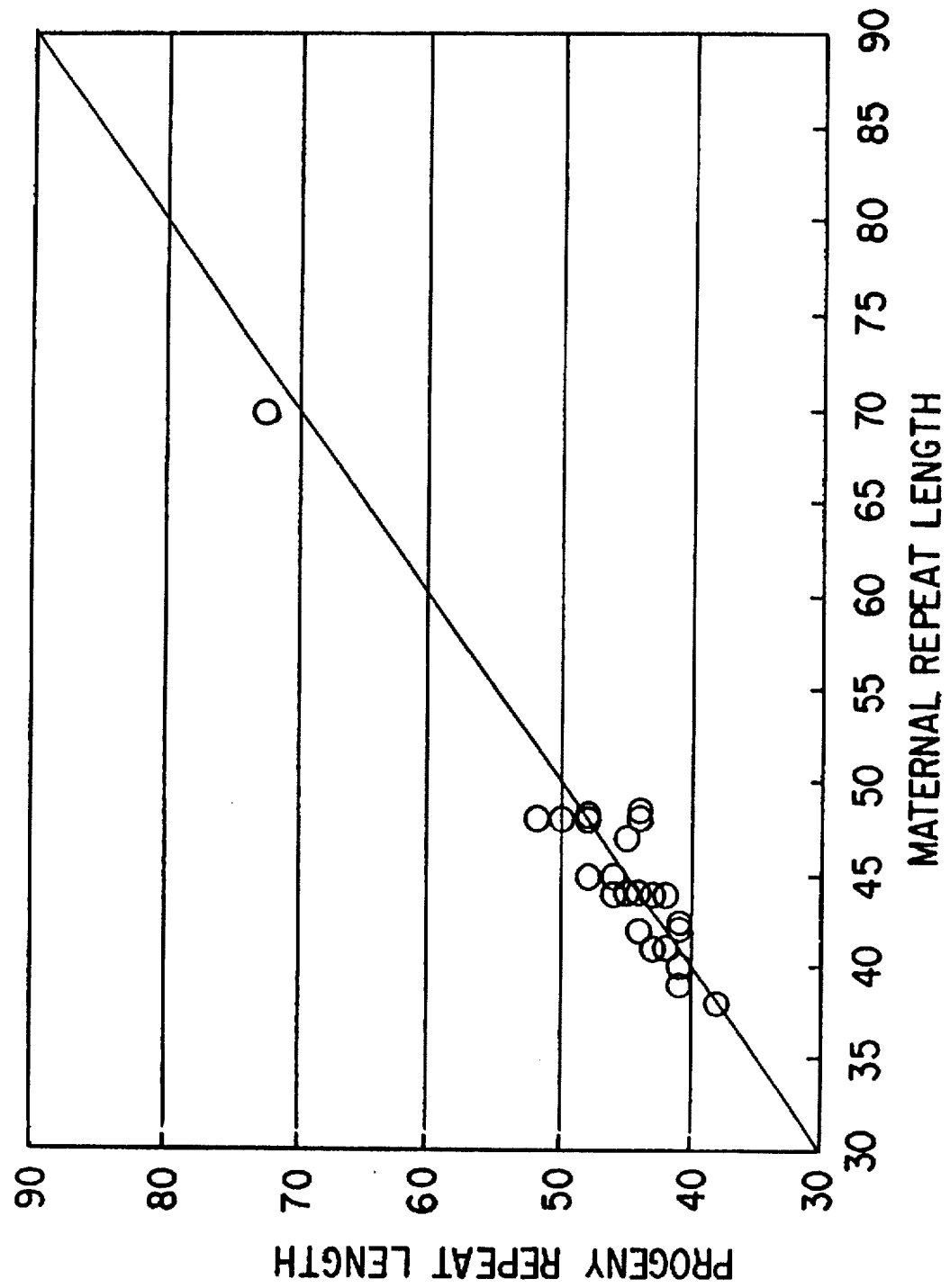
Figure 14B:
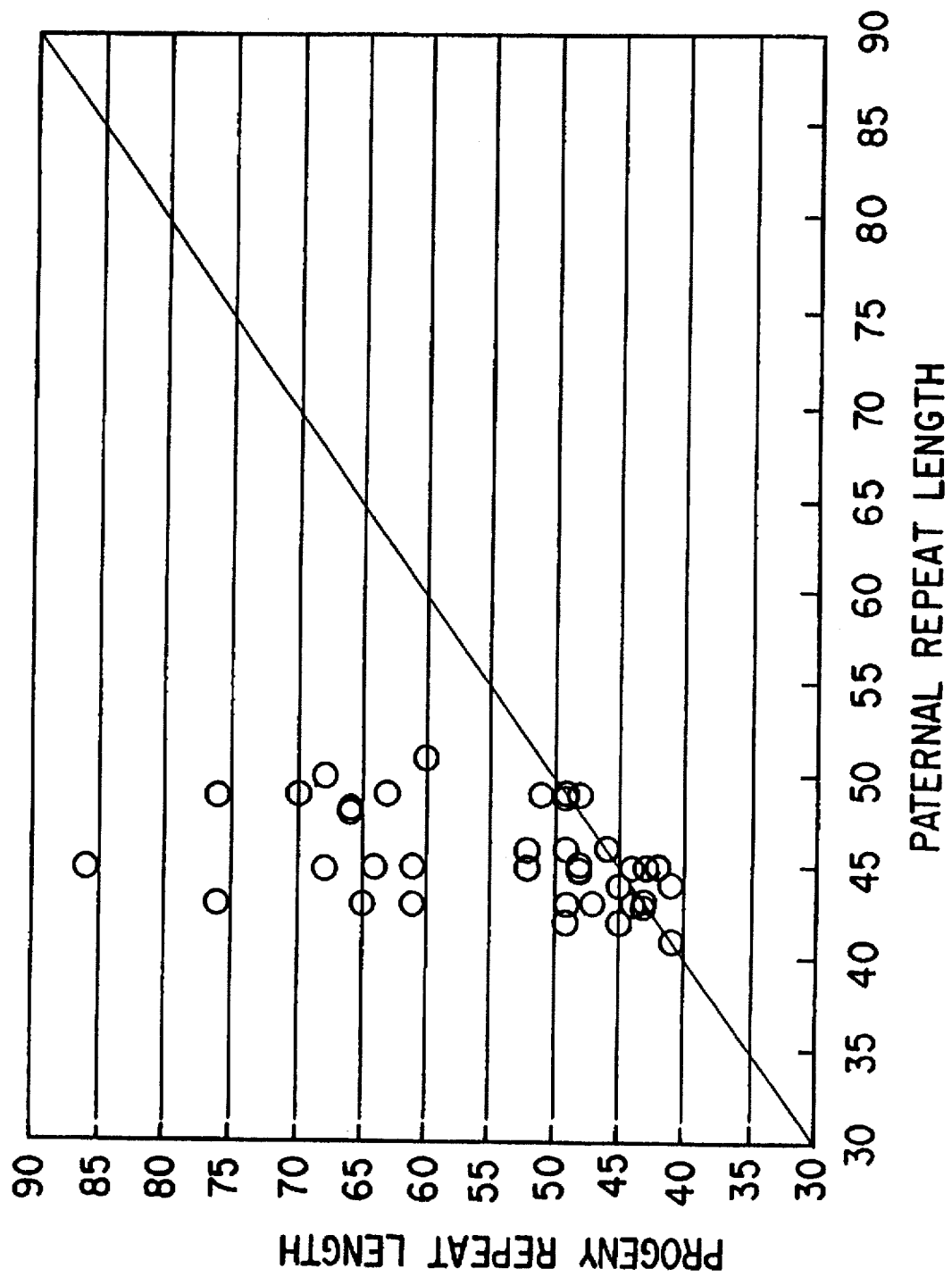

FIGS. 14A–B. Relationship of $(CAG)_n$ Repeat Length in Parents and Corresponding Progeny. Repeat length on the HD chromosome in mothers (Panel A) or fathers (Panel B) is plotted against the repeat length in the corresponding offspring. A total of 25 maternal transmissions and 37 paternal transmissions were available for typing.

Figure 15:
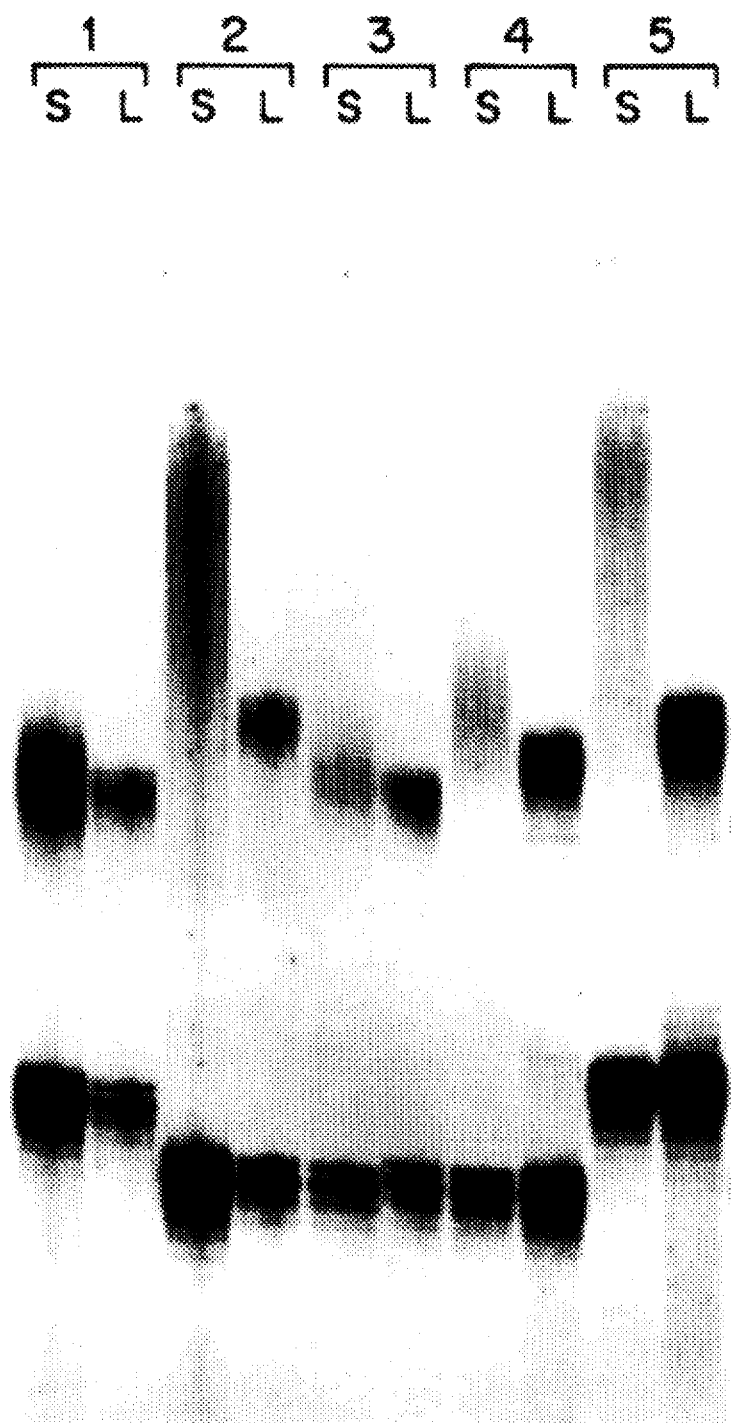

FIG. 15. Amplification of the HD $(CAG)_n$ Repeat From Sperm and Lymphoblast DNA. DNA from sperm (S) and lymphoblasts (L) for 5 members (pairs 1–5) of the Venezuelan HD pedigree aged 24–30 were used for PCR amplification of the HD $(CAG)_n$ repeat. The lower band in each lane derives from the normal chromosome.

Figure 16:
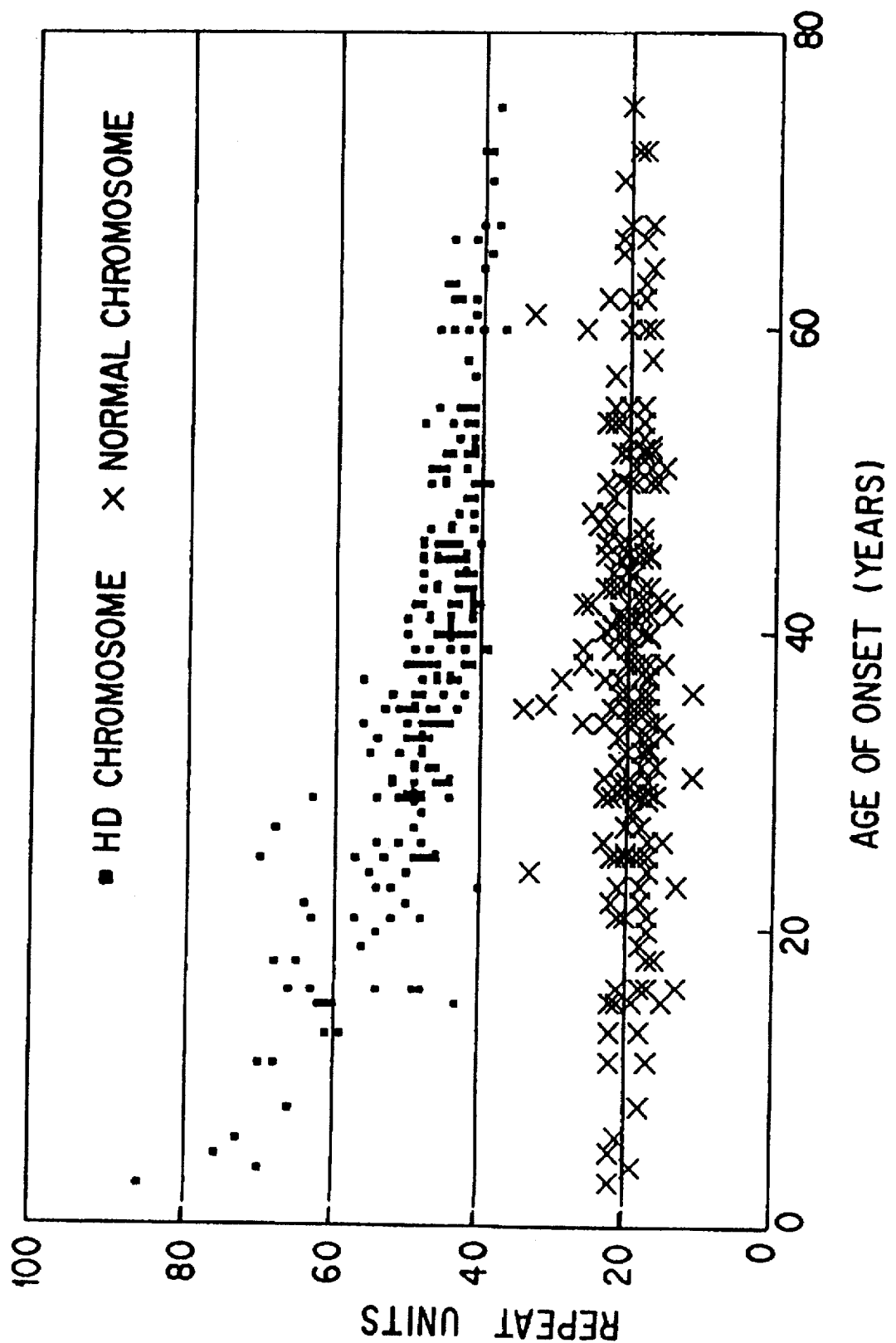

FIG. 16. Relationship of Repeat Unit Length with Age of Onset. Age of onset was established for 234 diagnosed HD gene carriers and plotted against the repeat length observed on both the HD and normal chromosomes in the corresponding lymphoblast lines.

Figure 17:
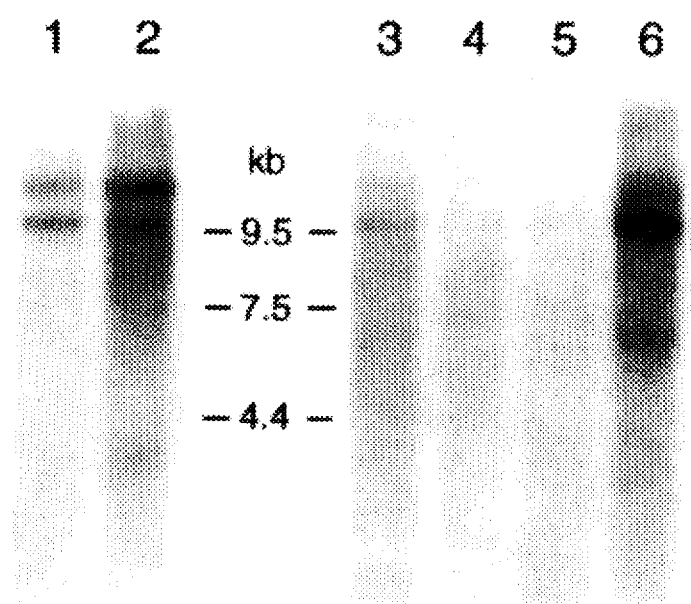

FIG. 17. Northern Blots Analysis of Mouse Hdh mRNAs. Northern blots containing 2 μg of polyA$^+$ mRNA from various adult mouse tissues were hybridized with human IT15B.1. Transcript sizes were estimated from RNA size markers as shown. Lanes: 1, heart; 2, brain; 3, liver; 4, skeletal muscle; 5, kidney, 6, testis.

FIG. 18. Schematic Diagram of Mouse Hdh Clones. The composite mouse Hdh cDNA sequence deposited in GenBank as accession #28827 is shown schematically over the clones from which it was derived. The 5' UTR and 3' UTR sequences are shown as thin lines, while the predicted coding sequence is depicted as a filled box. The sequences provided by each clone are: 129-1 genomic phage, nt 1-133; cDNA PCC4-8, nt 102-4469; PCC4-5, nt 3906-9765; and PCC4-3, nt 5781-9998. Only the latter clone displayed a polyA tail.

Figure 19:
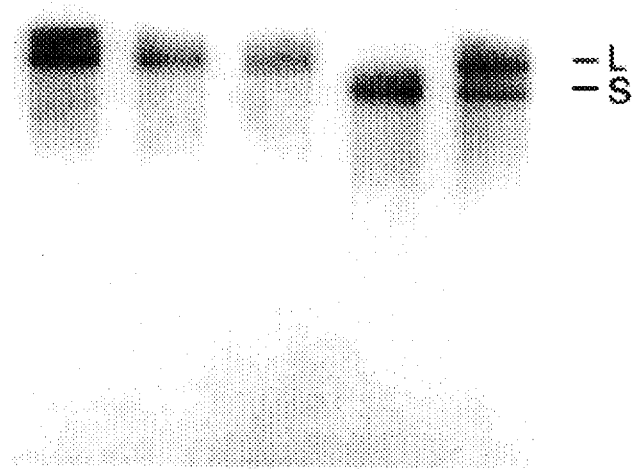

FIG. 19. CCG Polymorphism in Mus spretus. Mouse genomic or cloned DNA was amplified using PCR primers flanking the CAG-CCG rich region near the 5' end of the Hdh gene. Products were displayed on a 6% denaturing polyacrylamide gel. Lanes: 1:PCC4-8 cDNA; 2, C57BL/6J; 3, CBA/J; 4, M. spretus; 5, C57BL/6J+M. spretus. The laboratory mouse (L=190 bp) and M. spretus (S=187 bp) products differ by one CCG repeat unit as confirmed by DNA sequence analysis.

Figure 20:
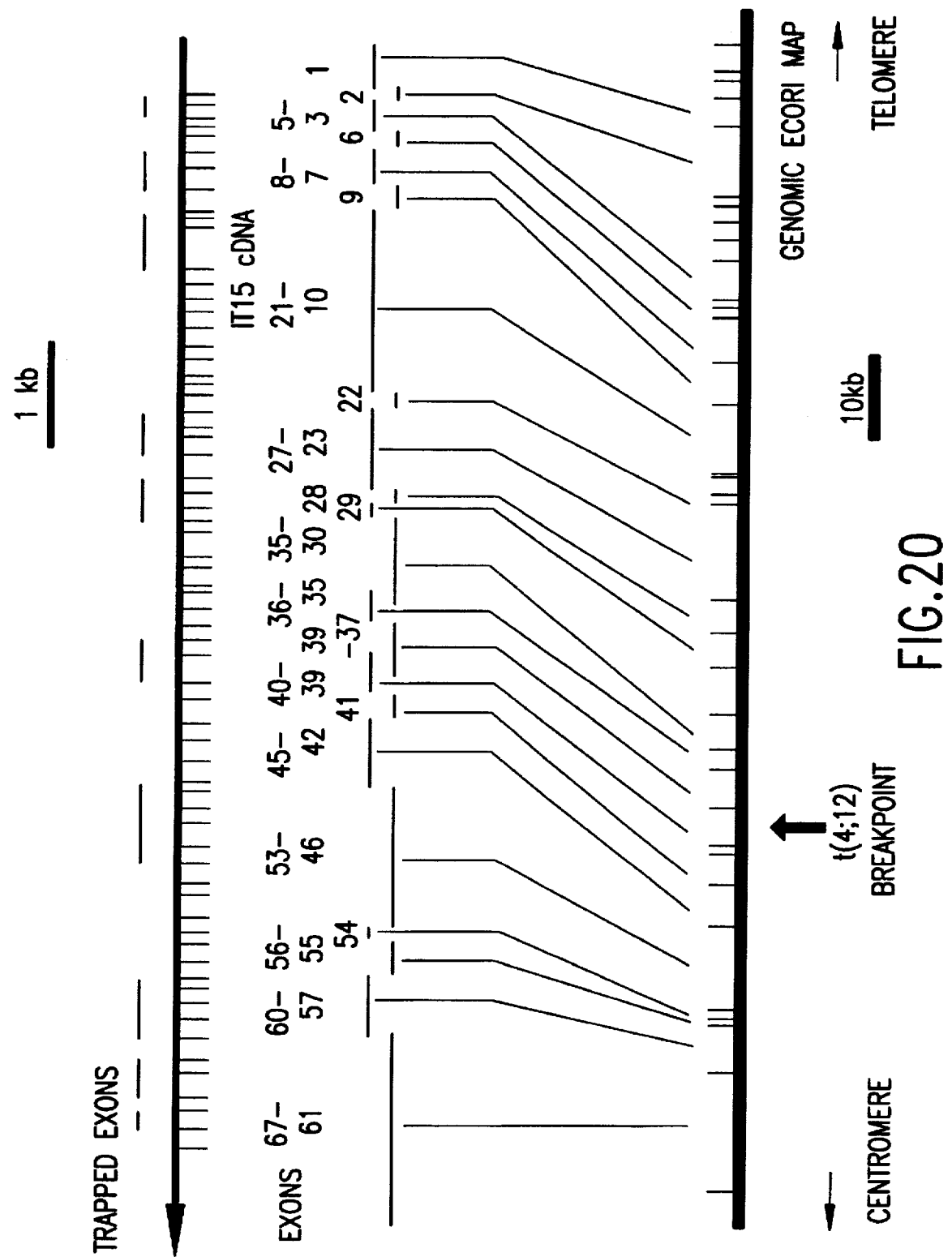

FIG. 20. Exon Structure of the HD Gene. A schematic of the IT15 cDNA is shown (top) with an arrow to denote the direction of transcription. Vertical lines below the cDNA correspond to exon junctions. Horizontal lines above the cDNA span those exons that were recovered from genomic DNA as cloned products in the exon amplification procedure. The genomic EcoRI map of the HD region of 4p16.3

(bottom) is shown, with vertical lines denoting EcoRI sites and centromere-telomere orientation provided below (Baxendale, S. et al., *Nature Genet.* 4:181–186 (1993)). Between the cDNA and the genomic map, exons 1–67 are shown as horizontal lines under the corresponding exon number. Contiguous horizontal lines denote exons which map to the same genomic EcoRI fragment as demonstrated by the vertical lines connecting to the physical map. The position of the t(4;12) breakpoint between exons 40 and 41 is shown by the vertical arrow below the genomic map.

Figure 21A:
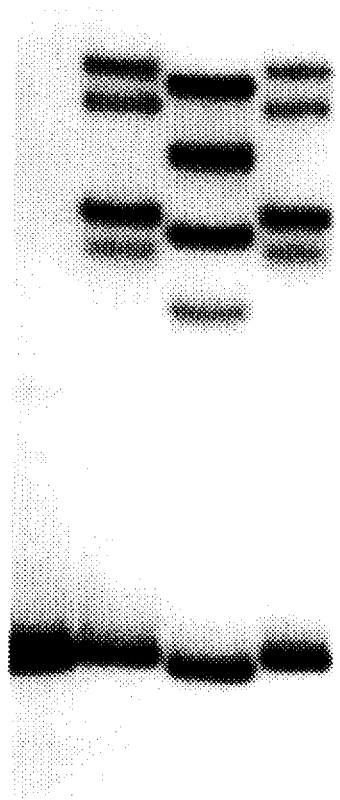
Figure 21B:
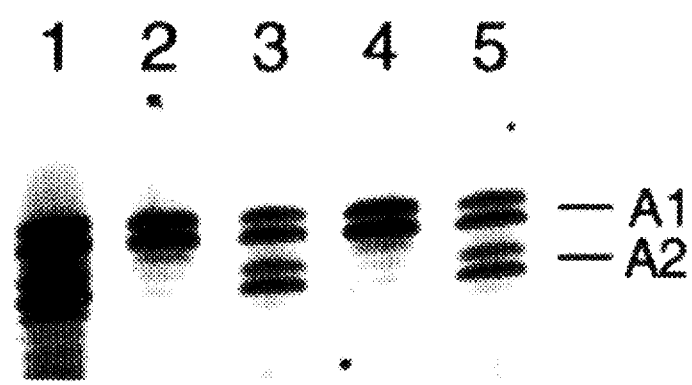

FIGS. 21A–B. The Δ2642 codon loss polymorphism.

A. SSCP analysis by RT-PCR of mRNA

First strand oligo (dT)-primed cDNA was amplified with primers 5' GGGAACAGCATCACACCC 3' (SEQ ID NO:17) and 5' GTTGCGCTCGGTGAACA 3' (SEQ ID NO:18) and the ~273 bp PCR products were analyzed under SSCP Conditions (Orita, M. et al., *Genomics* 5:874–879 (1989); Ambrose, C. et al., *Hum. Mol. Genet.* 1:697–703 (1992)). Lane 1=undenatured product from a normal individual; lane 2=denatured product from the same normal individual; lane 3=denatured product from an HD homozygote of the most common haplotype representing ⅓ of HD chromosomes (MacDonald, M. E. et al., *Nature Genet.* 1:99–103 (1992)); lane 4=denatured product from an HD homozygote of another less frequent haplotype.

B. Genomic PCR assay for the Δ2642 codon loss polymorphism

The region of the polymorphism was amplified from 10 ng of genomic DNA using primers within exon 58, 5' GCTGGGGAACAGCATCACACCC 3' (SEQ ID NO:19) and 5' CCTGGAGTTGACTGGAGACGTG 3' (SEQ ID NO:20), and the following amplification program: 2'@94° C., 30 cycles of 1'@58° C., 1'@72° C., followed by 10'@72° C. The products were displayed on a 6% denaturing urea-polyacrylamide gel. Lanes 1, 3 and 5 contain PCR products from HD heterozygotes of the major haplotype; lanes 2 and 4 contain PCR products from normal individuals bearing other 4p16.3 haplotypes. A1 denotes presence of codon 2642 (112 bp product; A2 denotes absence of codon 2642 (109 bp product).

Figure 22:
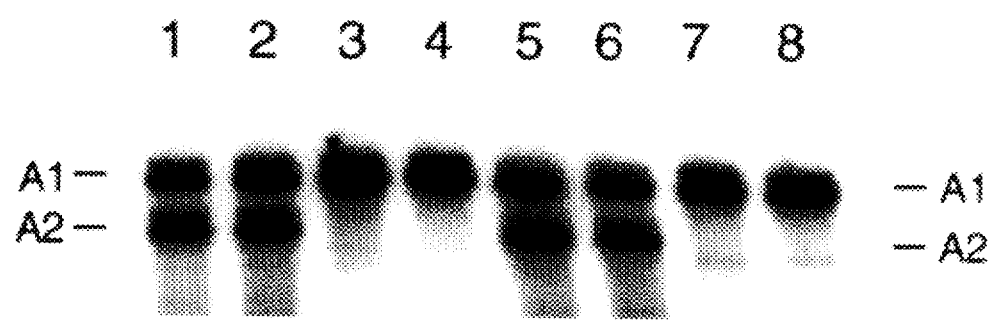
Figure 23A:
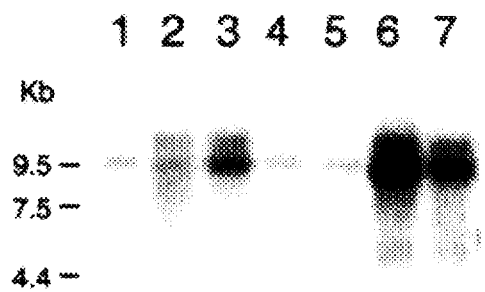
Figure 23B:
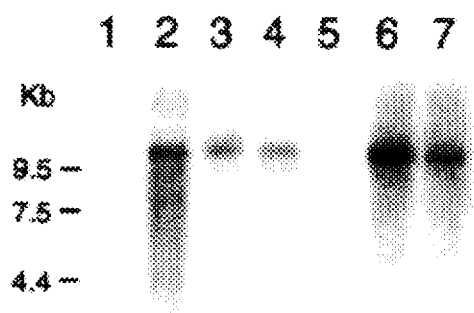
Figure 23C:
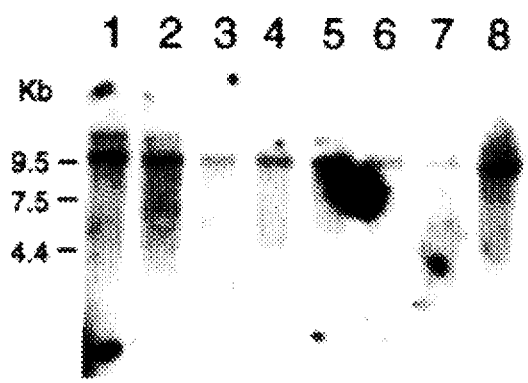
Figure 23D:
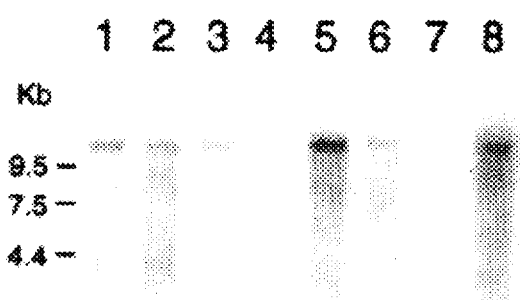

FIG. 22. Expression of both normal and HD alleles in mRNA. First strand cDNA primed with oligo(dT) (lanes 1–4) or an IT15 specific primer (5' CAGGTACTGAGC-GAGGAT 3') (SEQ ID NO:21 ) (lanes 5–8) was amplified using the same primers described in FIG. 21B. The PCR products spanning the Δ2642 codon polymorphism were resolved on a 6% denaturing urea-polyacrylamide gel. Lanes 1,5 and 2,6 represent 2 different HD heterozygotes with the major HD haplotype; lanes 3,7 and 4,8 represent 2 different HD heterozygotes with 2 other HD haplotypes. A1 denotes presence of codon 2642 (112 bp product); A2 denotes the absence of codon 2642 (109 by product).

FIGS. 23A–D. Northern blot survey of HD gene transcripts in adult tissues. Northern blots containing 2 μg of polyA$^+$ mRNA from various adult human tissues were hybridized with two probes. Panels A and C were hybridized with coding region 2,841 bp probe made by EcoRI digestion of cDNA clone IT15B. This probe spans nucleotides 2,028 to 4,868 of the published IT15 sequence (MacDonald, M. E. et al., *Cell* 72:971–983 (1993)). Panels B and D represent the same blots hybridized with a 292 bp genomic probe produced by PcR of cosmid L120D5 DNA using primers 5' GGAGAACACAGTCGTCTGTG 3' (SEQ ID NO:22) and 5' CGTGTAAAGTATGTGAATCGC 3' (SEQ ID NO:23). This probe derives from the sequence immediately 3' to the end of the 3'UTR reported in the published IT15 sequence. Panels A and B lanes: 1, heart; 2, brain; 3, placenta; 4, lung; 5, liver; 6, skeletal muscle; 7, kidney; Panels C and D lanes: 1, spleen; 2, thymus; 3, prostrate; 4, testis; 5, ovary; 6, small intestine; 7, colon; 8, peripheral blood leukocyte. Transcript sizes were estimated from RNA size markers as shown.

Figures 24A, 24B:
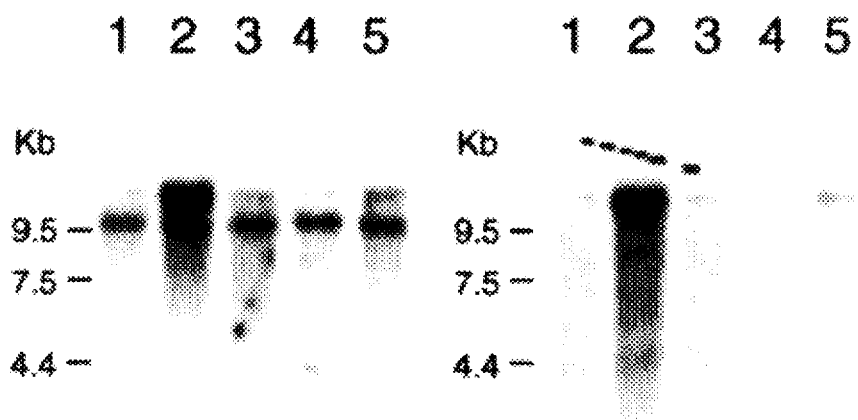

FIG. 24. Northern blot survey of HD gene transcripts in fetal tissues. Northern blot containing 2 ug of polyA$^+$ mRNA from various fetal human tissues were hybridized sequentially with the same two probes described in FIG. 4 (left and right, respectively). Lanes: 1, heart; 2, brain; 3, lung; 4, liver; 5, kidney.

Figure 25A:
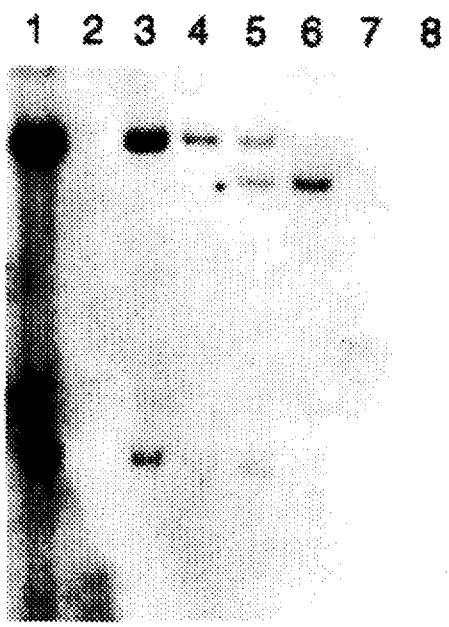
Figure 25B:
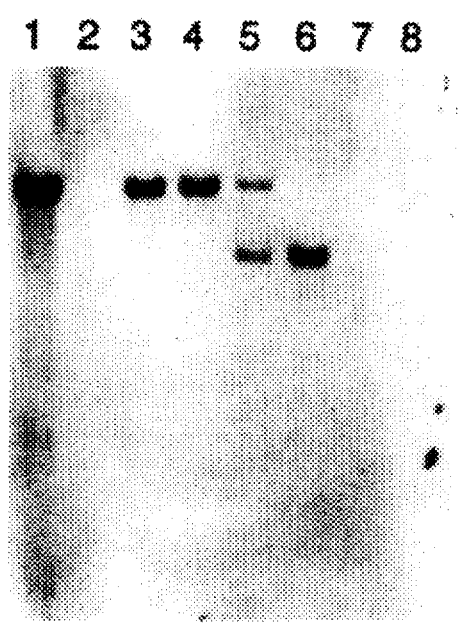

FIGS. 25A–B. The t(4;12) translocation disrupts the HD gene. Southern blots of HindIII (Panel A) and EcoRI (panel B) digested DNAs were hybridized with a 210 bp probe consisting of all of exon 40 and that portion of exon 39 3' to the EcoRI site contained with this exon. The probe was made by PCR from the cDNA using primers 5' CTTCAACGCTA-GAAGAAC 3' (SEQ ID NO:24) and 5' CAGACTTGAA-GATGTGGATC 3' (SEQ ID NO:25). Lane 1=normal human genomic lymphoblastoid cell DNA; lane 2= hamster DNA; lane 3=DNA from human-hamster hybrid HHW416 containing only human chromosome 4; lane 4=DNA from human-hamster hybrid HHW661 containing only a human t(4p15;5p15.1) chromosome; lane 5=DNA from lymphoblast line CV066 from the balanced t(4p16.3; 12p13.3) carrier (McKeown, C. et al., *J. Med. Genet.* 24:410–412 (1987)); lane 6=DNA from human-hamster hybrid HHW1071 containing the der(12) from CV066; lane 7=DNA from human-hamster hybrid HHW842 containing a chromosome 4 with an interstitial deletion that removes the entire HD gene; lane 8=DNA from human-hamster hybrid HHW847 containing a t(4;12) chromosome from which all of 4p16.3 is missing (Smith, B. et al., *Am. J. Hum. Genet.* 42:335–344 (1988); Lin, C. S. et al., *Somat. Cell Mol. Genet.* 17:481–488 (1991)). Both EcoRI and HindIII fragments are altered in CV066 and HHW1071. Since exons 39 and 40 reside on the same EcoRI fragment but different HindIII fragments (the small unaltered HindIII fragment is detected by exon 39), the t(4;12) breakpoint must map within the EcoRI fragment but proximal to both exons.

DETAILED DESCRIPTION OF THE INVENTION

In the following description, reference will be made to various methodologies known to those of skill in the art of molecular genetics and biology. Publications and other materials setting forth such known methodologies to which reference is made are incorporated herein by reference in their entireties as though set forth in full.

The IT15 gene described herein is a gene from the proximal portion of the 500 kb segment between human chromosome 4 markers D4S180 and D4S182. The huntingtin gene spans about 210 kb of DNA and encodes a previously undescribed protein of about 348 kDa. The huntingtin reading frame contains a polymorphic (CAG)$_n$ trinucleotide repeat with at least 17 alleles in the normal human population, where the repeat number varies from 11 to about 34 CAG copies in such alleles. This is the gene of the human chromosome that, as shown herein, suffers the presence of an unstable, expanded number of CAG trinucleotide repeats in Huntington's disease patients, such that the number of CAG repeats in the huntingtin gene increases to a range of 37 to at least 86 copies. These results are the basis of a conclusion that the huntingtin gene encodes a protein called "huntingtin," and that in such huntingtin gene the increase in the number of CAG repeats to a range of greater than about 37 repeats is the alteration that underlies the dominant phenotype of Huntington's disease. As used herein huntingtin gene is also called the Huntington's disease gene.

It is to be understood that the description below is applicable to any gene in which a CAG repeat within the gene is amplified in an aberrant manner resulting in a change in the regulation, localization, stability or translatability of the mRNA containing such amplified CAG repeat that is transcribed from such gene.

I. Cloning Of Huntingtin DNA And Expression Of Huntingtin Protein

The identification of huntingtin DNA and protein as the altered gene in Huntington's disease patients is exemplified below. In addition to utilizing the exemplified methods and results for the identification of deletions of the huntingtin gene in Huntington's disease patients, and for the isolation of the native human huntingtin gene, the sequence information presented in FIG. 4 represents a nucleic acid and protein sequence, that, when inserted into a linear or circular recombinant nucleic acid construct such as a vector, and used to transform a host cell, will provide copies of huntingtin DNA and huntingtin protein that are useful sources for the native huntingtin DNA and huntingtin protein for the methods of the invention. Such methods are known in the art and are briefly outlined below.

The process for genetically engineering the huntingtin coding sequence, for expression under a desired promoter, is facilitated through the cloning of genetic sequences which are capable of encoding such huntingtin protein. Such cloning technologies can utilize techniques known in the art for construction of a DNA sequence encoding the huntingtin protein, such as, for example, polymerase chain reaction technologies utilizing the huntingtin sequence disclosed herein to isolate the huntingtin gene anew, or an allele thereof that varies in the number of CAG repeats in such gene, or polynucleotide synthesis methods for constructing the nucleotide sequence using chemical methods. Expression of the cloned huntingtin DNA provides huntingtin protein.

As used herein, the term "genetic sequences" is intended to refer to a nucleic acid molecule of DNA or RNA, preferably DNA. Genetic sequences that are capable of being operably linked to DNA encoding huntingtin protein, so as to provide for its expression and maintenance in a host cell are obtained from a variety of sources, including commercial sources, genomic DNA, cDNA, synthetic DNA, and combinations thereof. Since the genetic code is universal, it is to be expected that any DNA encoding the huntingtin amino acid sequence of the invention will be useful to express huntingtin protein in any host, including prokaryotic (bacterial) hosts, eukaryotic hosts (plants, mammals (especially human), insects, yeast, and especially any cultured cell populations).

If it is desired to select anew a gene encoding huntingtin from a library that is thought to contain a huntingtin gene, such library can be screened and the desired gene sequence identified by any means which specifically selects for a sequence coding for the huntingtin gene or expressed huntingtin protein such as, for example, a) by hybridization (under stringent conditions for DNA:DNA hybridization) with an appropriate huntingtin DNA probe(s) containing a sequence specific for the DNA of this protein, such sequence being that provided in FIG. 4 or a functional derivative thereof that is, a shortened form that is of sufficient length to identify a clone containing the huntingtin gene, or b) by hybridization-selected translational analysis in which native huntingtin mRNA which hybridizes to the clone in question is translated in vitro and the translation products are further characterized for the presence of a biological activity of huntingtin, or c) by immunoprecipitation of a translated huntingtin protein product from the host expressing the huntingtin protein.

When a human allele does not encode the identical sequence to that of FIG. 4, it can be isolated and identified as being huntingtin DNA using the same techniques used herein, and especially PCR techniques to amplify the appropriate gene with primers based on the sequences disclosed herein. Many polymorphic probes useful in the fine localization of genes on chromosome 4 are known and available (see, for example, "ATCC/NIH Repository Catalogue of Human and Mouse DNA Probes and Libraries," fifth edition, 1991, pages 4–6. For example, a useful D4S10 probe is clone designation pTV20 (ATCC 57605 and 57604); H5.52 (ATCC 61107 and 61106) and F5.53 (ATCC 61108).

Human chromosome 4-specific libraries are known in the art and available from the ATCC for the isolation of probes ("ATCC/NIH Repository Catalogue of Human and Mouse DNA Probes and Libraries," fifth edition, 1991, pages 72–73), for example, LL04NS01 and LL04NS02 (ATCC 57719 and ATCC57718) are useful for these purposes.

It is not necessary to utilize the exact vector constructs exemplified in the invention; equivalent vectors can be constructed using techniques known in the art. For example, the sequence of the huntingtin DNA is provided herein, (see FIG. 4) and this sequence provides the specificity for the huntingan gene; it is only necessary that a desired probe contain this sequence, or a portion thereof sufficient to provide a positive indication of the presence of the huntingtin gene.

Huntingtin genomic DNA may or may not include naturally occurring introns. Moreover, such genomic DNA can be obtained in association with the native huntingtin 5' promoter region of the gene sequences and/or with the native huntingtin 3' transcriptional termination region.

Such huntingtin genomic DNA can also be obtained in association with the genetic sequences which encode the 5' non-translated region of the huntingtin mRNA and/or with the genetic sequences which encode the huntingtin 3' non-translated region. To the extent that a host cell can recognize the transcriptional and/or translational regulatory signals associated with the expression of huntingtin mRNA and protein, then the 5' and/or 3' non-transcribed regions of the native huntingan gene, and/or, the 5' and/or 3' non-translated regions of the huntingtin mRNA can be retained and employed for transcriptional and translational regulation.

Genomic DNA can be extracted and purified from any host cell, especially a human host cell possessing chromosome 4, by means well known in the art. Genomic DNA can be shortened by means known in the art, such as physical shearing or restriction digestion, to isolate the desired huntingtin gene from a chromosomal region that otherwise would contain more information than necessary for the utilization of the huntingtin gene in the hosts of the invention. For example, restriction digestion can be utilized to cleave the full-length sequence at a desired location. Alternatively, or in addition, nucleases that cleave from the 3'-end of a DNA molecule can be used to digest a certain sequence to a shortened form, the desired length then being identified and purified by polymerase chain reaction technologies, gel electrophoresis, and DNA sequencing. Such nucleases include, for example, Exonuclease III and Bal31. Other nucleases are well known in the art.

Alternatively, if it is known that a certain host cell population expresses huntingtin protein, then cDNA techniques known in the art can be utilized to synthesize a cDNA copy of the huntingtin mRNA present in such population.

For cloning the genomic or cDNA nucleic acid that encodes the amino acid sequence of the huntingtin protein into a vector, the DNA preparation can be ligated into an appropriate vector. The DNA sequence encoding huntingtin protein can be inserted into a DNA vector in accordance with conventional techniques, including blunt-ending or staggered-ending termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are well known in the art.

When the huntingtin DNA coding sequence and an operably linked promoter are introduced into a recipient eukaryotic cell (preferably a human host cell) as a non-replicating, non-integrating, molecule, the expression of the encoded huntingtin protein can occur through the transient (nonstable) expression of the introduced sequence.

Preferably the coding sequence is introduced on a DNA molecule, such as a closed circular or linear molecule that is capable of autonomous replication. If integration into the host chromosome is desired, it is preferable to use a linear molecule. If stable maintenance of the huntingtin gene is desired on an extrachromosomal element, then it is preferable to use a circular plasmid form, with the appropriate plasmid element for autonomous replication in the desired host.

The desired gene construct, providing a gene coding for the huntingtin protein, and the necessary regulatory elements operably linked thereto, can be introduced into a desired host cells by transformation, transfection, or any method capable of providing the construct to the host cell. A marker gene for the detection of a host cell that has accepted the huntingtin DNA can be on the same vector as the huntingtin DNA or on a separate construct for co-transformation with the huntingtin coding sequence construct into the host cell. The nature of the vector will depend on the host organism.

Suitable selection markers will depend upon the host cell. For example, the marker can provide biocide resistance, e.g., resistance to antibiotics, or heavy metals, such as copper, or the like.

Factors of importance in selecting a particular plasmid or viral vector include: the ease with which recipient cells that contain the vector can be recognized and selected from those recipient cells which do not contain the vector; the number of copies of the vector which are desired in a particular host; and whether it is desirable to be able to "shuttle" the vector between host cells of different species.

When it is desired to use *S. cerevisiae* as a host for a shuttle vector, preferred *S. cerevisiae* yeast plasmids include those containing the 2-micron circle, etc., or their derivatives. Such plasmids are well known in the art and are commercially available.

Oligonucleotide probes specific for the huntingtin sequence can be used to identify clones to huntingtin and can be designed de novo from the knowledge of the amino acid sequence of the protein as provided herein in FIG. 4 or from the knowledge of the nucleic acid sequence of the DNA encoding such protein as provided herein in FIG. 4 or of a related protein. Alternatively, antibodies can be raised against the huntingtin protein and used to identify the presence of unique protein determinants in transformants that express the desired cloned protein.

A nucleic acid molecule, such as DNA, is said to be "capable of expressing" a huntingtin protein if that nucleic acid contains expression control sequences which contain transcriptional regulatory information and such sequences are "operably linked" to the huntingtin nucleotide sequence which encode the huntingtin polypeptide.

An operable linkage is a linkage in which a sequence is connected to a regulatory sequence (or sequences) in such a way as to place expression of the sequence under the influence or control of the regulatory sequence. If the two DNA sequences are a coding sequence and a promoter region sequence linked to the 5' end of the coding sequence, they are operably linked if induction of promoter function results in the transcription of mRNA encoding the desired protein and if the nature of the linkage between the two DNA sequences does not (1) result in the introduction of a frame-shift mutation, (2) interfere with the ability of the expression regulatory sequences to direct the expression of the protein, antisense RNA, or (3) interfere with the ability of the DNA template to be transcribed. Thus, a promoter region would be operably linked to a DNA sequence if the promoter was capable of effecting transcription of that DNA sequence.

The precise nature of the regulatory regions needed for gene expression can vary between species or cell types, but shall in general include, as necessary, 5' non-transribing and 5' non-translating (non-coding) sequences involved with initiation of transcription and translation respectively, such as the TATA box, capping sequence, CAAT sequence, and the like, with those elements necessary for the promoter sequence being provided by the promoters of the invention. Such transcriptional control sequences can also include enhancer sequences or upstream activator sequences, as desired.

The vectors of the invention can further comprise other openly linked regulatory elements such as DNA elements which confer antibiotic resistance, or origins of replication for maintenance of the vector in one or more host cells.

In another embodiment, especially for maintenance of the vectors of the invention in prokaryotic cells, or in yeast *S. cerevisiae* cells, the introduced sequence is incorporated into a plasmid or viral vector capable of autonomous replication in the recipient host. Any of a wide variety of vectors can be employed for this purpose. In Bacillus hosts, integration of the desired DNA can be necessary.

Expression of a protein in eukaryotic hosts such as a human cell requires the use of regulatory regions functional in such hosts. A wide variety of transcriptional and translational regulatory sequences can be employed, depending upon the nature of the host. Preferably, these regulatory signals are associated in their native state with a particular gene which is capable of a high level of expression in the specific host cell, such as a specific human tissue type. In eukaryotes, where transcription is not linked to translation, such control regions may or may not provide an initiator methionine (AUG) codon, depending on whether the cloned sequence contains such a methionine. Such regions will, in general, include a promoter region sufficient to direct the initiation of RNA synthesis in the host cell.

If desired, the non-transcribed and/or non-translated regions 3' to the sequence coding for the huntingtin protein can be obtained by the above-described cloning methods. The 3'-non-transcribed region of the native human huntingtin gene can be retained for its transcriptional termination regulatory sequence elements, or for those elements which direct polyadenylation in eukaryotic cells. Where the native expression control sequences signals do not function satisfactorily in a host cell, then sequences functional in the host cell can be substituted.

It may be desired to construct a fusion product that contains a partial coding sequence (usually at the amino terminal end) of a first protein or small peptide and a second coding sequence (partial or complete) of the huntingtin protein at the carboxyl end. The coding sequence of the first protein can, for example, function as a signal sequence for secretion of the huntingtin protein from the host cell. Such first protein can also provide for tissue targeting or localization of the huntingtin protein if it is to be made in one cell type in a multicellular organism and delivered to another cell type in the same organism. Such fusion protein sequences can be designed with or without specific protease sites such that a desired peptide sequence is amenable to subsequent removal.

The expressed huntingtin protein can be isolated and purified from the medium of the host in accordance with conventional conditions, such as extraction, precipitation, chromatography, affinity chromatography, electrophoresis, or the like. For example, affinity purification with anti-huntingtin antibody can be used. A protein having the amino acid sequence shown in FIG. 3 can be made, or a shortened peptide of this sequence can be made, and used to raise antibodies using methods well known in the art. These antibodies can be used to affinity purify or quantitate huntingtin protein from any desired source.

If it is necessary to extract huntingtin protein from the intracellular regions of the host cells, the host cells can be collected by centrifugation, or with suitable buffers, lysed, and the protein isolated by column chromatography, for example, on DEAE-cellulose, phosphocellulose, polyribocytidylic acid-agarose, hydroxyapatite or by electrophoresis or immunoprecipitation.

II. Use Of Huntingan For Diagnostic And Treatment Purposes

It is to be understood that although the following discussion is specifically directed to human patients, the teachings are also applicable to any animal that expresses huntingtin and in which alteration of huntingtin, especially the amplification of CAG repeat copy number, leads to a defect in huntingtin gene (structure or function) or huntingtin protein (structure or function or expression), such that clinical manifectations such as those seen in Huntington's disease patients are found.

It is also to be understood that the methods referred to herein are applicable to any patient suspected of developing/having Huntington's disease, whether such condition is manifest at a young age or at a more advanced age in the patient's life. It is also to be understood that the term "patient" does not imply that symptoms are present, and patient includes any individual it is desired to examine or treat using the methods of the invention.

The diagnostic and screening methods of the invention are especially useful for a patient suspected of being at risk for developing Huntington's disease based on family history, or a patient in which it is desired to diagnose or eliminate the presence of the Huntington's disease condition as a causative agent behind a patient's symptoms.

It is to be understood that to the extent that a patient's symptoms arise due to the alteration of the CAG repeat copy numbers in the huntingtin gene, even without a diagnosis of Huntington's disease, the methods of the invention can identify the same as the underlying basis for such condition.

According to the invention, presymptomatic screening of an individual in need of such screening for their likelihood of developing Huntington's disease is now possible using DNA encoding the huntingtin gene of the invention, and specifically, DNA having the sequence of the normal human huntingtin gene. The screening method of the invention allows a presymptomatic diagnosis, including prenatal diagnosis, of the presence of an aberrant huntingtin gene in such individuals, and thus an opinion concerning the likelihood that such individual would develop or has developed Huntington's disease or symptoms thereof. This is especially valuable for the identification of carriers of altered huntingtin gene alleles where such alleles possess an increased number of CAG repeats in their huntingtin gene, for example, from individuals with a family history of Huntington's disease. Especially useful for the determination of the number of CAG repeats in the patient's huntingtin gene is the use of PCR to amplify such region or DNA blotting techniques.

For example, in the method of screening, a tissue sample would be taken from such individual, and screened for (1) the presence of the 'normal' human huntingtin gene, especially for the presence of a "normal" range of 11–34 CAG copies in such gene. The human huntingtin gene can be characterized based upon, for example, detection of restriction digestion patterns in 'normal' versus the patient's DNA, including RFLP analysis, using DNA probes prepared against the huntingtin sequence (or a functional fragment thereof) taught in the invention. Similarly, huntingtin mRNA can be characterized and compared to normal huntingtin mRNA (a) levels and/or (b) size as found in a human population not at risk of developing Huntington's disease using similar probes. Lastly, huntingtin protein can be (a) detected and/or (b) quantitated using a biological assay for huntingtin, for example, using an immunological assay and anti-huntingtin antibodies. When assaying huntingtin protein, the immunological assay is preferred for its speed. Methods of making antibody against the huntingtin are well known in the art.

An (1) aberrant huntingtin DNA size pattern, such as an aberrant huntingtin RFLP, and/or (2) aberrant huntingtin mRNA sizes or levels and/or (3) aberrant huntingtin protein levels would indicate that the patient has developed or is at risk for developing a huntingtin-associated symptom such as a symptom associated with Huntington's disease.

The screening and diagnostic methods of the invention do not require that the entire huntingtin DNA coding sequence be used for the probe. Rather, it is only necessary to use a fragment or length of nucleic acid that is sufficient to detect the presence of the huntingtin gene in a DNA preparation from a normal or affected individual, the absence of such gene, or an altered physical property of such gene (such as a change in electrophoretic migration pattern).

Prenatal diagnosis can be performed when desired, using any known method to obtain fetal cells, including amniocentesis, chorionic villous sampling (CVS), and fetoscopy. Prenatal chromosome analysis can be used to determine if the portion of chromosome 4 possessing the normal huntingtin gene is present in a heterozygous state, and PCR amplification or DNA blotting utilized for estimating the size of the CAG repeat in the huntingtin gene.

The huntingtin DNA can be synthesized, especially, the CAG repeat region can be amplified and, if desired, labeled with a radioactive or nonradioactive reporter group, using techniques known in the art (for example, see Eckstein, F., Ed., *Oligonucleotides and Analogues: A Practical Approach*, IRS Press at Oxford University Press, New York, 1992); and Kricka, L. J., Ed., *Nonisotopic DNA Probe Techniques*, Academic Press, San Diego, (1992)).

In one method of treating Huntington's disease in a patient in need of such treatment, functional huntingtin DNA is provided to the cells of such patient, preferably prior to such symptomatic state that indicates the death of many of the patient's neuronal cells which it is desired to target with the method of the invention. The replacement huntingtin DNA is provided in a manner and amount that permits the expression of the huntingtin protein provided by such gene, for a time and in a quantity sufficient to treat such patient. Many vector systems are known in the art to provide such delivery to human patients in need of a gene or protein missing from the cell. For example, adenovirus or retrovirus systems can be used, especially modified retrovirus systems and especially herpes simplex virus systems. Such methods are provided for, in, for example, the teachings of Breakefield, X. A. et al., *The New Biologist* 3:203–218 (1991) Huang, Q. et al., *Experimental Neurology* 115:303–316 (1992), WO93/03743 and WO90/09441 each incorporated herein fully by reference. Methods of antisense strategies are known in the art (see, for example, *Antisense Strategies*, Baserga, R. et al., Eds., Annals of the New York Academy of Sciences, volume 660, 1992).

In another method of treating Huntington's disease in a patient in need of such treatment, a gene encoding an expressible sequence that transcribes huntingtin antisense RNA is provided to the cells of such patient, preferably prior to such symptomatic state that indicates the death of many of the patient's neuronal cells which it is desired to target with the method of the invention. The replacement huntingtin antisense RNA gene is provided in a manner and amount that permits the expression of the antisense RNA provided by such gene, for a time and in a quantity sufficient to treat such patient, and especially in an amount to inhibit translation of the aberrant huntingtin mRNA that is being expressed in the cells of such patient. As above, many vector systems are known in the art to provide such delivery to human patients in need of a gene or protein which is altered in the patients' cells. For example, adenovirus or retrovirus systems can be used, especially modified retrovirus systems and especially herpes simplex virus systems. Such methods are provided for, in, for example, the teachings of Breakefield, X. A. et al., *The New Biologist* 3:203–218 (1991); Huang, Q. et al., *Experimental Neurology* 115:303–316 (1992), WO93/03743 and WO90/09441 each incorporated herein fully by reference.

Delivery of a DNA sequence encoding a functional huntingtin protein, such as the amino acid encoding sequence of FIG. 4, will effectively replace the altered huntingtin gene of the invention, and inhibit, and/or stop and/or regress the symptoms that are the result of the interference to huntingtin gene expression due to an increased number of CAG repeats, such as 37 to 86 repeats in the huntingtin gene as compared to the 11–34 CAG repeats found in human populations not at risk for developing Huntington's disease.

Because Huntington's disease is characterized by a loss of neurons that is most severe in the caudate and putamen regions of the brain, the method of treatment of the invention is most effective when the replacement huntingtin gene is provided to the patient early in the course of the disease, prior to the loss of many neurons due to cell death. For that reason, presymptomatic screening methods according to the invention are important in identifying those individuals in need of treatment by the method of the invention, and such treatment preferably is provided while such individual is presymptomatic.

In a further method of treating Huntington's disease in a patient in need of such treatment such method provides an antagonist to the aberrant huntingtin protein in the cells of such patient.

Although the method is specifically described for DNA-DNA probes, it is to be understood that RNA possessing the same sequence information as the DNA of the invention can be used when desired.

For diagnostic assays, huntingtin antibodies are useful for quantitating and evaluating levels of huntingtin protein, and are especially useful in immunoassays and diagnostic kits.

In another embodiment, the present invention relates to an antibody having binding affinity to an huntingtin polypeptide, or a binding fragment thereof. In a preferred embodiment, the polypeptide has the amino acid sequence set forth in SEQ ID NO:6, or mutant or species variation thereof, or at least 7 contiguous amino acids thereof (preferably, at least 10, 15, 20, or 30 contiguous amino acids thereof). Those which bind selectively to huntingtin would be chosen for use in methods which could include, but should not be limited to, the analysis of altered huntingtin expression in tissue containing huntingtin.

The antibodies of the present invention include monoclonal and polyclonal antibodies, as well fragments of these antibodies. Antibody fragments which contain the idiotype of the molecule can be generated by known techniques. For example, such fragments include but are not limited to: the $F(ab')_2$ fragment; the Fab' fragments, and the Fab fragments.

Of special interest to the present invention are antibodies to huntingtin (or their functional derivatives) which are produced in humans, or are "humanized" (i.e. non-immunogenic in a human) by recombinant or other technology. Humanized antibodies may be produced, for example by replacing an immunogenic portion of an antibody with a corresponding, but non-immunogenic portion (i.e. chimeric antibodies) (Robinson, R. R. et al., International Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., *Science* 240:1041–1043 (1988); Liu, A. Y. et al., *Proc. Natl. Acad. Sci. USA* 84:3439–3443 (1987); Liu, A. Y. et al., *J. Immunol.* 139:3521–3526 (1987); Sun, L. K. et al., *Proc. Natl. Acad. Sci. USA* 84:214–218 (1987); Nishimura, Y. et al., *Canc. Res.* 47:999–1005 (1987); Wood, C. R. et al., *Nature* 314:446–449 (1985)); Shaw et al., *J. Natl. Cancer Inst.* 80:1553–1559 (1988). General reviews of "humanized" chimeric antibodies are provided by Morrison, S. L. (*Science*, 229:1202–1207 (1985)) and by Oi, V. T. et al., *BioTechniques* 4:214 (1986)). Suitable "humanized" antibodies can be alternatively produced by CDR or CEA substitution (Jones, P. T. et al., *Nature* 321:552–525 (1986); Verhoeyan et al., *Science* 239:1534 (1988); Beidler, C. B. et al., *J. Immunol.* 141:4053–4060 (1988)).

In another embodiment, the present invention relates to a hybridoma which produces the above-described monoclonal antibody, or binding fragment thereof. A hybridoma is an immortalized cell line which is capable of secreting a specific monoclonal antibody.

In general, techniques for preparing monoclonal antibodies and hybridomas are well known in the art (Campbell, "*Monoclonal Antibody Technology: Laboratory Techniques in Biochemistry and Molecular Biology,*" Elsevier Science Publishers, Amsterdam, The Netherlands (1984); St. Groth et al., *J. Immunol. Methods* 35:1–21 (1980)).

Any animal (mouse, rabbit, and the like) which is known to produce antibodies can be immunized with the selected polypeptide. Methods for immunization are well known in the art. Such methods include subcutaneous or interperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Res.* 175:109–124 (1988)).

Hybridomas secreting the desired antibodies are cloned and the class and subclass is determined using procedures known in the art (Campbell, *Monoclonal Antibody Technology: Laboratory Techniques in Biochemistry and Molecular Biology*, supra (1984)).

For polyclonal antibodies, antibody containing antisera is isolated from the immunized animal and is screened for the presence of antibodies with the desired specificity using one of the above-described procedures.

In another embodiment of the present invention, the above-described antibodies are detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), pavagnetic atoms, and the like. Procedures for accomplishing such labeling are well-known in the art, for example, see (Sternberger et al., *J. Histochem. Cytochem.* 18:315 (1970); Bayer et al., *Meth. Enzym.* 62:308 (1979); Engval et al., *Immunol.* 109:129 (1972); Goding, *J. Immunol. Meth.* 13:215 (1976)). The labeled antibodies of the present invention can be used for in vitro, in vivo, and in situ assays to identify cells or tissues which express a specific peptide.

In another embodiment of the present invention the above-described antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., *"Handbook of Experimental Immunology"* 4th Ed., Blackwell Scientific Publications, Oxford, England, Chapter 10 (1986); Jacoby et al., *Meth. Enzym.* 34 Academic Press, N.Y. (1974)). The immobilized antibodies of the present invention can be used for in vitro, in vivo, and in situ assays as well as in immunochromotogmphy.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In *Synthetic Peptides, A User's Guide*, W. H. Freeman, N.Y., pp. 289–307 (1992), and Kaspczak et al., *Biochemistry* 28:9230–8 (1989).

Anti-peptide peptides can be generated in one of two fashions. First, the anti-peptide peptides can be generated by replacing the basic amino acid residues found in the huntingtin peptide sequence with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

The manner and method of carrying out the present invention can be more fully understood by those of skill by reference to the following examples, which examples are not intended in any manner to limit the scope of the present invention or of the claims directed thereto.

EXAMPLES

The gene causing Huntington's disease has been mapped in 4p16.3 but has previously eluded identification. The invention uses haplotype analysis of linkage disequilibrium to spotlight a small segment of 4p16.3 as the likely location of the defect. A new gene, huntingtin (IT15), isolated using cloned "trapped" exons from a cosmid contig of the target area contains a polymorphic trinucleotide repeat that is expanded and unstable on HD chromosomes. A $(CAG)_n$ repeat longer than the normal range of about 11 to about 34 copies was observed on HD chromosomes from all 75 disease families examined, comprising a wide range of ethnic backgrounds and 4p16.3 haplotypes. The $(CAG)_n$ repeat, which varies from 37 to at least 86 copies on HD chromosomes appears to be located within the coding sequence of a predicted about 348 kDa protein that is widely expressed but unrelated to any known gene. Thus, the Huntington's disease mutation involves an unstable DNA segment, similar to those described in fragile X syndrome and myotonic dystrophy, acting in the context of a novel 4p16.3 gene to produce a dominant phenotype.

The following protocols and experimental details are referenced in the examples that follow.

HD Cell Lines. Lymphoblast cell lines from HD families of varied ethnic backgrounds used for genetic linkage and disequilibrium studies (Conneally et al., *Genomics* 5:304–308 (1989); MacDonald et al., *Nature Genet.* 1:99–103 (1992)) have been established (Anderson and Gusella, *In Vitro* 20:856–858 (1984)) in the Molecular Neurogenetics Unit, Massachusetts General Hospital, over the past 13 years. The Venezuelan HD pedigree is an extended kindred of over 10,000 members in which all affected individuals have inherited the HD gene from a common founder (Gusella et al., *Nature* 306:234–238 (1983); Gusella et al., *Science* 225:1320–1326 (1984); Wexler et al., *Nature* 326:194–197 (1987)).

DNA/RNA Blotting. DNA was prepared from cultured cells and DNA blots prepared and hybridized as described (Gusella et al., *Proc. Natl. Acad. Sci. USA* 76:5239–5243 (1979); Gusella el al., *Nature* 306:234–238 (1983)). RNA was prepared and Northern blotting performed as described in Taylor et al., *Nature Genet.* 3:223–227 (1992).

Construction of Cosmid Contig. The initial construction of the cosmid contig was by chromosome walking from cosmids L19 and BJ56 (Allitto et al., *Genomics* 9:104–112 (1991); Lin et al., *Somat. Cell Mol. Genet.* 17:481–488 (1991)). Two libraries were employed, a collection of Alu-positive cosmids from the reduced cell hybrid H39-8C10 (Whaley et al., *Som. Cell Mol. Genet.* 17:83–91 (1991)) and an arrayed flow-sorted chromosome 4 cosmid library (NM87545) provided by the Los Alamos National Laboratory. Walking was accomplished by hybridization of whole cosmid DNA, using suppression of repetitive and vector sequences, to robot-generated high density filter grids (Nizetic, D. et al., *Proc. Natl. Acad. Sci. USA* 88:3233–3237 (1991); Lehrach, H. et al., in *Genome Analysis: Genetic and Physical Mapping*, Volume 1, Davies, K. E. et al., Ed., Cold Spring Harbor Laboratory Press, 1991, pp. 39–81). Cosmids L1C2, L69F7, L228B6 and L83D3 were first identified by hybridization of YAC clone YGA2 to the same arrayed library (Bates et al., *Nature Genet.* 1:180–187 (1992); Baxendale et al., *Nucleic Acids Res.* 19:6651 (1991)). HD cosmid GUS72-2130 was isolated by standard screening of a GUS72 cosmid library using a single-copy probe. Cosmid overlaps were confirmed by a combination of clone-to-clone and clone-to-genomic hybridizations, single-copy probe hybridizations and restriction mapping.

cDNA Isolation and Characterization. Exon probes were isolated and cloned as described (Buckler et al., *Proc. Natl. Acad. Sci. USA* 88:4005–4009 (1991)). Exon probes and cDNAs were used to screen human lambdaZAPII cDNA libraries constructed from adult frontal cortex, fetal brain, adenovirus transformed retinal cell line RCA, and liver RNA. cDNA clones, PCR products and trapped exons were sequenced as described (Sanger et al., *Proc. Natl. Acad. Sci. USA* 74:5463–5467 (1977)). Direct cosmid sequencing was performed as described (McClatchey et al., *Hum. Mol. Genet.* 1:521–527 (1992)). Database searches were performed using the BLAST network service of National Center for Biotechnology Information (Altschul et al., *J. Mol. Biol.* 215:403–410 (1990)).

PCR Assay of the $(CAG)_n$ Repeat. Genomic primers (SEQ ID NO:3 and SEQ ID NO:4) flanking the $(CAG)_n$ repeat are:

5' ATG AAG GCC TTC GAG TCC CTC AAG TCC TTC 3' and

5' AAA CTC ACG GTC GGT GCA GCG GCT CCT CAG 3'.

PCR amplification was performed in a reaction volume of 25 μl using 50 ng of genomic DNA, 5 μg of each primer, 10 mM Tris, pH 8.3, 5 mM KCl, 2 mM $MgCl_2$, 200 μM dNTPs, 10% DMSO, 0.1 unit Perfectmatch (Stratagene), 2.5 μCi $^{32}$P-dCTP (Amersham) and 1.25 units Taq polymerase (Boehringer Mannheim). After heating to 94° C. for 1.5 minutes, the reaction mix was cycled according to the following program: 40× [1'@94° C.; 1'@60° C.; 2'@72° C.]. 5 μl of each PCR reaction was dilute an equal volume of 95% formamide loading dye and heat denatured for 2 min. at 95° C. The products were resolved on 5% denaturing polyacrylamide gels. The PCR product from this reaction using cosmid L191F1 $(CAG_{18})$ as template was 247 bp. Allele sizes were estimated relative to a DNA sequencing ladder, the PCR products from sequenced cosmids, and the invariant background bands often present on the gel. Estimates of allelic variation were obtained by typing unrelated individuals of largely Western European ancestry, and normal parents of affected HD individuals from various pedigrees.

Typing of HD and normal chromosomes in Examples 5–8. HD chromosomes were derived from symptomatic individuals and "at risk" individuals known to be gene carriers by linkage marker analysis. All HD chromosomes were from members of well-characterized HD families of varied ethnic backgrounds used previously for genetic linkage and disequilibrium studies (MacDonald, M. E., et al., *Nature Genet.* 1:99–103 (1992); Conneally, P. M., et al., *Genomics* 5:304–308 (1989)). Three of the 150 families used were large pedigrees, each descended from a single founder. The large Venezuelan HD pedigree is an extended kindred of over 13,000 members from which we typed 75 HD chromosomes (Gusella, J. F., et al., *Nature* 306:234–238 (1983); Wexler, N. S., et al., *Nature* 326:194–197 (1987)). Two other large families that have been described previously as Family Z and Family D, provided 25 and 35 HD chromosomes, respectively (Folstein, S. E., et al., *Science* 229:776–779 (1985)). Normal chromosomes were taken from married-ins in the HD families and from unrelated normal individuals from non-HD families. The DNA tested for all individuals except four was prepared from lymphoblastoid cell lines or fresh blood (Gusella, J. F., et al., *Nature* 306:234–238 (1983); Anderson and Gusella, *In Vitro* 20:.856–858 (1984)). In the exceptional cases, DNA was prepared from frozen cerebellum. No difference in the characteristics of the PCR products were observed between lymphoblastoid, fresh blood, or brain DNAs. For five members of the Venezuelan pedigree aged 24–30, we also prepared DNA by extracting pelleted sperm from semen samples. The length of the HD gene $(CAG)_n$ repeat for all DNAs was assessed using polymerase chain reaction amplification.

Statistical analysis as set forth in Examples 5–8. Associations between repeat lengths and onset age were assessed by Pearson correlation coefficient and by multivariate regression to assess higher order associations. Comparisons of the distributions of repeat length for all HD chromosomes and those for individual families were made by analysis of variance and t-test contrasts between groups. The 95% confidence bands were computed around the regression line utilizing the general linear models procedure of SAS (SAS Institute Inc., SAS/STAT User's Guide, Version 6, Fourth Edition, Volume 2 (SAS Institute Inc., Cary, N.C., pp. 846, 1989)).

Hybridization as Set Forth in Example 9. Northern blots (Clontech polyA$^+$) were hybridized with $^{32}$P-labeled (Feinberg et al., *Anal. Biochem.* 137:266–267 (1984)) human cDNA clone IT15B. 1 (The Huntington's Disease Collaborative Research Group, *Cell* 72:971–983 (1993)) spanning nt 5345-10366 of the composite IT15 cDNA sequence (GenBank L12392). Hybridization conditions were: 50% formamide, 10% dextran sulfate, 0.8M NaCl, 5×Denhardt's, 50 mM Tris pH 7.5, 0.5% SDS, 100 μg/ml sheared single stranded fish DNA and 0.1% sodium pyrophosphate. Filters were hybridized for 48 hours at 42° C., then washed in 0.5×SSC, 0.1% SDS at 65° C.

The PCC4 embryonal carcinoma phage cDNA library (Stratagene) was hybridized with a pool of $^{32}$P-labeled (Feinberg et al., *Anal. Biochem.* 137:266–267 (1984)) human PCR and cDNA probes representing nt 933-1899 and 3028-10366. The 129 genomic phage library was screened similarly using a pair of probes flanking the CAG and CCG repeats prepared by PCR amplification from PCC4-8. The following primer pairs were used to amplify segments 5' and 3' to the repeats, respectively: primer set 1, 5'GAAAAGCT-GATGAAGGCT3' (SEQ ID NO: 7) and 5'CTGCTGAAAC-GACTTGAG3' (SEQ ID NO: 8); primer set 2, 5'CACCGC-CGCTGCCAGGTC3' (SEQ ID NO: 9) and 5'GGTCGGTGCAGCGGTTCC3' (SEQ ID NO: 10). Hybridization and washing were performed as above except 40% formamide, 1M NaCl, and 1×Denhardt's were used and washing was at room temperature.

DNA Sequencing as Set Forth in Example 9. Double stranded cDNA clones (1 μg), the 129-1 genomic phage clone (40 μg) and six pBSKII subclones (1 μg) of PCR product from M. spretus were sequenced by dideoxy chain termination (Sanger et al., *Proc. Natl. Acad. Sci. USA* 74:5463–5467 (1977)) using custom primers (Biosearch Cyclone) and 7-deazaguanosine/sequenase 2.0 (USB). Sequence comparisons with the human gene were performed using the GCG package (Genetics Computer Group, Program Manual for the GCG Package, Version Apr. 7, 1991, 575 Science Drive, Madison Wis. (1991)).

Polymorphism Analysis as Set Forth in Example 9. Genomic mouse DNA (200 ng) was amplified using the following primers flanking the CAG-CCG repeat region: 5'CTGATGAAGGCTTTCGAGTCGCTCAAGTCG3' (SEQ ID NO: 11) and 5'CCTTCTTTGGTCGGTGCAGCG-GTTCCTCTG3' (SEQ ID NO: 12). Reaction conditions were 200 μM dNTPs 10% DMSO, 1 μCi $^{32}$P dATP, 2 units Taq polymerase (Boehringer/Mannheim) and the buffer supplied by the manufacturer. The cycling program was: 1×2'@94° C.; 30×(1'@94° C.; 1'@60° C.; 1'@72° C.). Labeled PCR products were displayed on 6% denaturing polyacrylamide gels.

For subcloning of the *M. spretus* PCR product the above primers were resynthesized with (CUA)4 and (CAU)4, respectively on the 5' ends. After amplification, the product was cut from low-melt agarose and subcloned using uracil DNA glycosylase (UDG) (gibco/BRL) into pBSKII modified by digestion with ECORV and PCR amplification using primers 5'AGUAGUAGUAGAUCAAGCTTATC-GATACC3' (SEQ ID NO: 13) and 5'AUGAUGAUGAUGAUCGAATTCCTGCAGCC3' (SEQ ID NO: 14).

Cell Lines as Set Forth in Example 10. Cell lines from normal individuals, from HD heterozygotes and homozygotes and from the balanced t(4;12) carrier were established by EBV transformation of blood lymphocytes (Anderson & Guseila, *In Vitro* 20:.856–858 (1984)). Somatic cell hybrids have been described previously (Smith, B. et al., *Am. J. Hum. Genet.* 42:335–344 (1988); Lin, C. S. et al., *Somat. Cell Mol. Genet.* 17:481–488 (1991)).

Exon Amplification as Set Forth in Example 10. The exon amplification procedure was used to isolate coding sequences from a contig cosmid spanning the location of the HD gene (Baxendale, S. et al., *Nature Genet.* 4:181–186 (1993)). Exon products were obtained from either BamHI-BglII digests cloned into the first generation pSPL1 vector or by BamHI-BglII or PstI digests cloned into the second generation pSPL3 as described (Buckler, A. J. et al., *Proc. Natl. Acad. Sci. USA* 88:4005–4009 (1991)). PCR amplified exon products were cloned into pBSKII and sequenced using the double stranded template by dideoxy chain termination (Sanger & Coulson, *Proc. Natl. Acad. Sci. USA* 74:5463–5467 (1977)).

Exon-Intron Structure as Set Forth in Example 10. Exon-intron boundaries were sequenced directly from cosmid DNA using specific primers designed from the IT15 cDNA (McClatchey, A. I., *Hum. Mol. Genet.* 1:521–527 (1992)). Placement of the boundaries was achieved by comparison of the genomic and cDNA sequences. Some exon-intron boundaries were confirmed by sequencing of random cosmid subclones. To place exons on the physical map, 60 ng of two oligomers (21–23 base pairs each) corresponding to sequences at the edges of each exon were end-labeled with γ-$^{32}$-dATP using T4 polynucleotide kinase, and were hybridized independently at 42° C. to nylon filter membrane Southern blots of cosmid DNAs digest with EcoRI, followed by washing in 6×SSC at room temperature for 15 minutes (Gusella, J. F. et al., *Nature* 306:234–238 (1983)). Oligonucleotides for PCR, DNA sequencing and hybridization were synthesized using an automated DNA synthesizer (Applied Biosystems).

Blot Analyses as Set Forth in Example 10. DNA was prepared from cultured cells and Southern blots were prepared and hybridized as described (Gusella, J. F. et al., *Nature* 306:234–238 (1983); Gusella, J. F. et al., *Proc. Natl. Acad. Sci. USA* 76:5239–5243 (1979)). Northern blots were purchased from Clontech Laboratories, Inc. and were hybridized using the conditions provided by the manufacturer. Probes for Southern and Northern analyses were labeled with α-$^{32}$-dATP by the random priming method (Feinberg & Vogelstein, *Anal Biochem.* 137:266–267 (1984)).

Scanning for Polymorphism as Set Forth in Example 10. To scan for polymorphism, first strand cDNA was prepared by oligo(dT) priming of 1 μg of lymphoblast mRNA using cloned MuLV reverse transcriptase (BRL) as described (Buckler, A. J. et al., *Proc. Natl. Acad. Sci. USA* 88:4005–4009 (1991); Ambrose, C. et al., *Hum. Mol. Genet.* 1:697–703 (1992)). The composite IT15 sequence 3' to the CAG was then amplified by PCR in overlapping segments of ~1 kb using specific primer sets based on the cDNA sequence. Each PCR produce was directly sequenced (Sanger & Coulson, *Proc. Natl. Acad. Sci. USA* 74:5463–5467 (1977)) and was also used as template for production of ~200–300 bp $^{32}$P-labeled PCR products for SSCP analysis. PCR reactions, direct sequencing and SSCP analysis were all carried out as described previously (Ambrose, C. et al., *Hum. Mol. Genet.* 1:697–703 (1992)). A few PCR products which were refractory to direct sequencing were subcloned into pBSKII. Several independent subclones were then sequenced for each product.

Example 1

Application of Exon Amplification to Obtain Trapped Cloned Exons

Figure 1:
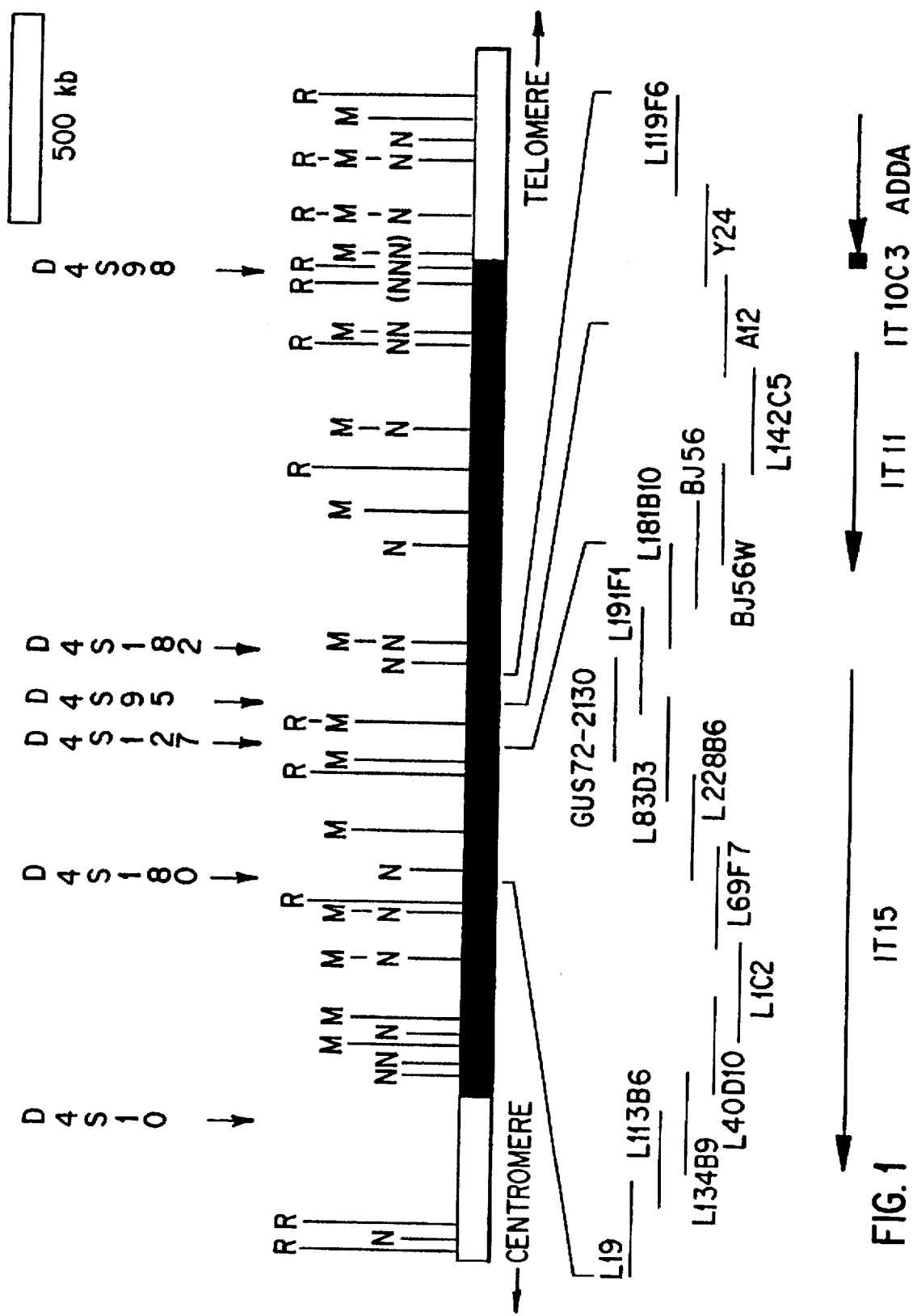
FIG. 1. Long-range restriction map of the HD candidate region. A partial long range restriction map of 4p16.3 is shown (adapted from Lin et al., Somat. Cell Mol. Genet. 17:481-488 (1991)). The HD candidate region determined by recombination events is depicted as a hatched line between D4S10 and D4S98. The portion of the HD candidate region implicated as the site of the defect by linkage disequilibrium haplotype analysis (MacDonald et al., Nature Genet. 1:99-103 (1992) is shown as a filled box. Below the map schematic, the region from D4S180 to D4S182 is expanded to show the cosmid config (averaging 40 kb/cosmid). The genomic coverage and where known the transcriptional orientation (arrow 5' to 3') of the huntingtin (IT15), IT11, IT10C3 and ADDA genes is also shown. Locus names above the map denote selected polymorphic markers that have been used in HD families. The positions of D4S127 and D4S95 which form the core of haplotype in the region of maximum disequilibrium are also shown in the cosmid contig. Restriction sites are given for Not I (N), Mlu I (M) and Nru I (R). Sites displaying complete digestion are shown in boldface while sites subject to frequent incomplete digestion are shown as lighter symbols. Brackets around the "N" symbols indicate the presence of additional clustered Not I sites.

The HD candidate region defined by discrete recombination events in well-characterized families spans 2.2 Mb between D4S10 and D4S98 as shown in FIG. 1. The 500 kb segment between D4S180 and D4S182 displays the strongest linkage disequilibrium with HD, with about ⅓ of disease chromosomes sharing a common haplotype, anchored by multi-allele polymorphisms at D4S127 and D4S95 (MacDonald et al., *Nature Genet.* 1:99–103 (1992)). Sixty-four overlapping cosmids spanning about 480 kb from D4S180 to a location between D4S95 and D4S182 have been isolated by a combination of information from YAC (Baxendale et al., *Nucleic Acids Res.* 19:6651 (1991)) and cosmid probe hybridization to high density filter grids of a chromosome 4 specific library, as well as additional libraries covering this region. Sixteen of these cosmids providing the complete contig are shown in FIG. 1. We have previously used exon amplification to identify ADDA, the α-adducin locus, IT10C3, a novel putative transporter gene, and IT11, a novel G protein-coupled receptor kinase gene in the region distal to D4S127 (FIG. 1).

We have now applied the exon amplification technique to cosmids from the region of the contig proximal to D4S127. This procedure produces "trapped" exon clones, which can represent single exons, or multiple exons spliced together and is an efficient method of obtaining probes for screening cDNA libraries. Individual cosmids were processed, yielding 9 exon clones in the region from cosmids L134B9 to L181B10.

Figure 2:
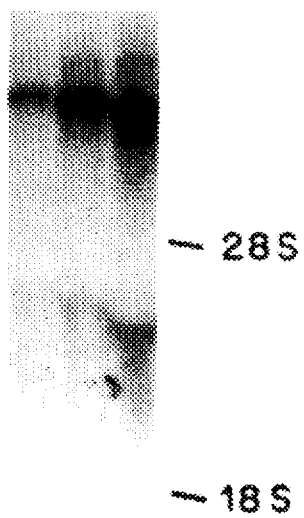
FIG. 2. Northern blot analysis of the huntingtin (IT15) transcript. Results of the hybridization of IT15A to a Northern blot of RNA from normal (lane 1) and HD homozygous (lane 2 and 3) lymphoblasts are shown. A single RNA of about 11 kb was detected in all three samples, with slight apparent variations being due to unequal RNA concentrations. The HD homozygotes are independent, deriving from the large American family (lane 2) and the large Venezuelan family (lane 3), respectively. The Venezuelan HD chromosome has a 4p16.3 haplotype of "5 2 2" defined by a $(GT)_n$ polymorphism at D4S127 and VNTR and TaqI RFLPs at D4S95. The American homozygote carries the most common 4p16.3 haplotype found on HD chromosomes: "2 11 1" (MacDonald et al., Nature Genet. 1:99-103

Two non-overlapping cDNAs were initially isolated using exon probes. IT15A was obtained by screening a transformed adult retinal cell cDNA library with exon clone DL118F5-U. IT16A was isolated by screening an adult frontal cortex cDNA library with a pool of three exon clones, DL83D3-8, DL83D3-1, and DL228B6-3. By Northern blot analysis, we discovered that IT15A and IT16A are in fact different portions of the same large approximately 10–11 kb transcript. FIG. 2 shows an example of a Northern blot containing RNA from lymphoblastoid cell lines representing a normal individual and 2 independent homozygotes for HD chromosomes of different haplotypes. The same approximately 10–11 kb transcript was also detected in RNA from a variety of human tissues (liver, spleen, kidney, muscle and various regions of adult brain).

Figure 3:
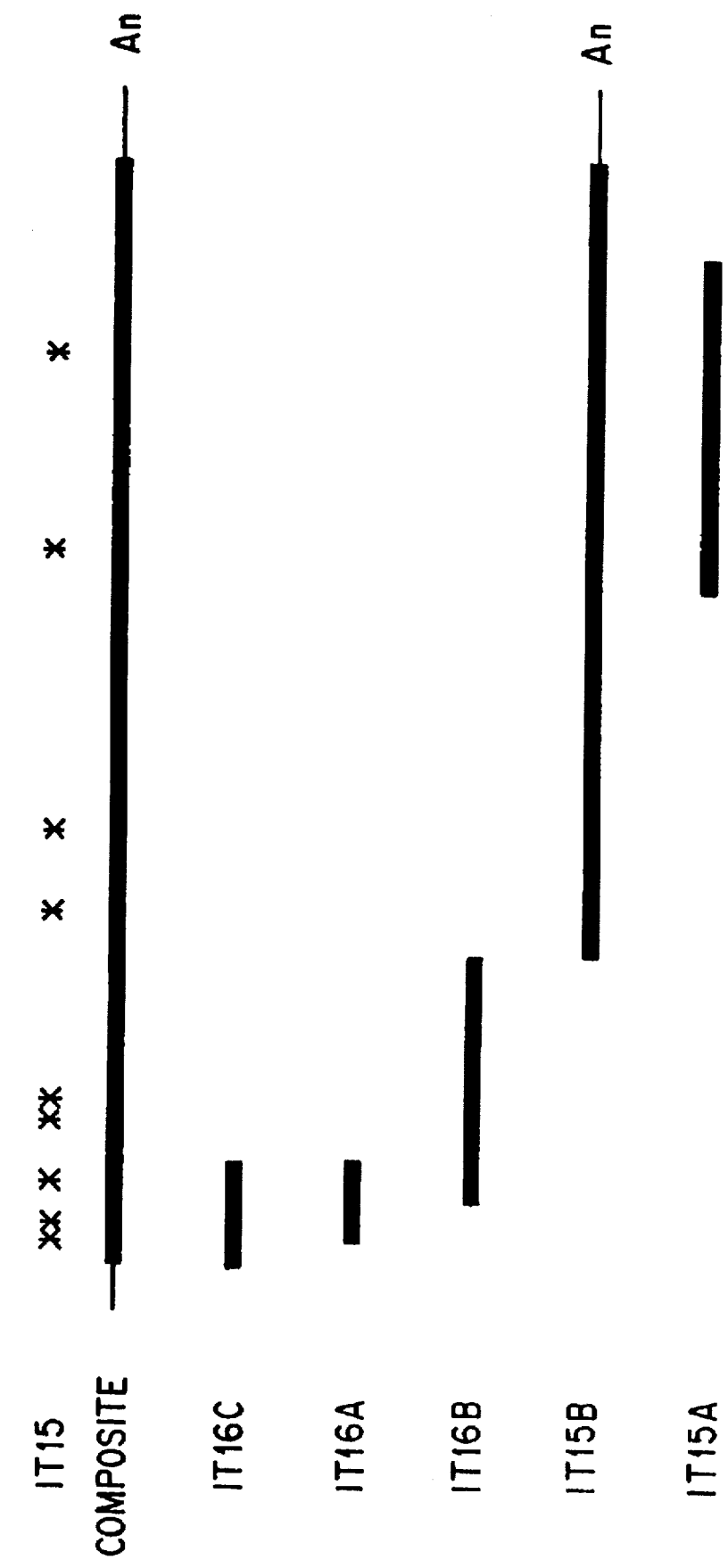
FIG. 3. Schematic of cDNA clones defining the IT15 transcript. Five cDNAs are represented under a schematic of the composite IT15 sequence. The thin line corresponds to untranslated regions. The thick line corresponds to coding sequence, assuming initiation of translation at the first Met codon in the open reading frame. Stars mark the positions of the following exon clones 5' to 3': DL83D3-8, DL83D3-1, DL228B6,-3, DL228B6-5, DL228B6-13, DL69F7-3, DL178H4-6, DL118F5-U and DL134B9-U4.

IT15A and IT16A were used to "walk" in a number of human tissue cDNA libraries in order to obtain the full-length transcript. FIG. 3 shows a representation of 5 cDNA clones which define the IT15 transcript, under a schematic of the composite sequence derived as described in the legend. FIG. 3 also displays the locations on the composite sequence of the 9 trapped exon clones.

The composite sequence of T15, containing the entire predicted coding sequence, spans 10,366 bases including a tail of 18 A's as shown in FIG. 4. An open reading frame of 9,432 bases begins with a potential initiator methionine codon at base 316, located in the context of an optimal translation initiation sequence. An in-frame stop codon is located 240 bases upstream from this site. The protein product of IT15 is predicted to be a 348 kDa protein containing 3,144 amino acids. Although the first Met codon in the long open reading frame has been chosen as the probable initiator codon, we cannot exclude that translation does not actually begin at a more 3' Met codon, producing a smaller protein.

Example 2

Polymorphic Variation of the $(CAG)_n$ Trinucleotide Repeat

Near its 5' end, the IT15 sequence contains 21 copies of the triplet CAG, encoding glutamine (FIG. 5). When this sequence was compared with genomic sequences that are known to surround simple sequence repeats (SSRs) in 4p16.3, it was found that normal cosmid L191F1 had 18 copies of the triplet indicating that the $(CAG)_n$ repeat is polymorphic (FIG. 5). Primers from the genomic sequence flanking the repeat were chosen to establish a PCR assay for this variation. In the normal population, this SSR polymorphism displays at least 17 discrete alleles (Table 1) ranging from about 11 to about 34 repeat units. Ninety-eight percent of the 173 normal chromosomes tested contained repeat lengths between 11 and 24 repeats. Two chromosomes were detected in the 25–30 repeat range and 2 normal chromosomes had 33 and 34 repeats respectively. The overall heterozygosity on normal chromosome was 80%. Based on sequence analysis of three clones, it appears that the variation is based entirely on the $(CAG)_n$, but the potential for variation of the smaller downstream $(CCG)_7$ which is also included in the PCR product, is also present.

Example 3

Instability of the Trinucleotide Repeat on HD chromosomes

Sequence analysis of cosmid GUS72-2130, derived from a chromosome with the major HD haplotype (see below), revealed 48 copies of the trinucleotide repeat, far greater than the largest normal allele (FIG. 5). When the PCR assay was applied to HD chromosomes, a pattern strikingly different from the normal variation was observed. HD heterozygotes contained one discrete allelic product in the normal size range, and one PCR product of much larger size, suggesting that the $(CAG)_n$ repeat on HD chromosomes is expanded relative to normal chromosomes.

FIG. 6 shows the patterns observed when the PCR assay was performed on lymphoblast DNA from a selected nuclear family in a large Venezuelan HD kindred. In this family, DNA marker analysis has shown previously that the HD chromosome was transmitted from the father (lane 2) to seven children (lanes 3, 5, 6, 7, 8, 10 and 11). The three normal chromosomes present in this mating yielded a PCR product in the normal size range (AN1, AN2, AN3) that was inherited in a Mendelian fashion. The HD chromosome in the father yielded a diffuse, "fuzzy"-appearing PCR product slightly smaller than the 48 repeat product of the non-Venezuelan HD cosmid. Except for the DNA in lane 5 which did not PCR amplify and in lane 11 which displayed only a single normal allele, each of the affected children's DNAs yielded a fuzzy PCR product of a different size (AE), indicating instability of the HD chromosome $(CAG)_n$ repeat. Lane 6 contained an HD-specific product slightly smaller than or equal to that of the father's DNA. Lanes 3, 7, 10 and 8, respectively, contained HD-specific PCR products of progressively larger size. The absence of an HD-specific PCR product in lane 11 suggested that this child's DNA possessed a $(CAG)_n$ repeat that was too long to amplify efficiently. This was verified by Southern blot analysis in which the expanded HD allele was easily detected and estimated to contain up to 100 copies of the repeat. Notably, this child had juvenile onset of HD at the very early age of 2 years. The onset of HD in the father was in his early 40s, typical of most adult HD patients in this population. The onset ages of children represented by lanes 3, 7, 10 and 8 were 26, 25, 14 and 11 years, respectively, suggesting a rough correlation between age at onset of HD and the length of the $(CAG)_n$ repeat on the HD chromosome. In keeping with this tread, the offspring represented in lane 6 with the fewest repeats remained asymptomatic when last examined at age of 30.

FIG. 7 shows PCR analysis for a second sibship from the Venezuelan pedigree in which both parents are HD heterozygotes carrying the same HD chromosome based on DNA marker studies. Several of the offspring are HD homozygotes (lanes 6+7, 10+11, 13+14, 17+18, 23+24) as reported previously (Wexler et al., Nature 326:194–197 (1987)). Each parent's DNA contained one allele in the normal range (AN1, AN2) which was transmitted in a Mendelian fashion. The HD-specific products (AE) from the DNA of both parents and children were all much larger than the normal allelic products and also showed extensive variation in mean size. A neurologic diagnosis for the offspring in this pedigree was not provided to maintain the blind status of investigators involved in the ongoing Venezuela HD project, although age of onset again appears to parallel repeat length. Paired samples under many of the individual symbols represent independent lymphoblast lines initiated at least one year apart. The variance between paired samples was not as great as between the different individuals, suggesting that the major differences in size of the PCR products resulted from meiotic transmission. Of special note is the result obtained in lanes 13 and 14. This HD homozygote's DNA yielded one PCR product larger and one smaller than the HD-specific PCR products of both parents.

To date, we have tested 75 independent HD families, representing all difference reported in MacDonald et al., Nature Genet. 1:99–103 (1992)) and a wide range of ethnic backgrounds. In all 75 cases, a PCR product larger than the normal size range was produced from the HD chromosome. The sizes of the HD-specific products ranged from 42 repeat copies to more than 66 copies, with a few individuals falling to yield a product because of the extreme length of the repeat. In these cases, Southern blot analysis revealed an increase in the length of an EcoRI fragment with the largest allele approximating 100 copies of the repeat. FIG. 8 shows the variation detected in members of an American family of Irish ancestry in which the major HD haplotype is segregating. Cosmid GUS72-2130 was cloned from the HD homozygous individual whose DNA was amplified in lane 2. As was observed in the Venezuelan HD pedigree (FIGS. 6 and 7), which segregates the disorder with a different 4p16.3 haplotype, the HD-specific PCR products for this family display considerable size variation.

Example 4

New Mutations to HD

The mutation rate in HD has been reported to be very low. To test whether the expansion of the $(CAG)_n$ repeat is the mechanism by which new HD mutations occur, two pedigrees with sporadic cases of HD have been examined in which intensive searching failed to reveal a family history of the disorder. In these cases, pedigree information sufficient to identify the same chromosomes in both the affected individual and unaffective relatives was gathered. FIGS. 9 and 10 show the results of PCR analysis of the $(CAG)_n$ repeat in these families. The chromosomes in each family were assigned an arbitrary number based on typing for a large number of RFLP and SSR markers in 4p16.3 defining distinct haplotypes and the presumed HD chromosome is starred.

In family #1, HD first appeared in individual II-3 who transmitted the disorder to III-1 along with chromosome 3*. This same chromosome was present in II-2, an elderly unaffected individual. PCR analysis revealed that chromosome 3* from II-2 produced a PCR product at the extreme high end of the normal range (about 36 CAG copies). However, the $(CAG)_n$ repeat on the same chromosome in II-3 and III-1 had undergone sequential expansions to about 44 and about 46 copies, respectively. A similar result was obtained in Family #2, where the presumed HD mutant III-2 had a considerably expanded repeat relative to the same chromosome in II-1 and III-1 (about 49 vs. about 33 CAG copies). In both family #1 and family #2, the ultimate HD chromosome displays the marker haplotype characteristic of ⅓ of all HD chromosomes, suggesting that this haplotype may be predisposed to undergoing repeat expansion.

Discussion

The discovery of an expanded, unstable trinucleotide repeat on HD chromosomes within the IT15 gene is the basis for utilizing this gene as the HD gene of the invention. These results are consistent with the interpretation that HD constitutes the latest example of a mutational mechanism that may prove quite common in human genetic disease. Elongation of a trinucleotide repeat sequence has been implicated previously as the cause of three quite different human disorders, the fragile X syndrome, myotonic dystrophy and spino-bulbar muscular atrophy. The initial observations of repeat expansion in HD indicate that this phenomenon shares features in common with each of these disorders.

In the fragile X syndrome, expression of a constellation of symptoms that includes mental retardation and a fragile site at Xq27.3 is associated with expansion of a $(CGG)_n$ repeat thought to be in the 5' untranslated region of the FMR1 gene (Fu et al., *Cell* 67:1047–1058 (1991); Kremer et al., *Science* 252:1711–1714 (1991); Verkerk et al., *Cell* 65:904–914 (1991)). In myotonic dystrophy, a dominant disorder involving muscle weakness with myotonia that typically is present in early adulthood, the unstable trinucleotide repeat, $(CTG)_n$, is located in the 3' untranslated region of the mysotonin protein kinase gene (Aslanidis et al., *Nature* 355:548–551 (1992); Brook et al., *Cell* 68:799–808 (1992); Buxton et al., *Nature* 355:547–548 (1992); Fu et al., *Science* 255:1256–1259 (1992); Harley et al., *Lancet* 339:1125–1128 (1992); Mahadevan et al., *Science* 255:1253–1255 (1992)). The unstable $(CAG)_n$ repeat in HD may be within the coding sequence of the IT15 gene, a feature shared with spino-bulbar muscular atrophy, an X-linked recessive adult-onset disorder of the motor neurons caused by expansion of a $(CAG)_n$ repeat in the coding sequence of the androgen receptor gene (LaSpada et al., *Nature* 352:77–79 (1991)). The repeat length in both the fragile X syndrome and myotonic dystrophy tends to increase in successive generations, sometimes quite dramatically. Occasionally, decreases in the average repeat length are observed (Fu et al., *Science* 255:1256–1259 (1992); Yu et al., *Am. J. Hum. Genet.* 50:968–980 (1992); Bruner et al., *N. Engl. J. Med.* :476–480 (1993)). The HD trinuclcotide repeat is also unstable, usually expanding when transmitted to the next generation, but contracting on occasion. In HD, as in the other disorders, change in copy number occurs in the absence of recombination. Compared with the fragile X syndrome, myotonic dystrophy, and HD, the instability of the disease allele in spino-bulbar muscular atrophy is more limited, and dramatic expansions of repeat length have not been seen (Biancalana et al., *Hum. Mol. Genet.* 1:255–258 (1992)).

Expansion of the repeat length in myotonic dystrophy is associated with a particular chromosomal haplotype, suggesting the existence of a primordial predisposing mutation (Harley et al., *Am. J. Hum. Genet.* 49:68–75 (1991); Harley et al., *Nature* 355:545–546 (1992); Ashizawa, *Lancet* 338:642–643 (1991). In the fragile X syndrome, there may be a limited number of ancestral mutations that predispose to increases in trinucleotide repeat number (Richards et al., *Nature Genet.* 1:257–260 (1992); Oudet et al., *Am. J. Hum. Genet.* 52:297–304 (1993)). The linkage disequilibrium analysis used to identify IT15 indicates that there are several haplotypes associated with HD, but that at least ⅓ of HD chromosomes are ancestrally related (MacDonald et al., *Nature Genet.* 1:99–103 (1992)). These data, combined with the reported low rate of new mutation to HD (Harper, *J. Med. Genet.* 89:365–376 (1992)), suggest that expansion of the trinucleotide repeat may only occur on select chromosomes. The analysis of two families presented herein, in which new mutation was supposed to have occurred, is consistent with the view that there may be particular normal chromosomes that have the capacity to undergo expansion of the repeat into the HD range. In each of these families, a chromosome with a $(CAG)_n$ repeat length in the upper end of the normal range was segregating on a chromosome whose 4p16.3 haplotype matched the most common haplotype seen on HD chromosomes and the clinical appearance of HD in these two cases was associated with expansion of the trinucleotide repeat.

The recent application of haplotype analysis to explore the linkage disequilibrium on HD chromosomes pointed to a portion of a 2.2 Mb candidate region defined by the majority of recombination events described in HD pedigrees (MacDonald et al., *Nature Genet* 1:99–103 (1992)). Previously, the search for the gene was confounded by three matings in which the genetic inheritance pattern was inconsistent with the remainder of the family (MacDonald et al., *Neuron* 3:183–190 (1989b); Pilehard et al., *Am. J. Hum. Genet.* 50:1218–1230 (1992)). These matings produced apparently affected HD individuals despite the inheritance of only normal alleles for markers throughout 4p16.3, effectively excluding inheritance of the HD chromosome present in the rest of the pedigree. Using PCR assay disclosed above, each of these families was tested and it was determined that like other HD kindreds, an expanded allele segregates with HD in affected individuals of all three pedigrees. However, an expanded allele was not present in those specific individuals with the inconsistent 4p16.3 genotypes. Instead, these individuals displayed the normal alleles expected based on analysis of other markers in 4p16.3. It is conceivable that these inconsistent individuals do not, in fact, have HD, but some other disorder. Alternatively, they might represent genetic mosaics in which the HD allele is more heavily represented and/or more expanded in brain tissue than in the lymphoblast DNA used for genotyping.

The capacity to monitor directly the size of the trinucleotide repeat in individuals "at risk" for HD provides significant advantages over current methods, eliminating the need for complicated linkage analyses, facilitating genetic counseling, and extending the applicability of presymptomatic and prenatal diagnosis to "at risk" individuals with no living affected relatives. however, it is of the utmost importance that the current internationally accepted guidelines and counseling protocols for testing those "at risk" continue to be observed, and that samples from unaffected relatives should not be tested inadvertently or without full consent. In the series of patients examined in this study, there is an apparent correlation between repeat length and age of onset of the disease, reminiscent of that reported in myotonic dystrophy (Harley et al., *Lancet* 339:1125–1128 (1992); Tsilfidis et al., *Nature Genet.* 1:192–195 (1992)). The largest HD trinucleotide repeat segments were found in juvenile onset cases, where there is a known preponderance of male transmission (Merrit et al., *Excerpta Medica*, Amsterdam, pp. 645–650 (1969)).

The expression of fragile X syndrome is associated with direct inactivation of the FMRI gene (Pierretti et al., *Cell* 66:817–822 (1991); DeBoulle et al., *Nature Genet.* 3:31–35 (1993)). The recessive inheritance pattern of spino-bulbar muscular atrophy suggests that in this disorder, an inactive gene product is produced. In myotonic dystrophy, the manner in which repeat expansion leads to the dominant disease phenotype is unknown. There are numerous possibilities for the mechanism of pathogenesis of the expanded trinucleotide repeat in HD. Without intending to be held to this theory, nevertheless notice can be taken that since Wolf-Hirschhorn patients hemizygous for 4p16.3 do not display features of HD, and IT15 mRNA is present in HD homozygotes, the expanded trinucleotide repeat does not cause simple inactivation of the gene containing it. The observation that the phenotype of HD is completely dominant, since homozygotes for the disease allele do not differ clinically from heterozygotes, has suggested that HD results from a gain of function mutation, in which either the mRNA product or the protein product of the disease allele would have some new property, or be expressed inappropriately (Wexler et al., *Nature* 326:194–197 (1987); Myers et al., *Am. J. Hum. Genet.* 43:615–618 (1989)). If the expanded trinucleotide repeat were translated, the consequences on the protein product would be dramatic, increasing the length of the poly-glutamine stretch near the N-terminus. It is possible, however, that despite the presence of an upstream Met codon, the normal translational start occurs 3' to the $(CAG)_n$ repeat and there is no poly-glutamine stretch in the protein product. In this case, the repeat would be in the 5' untranslated region and might be expected to have its dominant effect at the mRNA level. The presence of an expanded repeat might directly alter regulation, localization, stability or translatability of the mRNA containing it, and could indirectly affect its counterpart from the normal allele in HD heterozygotes. Other conceivable scenarios are that the presence of an expanded repeat might alter the effective translation start site for the HD transcript, thereby truncating the protein, or alter the transcription start site for the IT15 gene, disrupting control of mRNA expression. Finally, although the repeat is located within the IT15 transcript, the possibility that it leads to HD by virtue of an action on the expression of an adjacent gene cannot be excluded.

Despite this final caveat, it is consistent with the above results and most likely that the trinucleotide repeat expansion causes HD by its effect, either at the mRNA or protein level, on the expression and/or structure of the protein product of the IT15 gene, which has been named huntingtin. Outside of the region of the triplet repeat, the IT15 DNA sequence detected no significant similarity to any previously reported gene in the GenBank database. Except for the stretches of glutamine and proline near the N-terminus, the amino acid sequence displayed no similarity to known proteins, providing no conspicuous clues to huntingtin's function. The poly-glutamine and poly-proline region near the N-terminus detect similarity with a large number of proteins which also contain long stretches of these amino acids. It is difficult to assess the significance of such similarities, although it is notable that many of these are DNA binding proteins and that huntingtin does have a single leucine zipper motiff at residue 1,443. Huntingtin appears to be widely expressed, and yet cell death in HD is confined to specific neurons in particular regions of the brain.

TABLE 1

COMPARISON OF HD AND NORMAL REPEAT SIZES

| RANGE OF ALLELE SIZES (# REPEATS) | NORMAL CHROMOSOMES NUMBER AND FREQUENCY | | HD CHROMOSOMES NUMBER AND FREQUENCY | |
|---|---|---|---|---|
| ≧48 | 0 | 0 | 44 | 0.59 |
| 42–47 | 0 | 0 | 30 | 0.41 |
| 30–41 | 2 | 0.01 | 0 | 0 |
| 25–30 | 2 | 0.01 | 0 | 0 |
| ≦24 | 169 | 0.98 | 0 | 0 |
| TOTAL | 173 | 1.00 | 74 | 1.0 |

Example 5

Distribution of Trinucleotide Repeat Lengths on Normal and HD Chromosomes

The number of copies of the HD triplet repeat has been examined in a total of 425 HD chromosomes from 150 independent families and compared with the copy number of the HD triplet repeat of 545 normal chromosomes. The results are displayed in FIG. 11. Two non-overlapping distributions of repeat length were observed, wherein the upper end of the normal range and the lower end of the HD range were separated by 3 repeat units. The normal chromosomes displayed 24 alleles producing PCR products ranging from 11 to 34 repeat units, with a median of 19 units (mean 19.71, s.d. 3.21). The HD chromosomes yielded 54 discrete PCR products corresponding to repeat lengths of 37 to 86 units, with a median of 45 units (mean 46.42, s.d. 6.68).

Of the HD chromosomes, 134 and 161 were known to be maternally or paternally-derived, respectively. To investigate whether the sex of the transmitting parent might influence the distribution of repeat lengths, these two sets of chromosomes were plotted separately in FIG. 12. The maternally-derived chromosomes displayed repeat lengths ranging from 37 to 73 units, with a median of 44 (mean 44.93, s.d. 5.14). The paternally-derived chromosomes had 37 to 86 copies of the repeat unit, with a median of 48 units (mean 49.14, s.d. 8.27). However, a higher proportion of the paternally-derived HD chromosomes had repeat lengths greater than 55 units (16% vs. 2%), suggesting the possibility of a differential effect of paternal versus maternal transmission.

The data set used excluded chromosomes from a few clinically diagnosed individuals who have previously been shown not to have inherited the HD chromosome by DNA marker linkage studies (MacDonald, M. E., et al., *Neuron* 3:183–190 (1989); Pritchard, C., et al., *Am. J. Hum. Genet.* 50:1218–1230 (1992)). These individuals have repeat lengths well within the normal range. Their disease manifestations have not been explained, and they may represent phenocopies of HD. Regardless of the mechanism involved, the occurrence at low frequency of such individuals within known HD families must be considered if diagnostic conclusions are based solely on repeat length.

The control data set also excludes a number of chromosomes from phenotypically normal individuals who are related to "spontaneous" cases of HD or "new mutations". Chromosomes from these individuals who are not clinically affected and have no family history of the disorder cannot be designated as HD. However, these chromosomes cannot be classified as unambiguously normal because they are essentially the same chromosome as that of an affected relative, the diagnosed "spontaneous" HD proband, except with respect to repeat length. The lengths of repeat found on these ambiguous chromosomes (34–38 units) span the gap between the control and HD distributions, confounding a decision on the status of any individual with a repeat in the high normal to low HD range.

Example 6

Instability of the Trinucleotide Repeat

Figure 13C:
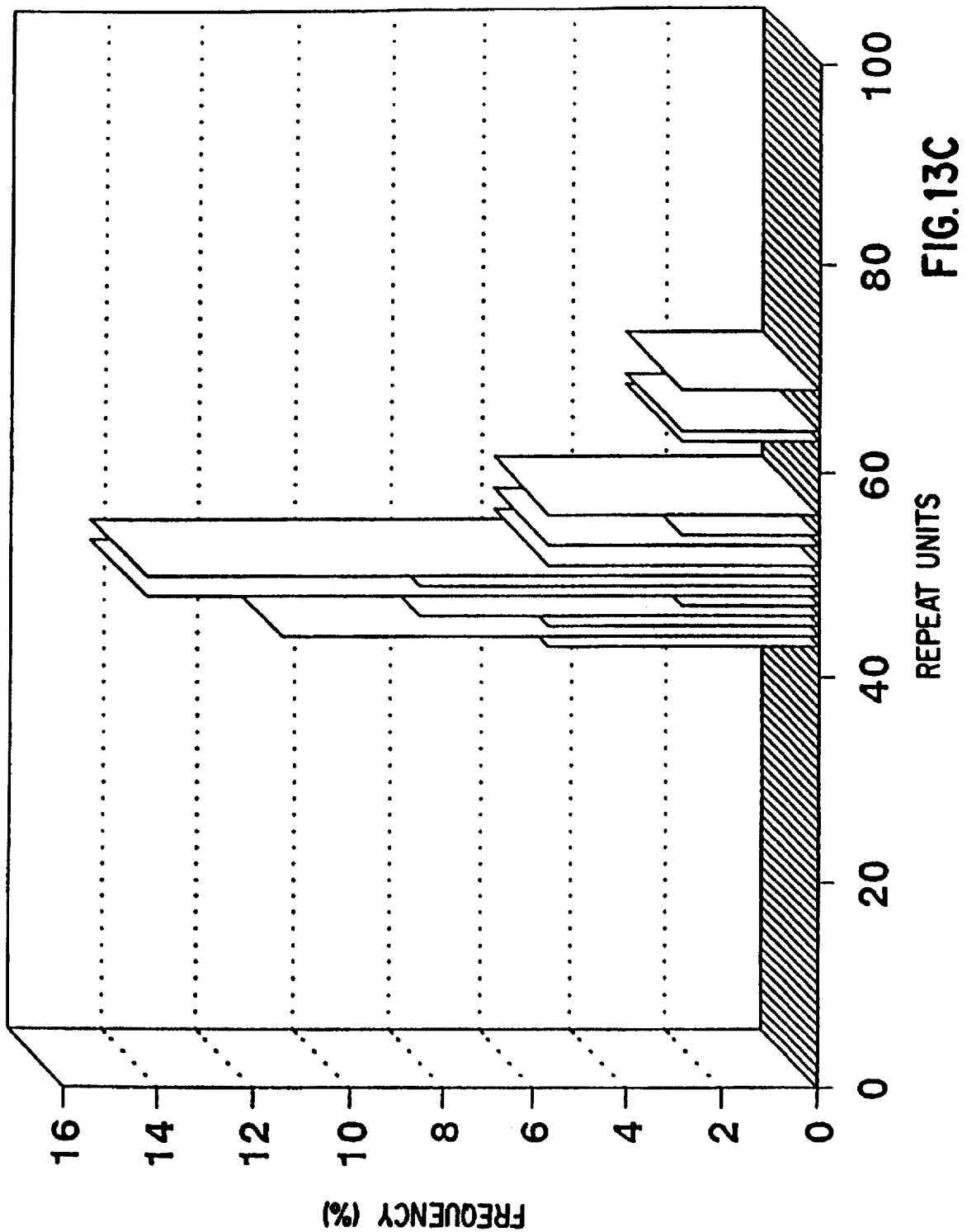

The data in FIG. 11 combine repeat lengths from 150 different HD families representing many potentially independent origins of the defect. To examine the variation in repeat lengths on sets of HD chromosomes known to descend from a common founder, the data from three large HD kindreds (Gusella, J. F., et al., *Nature* 306:234–238 (1983); Wexler, N. S., et al., *Nature* 326:194–197 (1987); Folstein, S. E., et al., *Science* 229:776–779 (1985)) with different 4p16.3 haplotypes (MacDonald, M. E., et al., *Nature Genet.* 1:99–103 (1992)), typed for 75, 25 and 35 individuals, respectively, were separated. Despite the single origin of the founder HD chromosome within each pedigree, members of the separate pedigrees display a wide range of repeat lengths (FIG. 13). This instability of the HD chromosome repeat is most prominent in members of a large Venezuelan HD kindred (panel A) In which the common HD ancestor has produced 10 generations of descendants, numbering over 13,000 individuals. The distribution of repeat lengths in this sampling of the Venezuelan pedigree (median 46, mean 48.26, s.d. 9.3) is not significantly different from that of the larger sample of HD chromosomes from all families. Panels B and C. display results for two extended families in which HD was introduced more recently than in the Venezuelan kindred. These families have been reported to exhibit different age of onset distributions and varied phenotypic features of HD (Folstein, S. E., et al., *Science* 229:776–779 (1985)). Both revealed extensive repeat length variation, with a median of 41 and 49 repeat units, respectively. The distribution of repeat lengths in the members of the family in Panel B was significantly different from the distribution of all HD chromosome repeat lengths (p<0.0001), with a smaller mean of 42.04 repeat units (s.d. 2.82). The repeat distribution from HD chromosomes of Panel C. was also significantly different from the total data set (p<0.004), but with a higher mean of 49.80(s.d. 5.86).

Example 7

Parental Source Effects on Repeat Length Variation

For 62 HD chromosomes in FIG. 11, the length of the trinucleotide repeat also could be examined on the corresponding parental HD chromosome. In 20 of 25 maternal transmissions, and in 31 of 37 paternal transmissions, the repeat length was altered, indicating considerable instability. A similar phenomenon was not observed for normal chromosomes, where more than 500 meiotic transmissions revealed no changes in repeat length, although the very existence of such a large number of normal alleles suggests at least a low degree of instability.

FIG. 14 shows the relationship between the repeat lengths on the HD chromosomes in the affected parent and corresponding progeny. For the 20 maternally-inherited chromosomes on which the repeat length was altered, 13 changes were increases in length and 7 were decreases. Both increases and decreases involved changes of less than 5 repeat units and the overall correlation between the mother's repeat length and that of her child was r=0.95 (p<0.0001). The average change in repeat length in the 25 maternal transmissions was an increase of 0.4 repeats.

On paternally-derived chromosomes, the 31 transmissions in which the repeat length changes comprised 26 length increases and 5 length decreases. Although the decreases in size were only slightly smaller than those observed on maternally-derived chromosomes, ranging from 1 to 3 repeat units, the increases were often dramatically larger. Thus, the correlation of the repeat length in the father with that of his offspring was only r=0.35 (p<0.04). The average change in the 37 paternal transmissions was an increase of 9 repeat units. The maximum length increase observed through paternal transmission was 41 repeat units, a near doubling of the parental repeat.

For both male and female transmissions, there was no correlation between the size of the parental repeat and either the magnitude or frequency of changes.

To determine whether the variation in the length of the repeat observed through male transmission of HD chromosomes is reflected in the male germ cells, we amplified the repeat from sperm DNA and from DNA of the corresponding lymphoblast from 5 HD gene carriers. The results, shown in FIG. 15, reveal striking differences between the lymphoblast and sperm DNA for the HD chromosome repeat, but not for the repeat on the normal chromosome. All the sperm donors are members of the Venezuelan HD family and range in age from 24 to 30 years. Individuals 1 and 2 are siblings with HD chromosome repeat lengths based on lymphoblast DNA of 45 and 52, respectively. Individuals 3 and 4 are also siblings, with HD repeat lengths of 46 and 49, respectively. Individual 5, from a different sibship than either of the other two pairs, has an HD repeat of 52 copies. In all 5 cases, the PCR amplification of sperm DNA and lymphoblast DNA yielded identical products from the normal chromosome. However, in comparison with lymphoblast DNA, the HD gene from sperm DNA yielded a diffuse array of products. In 3 of the 5 cases (2,4 and 5), the diffuse array spread to much larger allelic products than the corresponding lymphoblast product. Subject 2 showed the greatest range of expansion, with the sperm DNA product extending to over 80 repeat units. Interestingly, the 3 individuals displaying the greatest variation have the longest repeats and are currently symptomatic. The other two donors have shorter repeat lengths in the HD range, and remain at risk at this time.

The striking difference in the high repeat length range (>55) between HD chromosomes transmitted from the father and those transmitted from the mother indicated a potential parental source effect. When this was examined directly, the HD chromosome repeat length changed in about 85% of transmissions. Most changes involved a fluctuation of only a few repeat units, with larger increases occurring only in male transmissions. The greater size increases in male transmission appear to be caused by particular instability of the HD trinucleotide repeat during male gametogenesis, based on the amplification of the repeat from sperm DNA.

Example 8

Relationship Between Repeat Length and Age of Onset

Increased repeat length might correlate with a reduced age of onset of HD. Accordingly, age of onset data was determined for 234 of the individuals represented in FIG. 11. FIG. 16 displays the repeat lengths found on the HD and normal chromosomes of these individuals relative to their age of onset. Indeed, age of onset is inversely correlated with the HD repeat length. A Pearson correlation coefficient of $r=-0.75$, $p<0.0001$ was obtained assuming a linear relationship between age of onset and repeat length. When a polynomial function was used, a better fit was obtained ($R^2=0.61$, $F=121.45$), suggesting a higher order association between age of onset and repeat length.

There is considerable variation in the age of onset associated with any specific number of repeat units, particularly for trinucleotide repeats in the 37–52 unit zone (88% of HD chromosomes) where onset ranged from 15 to 75 years. In this range, a linear relationship between age of onset and repeat length provided as good a fit as a higher order relationship. The 95% confidence interval surrounding the predicted regression line was estimated at ±18 years. In the 37 to 52 unit range, the association of repeat length to onset age is only half as strong as in the overall distribution ($r=-0.40$, $p<0.0001$), indicating that much of the predictive power is contributed by repeats longer than 52 units. In this increased range, onset is likely to be very young and consequently not relevant to most persons seeking testing.

For the 178 cases in the 37–52 repeat unit range for which it was possible to subdivide the data set based on parental origin of the HD gene, multivariate regression analysis suggested a significant effect of parental origin on age of onset ($p<0.05$) independent of repeat length in this range. HD gene carriers from maternal transmissions had an average age of onset two years later than those from paternal transmissions.

In both univariate and multivariate analyses, no association between age of onset and the repeat length on the normal chromosome was detected, either in the total data set, or when it was subdivided into chromosomes of maternal or paternal origin.

Example 9

The Mouse Huntington's Disease Gene Homologue (Hdh)

A. Northern Blot Analysis of Hdh Expression

The HD gene is expressed in all human tissues tested to date as two different mRNAs of 10.5 and 13.5 kb that encode the same huntingtin protein, but differ in their 3' untranslated regions (UTRs) due to alternative polyadenylation (Lin et al., Hum. Mol. Genet. 2:1541–1545 (1993)). In DNA blot analyses used to map the Hdh locus on Chr 5, it was determined that the mouse gene is sufficiently conserved to be easily detected using a human probe. FIG. 17 displays the results of hybridizing a human HD probe to Northern blots containing polyA+RNA from a variety of mouse tissues. The pattern of expression is remarkably similar to the expression of HD in man, with two different RNAs also of 10.5 and 13.5 kb. These RNAs are expressed in all tissues tested, but at varying ratios. As in man, mouse brain RNA displays the highest proportion of the larger transcript. A novel band of variable intensity is also seen on the mouse Northern blots at ~7 kb. This signal is removed by stringent washing suggesting the possibility of a related locus.

B. Isolation of Overlapping cDNA Clones for Hdh

To permit direct comparison of the human and mouse homologoues, a mouse PCC4 embryonal carcinoma cDNA library was screened with a pool of cDNA and PCR probes spanning almost the entire published composite IT15 sequence of 10,355 bp (GenBank #L12392) to isolate overlapping clones representing the Hdh mRNAs. A summary of the cDNAs obtained is displayed in FIG. 18. Three cDNA clones provided overlapping sequence coverage from a few bases 3' to the initiator ATG codon through the entire coding sequence. Clone PCC4-3 also possessed a polyA tail attached to a 3' UTR similar in length to that of the shorter of the two human transcripts. The larger mouse Hdh transcript, like that in man, is possibly generated by alternative polyadenylation.

The 5' UTR and the first few bases of coding sequence were not recovered in any cDNA clones. To obtain these sequences, a genomic clone was isolated by screening a 129 phage library with probes from the 5' end of PCC4-8. Direct sequencing of the phage insert provided Hdh sequence from 89 bp upstream of the initiator ATG through the first 44 bases of the coding sequence.

C. Composite Hdh cDNA and Huntingtin Sequences

The composite DNA sequence generated from the clones shown in FIG. 18 spans 9998 nucleotides (nt) and has been deposited in GenBank, with accession #L28827 (SEQ ID NO:15). The putative initiator ATG codon at nt 90 and the TGA stop codon at nt 9447 bracket an open reading frame (SEQ. ID NO: 15) that predicts a mouse huntingtin protein of 3,119 amino acids (SEQ. ID NO: 16). Like human huntingtin, mouse huntingtin has a region with stretches polyglutamine and polyproline near its N-terminus. Across the coding sequence 5' (nt 90-143) and 3' (nt 267-9446) to the glutamine/proline-rich region, respectively, the DNA sequence is 90% and 86% identical to the human cDNA. In the 89 nt of 5' UTR, identity to the human sequence declines to 67%, with the mouse sequence having an insert of 7 bases 48 nt upstream from the ATG. The 552 nt of 3' UTR is less conserved overall (64%) with many gaps required to match the sequences from the two species. Interestingly, however, the 75 nt segment immediately upstream from the site of polyA addition shows 90% identity in man and mouse, perhaps indicative of a common structural basis for alternative polyadenylation at this site.

At the protein level, human and mouse huntingtin are 100% and 91% identical N-terminal and C-terminal to the glutamine/proline-rich region, respectively. The mouse protein is shorter than the human protein, owing largely to a smaller glutamine/proline-rich region. The remainder of the mouse protein displays 238 conservative amino acid substitutions, 29 non-conservative substitutions, 5 residue deletions and 1 residue addition relative to its human counterpart.

Features of DNA encoding the glutamine/proline-rich region of human huntingtin are the polymorphic CAG repeat that is expanded on disease chromosomes, and the adjacent polymorphic CCG repeat. In man, the polyglutamine stretch varies from 13 to 36 residues, and is encoded almost entirely by CAG except for a penultimate CAA codon. The mouse gene encodes 7 consecutive glutamines in an imperfect repeat with a CAA codon flanked on 5' and 3' sides by 2 and 4 CAG codons, respectively. In both species, the glutamine stretch is followed by a segment with runs of proline with the occasional glutamine or other amino acid residue interspersed. In man, the CCG repeat located just downstream from the polymorphic CAG repeat is also polymorphic (Rubinsztein et al., *Nature Genet.* 5:214–215 (1993)).

D. Polymorphisms of a CCG Repeat in Hdh

To determine whether the repeat sequences displayed polymorphism in the mouse comparable to that on human chromosomes, the corresponding region was amplified from various strains of laboratory mouse and from *M. spretus*. A typical result is shown in FIG. 19, in which 129 (represented by clone PCC4-8), C57BL/6J and CBA/J all yield an identical product. The shorter product generated from *M. spretus* was sequenced for comparison with PCC4-8. The difference in length is not due to any change in CAG number, but rather to a decrease of one CCG in the *M. spretus*. Thus, the CAG repeat is not only shorter in mouse than in man, it also does not display any evidence of significant length variation.

E. Discussion

The mouse Hdh gene is located on Chr 5, in a region of synergy conservation with human chromosome 4 (Cheng et al., *Genomics* 4:419–426 (1989)). Although the genomic structure of Hdh is unknown, the human HD gene contains 67 exons, spread across 180 kb of 4p16.3. The human and mouse genes are extremely similar, showing an overall amino acid identity of more than 90% over most of the predicted protein. A comparison of the differences indicates that they are not confined to alterations affecting a few exons, but are found throughout the gene. However, neither are they equally distributed. The regions encompassing amino acids 373–403, 567–641, 1684–1717, and 2136–2374 seem particularly rich in amino acid substitutions in contrast to segments such as residues 60–372, and 1190–1637. The latter might indicate the locations of critical functional domains of huntingtin.

More extensive differences are found in the DNA of the 5' and particularly the 3' UTRs, suggesting less stringent selective pressures overall on these sequences. However, the relatively high level of conservation of the DNA sequence immediately upstream from one site of polyA addition in man indicates that this segment may be involved in regulating alternative polyadenylation. Although the existence of alternative polyadenylation has not been demonstrated unequivocally in the mouse, the ubiquitous expression of two Hdh RNAs comparable in size to the human HD RNAs supports this supposition.

Lin et al. (Linet al., *Hum. Mol. Genet.* 3:85–92 (1994)) has also reported a cDNA sequence for mouse Hdh spanning 9992 bp, also encoding a huntingtin protein of 3119 residues. However, the composite cDNA sequence reported herein has notable differences. These are best compared at the protein level, where the two sequences differ at 28 residues spread across the entire protein, from position 2 to position 3096. In 24 of these cases, the mouse huntingtin sequence described herein matches the amino acid sequence found in man. In the remaining 4 cases, Lin et al. (Lin et al., *Hum. Mol. Genet.* 3:85–92 (1994)) matches the human sequence. Our 3' UTR sequence has seven mismatches, additions, or deletions of single bases compared to Lin et al. (Lin et al., *Hum. Mol. Genet.* 3:85–92 (1994)). In addition, both of the clones PCC4-3 and PCC4-5 described herein contain a stretch of 35 bp not present in Lin et al.'s sequence. Lin et al. also found that in their cDNA clones the CCG repeat beginning at codon 32 varies between C57BL6 and random outbred laboratory mice, displaying 3 and 4 repeat units, respectively. While the amplification described herein of genomic DNA agrees with the site of this polymorphism, it does not yield the same strain-specific pattern. In the experiments described herein, all 3 strains of laboratory mice, including 129, C57BL/6J and CBA/J, possessed 4 CCG units while only *M. spretus* revealed 3 CCGs.

Finally, Lin et al. (Lin et al., *Hum. Mol. Genet.* 3:85–92 (1994)) reported the identification of a putative alternative splicing event that removed nt 4562 to 6091, and therefore amino acids 1522 to 2001 from the protein. An examination of FIG. 18 reveals that this segment begins in exon 35 and ends in exon 44 of the human gene. Thus, unless the exon structure of the mouse gene differs radically from that of the human gene, the clone isolated by Lin et al. (Lin et al., *Hum. Mol. Genet.* 3:85–92 (1994)) cannot be explained by simple alternative splicing. Indeed, these authors suggest that the same variant sequence is also expressed in man. For this to occur would require a complex change, including the recognition of a segment in exon 35 as a splice donor, the use of a different sequence in exon 44 as a splice acceptor, and the bypassing of conventional splicing signals in exons 36–44. Alternatively, the sequence reported by Lin et al. could have resulted from a cloning artifact.

Human huntingtin is predicted to be a large protein of greater than~3,130 amino acids that does not display significant homology to any known protein. The high level of conservation of mouse huntingtin (91% identity) suggests that there are tight evolutionary constraints on its sequence. The decline in DNA sequence conservation upstream from the putative initiator ATG suggests that the coding sequence indeed begins as predicted, and includes the polyglutamine segment encoded by the CAG repeat.

The fact that mouse huntingtin also contains a short stretch of polyglutamine argues for a role of this segment in the normal function of the protein. However, there must be considerable leeway in the fulfillment of this role and of the role of the adjacent polyproline stretch, given the extensive CAG repeat variation on normal human chromosomes. The failure to observe similar variation in the mouse gene, with the exception of one codon change in a CCG repeat, may indicate a stronger selective pressure for maintaining the length of these repeats in the model organism. Alternatively, the variation in the human repeats may indicate that a greater mean length, the particular chromosomal context in which they are found, or species differences in characteristics of the replication process produce a higher mutation rate in man.

Because RNA is produced at normal levels from the HD allele and heterozygous disruption of the gene by translocation does not produce any phenotype the expanded CAG mutation does not entail simple cis-inactivation of the HD gene (although its effects on adjacent genes remain to be determined). The dominant nature of the HD phenotype (Wexler et al., *Nature* 326:194–197 (1987); Myers et al., *Am. J. Hum. Genet.* 4,5:615–618 (1989)) indicates that the effect of the expanded repeat must include either trans-inactivation of the normal product or conference of a new property on the abnormal product. Both of these possibilities seem more likely to operate at the protein than at the RNA level, particularly since initial antibody studies of huntingtin have not revealed grossly altered expression in HD (Hoogeveen et al., *Hum. Mol. Genet.* 2:2069–2073 (1993)). The small size and apparent stability of the CAG repeat in mouse is consistent with the absence of an HD-like disorder in this model organism. However, the overall conservation of the Hdh gene suggests that genetic manipulation in the mouse, either to produce homozygous "knock-outs" or to introduce an expanded CAG repeat, provides a reasonable hope of resolving the mechanistic issues and of generating an accurate animal model of HD.

Example 10

Exon-Intron Structure of the HD Gene

In the initial search for the HD gene, exons from cosmids spanning a region of 4p16.3 that displayed a common haplotype on approximately ⅓ of HD chromosomes were cloned (MacDonald, M. E. et al., *Nature Genet.* 1:99–103 (1992)). Initially, the first generation exon amplification system developed by Buckler, A. J. et al. (*Proc. Natl. Acad. Sci. USA* 88:4005–4009 (1991)) was employed to produce cloned exons from individual cosmids isolated by sequential walking steps from D4S180 and D4S156 (Baxendale, S. et al., *Nature Genet.* 4:181–186 (1993)). These exons were used to identify the IT15 cDNA clones (MacDonald, M. E. et al., *Cell* 72:971–983 (1993)).

To determine intron-exon junctions, DNA primers located every 200–300 bp in the cDNAs were used to directly sequence the corresponding cosmid DNAs and designed new primers as needed based on the evolving knowledge of the exon structure. As this work progressed, a second-generation vector system that eliminated false-positive products, and allowed cloning of genomic DNA with multiple restriction enzymes was applied in multiple experiments to saturate the region with cloned exons. The products obtained in this system have the additional advantage that 5'-3' orientation is immediately discernible. To position all exons on the physical map, two primers from each exon were hybridized to EcoRI digests of all overlapping cosmids from the region, representing an average 3-fold redundancy.

The composite IT 15 cDNA sequence corresponds to a genomic segment of 180 kb and is encoded in 67 exons as shown in FIG. 20. The internal exons ranged in size from 48 bp to 341 bp with an average of 138 bp. All cloned, sequenced exons are aligned with the composite cDNA sequence in FIG. 20, and together constitute 36% of the transcript. Of the 65 internal exons, 27 were trapped by exon amplification using PstI or BamHI-BglII digests, 15 as single exon products and 12 as multiple adjacent exons spliced together in the amplification procedure. The minimum and maximum sized exons were both represented in this collection, which averaged 139 bp/exon, indicating no apparent size bias in the procedure.

A codon loss polymorphism in IT15

To search for DNA changes other than the trinucleotide repeat expansion that might also be associated with HD, the normal and HD transcripts were compared by sequence analysis of partial cDNA clones and by single strand conformational polymorphism analysis (SSCP) of PCR products from first strand cDNA (Orita, M. et al., *Genomics* 5:874–879 (1989)). Sequencing of individual normal cDNAs revealed four single base pair differences from the consensus sequence, at positions 1949 (C to G, Leu to Val), 2372 (C to G, Ser to Cys), 4034 (G to A, Arg to Lys), and 8677 (A to G, Ile to Val) (See: SEQ ID No: 5). No sequence differences other than the CAG repeat length were found exclusively in the HD cDNAs.

For SSCP analysis, two HD homozygotes of different haplotypes, both alleles from a single normal individual, and the normal sequence represented in a corresponding cDNA clone were scanned. Variant SSCP bands were detected in exons 58, 60 and 67. The exon 67 difference involved a choice of either C. or T at position 9809 of the composite cDNA sequence (SEQ ID No: 5). This change occurred in the 3' untranslated region and both forms were represented on at least one normal and one HD allele. The exon 60 difference was found only on one of the normal alleles.

The exon 58 difference (FIG. 21A) was present in the HD homozygote representing the most common disease haplotype, but absent from an HD homozygote of another haplotype (MacDonald, M. E. et al., *Nature Genet.* 1:99–103 (1992); Myers, R. H. et al., *Am. J. Hum. Genet.* 45:615–618 (1989)). Sequence analysis of multiple cloned PCR products revealed the loss of a single codon from a run of our consecutive GAG (Glu) codons at positions 2642–2645 of the predicted amino acid sequence ((SEQ ID No: 6). For convenience, this change is referred to as Δ2642. A genomic PCR assay for Δ2642 was developed in order to scan additional HD and normal chromosomes to test its disease specificity ((FIG. 21B). This analysis revealed that the codon loss represents a normal, infrequent polymorphism with allele frequencies of 0.93 and 0.07 for presence or absence or codon 2642, respective (N=175 normal chromosomes). The Δ2642 change showed linkage disequilibrium with HD ($\chi^2$=37.47, 1 d.f., p<0.0001), where the codon loss was represented on 38.55 of disease chromosomes (N=80 independent HD chromosomes).
Both HD alleles are expressed The Δ2642 polymorphism provided a ready means to assay whether both alleles of the HD gene are expressed in the cells of affected individuals. FIG. 22 shows the analysis of two independent preparations of first strand cDNA from lymphoblast lines of four unrelated HD patients, two of whom were heterozygous for the polymorphism, with the codon loss segregating with the disease chromosome. Both of these individuals clearly expressed both the normal and disease alleles. Similar results have been observed in RNA from normal individuals, HD heterozygotes and HD homozygotes using the CAG repeat assay.
Expression of the HD mRNA The pathology of HD appears to be confined to the brain. However, the expression of the IT15 transcript is not confined to this tissue. FIGS. 23 and 24 show a Northern blot survey of 15 adult and 5 fetal tissue RNAs, respectively. Hybridization with an IT15 probe revealed two RNA species that were present in all tissues tested but varied in relative abundance. The size of these RNAs were estimated as 13.5 kb and 10.5 kb with the latter being the more abundant in most tissues. Interestingly, the apparent ratio of larger to the smaller transcript was greatest in fetal and adult brain. By contrast, the larger transcript was barely detectable in adult liver and colon.

The smaller RNA species probably corresponds to the composite cDNA sequence (SEQ ID No: 5), and the larger could result either from alternative splicing or from alternative polyadenylation. The SSCP analysis of first strand cDNA had failed to yield any evidence of extensive alternative splicing, and an exon 2 probe detected both RNA species. Therefore, a genomic probe was prepared from the region of cosmid L120D5 located immediately downstream from the sequence at the site of the polyA tail in cDNA clone IT15B (Baxendale, S. et al ., *Nature Genet.* 4:181–186 (1993)). Hybridization of this second probe to the Northern blots is also shown in FIGS. 23 and 24. The extended 3' probe detected only the larger of the two IT15 RNA species suggesting that this transcript arises by use of a downstream polyA addition site. Thus, screening of additional cDNA libraries, particularly from fetal brain, would likely yield a cDNA containing an additional ~3 kb of 3' untranslated region contiguous with the current exon 67 sequence.

A balanced translocation disrupting the HD gene

The HD gene search produced a panel of somatic cell hybrid lines dissecting 4p into several regions (Smith, B. et al., *Am. J. Hum. Genet.* 42:335–344 (1988); Lin, C. S. et al., *Somat. Cell Mol. Genet.* 17:481–488 (1991)). One of the chromosomes from this panel has a t(4p16.3; 12p13.3) with a breakpoint between D4S180 and D4S127 (McKeown, C. et al. , *J. Med. Genet.* 24:410–412 (1987)). To establish whether this chromosome bisects the HD gene, exon probes were hybridized to genomic blots of DNA from a lymphoblast cell line (CV066) with the balanced translocation and from a hybrid line (HHW1071) containing only the region of 4p16.3 between the translocation breakpoint and the 4p telomere as part of the der(12) chromosome. Exons 41–67 are absent from the hybrid, indicating that the breakpoint maps between exons 40 and 41. Indeed, the EcoRI and HindIII fragments containing exon 40 are altered in size in CV066 and in HHW1071 (FIG. 25) positioning the t(4;12) breakpoint within the HD gene as depicted in FIG. 20.

The CV066 lymphoblast line was derived from a balanced carrier of the t(4; 12) who was first identified as the mother of a Wolf-Hirschhorn child produced by transmission of only the der(4) chromosome (McKeown, C. et al. , *J. Med. Genet.* 24:410–412 (1987)). Therefore, this woman possesses one intact HD gene which will produce a normal product, and a bisected HD gene which at best could produce a partial protein, or partial fusion protein. This balanced translocation is not associated with any detectable abnormal phenotype either in the woman or in one of her offspring. Thus, heterozygous disruption of the HD gene does not have catastrophic consequences for development or cause juvenile HD. Moreover, this translocation makes it unlikely that the expanded CAG repeat in HD acts by simply inactivating the allele containing it. At age 46, the woman, who possesses only one intact copy of this locus, is already beyond the age of onset of the majority of HD cases and does not display any signs of the disorder. She has also passed the balanced translocation to one offspring who is similarly phenotypically normal.

Discussion

The number of exons comprising the HD gene is one of the highest report to date for any human locus. However, the exons are arrayed across a relatively compact genomic region of 180 kb. The initial identification and detailed analysis of this locus was aided tremendously by the development of the exon amplification procedure (Buckler, A. J. et al., *Proc. Natl. Acad. Sci. USA* 88:4005–4009 (1991)). Cloned trapped exons provided probes for the isolation of cDNA clones and multiple sequenced, oriented entry points for aligning the cDNA. The knowledge of the cosmid of origin of each trapped exon included in a cDNA clone gave an immediate assessment of genomic coverage, and provided the basis for complete sequence analysis and rapid determination of exon-intron junctions. The fact that 42% of the internal exons susceptible to exon amplification were recovered as cloned segments demonstrates that it is remarkably easy to isolate a significant portion of a gene using this procedure. In fact, only two of several possible enzyme combinations for cloning the genomic DNA were employed. It is likely that many of the exons that were missed could be isolated using an alternative restriction digest with the same vector system. Thus, exon amplification appears to be an excellent means of saturating a particular genomic region with expressed sequences and quickly relating the corresponding transcripts to the physical map.

The HD gene is expressed in every tissue tested to date, with at least two alternative forms that differ in the extent of their 3' untranslated region. There might be alternative splicing of the transcript in some tissues, but RNA-PCR SSCP analysis of lymphoblastoid cell RNA failed to reveal any evidence of alternative forms within the coding sequence. Moreover, the exon trapping did not yield any other putative exons from this region that could be a part of a transcript from this gene. Finally, all of the overlapping cDNAs so far isolated from brain and other tissues have been colinear, except when they contain unspliced intronic sequence. Thus, if alternative splicing occurs it is unlikely to be extensive unless it is restricted to a specific cell type not yet explored.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. An isolated nucleic acid encoding huntingtin protein.

2. The nucleic acid of claim 1, wherein said huntingtin protein has the amino acid sequence shown in SEQ ID NO:6.

3. The nucleic acid of claim 2, wherein said nucleic acid has the DNA sequence shown encoding amino acids in SEQ ID NO:5.

4. The nucleic acid according to claim 1, wherein the nucleic acid encoding huntingtin protein is operably linked to transcriptional and/or translational expression signals.

5. A recombinant nucleic acid molecule comprising a transcriptional control region operably linked to a reverse complement sequence of the nucleic acid of claim 1.

6. An isolated vector comprising the nucleic acid of claim 5.

7. A host cell transformed with the vector according to claim 6.

* * * * *

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:1:

GGCGGGAGAC CGCCATGGCG                                                                            20

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

AATACGACTC ACTATAG                                                                               17

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

ATGAAGGCCT TCGAGTCCCT CAAGTCCTTC                                                                  30

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

AAACTCACGG TCGGTGCAGC GGCTCCTCAG                                                                  30

( 2 ) INFORMATION FOR SEQ ID NO:5:

( i ) SEQUENCE CHARACTERISTICS:
        ( A ) LENGTH: 10366 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 316..9748

( x i ) SEQUENCE DESCRIPTION: SEQ ID NO:5:

```
TTGCTGTGTG AGGCAGAACC TGCGGGGGCA GGGGCGGGCT GGTTCCCTGG CCAGCCATTG          60

GCAGAGTCCG CAGGCTAGGG CTGTCAATCA TGCTGGCCGG CGTGGCCCCG CCTCCGCCGG         120

CGCGGCCCCG CCTCCGCCGG CGCACGTCTG GGACGCAAGG CGCCGTGGGG GCTGCCGGGA         180

CGGGTCCAAG ATGGACGGCC GCTCAGGTTC TGCTTTTACC TGCGGCCCAG AGCCCCATTC         240

ATTGCCCCGG TGCTGAGCGG CGCCGCGAGT CGGCCCGAGG CCTCCGGGGA CTGCCGTGCC         300

GGGCGGGAGA CCGCC ATG GCG ACC CTG GAA AAG CTG ATG AAG GCC TTC GAG          351
                Met Ala Thr Leu Glu Lys Leu Met Lys Ala Phe Glu
                  1               5                  10

TCC CTC AAG TCC TTC CAG CAG CAG CAG CAG CAG CAG CAG CAG CAG              399
Ser Leu Lys Ser Phe Gln Gln Gln Gln Gln Gln Gln Gln Gln Gln
         15                  20                  25

CAG CAG CAG CAG CAG CAG CAG CAG CAG CAG CAA CAG CCG CCA CCG CCG          447
Gln Gln Gln Gln Gln Gln Gln Gln Gln Gln Gln Gln Pro Pro Pro Pro
         30                  35                  40
```

-continued

| | | | | | | | | | | | | | | | |
|---|---|---|---|---|---|---|---|---|---|---|---|---|---|---|---|
| CCG | CCG | CCG | CCG | CCG | CCT | CCT | CAG | CTT | CCT | CAG | CCG | CCG | CCG | CAG | GCA | 495 |
| Pro | Pro | Pro | Pro | Pro | Pro | Pro | Gln | Leu | Pro | Gln | Pro | Pro | Pro | Gln | Ala |
| 45 | | | | 50 | | | | | | 55 | | | | | 60 |

| CAG | CCG | CTG | CTG | CCT | CAG | CCG | CAG | CCG | CCC | CCG | CCG | CCG | CCC | CCG | CCG | 543 |
| Gln | Pro | Leu | Leu | Pro | Gln | Pro | Gln | Pro | Pro | Pro | Pro | Pro | Pro | Pro | Pro |
| | | | | 65 | | | | 70 | | | | | 75 | | |

| CCA | CCC | GGC | CCG | GCT | GTG | GCT | GAG | GAG | CCG | CTG | CAC | CGA | CCA | AAG | AAA | 591 |
| Pro | Pro | Gly | Pro | Ala | Val | Ala | Glu | Glu | Pro | Leu | His | Arg | Pro | Lys | Lys |
| | | | 80 | | | | | 85 | | | | | 90 | | |

| GAA | CTT | TCA | GCT | ACC | AAG | AAA | GAC | CGT | GTG | AAT | CAT | TGT | CTG | ACA | ATA | 639 |
| Glu | Leu | Ser | Ala | Thr | Lys | Lys | Asp | Arg | Val | Asn | His | Cys | Leu | Thr | Ile |
| | | 95 | | | | 100 | | | | | 105 | | | | |

| TGT | GAA | AAC | ATA | GTG | GCA | CAG | TCT | GTC | AGA | AAT | TCT | CCA | GAA | TTT | CAG | 687 |
| Cys | Glu | Asn | Ile | Val | Ala | Gln | Ser | Val | Arg | Asn | Ser | Pro | Glu | Phe | Gln |
| 110 | | | | | 115 | | | | | | 120 | | | | |

| AAA | CTT | CTG | GGC | ATC | GCT | ATG | GAA | CTT | TTT | CTG | CTG | TGC | AGT | GAT | GAC | 735 |
| Lys | Leu | Leu | Gly | Ile | Ala | Met | Glu | Leu | Phe | Leu | Leu | Cys | Ser | Asp | Asp |
| 125 | | | | | 130 | | | | | 135 | | | | | 140 |

| GCA | GAG | TCA | GAT | GTC | AGG | ATG | GTG | GCT | GAC | GAA | TGC | CTC | AAC | AAA | GTT | 783 |
| Ala | Glu | Ser | Asp | Val | Arg | Met | Val | Ala | Asp | Glu | Cys | Leu | Asn | Lys | Val |
| | | | | 145 | | | | | 150 | | | | | 155 | |

| ATC | AAA | GCT | TTG | ATG | GAT | TCT | AAT | CTT | CCA | AGG | TTA | CAG | CTC | GAG | CTC | 831 |
| Ile | Lys | Ala | Leu | Met | Asp | Ser | Asn | Leu | Pro | Arg | Leu | Gln | Leu | Glu | Leu |
| | | | 160 | | | | | 165 | | | | | 170 | | |

| TAT | AAG | GAA | ATT | AAA | AAG | AAT | GGT | GCC | CCT | CGG | AGT | TTG | CGT | GCT | GCC | 879 |
| Tyr | Lys | Glu | Ile | Lys | Lys | Asn | Gly | Ala | Pro | Arg | Ser | Leu | Arg | Ala | Ala |
| | | 175 | | | | | 180 | | | | | 185 | | | |

| CTG | TGG | AGG | TTT | GCT | GAG | CTG | GCT | CAC | CTG | GTT | CGG | CCT | CAG | AAA | TGC | 927 |
| Leu | Trp | Arg | Phe | Ala | Glu | Leu | Ala | His | Leu | Val | Arg | Pro | Gln | Lys | Cys |
| | 190 | | | | | 195 | | | | | 200 | | | | |

| AGG | CCT | TAC | CTG | GTG | AAC | CTT | CTG | CCG | TGC | CTG | ACT | CGA | ACA | AGC | AAG | 975 |
| Arg | Pro | Tyr | Leu | Val | Asn | Leu | Leu | Pro | Cys | Leu | Thr | Arg | Thr | Ser | Lys |
| 205 | | | | | 210 | | | | | 215 | | | | | 220 |

| AGA | CCC | GAA | GAA | TCA | GTC | CAG | GAG | ACC | TTG | GCT | GCA | GCT | GTT | CCC | AAA | 1023 |
| Arg | Pro | Glu | Glu | Ser | Val | Gln | Glu | Thr | Leu | Ala | Ala | Ala | Val | Pro | Lys |
| | | | | 225 | | | | | 230 | | | | | 235 | |

| ATT | ATG | GCT | TCT | TTT | GGC | AAT | TTT | GCA | AAT | GAC | AAT | GAA | ATT | AAG | GTT | 1071 |
| Ile | Met | Ala | Ser | Phe | Gly | Asn | Phe | Ala | Asn | Asp | Asn | Glu | Ile | Lys | Val |
| | | | 240 | | | | | 245 | | | | | 250 | | |

| TTG | TTA | AAG | GCC | TTC | ATA | GCG | AAC | CTG | AAG | TCA | AGC | TCC | CCC | ACC | ATT | 1119 |
| Leu | Leu | Lys | Ala | Phe | Ile | Ala | Asn | Leu | Lys | Ser | Ser | Ser | Pro | Thr | Ile |
| | | 255 | | | | | 260 | | | | | 265 | | | |

| CGG | CGG | ACA | GCG | GCT | GGA | TCA | GCA | GTG | AGC | ATC | TGC | CAG | CAC | TCA | AGA | 1167 |
| Arg | Arg | Thr | Ala | Ala | Gly | Ser | Ala | Val | Ser | Ile | Cys | Gln | His | Ser | Arg |
| | 270 | | | | | 275 | | | | | 280 | | | | |

| AGG | ACA | CAA | TAT | TTC | TAT | AGT | TGG | CTA | CTA | AAT | GTG | CTC | TTA | GGC | TTA | 1215 |
| Arg | Thr | Gln | Tyr | Phe | Tyr | Ser | Trp | Leu | Leu | Asn | Val | Leu | Leu | Gly | Leu |
| 285 | | | | | 290 | | | | | 295 | | | | | 300 |

| CTC | GTT | CCT | GTC | GAG | GAT | GAA | CAC | TCC | ACT | CTG | CTG | ATT | CTT | GGC | GTG | 1263 |
| Leu | Val | Pro | Val | Glu | Asp | Glu | His | Ser | Thr | Leu | Leu | Ile | Leu | Gly | Val |
| | | | | 305 | | | | | 310 | | | | | 315 | |

| CTG | CTC | ACC | CTG | AGG | TAT | TTG | GTG | CCC | TTG | CTG | CAG | CAG | CAG | GTC | AAG | 1311 |
| Leu | Leu | Thr | Leu | Arg | Tyr | Leu | Val | Pro | Leu | Leu | Gln | Gln | Gln | Val | Lys |
| | | | 320 | | | | | 325 | | | | | 330 | | |

| GAC | ACA | AGC | CTG | AAA | GGC | AGC | TTC | GGA | GTG | ACA | AGG | AAA | GAA | ATG | GAA | 1359 |
| Asp | Thr | Ser | Leu | Lys | Gly | Ser | Phe | Gly | Val | Thr | Arg | Lys | Glu | Met | Glu |
| | | 335 | | | | | 340 | | | | | 345 | | | |

| GTC | TCT | CCT | TCT | GCA | GAG | CAG | CTT | GTC | CAG | GTT | TAT | GAA | CTG | ACG | TTA | 1407 |
| Val | Ser | Pro | Ser | Ala | Glu | Gln | Leu | Val | Gln | Val | Tyr | Glu | Leu | Thr | Leu |
| | | 350 | | | | | 355 | | | | | 360 | | | |

-continued

| | | | | | | | | | | | | | | | | |
|---|---|---|---|---|---|---|---|---|---|---|---|---|---|---|---|---|
| CAT | CAT | ACA | CAG | CAC | CAA | GAC | CAC | AAT | GTT | GTG | ACC | GGA | GCC | CTG | GAG | 1455 |
| His | His | Thr | Gln | His | Gln | Asp | His | Asn | Val | Val | Thr | Gly | Ala | Leu | Glu | |
| 365 | | | | 370 | | | | | 375 | | | | | | 380 | |
| CTG | TTG | CAG | CAG | CTC | TTC | AGA | ACG | CCT | CCA | CCC | GAG | CTT | CTG | CAA | ACC | 1503 |
| Leu | Leu | Gln | Gln | Leu | Phe | Arg | Thr | Pro | Pro | Pro | Glu | Leu | Leu | Gln | Thr | |
| | | | | 385 | | | | 390 | | | | | | 395 | | |
| CTG | ACC | GCA | GTC | GGG | GGC | ATT | GGG | CAG | CTC | ACC | GCT | GCT | AAG | GAG | GAG | 1551 |
| Leu | Thr | Ala | Val | Gly | Gly | Ile | Gly | Gln | Leu | Thr | Ala | Ala | Lys | Glu | Glu | |
| | | | 400 | | | | | 405 | | | | | 410 | | | |
| TCT | GGT | GGC | CGA | AGC | CGT | AGT | GGG | AGT | ATT | GTG | GAA | CTT | ATA | GCT | GGA | 1599 |
| Ser | Gly | Gly | Arg | Ser | Arg | Ser | Gly | Ser | Ile | Val | Glu | Leu | Ile | Ala | Gly | |
| | | 415 | | | | 420 | | | | | 425 | | | | | |
| GGG | GGT | TCC | TCA | TGC | AGC | CCT | GTC | CTT | TCA | AGA | AAA | CAA | AAA | GGC | AAA | 1647 |
| Gly | Gly | Ser | Ser | Cys | Ser | Pro | Val | Leu | Ser | Arg | Lys | Gln | Lys | Gly | Lys | |
| | 430 | | | | | 435 | | | | | 440 | | | | | |
| GTG | CTC | TTA | GGA | GAA | GAA | GAA | GCC | TTG | GAG | GAT | GAC | TCT | GAA | TCG | AGA | 1695 |
| Val | Leu | Leu | Gly | Glu | Glu | Glu | Ala | Leu | Glu | Asp | Asp | Ser | Glu | Ser | Arg | |
| 445 | | | | 450 | | | | | 455 | | | | | | 460 | |
| TCG | GAT | GTC | AGC | AGC | TCT | GCC | TTA | ACA | GCC | TCA | GTG | AAG | GAT | GAG | ATC | 1743 |
| Ser | Asp | Val | Ser | Ser | Ser | Ala | Leu | Thr | Ala | Ser | Val | Lys | Asp | Glu | Ile | |
| | | | | 465 | | | | | 470 | | | | | 475 | | |
| AGT | GGA | GAG | CTG | GCT | GCT | TCT | TCA | GGG | GTT | TCC | ACT | CCA | GGG | TCA | GCA | 1791 |
| Ser | Gly | Glu | Leu | Ala | Ala | Ser | Ser | Gly | Val | Ser | Thr | Pro | Gly | Ser | Ala | |
| | | | 480 | | | | | 485 | | | | | 490 | | | |
| GGT | CAT | GAC | ATC | ATC | ACA | GAA | CAG | CCA | CGG | TCA | CAG | CAC | ACA | CTG | CAG | 1839 |
| Gly | His | Asp | Ile | Ile | Thr | Glu | Gln | Pro | Arg | Ser | Gln | His | Thr | Leu | Gln | |
| | | 495 | | | | 500 | | | | | 505 | | | | | |
| GCG | GAC | TCA | CTG | GAT | CTG | GCC | AGC | TGT | GAC | TTG | ACA | AGC | TCT | GCC | ACT | 1887 |
| Ala | Asp | Ser | Leu | Asp | Leu | Ala | Ser | Cys | Asp | Leu | Thr | Ser | Ser | Ala | Thr | |
| | 510 | | | | | 515 | | | | | 520 | | | | | |
| GAT | GGG | GAT | GAG | GAG | GAT | ATC | TTG | AGC | CAC | AGC | TCC | AGC | CAG | GTC | AGC | 1935 |
| Asp | Gly | Asp | Glu | Glu | Asp | Ile | Leu | Ser | His | Ser | Ser | Ser | Gln | Val | Ser | |
| 525 | | | | | 530 | | | | | 535 | | | | | 540 | |
| GCC | GTC | CCA | TCT | GAC | CCT | GCC | ATG | GAC | CTG | AAT | GAT | GGG | ACC | CAG | GCC | 1983 |
| Ala | Val | Pro | Ser | Asp | Pro | Ala | Met | Asp | Leu | Asn | Asp | Gly | Thr | Gln | Ala | |
| | | | | 545 | | | | | 550 | | | | | 555 | | |
| TCG | TCG | CCC | ATC | AGC | GAC | AGC | TCC | CAG | ACC | ACC | ACC | GAA | GGG | CCT | GAT | 2031 |
| Ser | Ser | Pro | Ile | Ser | Asp | Ser | Ser | Gln | Thr | Thr | Thr | Glu | Gly | Pro | Asp | |
| | | | 560 | | | | | 565 | | | | | 570 | | | |
| TCA | GCT | GTT | ACC | CCT | TCA | GAC | AGT | TCT | GAA | ATT | GTG | TTA | GAC | GGT | ACC | 2079 |
| Ser | Ala | Val | Thr | Pro | Ser | Asp | Ser | Ser | Glu | Ile | Val | Leu | Asp | Gly | Thr | |
| | | 575 | | | | | 580 | | | | | 585 | | | | |
| GAC | AAC | CAG | TAT | TTG | GGC | CTG | CAG | ATT | GGA | CAG | CCC | CAG | GAT | GAA | GAT | 2127 |
| Asp | Asn | Gln | Tyr | Leu | Gly | Leu | Gln | Ile | Gly | Gln | Pro | Gln | Asp | Glu | Asp | |
| | 590 | | | | | 595 | | | | | 600 | | | | | |
| GAG | GAA | GCC | ACA | GGT | ATT | CTT | CCT | GAT | GAA | GCC | TCG | GAG | GCC | TTC | AGG | 2175 |
| Glu | Glu | Ala | Thr | Gly | Ile | Leu | Pro | Asp | Glu | Ala | Ser | Glu | Ala | Phe | Arg | |
| 605 | | | | | 610 | | | | | 615 | | | | | 620 | |
| AAC | TCT | TCC | ATG | GCC | CTT | CAA | CAG | GCA | CAT | TTA | TTG | AAA | AAC | ATG | AGT | 2223 |
| Asn | Ser | Ser | Met | Ala | Leu | Gln | Gln | Ala | His | Leu | Leu | Lys | Asn | Met | Ser | |
| | | | | 625 | | | | | 630 | | | | | 635 | | |
| CAC | TGC | AGG | CAG | CCT | TCT | GAC | AGC | AGT | GTT | GAT | AAA | TTT | GTG | TTG | AGA | 2271 |
| His | Cys | Arg | Gln | Pro | Ser | Asp | Ser | Ser | Val | Asp | Lys | Phe | Val | Leu | Arg | |
| | | | 640 | | | | | 645 | | | | | 650 | | | |
| GAT | GAA | GCT | ACT | GAA | CCG | GGT | GAT | CAA | GAA | AAC | AAG | CCT | TGC | CGC | ATC | 2319 |
| Asp | Glu | Ala | Thr | Glu | Pro | Gly | Asp | Gln | Glu | Asn | Lys | Pro | Cys | Arg | Ile | |
| | | | 655 | | | | | 660 | | | | | 665 | | | |
| AAA | GGT | GAC | ATT | GGA | CAG | TCC | ACT | GAT | GAT | GAC | TCT | GCA | CCT | CTT | GTC | 2367 |
| Lys | Gly | Asp | Ile | Gly | Gln | Ser | Thr | Asp | Asp | Asp | Ser | Ala | Pro | Leu | Val | |
| | | 670 | | | | 675 | | | | | 680 | | | | | |

```
CAT TCT GTC CGC CTT TTA TCT GCT TCG TTT TTG CTA ACA GGG GGA AAA         2415
His Ser Val Arg Leu Leu Ser Ala Ser Phe Leu Leu Thr Gly Gly Lys
685             690                 695                 700

AAT GTG CTG GTT CCG GAC AGG GAT GTG AGG GTC AGC GTG AAG GCC CTG         2463
Asn Val Leu Val Pro Asp Arg Asp Val Arg Val Ser Val Lys Ala Leu
            705                 710                 715

GCC CTC AGC TGT GTG GGA GCA GCT GTG GCC CTC CAC CCG GAA TCT TTC         2511
Ala Leu Ser Cys Val Gly Ala Ala Val Ala Leu His Pro Glu Ser Phe
        720                 725                 730

TTC AGC AAA CTC TAT AAA GTT CCT CTT GAC ACC ACG GAA TAC CCT GAG         2559
Phe Ser Lys Leu Tyr Lys Val Pro Leu Asp Thr Thr Glu Tyr Pro Glu
        735                 740                 745

GAA CAG TAT GTC TCA GAC ATC TTG AAC TAC ATC GAT CAT GGA GAC CCA         2607
Glu Gln Tyr Val Ser Asp Ile Leu Asn Tyr Ile Asp His Gly Asp Pro
750                 755                 760

CAG GTT CGA GGA GCC ACT GCC ATT CTC TGT GGG ACC CTC ATC TGC TCC         2655
Gln Val Arg Gly Ala Thr Ala Ile Leu Cys Gly Thr Leu Ile Cys Ser
765             770                 775                 780

ATC CTC AGC AGG TCC CGC TTC CAC GTG GGA GAT TGG ATG GGC ACC ATT         2703
Ile Leu Ser Arg Ser Arg Phe His Val Gly Asp Trp Met Gly Thr Ile
            785                 790                 795

AGA ACC CTC ACA GGA AAT ACA TTT TCT TTG GCG GAT TGC ATT CCT TTG         2751
Arg Thr Leu Thr Gly Asn Thr Phe Ser Leu Ala Asp Cys Ile Pro Leu
        800                 805                 810

CTG CGG AAA ACA CTG AAG GAT GAG TCT TCT GTT ACT TGC AAG TTA GCT         2799
Leu Arg Lys Thr Leu Lys Asp Glu Ser Ser Val Thr Cys Lys Leu Ala
        815                 820                 825

TGT ACA GCT GTG AGG AAC TGT GTC ATG AGT CTC TGC AGC AGC AGC TAC         2847
Cys Thr Ala Val Arg Asn Cys Val Met Ser Leu Cys Ser Ser Ser Tyr
830                 835                 840

AGT GAG TTA GGA CTG CAG CTG ATC ATC GAT GTG CTG ACT CTG AGG AAC         2895
Ser Glu Leu Gly Leu Gln Leu Ile Ile Asp Val Leu Thr Leu Arg Asn
845             850                 855                 860

AGT TCC TAT TGG CTG GTG AGG ACA GAG CTT CTG GAA ACC CTT GCA GAG         2943
Ser Ser Tyr Trp Leu Val Arg Thr Glu Leu Leu Glu Thr Leu Ala Glu
            865                 870                 875

ATT GAC TTC AGG CTG GTG AGC TTT TTG GAG GCA AAA GCA GAA AAC TTA         2991
Ile Asp Phe Arg Leu Val Ser Phe Leu Glu Ala Lys Ala Glu Asn Leu
        880                 885                 890

CAC AGA GGG GCT CAT CAT TAT ACA GGG CTT TTA AAA CTG CAA GAA CGA         3039
His Arg Gly Ala His His Tyr Thr Gly Leu Leu Lys Leu Gln Glu Arg
        895                 900                 905

GTG CTC AAT AAT GTT GTC ATC CAT TTG CTT GGA GAT GAA GAC CCC AGG         3087
Val Leu Asn Asn Val Val Ile His Leu Leu Gly Asp Glu Asp Pro Arg
910                 915                 920

GTG CGA CAT GTT GCC GCA GCA TCA CTA ATT AGG CTT GTC CCA AAG CTG         3135
Val Arg His Val Ala Ala Ala Ser Leu Ile Arg Leu Val Pro Lys Leu
925             930                 935                 940

TTT TAT AAA TGT GAC CAA GGA CAA GCT GAT CCA GTA GTG GCC GTG GCA         3183
Phe Tyr Lys Cys Asp Gln Gly Gln Ala Asp Pro Val Val Ala Val Ala
            945                 950                 955

AGA GAT CAA AGC AGT GTT TAC CTG AAA CTT CTC ATG CAT GAG ACG CAG         3231
Arg Asp Gln Ser Ser Val Tyr Leu Lys Leu Leu Met His Glu Thr Gln
        960                 965                 970

CCT CCA TCT CAT TTC TCC GTC AGC ACA ATA ACC AGA ATA TAT AGA GGC         3279
Pro Pro Ser His Phe Ser Val Ser Thr Ile Thr Arg Ile Tyr Arg Gly
        975                 980                 985

TAT AAC CTA CTA CCA AGC ATA ACA GAC GTC ACT ATG GAA AAT AAC CTT         3327
Tyr Asn Leu Leu Pro Ser Ile Thr Asp Val Thr Met Glu Asn Asn Leu
990                 995                 1000
```

| | | | | | | | | | | | | | | | | |
|---|---|---|---|---|---|---|---|---|---|---|---|---|---|---|---|---|
| TCA | AGA | GTT | ATT | GCA | GCA | GTT | TCT | CAT | GAA | CTA | ATC | ACA | TCA | ACC | ACC | 3375 |
| Ser | Arg | Val | Ile | Ala | Ala | Val | Ser | His | Glu | Leu | Ile | Thr | Ser | Thr | Thr | |
| 1005 | | | | 1010 | | | | | 1015 | | | | | | 1020 | |
| AGA | GCA | CTC | ACA | TTT | GGA | TGC | TGT | GAA | GCT | TTG | TGT | CTT | CTT | TCC | ACT | 3423 |
| Arg | Ala | Leu | Thr | Phe | Gly | Cys | Cys | Glu | Ala | Leu | Cys | Leu | Leu | Ser | Thr | |
| | | | | 1025 | | | | | 1030 | | | | | | 1035 | |
| GCC | TTC | CCA | GTT | TGC | ATT | TGG | AGT | TTA | GGT | TGG | CAC | TGT | GGA | GTG | CCT | 3471 |
| Ala | Phe | Pro | Val | Cys | Ile | Trp | Ser | Leu | Gly | Trp | His | Cys | Gly | Val | Pro | |
| | | | | 1040 | | | | | 1045 | | | | | | 1050 | |
| CCA | CTG | AGT | GCC | TCA | GAT | GAG | TCT | AGG | AAG | AGC | TGT | ACC | GTT | GGG | ATG | 3519 |
| Pro | Leu | Ser | Ala | Ser | Asp | Glu | Ser | Arg | Lys | Ser | Cys | Thr | Val | Gly | Met | |
| | | | | 1055 | | | | | 1060 | | | | | | 1065 | |
| GCC | ACA | ATG | ATT | CTG | ACC | CTG | CTC | TCG | TCA | GCT | TGG | TTC | CCA | TTG | GAT | 3567 |
| Ala | Thr | Met | Ile | Leu | Thr | Leu | Leu | Ser | Ser | Ala | Trp | Phe | Pro | Leu | Asp | |
| | 1070 | | | | | 1075 | | | | | 1080 | | | | | |
| CTC | TCA | GCC | CAT | CAA | GAT | GCT | TTG | ATT | TTG | GCC | GGA | AAC | TTG | CTT | GCA | 3615 |
| Leu | Ser | Ala | His | Gln | Asp | Ala | Leu | Ile | Leu | Ala | Gly | Asn | Leu | Leu | Ala | |
| 1085 | | | | | 1090 | | | | | 1095 | | | | | 1100 | |
| GCC | AGT | GCT | CCC | AAA | TCT | CTG | AGA | AGT | TCA | TGG | GCC | TCT | GAA | GAA | GAA | 3663 |
| Ala | Ser | Ala | Pro | Lys | Ser | Leu | Arg | Ser | Ser | Trp | Ala | Ser | Glu | Glu | Glu | |
| | | | | 1105 | | | | | 1110 | | | | | | 1115 | |
| GCC | AAC | CCA | GCA | GCC | ACC | AAG | CAA | GAG | GAG | GTC | TGG | CCA | GCC | CTG | GGG | 3711 |
| Ala | Asn | Pro | Ala | Ala | Thr | Lys | Gln | Glu | Glu | Val | Trp | Pro | Ala | Leu | Gly | |
| | | | | 1120 | | | | | 1125 | | | | | | 1130 | |
| GAC | CGG | GCC | CTG | GTG | CCC | ATG | GTG | GAG | CAG | CTC | TTC | TCT | CAC | CTG | CTG | 3759 |
| Asp | Arg | Ala | Leu | Val | Pro | Met | Val | Glu | Gln | Leu | Phe | Ser | His | Leu | Leu | |
| | | | | 1135 | | | | | 1140 | | | | | | 1145 | |
| AAG | GTG | ATT | AAC | ATT | TGT | GCC | CAC | GTC | CTG | GAT | GAC | GTG | GCT | CCT | GGA | 3807 |
| Lys | Val | Ile | Asn | Ile | Cys | Ala | His | Val | Leu | Asp | Asp | Val | Ala | Pro | Gly | |
| | 1150 | | | | | 1155 | | | | | 1160 | | | | | |
| CCC | GCA | ATA | AAG | GCA | GCC | TTG | CCT | TCT | CTA | ACA | AAC | CCC | CCT | TCT | CTA | 3855 |
| Pro | Ala | Ile | Lys | Ala | Ala | Leu | Pro | Ser | Leu | Thr | Asn | Pro | Pro | Ser | Leu | |
| 1165 | | | | | 1170 | | | | | 1175 | | | | | 1180 | |
| AGT | CCC | ATC | CGA | CGA | AAG | GGG | AAG | GAG | AAA | GAA | CCA | GGA | GAA | CAA | GCA | 3903 |
| Ser | Pro | Ile | Arg | Arg | Lys | Gly | Lys | Glu | Lys | Glu | Pro | Gly | Glu | Gln | Ala | |
| | | | | 1185 | | | | | 1190 | | | | | | 1195 | |
| TCT | GTA | CCG | TTG | AGT | CCC | AAG | AAA | GGC | AGT | GAG | GCC | AGT | GCA | GCT | TCT | 3951 |
| Ser | Val | Pro | Leu | Ser | Pro | Lys | Lys | Gly | Ser | Glu | Ala | Ser | Ala | Ala | Ser | |
| | | | | 1200 | | | | | 1205 | | | | | | 1210 | |
| AGA | CAA | TCT | GAT | ACC | TCA | GGT | CCT | GTT | ACA | ACA | AGT | AAA | TCC | TCA | TCA | 3999 |
| Arg | Gln | Ser | Asp | Thr | Ser | Gly | Pro | Val | Thr | Thr | Ser | Lys | Ser | Ser | Ser | |
| | | | | 1215 | | | | | 1220 | | | | | | 1225 | |
| CTG | GGG | AGT | TTC | TAT | CAT | CTT | CCT | TCA | TAC | CTC | AGA | CTG | CAT | GAT | GTC | 4047 |
| Leu | Gly | Ser | Phe | Tyr | His | Leu | Pro | Ser | Tyr | Leu | Arg | Leu | His | Asp | Val | |
| | 1230 | | | | | 1235 | | | | | 1240 | | | | | |
| CTG | AAA | GCT | ACA | CAC | GCT | AAC | TAC | AAG | GTC | ACG | CTG | GAT | CTT | CAG | AAC | 4095 |
| Leu | Lys | Ala | Thr | His | Ala | Asn | Tyr | Lys | Val | Thr | Leu | Asp | Leu | Gln | Asn | |
| 1245 | | | | | 1250 | | | | | 1255 | | | | | 1260 | |
| AGC | ACG | GAA | AAG | TTT | GGA | GGG | TTT | CTC | CGC | TCA | GCC | TTG | GAT | GTT | CTT | 4143 |
| Ser | Thr | Glu | Lys | Phe | Gly | Gly | Phe | Leu | Arg | Ser | Ala | Leu | Asp | Val | Leu | |
| | | | | 1265 | | | | | 1270 | | | | | | 1275 | |
| TCT | CAG | ATA | CTA | GAG | CTG | GCC | ACA | CTG | CAG | GAC | ATT | GGG | AAG | TGT | GTT | 4191 |
| Ser | Gln | Ile | Leu | Glu | Leu | Ala | Thr | Leu | Gln | Asp | Ile | Gly | Lys | Cys | Val | |
| | | | | 1280 | | | | | 1285 | | | | | | 1290 | |
| GAA | GAG | ATC | CTA | GGA | TAC | CTG | AAA | TCC | TGC | TTT | AGT | CGA | GAA | CCA | ATG | 4239 |
| Glu | Glu | Ile | Leu | Gly | Tyr | Leu | Lys | Ser | Cys | Phe | Ser | Arg | Glu | Pro | Met | |
| | | | | 1295 | | | | | 1300 | | | | | | 1305 | |
| ATG | GCA | ACT | GTT | TGT | GTT | CAA | CAA | TTG | TTG | AAG | ACT | CTC | TTT | GGC | ACA | 4287 |
| Met | Ala | Thr | Val | Cys | Val | Gln | Gln | Leu | Leu | Lys | Thr | Leu | Phe | Gly | Thr | |
| | 1310 | | | | | 1315 | | | | | 1320 | | | | | |

```
AAC TTG GCC TCC CAG TTT GAT GGC TTA TCT TCC AAC CCC AGC AAG TCA         4335
Asn Leu Ala Ser Gln Phe Asp Gly Leu Ser Ser Asn Pro Ser Lys Ser
1325                1330                1335                1340

CAA GGC CGA GCA CAG CGC CTT GGC TCC TCC AGT GTG AGG CCA GGC TTG         4383
Gln Gly Arg Ala Gln Arg Leu Gly Ser Ser Ser Val Arg Pro Gly Leu
            1345                1350                1355

TAC CAC TAC TGC TTC ATG GCC CCG TAC ACC CAC TTC ACC CAG GCC CTC         4431
Tyr His Tyr Cys Phe Met Ala Pro Tyr Thr His Phe Thr Gln Ala Leu
                1360                1365                1370

GCT GAC GCC AGC CTG AGG AAC ATG GTG CAG GCG GAG CAG GAG AAC GAC         4479
Ala Asp Ala Ser Leu Arg Asn Met Val Gln Ala Glu Gln Glu Asn Asp
1375                1380                1385

ACC TCG GGA TGG TTT GAT GTC CTC CAG AAA GTG TCT ACC CAG TTG AAG         4527
Thr Ser Gly Trp Phe Asp Val Leu Gln Lys Val Ser Thr Gln Leu Lys
            1390                1395                1400

ACA AAC CTC ACG AGT GTC ACA AAG AAC CGT GCA GAT AAG AAT GCT ATT         4575
Thr Asn Leu Thr Ser Val Thr Lys Asn Arg Ala Asp Lys Asn Ala Ile
1405                1410                1415                1420

CAT AAT CAC ATT CGT TTG TTT GAA CCT CTT GTT ATA AAA GCT TTA AAA         4623
His Asn His Ile Arg Leu Phe Glu Pro Leu Val Ile Lys Ala Leu Lys
                1425                1430                1435

CAG TAC ACG ACT ACA ACA TGT GTG CAG TTA CAG AAG CAG GTT TTA GAT         4671
Gln Tyr Thr Thr Thr Thr Cys Val Gln Leu Gln Lys Gln Val Leu Asp
            1440                1445                1450

TTG CTG GCG CAG CTG GTT CAG TTA CGG GTT AAT TAC TGT CTT CTG GAT         4719
Leu Leu Ala Gln Leu Val Gln Leu Arg Val Asn Tyr Cys Leu Leu Asp
            1455                1460                1465

TCA GAT CAG GTG TTT ATT GGC TTT GTA TTG AAA CAG TTT GAA TAC ATT         4767
Ser Asp Gln Val Phe Ile Gly Phe Val Leu Lys Gln Phe Glu Tyr Ile
1470                1475                1480

GAA GTG GGC CAG TTC AGG GAA TCA GAG GCA ATC ATT CCA AAC ATC TTT         4815
Glu Val Gly Gln Phe Arg Glu Ser Glu Ala Ile Ile Pro Asn Ile Phe
1485                1490                1495                1500

TTC TTC TTG GTA TTA CTA TCT TAT GAA CGC TAT CAT TCA AAA CAG ATC         4863
Phe Phe Leu Val Leu Leu Ser Tyr Glu Arg Tyr His Ser Lys Gln Ile
                1505                1510                1515

ATT GGA ATT CCT AAA ATC ATT CAG CTC TGT GAT GGC ATC ATG GCC AGT         4911
Ile Gly Ile Pro Lys Ile Ile Gln Leu Cys Asp Gly Ile Met Ala Ser
            1520                1525                1530

GGA AGG AAG GCT GTG ACA CAT GCC ATA CCG GCT CTG CAG CCC ATA GTC         4959
Gly Arg Lys Ala Val Thr His Ala Ile Pro Ala Leu Gln Pro Ile Val
            1535                1540                1545

CAC GAC CTC TTT GTA TTA AGA GGA ACA AAT AAA GCT GAT GCA GGA AAA         5007
His Asp Leu Phe Val Leu Arg Gly Thr Asn Lys Ala Asp Ala Gly Lys
            1550                1555                1560

GAG CTT GAA ACC CAA AAA GAG GTG GTG GTG TCA ATG TTA CTG AGA CTC         5055
Glu Leu Glu Thr Gln Lys Glu Val Val Val Ser Met Leu Leu Arg Leu
1565                1570                1575                1580

ATC CAG TAC CAT CAG GTG TTG GAG ATG TTC ATT CTT GTC CTG CAG CAG         5103
Ile Gln Tyr His Gln Val Leu Glu Met Phe Ile Leu Val Leu Gln Gln
            1585                1590                1595

TGC CAC AAG GAG AAT GAA GAC AAG TGG AAG CGA CTG TCT CGA CAG ATA         5151
Cys His Lys Glu Asn Glu Asp Lys Trp Lys Arg Leu Ser Arg Gln Ile
                1600                1605                1610

GCT GAC ATC ATC CTC CCA ATG TTA GCC AAA CAG CAG ATG CAC ATT GAC         5199
Ala Asp Ile Ile Leu Pro Met Leu Ala Lys Gln Gln Met His Ile Asp
            1615                1620                1625

TCT CAT GAA GCC CTT GGA GTG TTA AAT ACA TTA TTT GAG ATT TTG GCC         5247
Ser His Glu Ala Leu Gly Val Leu Asn Thr Leu Phe Glu Ile Leu Ala
            1630                1635                1640
```

```
CCT TCC TCC CTC CGT CCG GTA GAC ATG CTT TTA CGG AGT ATG TTC GTC        5295
Pro Ser Ser Leu Arg Pro Val Asp Met Leu Leu Arg Ser Met Phe Val
1645                1650                1655                1660

ACT CCA AAC ACA ATG GCG TCC GTG AGC ACT GTT CAA CTG TGG ATA TCG        5343
Thr Pro Asn Thr Met Ala Ser Val Ser Thr Val Gln Leu Trp Ile Ser
            1665                1670                1675

GGA ATT CTG GCC ATT TTG AGG GTT CTG ATT TCC CAG TCA ACT GAA GAT        5391
Gly Ile Leu Ala Ile Leu Arg Val Leu Ile Ser Gln Ser Thr Glu Asp
        1680                1685                1690

ATT GTT CTT TCT CGT ATT CAG GAG CTC TCC TTC TCT CCG TAT TTA ATC        5439
Ile Val Leu Ser Arg Ile Gln Glu Leu Ser Phe Ser Pro Tyr Leu Ile
    1695                1700                1705

TCC TGT ACA GTA ATT AAT AGG TTA AGA GAT GGG GAC AGT ACT TCA ACG        5487
Ser Cys Thr Val Ile Asn Arg Leu Arg Asp Gly Asp Ser Thr Ser Thr
1710                1715                1720

CTA GAA GAA CAC AGT GAA GGG AAA CAA ATA AAG AAT TTG CCA GAA GAA        5535
Leu Glu Glu His Ser Glu Gly Lys Gln Ile Lys Asn Leu Pro Glu Glu
1725                1730                1735                1740

ACA TTT TCA AGG TTT CTA TTA CAA CTG GTT GGT ATT CTT TTA GAA GAC        5583
Thr Phe Ser Arg Phe Leu Leu Gln Leu Val Gly Ile Leu Leu Glu Asp
            1745                1750                1755

ATT GTT ACA AAA CAG CTG AAG GTG GAA ATG AGT GAG CAG CAA CAT ACT        5631
Ile Val Thr Lys Gln Leu Lys Val Glu Met Ser Glu Gln Gln His Thr
        1760                1765                1770

TTC TAT TGC CAG GAA CTA GGC ACA CTG CTA ATG TGT CTG ATC CAC ATC        5679
Phe Tyr Cys Gln Glu Leu Gly Thr Leu Leu Met Cys Leu Ile His Ile
    1775                1780                1785

TTC AAG TCT GGA ATG TTC CGG AGA ATC ACA GCA GCT GCC ACT AGG CTG        5727
Phe Lys Ser Gly Met Phe Arg Arg Ile Thr Ala Ala Ala Thr Arg Leu
1790                1795                1800

TTC CGC AGT GAT GGC TGT GGC GGC AGT TTC TAC ACC CTG GAC AGC TTG        5775
Phe Arg Ser Asp Gly Cys Gly Gly Ser Phe Tyr Thr Leu Asp Ser Leu
1805                1810                1815                1820

AAC TTG CGG GCT CGT TCC ATG ATC ACC ACC CAC CCG GCC CTG GTG CTG        5823
Asn Leu Arg Ala Arg Ser Met Ile Thr Thr His Pro Ala Leu Val Leu
            1825                1830                1835

CTC TGG TGT CAG ATA CTG CTG CTT GTC AAC CAC ACC GAC TAC CGC TGG        5871
Leu Trp Cys Gln Ile Leu Leu Leu Val Asn His Thr Asp Tyr Arg Trp
        1840                1845                1850

TGG GCA GAA GTG CAG CAG ACC CCG AAA AGA CAC AGT CTG TCC AGC ACA        5919
Trp Ala Glu Val Gln Gln Thr Pro Lys Arg His Ser Leu Ser Ser Thr
    1855                1860                1865

AAG TTA CTT AGT CCC CAG ATG TCT GGA GAA GAG GAG GAT TCT GAC TTG        5967
Lys Leu Leu Ser Pro Gln Met Ser Gly Glu Glu Glu Asp Ser Asp Leu
1870                1875                1880

GCA GCC AAA CTT GGA ATG TGC AAT AGA GAA ATA GTA CGA AGA GGG GCT        6015
Ala Ala Lys Leu Gly Met Cys Asn Arg Glu Ile Val Arg Arg Gly Ala
1885                1890                1895                1900

CTC ATT CTC TTC TGT GAT TAT GTC TGT CAG AAC CTC CAT GAC TCC GAG        6063
Leu Ile Leu Phe Cys Asp Tyr Val Cys Gln Asn Leu His Asp Ser Glu
            1905                1910                1915

CAC TTA ACG TGG CTC ATT GTA AAT CAC ATT CAA GAT CTG ATC AGC CTT        6111
His Leu Thr Trp Leu Ile Val Asn His Ile Gln Asp Leu Ile Ser Leu
        1920                1925                1930

TCC CAC GAG CCT CCA GTA CAG GAC TTC ATC AGT GCC GTT CAT CGG AAC        6159
Ser His Glu Pro Pro Val Gln Asp Phe Ile Ser Ala Val His Arg Asn
    1935                1940                1945

TCT GCT GCC AGC GGC CTG TTC ATC CAG GCA ATT CAG TCT CGT TGT GAA        6207
Ser Ala Ala Ser Gly Leu Phe Ile Gln Ala Ile Gln Ser Arg Cys Glu
1950                1955                1960
```

```
AAC CTT TCA ACT CCA ACC ATG CTG AAG AAA ACT CTT CAG TGC TTG GAG         6255
Asn Leu Ser Thr Pro Thr Met Leu Lys Lys Thr Leu Gln Cys Leu Glu
1965                1970                1975                1980

GGG ATC CAT CTC AGC CAG TCG GGA GCT GTG CTC ACG CTG TAT GTG GAC         6303
Gly Ile His Leu Ser Gln Ser Gly Ala Val Leu Thr Leu Tyr Val Asp
                1985                1990                1995

AGG CTT CTG TGC ACC CCT TTC CGT GTG CTG GCT CGC ATG GTC GAC ATC         6351
Arg Leu Leu Cys Thr Pro Phe Arg Val Leu Ala Arg Met Val Asp Ile
            2000                2005                2010

CTT GCT TGT CGC CGG GTA GAA ATG CTT CTG GCT GCA AAT TTA CAG AGC         6399
Leu Ala Cys Arg Arg Val Glu Met Leu Leu Ala Ala Asn Leu Gln Ser
        2015                2020                2025

AGC ATG GCC CAG TTG CCA ATG GAA GAA CTC AAC AGA ATC CAG GAA TAC         6447
Ser Met Ala Gln Leu Pro Met Glu Glu Leu Asn Arg Ile Gln Glu Tyr
    2030                2035                2040

CTT CAG AGC AGC GGG CTC GCT CAG AGA CAC CAA AGG CTC TAT TCC CTG         6495
Leu Gln Ser Ser Gly Leu Ala Gln Arg His Gln Arg Leu Tyr Ser Leu
2045                2050                2055                2060

CTG GAC AGG TTT CGT CTC TCC ACC ATG CAA GAC TCA CTT AGT CCC TCT         6543
Leu Asp Arg Phe Arg Leu Ser Thr Met Gln Asp Ser Leu Ser Pro Ser
                2065                2070                2075

CCT CCA GTC TCT TCC CAC CCG CTG GAC GGG GAT GGG CAC GTG TCA CTG         6591
Pro Pro Val Ser Ser His Pro Leu Asp Gly Asp Gly His Val Ser Leu
            2080                2085                2090

GAA ACA GTG AGT CCG GAC AAA GAC TGG TAC GTT CAT CTT GTC AAA TCC         6639
Glu Thr Val Ser Pro Asp Lys Asp Trp Tyr Val His Leu Val Lys Ser
        2095                2100                2105

CAG TGT TGG ACC AGG TCA GAT TCT GCA CTG CTG GAA GGT GCA GAG CTG         6687
Gln Cys Trp Thr Arg Ser Asp Ser Ala Leu Leu Glu Gly Ala Glu Leu
    2110                2115                2120

GTG AAT CGG ATT CCT GCT GAA GAT ATG AAT GCC TTC ATG ATG AAC TCG         6735
Val Asn Arg Ile Pro Ala Glu Asp Met Asn Ala Phe Met Met Asn Ser
2125                2130                2135                2140

GAG TTC AAC CTA AGC CTG CTA GCT CCA TGC TTA AGC CTA GGG ATG AGT         6783
Glu Phe Asn Leu Ser Leu Leu Ala Pro Cys Leu Ser Leu Gly Met Ser
                2145                2150                2155

GAA ATT TCT GGT GGC CAG AAG AGT GCC CTT TTT GAA GCA GCC CGT GAG         6831
Glu Ile Ser Gly Gly Gln Lys Ser Ala Leu Phe Glu Ala Ala Arg Glu
            2160                2165                2170

GTG ACT CTG GCC CGT GTG AGC GGC ACC GTG CAG CAG CTC CCT GCT GTC         6879
Val Thr Leu Ala Arg Val Ser Gly Thr Val Gln Gln Leu Pro Ala Val
        2175                2180                2185

CAT CAT GTC TTC CAG CCC GAG CTG CCT GCA GAG CCG GCG GCC TAC TGG         6927
His His Val Phe Gln Pro Glu Leu Pro Ala Glu Pro Ala Ala Tyr Trp
    2190                2195                2200

AGC AAG TTG AAT GAT CTG TTT GGG GAT GCT GCA CTG TAT CAG TCC CTG         6975
Ser Lys Leu Asn Asp Leu Phe Gly Asp Ala Ala Leu Tyr Gln Ser Leu
2205                2210                2215                2220

CCC ACT CTG GCC CGG GCC CTG GCA CAG TAC CTG GTG GTG GTC TCC AAA         7023
Pro Thr Leu Ala Arg Ala Leu Ala Gln Tyr Leu Val Val Val Ser Lys
                2225                2230                2235

CTG CCC AGT CAT TTG CAC CTT CCT CCT GAG AAA GAG AAG GAC ATT GTG         7071
Leu Pro Ser His Leu His Leu Pro Pro Glu Lys Glu Lys Asp Ile Val
            2240                2245                2250

AAA TTC GTG GTG GCA ACC CTT GAG GCC CTG TCC TGG CAT TTG ATC CAT         7119
Lys Phe Val Val Ala Thr Leu Glu Ala Leu Ser Trp His Leu Ile His
        2255                2260                2265

GAG CAG ATC CCG CTG AGT CTG GAT CTC CAG GCA GGG CTG GAC TGC TGC         7167
Glu Gln Ile Pro Leu Ser Leu Asp Leu Gln Ala Gly Leu Asp Cys Cys
    2270                2275                2280
```

| | |
|---|---|
| TGC CTG GCC CTG CAG CTG CCT GGC CTC TGG AGC GTG GTC TCC TCC ACA<br>Cys Leu Ala Leu Gln Leu Pro Gly Leu Trp Ser Val Val Ser Ser Thr<br>2285                      2290                  2295                2300 | 7215 |
| GAG TTT GTG ACC CAC GCC TGC TCC CTC ATC TAC TGT GTG CAC TTC ATC<br>Glu Phe Val Thr His Ala Cys Ser Leu Ile Tyr Cys Val His Phe Ile<br>                    2305                  2310                2315 | 7263 |
| CTG GAG GCC GTT GCA GTG CAG CCT GGA GAG CAG CTT CTT AGT CCA GAA<br>Leu Glu Ala Val Ala Val Gln Pro Gly Glu Gln Leu Leu Ser Pro Glu<br>2320                      2325                  2330 | 7311 |
| AGA AGG ACA AAT ACC CCA AAA GCC ATC AGC GAG GAG GAG GAG GAA GTA<br>Arg Arg Thr Asn Thr Pro Lys Ala Ile Ser Glu Glu Glu Glu Glu Val<br>                    2335                  2340                2345 | 7359 |
| GAT CCA AAC ACA CAG AAT CCT AAG TAT ATC ACT GCA GCC TGT GAG ATG<br>Asp Pro Asn Thr Gln Asn Pro Lys Tyr Ile Thr Ala Ala Cys Glu Met<br>2350                      2355                  2360 | 7407 |
| GTG GCA GAA ATG GTG GAG TCT CTG CAG TCG GTG TTG GCC TTG GGT CAT<br>Val Ala Glu Met Val Glu Ser Leu Gln Ser Val Leu Ala Leu Gly His<br>2365                      2370                  2375                2380 | 7455 |
| AAA AGG AAT AGC GGC GTG CCG GCG TTT CTC ACG CCA TTG CTC AGG AAC<br>Lys Arg Asn Ser Gly Val Pro Ala Phe Leu Thr Pro Leu Leu Arg Asn<br>                    2385                  2390                2395 | 7503 |
| ATC ATC ATC AGC CTG GCC CGC CTG CCC CTT GTC AAC AGC TAC ACA CGT<br>Ile Ile Ile Ser Leu Ala Arg Leu Pro Leu Val Asn Ser Tyr Thr Arg<br>2400                      2405                  2410 | 7551 |
| GTG CCC CCA CTG GTG TGG AAG CTT GGA TGG TCA CCC AAA CCG GGA GGG<br>Val Pro Pro Leu Val Trp Lys Leu Gly Trp Ser Pro Lys Pro Gly Gly<br>                    2415                  2420                2425 | 7599 |
| GAT TTT GGC ACA GCA TTC CCT GAG ATC CCC GTG GAG TTC CTC CAG GAA<br>Asp Phe Gly Thr Ala Phe Pro Glu Ile Pro Val Glu Phe Leu Gln Glu<br>2430                      2435                  2440 | 7647 |
| AAG GAA GTC TTT AAG GAG TTC ATC TAC CGC ATC AAC ACA CTA GGC TGG<br>Lys Glu Val Phe Lys Glu Phe Ile Tyr Arg Ile Asn Thr Leu Gly Trp<br>2445                      2450                  2455                2460 | 7695 |
| ACC AGT CGT ACT CAG TTT GAA GAA ACT TGG GCC ACC CTC CTT GGT GTC<br>Thr Ser Arg Thr Gln Phe Glu Glu Thr Trp Ala Thr Leu Leu Gly Val<br>                    2465                  2470                2475 | 7743 |
| CTG GTG ACG CAG CCC CTC GTG ATG GAG CAG GAG GAG AGC CCA CCA GAA<br>Leu Val Thr Gln Pro Leu Val Met Glu Gln Glu Glu Ser Pro Pro Glu<br>2480                      2485                  2490 | 7791 |
| GAA GAC ACA GAG AGG ACC CAG ATC AAC GTC CTG GCC GTG CAG GCC ATC<br>Glu Asp Thr Glu Arg Thr Gln Ile Asn Val Leu Ala Val Gln Ala Ile<br>                    2495                  2500                2505 | 7839 |
| ACC TCA CTG GTG CTC AGT GCA ATG ACT GTG CCT GTG GCC GGC AAC CCA<br>Thr Ser Leu Val Leu Ser Ala Met Thr Val Pro Val Ala Gly Asn Pro<br>2510                      2515                  2520 | 7887 |
| GCT GTA AGC TGC TTG GAG CAG CAG CCC CGG AAC AAG CCT CTG AAA GCT<br>Ala Val Ser Cys Leu Glu Gln Gln Pro Arg Asn Lys Pro Leu Lys Ala<br>2525                      2530                  2535                2540 | 7935 |
| CTC GAC ACC AGG TTT GGG AGG AAG CTG AGC ATT ATC AGA GGG ATT GTG<br>Leu Asp Thr Arg Phe Gly Arg Lys Leu Ser Ile Ile Arg Gly Ile Val<br>                    2545                  2550                2555 | 7983 |
| GAG CAA GAG ATT CAA GCA ATG GTT TCA AAG AGA GAG AAT ATT GCC ACC<br>Glu Gln Glu Ile Gln Ala Met Val Ser Lys Arg Glu Asn Ile Ala Thr<br>2560                      2565                  2570 | 8031 |
| CAT CAT TTA TAT CAG GCA TGG GAT CCT GTC CCT TCT CTG TCT CCG GCT<br>His His Leu Tyr Gln Ala Trp Asp Pro Val Pro Ser Leu Ser Pro Ala<br>2575                      2580                  2585 | 8079 |
| ACT ACA GGT GCC CTC ATC AGC CAC GAG AAG CTG CTG CTA CAG ATC AAC<br>Thr Thr Gly Ala Leu Ile Ser His Glu Lys Leu Leu Leu Gln Ile Asn<br>2590                      2595                  2600 | 8127 |

```
CCC GAG CGG GAG CTG GGG AGC ATG AGC TAC AAA CTC GGC CAG GTG TCC      8175
Pro Glu Arg Glu Leu Gly Ser Met Ser Tyr Lys Leu Gly Gln Val Ser
2605                2610                2615                2620

ATA CAC TCC GTG TGG CTG GGG AAC AGC ATC ACA CCC CTG AGG GAG GAG      8223
Ile His Ser Val Trp Leu Gly Asn Ser Ile Thr Pro Leu Arg Glu Glu
                2625                2630                2635

GAA TGG GAC GAG GAA GAG GAG GAG GAG GCC GAC GCC CCT GCA CCT TCG      8271
Glu Trp Asp Glu Glu Glu Glu Glu Glu Ala Asp Ala Pro Ala Pro Ser
            2640                2645                2650

TCA CCA CCC ACG TCT CCA GTC AAC TCC AGG AAA CAC CGG GCT GGA GTT      8319
Ser Pro Pro Thr Ser Pro Val Asn Ser Arg Lys His Arg Ala Gly Val
        2655                2660                2665

GAC ATC CAC TCC TGT TCG CAG TTT TTG CTT GAG TTG TAC AGC CGC TGG      8367
Asp Ile His Ser Cys Ser Gln Phe Leu Leu Glu Leu Tyr Ser Arg Trp
    2670                2675                2680

ATC CTG CCG TCC AGC TCA GCC AGG AGG ACC CCG GCC ATC CTG ATC AGT      8415
Ile Leu Pro Ser Ser Ser Ala Arg Arg Thr Pro Ala Ile Leu Ile Ser
2685                2690                2695                2700

GAG GTG GTC AGA TCC CTT CTA GTG GTC TCA GAC TTG TTC ACC GAG CGC      8463
Glu Val Val Arg Ser Leu Leu Val Val Ser Asp Leu Phe Thr Glu Arg
                2705                2710                2715

AAC CAG TTT GAG CTG ATG TAT GTG ACG CTG ACA GAA CTG CGA AGG GTG      8511
Asn Gln Phe Glu Leu Met Tyr Val Thr Leu Thr Glu Leu Arg Arg Val
            2720                2725                2730

CAC CCT TCA GAA GAC GAG ATC CTC GCT CAG TAC CTG GTG CCT GCC ACC      8559
His Pro Ser Glu Asp Glu Ile Leu Ala Gln Tyr Leu Val Pro Ala Thr
        2735                2740                2745

TGC AAG GCA GCT GCC GTC CTT GGG ATG GAC AAG GCC GTG GCG GAG CCT      8607
Cys Lys Ala Ala Ala Val Leu Gly Met Asp Lys Ala Val Ala Glu Pro
    2750                2755                2760

GTC AGC CGC CTG CTG GAG AGC ACG CTC AGG AGC AGC CAC CTG CCC AGC      8655
Val Ser Arg Leu Leu Glu Ser Thr Leu Arg Ser Ser His Leu Pro Ser
2765                2770                2775                2780

AGG GTT GGA GCC CTG CAC GGC ATC CTC TAT GTG CTG GAG TGC GAC CTG      8703
Arg Val Gly Ala Leu His Gly Ile Leu Tyr Val Leu Glu Cys Asp Leu
                2785                2790                2795

CTG GAC GAC ACT GCC AAG CAG CTC ATC CCG GTC ATC AGC GAC TAT CTC      8751
Leu Asp Asp Thr Ala Lys Gln Leu Ile Pro Val Ile Ser Asp Tyr Leu
            2800                2805                2810

CTC TCC AAC CTG AAA GGG ATC GCC CAC TGC GTG AAC ATT CAC AGC CAG      8799
Leu Ser Asn Leu Lys Gly Ile Ala His Cys Val Asn Ile His Ser Gln
        2815                2820                2825

CAG CAC GTA CTG GTC ATG TGT GCC ACT GCG TTT TAC CTC ATT GAG AAC      8847
Gln His Val Leu Val Met Cys Ala Thr Ala Phe Tyr Leu Ile Glu Asn
    2830                2835                2840

TAT CCT CTG GAC GTA GGG CCG GAA TTT TCA GCA TCA ATA ATA CAG ATG      8895
Tyr Pro Leu Asp Val Gly Pro Glu Phe Ser Ala Ser Ile Ile Gln Met
2845                2850                2855                2860

TGT GGG GTG ATG CTG TCT GGA AGT GAG GAG TCC ACC CCC TCC ATC ATT      8943
Cys Gly Val Met Leu Ser Gly Ser Glu Glu Ser Thr Pro Ser Ile Ile
                2865                2870                2875

TAC CAC TGT GCC CTC AGA GGC CTG GAG CGC CTC CTG CTC TCT GAG CAG      8991
Tyr His Cys Ala Leu Arg Gly Leu Glu Arg Leu Leu Leu Ser Glu Gln
            2880                2885                2890

CTC TCC CGC CTG GAT GCA GAA TCG CTG GTC AAG CTG AGT GTG GAC AGA      9039
Leu Ser Arg Leu Asp Ala Glu Ser Leu Val Lys Leu Ser Val Asp Arg
        2895                2900                2905

GTG AAC GTG CAC AGC CCG CAC CGG GCC ATG GCG GCT CTG GGC CTG ATG      9087
Val Asn Val His Ser Pro His Arg Ala Met Ala Ala Leu Gly Leu Met
    2910                2915                2920
```

```
CTC  ACC  TGC  ATG  TAC  ACA  GGA  AAG  GAG  AAA  GTC  AGT  CCG  GGT  AGA  ACT       9135
Leu  Thr  Cys  Met  Tyr  Thr  Gly  Lys  Glu  Lys  Val  Ser  Pro  Gly  Arg  Thr
2925                2930                2935                2940

TCA  GAC  CCT  AAT  CCT  GCA  GCC  CCC  GAC  AGC  GAG  TCA  GTG  ATT  GTT  GCT       9183
Ser  Asp  Pro  Asn  Pro  Ala  Ala  Pro  Asp  Ser  Glu  Ser  Val  Ile  Val  Ala
                    2945                2950                2955

ATG  GAG  CGG  GTA  TCT  GTT  CTT  TTT  GAT  AGG  ATC  AGG  AAA  GGC  TTT  CCT       9231
Met  Glu  Arg  Val  Ser  Val  Leu  Phe  Asp  Arg  Ile  Arg  Lys  Gly  Phe  Pro
               2960                2965                2970

TGT  GAA  GCC  AGA  GTG  GTG  GCC  AGG  ATC  CTG  CCC  CAG  TTT  CTA  GAC  GAC       9279
Cys  Glu  Ala  Arg  Val  Val  Ala  Arg  Ile  Leu  Pro  Gln  Phe  Leu  Asp  Asp
          2975                2980                2985

TTC  TTC  CCA  CCC  CAG  GAC  ATC  ATG  AAC  AAA  GTC  ATC  GGA  GAG  TTT  CTG       9327
Phe  Phe  Pro  Pro  Gln  Asp  Ile  Met  Asn  Lys  Val  Ile  Gly  Glu  Phe  Leu
     2990                2995                3000

TCC  AAC  CAG  CAG  CCA  TAC  CCC  CAG  TTC  ATG  GCC  ACC  GTG  GTG  TAT  AAG       9375
Ser  Asn  Gln  Gln  Pro  Tyr  Pro  Gln  Phe  Met  Ala  Thr  Val  Val  Tyr  Lys
3005                 3010                3015                3020

GTG  TTT  CAG  ACT  CTG  CAC  AGC  ACC  GGG  CAG  TCG  TCC  ATG  GTC  CGG  GAC       9423
Val  Phe  Gln  Thr  Leu  His  Ser  Thr  Gly  Gln  Ser  Ser  Met  Val  Arg  Asp
               3025                3030                3035

TGG  GTC  ATG  CTG  TCC  CTC  TCC  AAC  TTC  ACG  CAG  AGG  GCC  CCG  GTC  GCC       9471
Trp  Val  Met  Leu  Ser  Leu  Ser  Asn  Phe  Thr  Gln  Arg  Ala  Pro  Val  Ala
          3040                3045                3050

ATG  GCC  ACG  TGG  AGC  CTC  TCC  TGC  TTC  TTT  GTC  AGC  GCG  TCC  ACC  AGC       9519
Met  Ala  Thr  Trp  Ser  Leu  Ser  Cys  Phe  Phe  Val  Ser  Ala  Ser  Thr  Ser
     3055                3060                3065

CCG  TGG  GTC  GCG  GCG  ATC  CTC  CCA  CAT  GTC  ATC  AGC  AGG  ATG  GGC  AAG       9567
Pro  Trp  Val  Ala  Ala  Ile  Leu  Pro  His  Val  Ile  Ser  Arg  Met  Gly  Lys
3070                 3075                3080

CTG  GAG  CAG  GTG  GAC  GTG  AAC  CTT  TTC  TGC  CTG  GTC  GCC  ACA  GAC  TTC       9615
Leu  Glu  Gln  Val  Asp  Val  Asn  Leu  Phe  Cys  Leu  Val  Ala  Thr  Asp  Phe
3085                 3090                3095                3100

TAC  AGA  CAC  CAG  ATA  GAG  GAG  GAG  CTC  GAC  CGC  AGG  GCC  TTC  CAG  TCT       9663
Tyr  Arg  His  Gln  Ile  Glu  Glu  Glu  Leu  Asp  Arg  Arg  Ala  Phe  Gln  Ser
               3105                3110                3115

GTG  CTT  GAG  GTG  GTT  GCA  GCC  CCA  GGA  AGC  CCA  TAT  CAC  CGG  CTG  CTG       9711
Val  Leu  Glu  Val  Val  Ala  Ala  Pro  Gly  Ser  Pro  Tyr  His  Arg  Leu  Leu
               3120                3125                3130

ACT  TGT  TTA  CGA  AAT  GTC  CAC  AAG  GTC  ACC  ACC  TGC  T GAGCGCCATG            9758
Thr  Cys  Leu  Arg  Asn  Val  His  Lys  Val  Thr  Thr  Cys
               3135                3140

GTGGGAGAGA  CTGTGAGGCG  GCAGCTGGGG  CCGGAGCCTT  TGGAAGTCTG  TGCCCTTGTG            9818
CCCTGCCTCC  ACCGAGCCAG  CTTGGTCCCT  ATGGGCTTCC  GCACATGCCG  CGGGCGGCCA            9878
GGCAACGTGC  GTGTCTCTGC  CATGTGGCAG  AAGTGCTCTT  TGTGGCAGTG  GCCAGGCAGG            9938
GAGTGTCTGC  AGTCCTGGTG  GGGCTGAGCC  TGAGGCCTTC  CAGAAAGCAG  GAGCAGCTGT            9998
GCTGCACCCC  ATGTGGGTGA  CCAGGTCCTT  TCTCCTGATA  GTCACCTGCT  GGTTGTTGCC           10058
AGGTTGCAGC  TGCTCTTGCA  TCTGGGCCAG  AAGTCCTCCC  TCCTGCAGGC  TGGCTGTTGG           10118
CCCCTCTGCT  GTCCTGCAGT  AGAAGGTGCC  GTGAGCAGGC  TTTGGGAACA  CTGGCCTGGG           10178
TCTCCCTGGT  GGGGTGTGCA  TGCCACGCCC  CGTGTCTGGA  TGCACAGATG  CCATGGCCTG           10238
TGCTGGGCCA  GTGGCTGGGG  GTGCTAGACA  CCCGGCACCA  TTCTCCCTTC  TCTCTTTTCT           10298
TCTCAGGATT  TAAAATTTAA  TTATATCAGT  AAAGAGATTA  ATTTAACGT   AAAAAAAAAA           10358
AAAAAAA                                                                         10366
```

( 2 ) INFORMATION FOR SEQ ID NO:6:

( i ) SEQUENCE CHARACTERISTICS:
        ( A ) LENGTH: 3144 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Ala Thr Leu Glu Lys Leu Met Lys Ala Phe Glu Ser Leu Lys Ser
 1               5                  10                  15

Phe Gln Gln Gln Gln Gln Gln Gln Gln Gln Gln Gln Gln Gln Gln Gln
            20                  25                  30

Gln Gln Gln Gln Gln Gln Gln Gln Pro Pro Pro Pro Pro Pro Pro Pro
            35                  40                  45

Pro Pro Pro Gln Leu Pro Gln Pro Pro Pro Gln Ala Gln Pro Leu Leu
        50              55                  60

Pro Gln Pro Gln Pro Pro Pro Pro Pro Pro Pro Pro Pro Pro Gly Pro
65                  70                  75                  80

Ala Val Ala Glu Glu Pro Leu His Arg Pro Lys Lys Glu Leu Ser Ala
                85                  90                  95

Thr Lys Lys Asp Arg Val Asn His Cys Leu Thr Ile Cys Glu Asn Ile
                100                 105                 110

Val Ala Gln Ser Val Arg Asn Ser Pro Glu Phe Gln Lys Leu Leu Gly
            115                 120                 125

Ile Ala Met Glu Leu Phe Leu Leu Cys Ser Asp Asp Ala Glu Ser Asp
        130                 135                 140

Val Arg Met Val Ala Asp Glu Cys Leu Asn Lys Val Ile Lys Ala Leu
145                 150                 155                 160

Met Asp Ser Asn Leu Pro Arg Leu Gln Leu Glu Leu Tyr Lys Glu Ile
                165                 170                 175

Lys Lys Asn Gly Ala Pro Arg Ser Leu Arg Ala Ala Leu Trp Arg Phe
            180                 185                 190

Ala Glu Leu Ala His Leu Val Arg Pro Gln Lys Cys Arg Pro Tyr Leu
        195                 200                 205

Val Asn Leu Leu Pro Cys Leu Thr Arg Thr Ser Lys Arg Pro Glu Glu
    210                 215                 220

Ser Val Gln Glu Thr Leu Ala Ala Ala Val Pro Lys Ile Met Ala Ser
225                 230                 235                 240

Phe Gly Asn Phe Ala Asn Asp Asn Glu Ile Lys Val Leu Leu Lys Ala
                245                 250                 255

Phe Ile Ala Asn Leu Lys Ser Ser Pro Thr Ile Arg Arg Thr Ala Ala
            260                 265                 270

Ala Gly Ser Ala Val Ser Ile Cys Gln His Ser Arg Arg Thr Gln Tyr
        275                 280                 285

Phe Tyr Ser Trp Leu Leu Asn Val Leu Leu Gly Leu Leu Val Pro Val
    290                 295                 300

Glu Asp Glu His Ser Thr Leu Leu Ile Leu Gly Val Leu Leu Thr Leu
305                 310                 315                 320

Arg Tyr Leu Val Pro Leu Leu Gln Gln Gln Val Lys Asp Thr Ser Leu
                325                 330                 335

Lys Gly Ser Phe Gly Val Thr Arg Lys Glu Met Glu Val Ser Pro Ser
            340                 345                 350

Ala Glu Gln Leu Val Gln Val Tyr Glu Leu Thr Leu His His Thr Gln
        355                 360                 365
```

-continued

| | | | | | | | | | | | | | | |
|---|---|---|---|---|---|---|---|---|---|---|---|---|---|---|
| His | Gln | Asp | His | Asn | Val | Val | Thr | Gly | Ala | Leu | Glu | Leu | Leu | Gln | Gln |
| 370 | | | | | 375 | | | | | 380 | | | | | |
| Leu | Phe | Arg | Thr | Pro | Pro | Pro | Glu | Leu | Leu | Thr | Leu | Thr | Ala | Val | |
| 385 | | | | | 390 | | | | | 395 | | | | | 400 |
| Gly | Gly | Ile | Gly | Gln | Leu | Thr | Ala | Ala | Lys | Glu | Glu | Ser | Gly | Gly | Arg |
| | | | | 405 | | | | | 410 | | | | | 415 | |
| Ser | Arg | Ser | Gly | Ser | Ile | Val | Glu | Leu | Ile | Ala | Gly | Gly | Gly | Ser | Ser |
| | | | 420 | | | | | 425 | | | | | 430 | | |
| Cys | Ser | Pro | Val | Leu | Ser | Arg | Lys | Gln | Lys | Gly | Lys | Val | Leu | Leu | Gly |
| | | 435 | | | | | 440 | | | | | 445 | | | |
| Glu | Glu | Glu | Ala | Leu | Glu | Asp | Asp | Ser | Glu | Ser | Arg | Ser | Asp | Val | Ser |
| 450 | | | | | 455 | | | | | 460 | | | | | |
| Ser | Ser | Ala | Leu | Thr | Ala | Ser | Val | Lys | Asp | Glu | Ile | Ser | Gly | Glu | Leu |
| 465 | | | | | 470 | | | | | 475 | | | | | 480 |
| Ala | Ala | Ser | Ser | Gly | Val | Ser | Thr | Pro | Gly | Ser | Ala | Gly | His | Asp | Ile |
| | | | | 485 | | | | | 490 | | | | | 495 | |
| Ile | Thr | Glu | Gln | Pro | Arg | Ser | Gln | His | Thr | Leu | Gln | Ala | Asp | Ser | Leu |
| | | | 500 | | | | | 505 | | | | | 510 | | |
| Asp | Leu | Ala | Ser | Cys | Asp | Leu | Thr | Ser | Ser | Ala | Thr | Asp | Gly | Asp | Glu |
| | | 515 | | | | | 520 | | | | | 525 | | | |
| Glu | Asp | Ile | Leu | Ser | His | Ser | Ser | Ser | Gln | Val | Ser | Ala | Val | Pro | Ser |
| 530 | | | | | 535 | | | | | 540 | | | | | |
| Asp | Pro | Ala | Met | Asp | Leu | Asn | Asp | Gly | Thr | Gln | Ala | Ser | Ser | Pro | Ile |
| 545 | | | | | 550 | | | | | 555 | | | | | 560 |
| Ser | Asp | Ser | Ser | Gln | Thr | Thr | Thr | Glu | Gly | Pro | Asp | Ser | Ala | Val | Thr |
| | | | | 565 | | | | | 570 | | | | | 575 | |
| Pro | Ser | Asp | Ser | Ser | Glu | Ile | Val | Leu | Asp | Gly | Thr | Asp | Asn | Gln | Tyr |
| | | | 580 | | | | | 585 | | | | | 590 | | |
| Leu | Gly | Leu | Gln | Ile | Gly | Gln | Pro | Gln | Asp | Glu | Asp | Glu | Glu | Ala | Thr |
| | | | | 595 | | | | | 600 | | | | | 605 | |
| Gly | Ile | Leu | Pro | Asp | Glu | Ala | Ser | Glu | Ala | Phe | Arg | Asn | Ser | Ser | Met |
| | | 610 | | | | | 615 | | | | | 620 | | | |
| Ala | Leu | Gln | Gln | Ala | His | Leu | Leu | Lys | Asn | Met | Ser | His | Cys | Arg | Gln |
| 625 | | | | | 630 | | | | | 635 | | | | | 640 |
| Pro | Ser | Asp | Ser | Ser | Val | Asp | Lys | Phe | Val | Leu | Arg | Asp | Glu | Ala | Thr |
| | | | | 645 | | | | | 650 | | | | | 655 | |
| Glu | Pro | Gly | Asp | Gln | Glu | Asn | Lys | Pro | Cys | Arg | Ile | Lys | Gly | Asp | Ile |
| | | | 660 | | | | | 665 | | | | | 670 | | |
| Gly | Gln | Ser | Thr | Asp | Asp | Asp | Ser | Ala | Pro | Leu | Val | His | Ser | Val | Arg |
| | | | 675 | | | | | 680 | | | | | 685 | | |
| Leu | Leu | Ser | Ala | Ser | Phe | Leu | Leu | Thr | Gly | Gly | Lys | Asn | Val | Leu | Val |
| | | 690 | | | | | 695 | | | | | 700 | | | |
| Pro | Asp | Arg | Asp | Val | Arg | Val | Ser | Val | Lys | Ala | Leu | Ala | Leu | Ser | Cys |
| 705 | | | | | 710 | | | | | 715 | | | | | 720 |
| Val | Gly | Ala | Ala | Val | Ala | Leu | His | Pro | Glu | Ser | Phe | Phe | Ser | Lys | Leu |
| | | | | 725 | | | | | 730 | | | | | 735 | |
| Tyr | Lys | Val | Pro | Leu | Asp | Thr | Thr | Glu | Tyr | Pro | Glu | Glu | Gln | Tyr | Val |
| | | | 740 | | | | | 745 | | | | | 750 | | |
| Ser | Asp | Ile | Leu | Asn | Tyr | Ile | Asp | His | Gly | Asp | Pro | Gln | Val | Arg | Gly |
| | | | 755 | | | | | 760 | | | | | 765 | | |
| Ala | Thr | Ala | Ile | Leu | Cys | Gly | Thr | Leu | Ile | Cys | Ser | Ile | Leu | Ser | Arg |
| | | | 770 | | | | | 775 | | | | | 780 | | |
| Ser | Arg | Phe | His | Val | Gly | Asp | Trp | Met | Gly | Thr | Ile | Arg | Thr | Leu | Thr |
| 785 | | | | | 790 | | | | | 795 | | | | | 800 |

-continued

| | | | | | | | | | | | | | | |
|---|---|---|---|---|---|---|---|---|---|---|---|---|---|---|
|Gly|Asn|Thr|Phe|Ser<br>805|Leu|Ala|Asp|Cys<br>810|Ile|Pro|Leu|Leu|Arg|Lys<br>815|Thr|
|Leu|Lys|Asp|Glu<br>820|Ser|Ser|Val|Thr|Cys<br>825|Lys|Leu|Ala|Cys|Thr<br>830|Ala|Val|
|Arg|Asn|Cys<br>835|Val|Met|Ser|Leu|Cys<br>840|Ser|Ser|Ser|Tyr|Ser<br>845|Glu|Leu|Gly|
|Leu|Gln<br>850|Leu|Ile|Ile|Asp|Val<br>855|Leu|Thr|Leu|Arg|Asn<br>860|Ser|Ser|Tyr|Trp|
|Leu<br>865|Val|Arg|Thr|Glu|Leu<br>870|Leu|Glu|Thr|Leu|Ala<br>875|Glu|Ile|Asp|Phe|Arg<br>880|
|Leu|Val|Ser|Phe|Leu<br>885|Glu|Ala|Lys|Ala|Glu<br>890|Asn|Leu|His|Arg|Gly<br>895|Ala|
|His|His|Tyr|Thr<br>900|Gly|Leu|Leu|Lys|Leu<br>905|Gln|Glu|Arg|Val|Leu<br>910|Asn|Asn|
|Val|Val|Ile<br>915|His|Leu|Leu|Gly|Asp<br>920|Glu|Asp|Pro|Arg|Val<br>925|Arg|His|Val|
|Ala|Ala<br>930|Ala|Ser|Leu|Ile|Arg<br>935|Leu|Val|Pro|Lys|Leu<br>940|Phe|Tyr|Lys|Cys|
|Asp<br>945|Gln|Gly|Gln|Ala|Asp<br>950|Pro|Val|Val|Ala|Val<br>955|Ala|Arg|Asp|Gln|Ser<br>960|
|Ser|Val|Tyr|Leu|Lys<br>965|Leu|Leu|Met|His|Glu<br>970|Thr|Gln|Pro|Pro|Ser<br>975|His|
|Phe|Ser|Val|Ser<br>980|Thr|Ile|Thr|Arg|Ile<br>985|Tyr|Arg|Gly|Tyr|Asn<br>990|Leu|Leu|
|Pro|Ser|Ile|Thr<br>995|Asp|Val|Thr|Met|Glu<br>1000|Asn|Asn|Leu|Ser|Arg<br>1005|Val|Ile|
|Ala|Ala|Val<br>1010|Ser|His|Glu|Leu|Ile<br>1015|Thr|Ser|Thr|Thr|Arg<br>1020|Ala|Leu|Thr|
|Phe|Gly|Cys|Cys<br>1025|Glu|Ala|Leu|Cys|Leu<br>1030|Leu|Ser|Thr|Ala|Phe<br>1035|Pro|Val<br>1040|
|Cys|Ile|Trp|Ser|Leu<br>1045|Gly|Trp|His|Cys|Gly<br>1050|Val|Pro|Pro|Leu|Ser<br>1055|Ala|
|Ser|Asp|Glu|Ser<br>1060|Arg|Lys|Ser|Cys|Thr<br>1065|Val|Gly|Met|Ala|Thr<br>1070|Met|Ile|
|Leu|Thr|Leu|Leu<br>1075|Ser|Ser|Ala|Trp|Phe<br>1080|Pro|Leu|Asp|Leu|Ser<br>1085|Ala|His|
|Gln|Asp<br>1090|Ala|Leu|Ile|Leu|Ala<br>1095|Gly|Asn|Leu|Leu|Ala<br>1100|Ala|Ser|Ala|Pro|
|Lys|Ser<br>1105|Leu|Arg|Ser|Ser|Trp<br>1110|Ala|Ser|Glu|Glu|Glu<br>1115|Ala|Asn|Pro|Ala<br>1120|
|Ala|Thr|Lys|Gln|Glu<br>1125|Glu|Val|Trp|Pro|Ala<br>1130|Leu|Gly|Asp|Arg|Ala<br>1135|Leu|
|Val|Pro|Met|Val|Glu<br>1140|Gln|Leu|Phe|Ser|His<br>1145|Leu|Leu|Lys|Val|Ile<br>1150|Asn|
|Ile|Cys|Ala|His|Val<br>1155|Leu|Asp|Asp|Val|Ala<br>1160|Pro|Gly|Pro|Ala|Ile<br>1165|Lys|
|Ala|Ala|Leu|Pro<br>1170|Ser|Leu|Thr|Asn|Pro<br>1175|Pro|Ser|Leu|Ser|Pro<br>1180|Ile|Arg|
|Arg|Lys<br>1185|Gly|Lys|Glu|Lys|Glu<br>1190|Pro|Gly|Glu|Gln|Ala<br>1195|Ser|Val|Pro|Leu<br>1200|
|Ser|Pro|Lys|Lys|Gly<br>1205|Ser|Glu|Ala|Ser|Ala<br>1210|Ala|Ser|Arg|Gln|Ser<br>1215|Asp|
|Thr|Ser|Gly|Pro|Val|Thr|Thr|Ser|Lys|Ser|Ser|Ser|Leu|Gly|Ser|Phe|

-continued

```
              1220                    1225                    1230
Tyr His Leu Pro Ser Tyr Leu Arg Leu His Asp Val Leu Lys Ala Thr
         1235                    1240                    1245
His Ala Asn Tyr Lys Val Thr Leu Asp Leu Gln Asn Ser Thr Glu Lys
         1250                    1255                    1260
Phe Gly Gly Phe Leu Arg Ser Ala Leu Asp Val Leu Ser Gln Ile Leu
1265                    1270                    1275                    1280
Glu Leu Ala Thr Leu Gln Asp Ile Gly Lys Cys Val Glu Glu Ile Leu
                   1285                    1290                    1295
Gly Tyr Leu Lys Ser Cys Phe Ser Arg Glu Pro Met Met Ala Thr Val
              1300                    1305                    1310
Cys Val Gln Gln Leu Leu Lys Thr Leu Phe Gly Thr Asn Leu Ala Ser
         1315                    1320                    1325
Gln Phe Asp Gly Leu Ser Ser Asn Pro Ser Lys Ser Gln Gly Arg Ala
         1330                    1335                    1340
Gln Arg Leu Gly Ser Ser Ser Val Arg Pro Gly Leu Tyr His Tyr Cys
1345                    1350                    1355                    1360
Phe Met Ala Pro Tyr Thr His Phe Thr Gln Ala Leu Ala Asp Ala Ser
                   1365                    1370                    1375
Leu Arg Asn Met Val Gln Ala Glu Gln Glu Asn Asp Thr Ser Gly Trp
              1380                    1385                    1390
Phe Asp Val Leu Gln Lys Val Ser Thr Gln Leu Lys Thr Asn Leu Thr
         1395                    1400                    1405
Ser Val Thr Lys Asn Arg Ala Asp Lys Asn Ala Ile His Asn His Ile
         1410                    1415                    1420
Arg Leu Phe Glu Pro Leu Val Ile Lys Ala Leu Lys Gln Tyr Thr Thr
1425                    1430                    1435                    1440
Thr Thr Cys Val Gln Leu Gln Lys Gln Val Leu Asp Leu Leu Ala Gln
                   1445                    1450                    1455
Leu Val Gln Leu Arg Val Asn Tyr Cys Leu Leu Asp Ser Asp Gln Val
              1460                    1465                    1470
Phe Ile Gly Phe Val Leu Lys Gln Phe Glu Tyr Ile Glu Val Gly Gln
         1475                    1480                    1485
Phe Arg Glu Ser Glu Ala Ile Ile Pro Asn Ile Phe Phe Phe Leu Val
         1490                    1495                    1500
Leu Leu Ser Tyr Glu Arg Tyr His Ser Lys Gln Ile Ile Gly Ile Pro
1505                    1510                    1515                    1520
Lys Ile Ile Gln Leu Cys Asp Gly Ile Met Ala Ser Gly Arg Lys Ala
                   1525                    1530                    1535
Val Thr His Ala Ile Pro Ala Leu Gln Pro Ile Val His Asp Leu Phe
              1540                    1545                    1550
Val Leu Arg Gly Thr Asn Lys Ala Asp Ala Gly Lys Glu Leu Glu Thr
         1555                    1560                    1565
Gln Lys Glu Val Val Val Ser Met Leu Leu Arg Leu Ile Gln Tyr His
         1570                    1575                    1580
Gln Val Leu Glu Met Phe Ile Leu Val Leu Gln Gln Cys His Lys Glu
1585                    1590                    1595                    1600
Asn Glu Asp Lys Trp Lys Arg Leu Ser Arg Gln Ile Ala Asp Ile Ile
                   1605                    1610                    1615
Leu Pro Met Leu Ala Lys Gln Gln Met His Ile Asp Ser His Glu Ala
              1620                    1625                    1630
Leu Gly Val Leu Asn Thr Leu Phe Glu Ile Leu Ala Pro Ser Ser Leu
         1635                    1640                    1645
```

-continued

```
Arg Pro Val Asp Met Leu Leu Arg Ser Met Phe Val Thr Pro Asn Thr
    1650                1655                1660
Met Ala Ser Val Ser Thr Val Gln Leu Trp Ile Ser Gly Ile Leu Ala
1665            1670                1675                1680
Ile Leu Arg Val Leu Ile Ser Gln Ser Thr Glu Asp Ile Val Leu Ser
        1685                1690                1695
Arg Ile Gln Glu Leu Ser Phe Ser Pro Tyr Leu Ile Ser Cys Thr Val
        1700                1705                1710
Ile Asn Arg Leu Arg Asp Gly Asp Ser Thr Ser Thr Leu Glu Glu His
        1715                1720                1725
Ser Glu Gly Lys Gln Ile Lys Asn Leu Pro Glu Glu Thr Phe Ser Arg
        1730                1735                1740
Phe Leu Leu Gln Leu Val Gly Ile Leu Leu Glu Asp Ile Val Thr Lys
1745            1750                1755                1760
Gln Leu Lys Val Glu Met Ser Glu Gln Gln His Thr Phe Tyr Cys Gln
        1765                1770                1775
Glu Leu Gly Thr Leu Leu Met Cys Leu Ile His Ile Phe Lys Ser Gly
        1780                1785                1790
Met Phe Arg Arg Ile Thr Ala Ala Ala Thr Arg Leu Phe Arg Ser Asp
        1795                1800                1805
Gly Cys Gly Gly Ser Phe Tyr Thr Leu Asp Ser Leu Asn Leu Arg Ala
        1810                1815                1820
Arg Ser Met Ile Thr Thr His Pro Ala Leu Val Leu Leu Trp Cys Gln
1825            1830                1835                1840
Ile Leu Leu Leu Val Asn His Thr Asp Tyr Arg Trp Trp Ala Glu Val
            1845                1850                1855
Gln Gln Thr Pro Lys Arg His Ser Leu Ser Ser Thr Lys Leu Leu Ser
        1860                1865                1870
Pro Gln Met Ser Gly Glu Glu Asp Ser Asp Leu Ala Ala Lys Leu
        1875                1880                1885
Gly Met Cys Asn Arg Glu Ile Val Arg Arg Gly Ala Leu Ile Leu Phe
        1890                1895                1900
Cys Asp Tyr Val Cys Gln Asn Leu His Asp Ser Glu His Leu Thr Trp
1905            1910                1915                1920
Leu Ile Val Asn His Ile Gln Asp Leu Ile Ser Leu Ser His Glu Pro
            1925                1930                1935
Pro Val Gln Asp Phe Ile Ser Ala Val His Arg Asn Ser Ala Ala Ser
            1940                1945                1950
Gly Leu Phe Ile Gln Ala Ile Gln Ser Arg Cys Glu Asn Leu Ser Thr
        1955                1960                1965
Pro Thr Met Leu Lys Lys Thr Leu Gln Cys Leu Glu Gly Ile His Leu
    1970                1975                1980
Ser Gln Ser Gly Ala Val Leu Thr Leu Tyr Val Asp Arg Leu Leu Cys
1985            1990                1995                2000
Thr Pro Phe Arg Val Leu Ala Arg Met Val Asp Ile Leu Ala Cys Arg
            2005                2010                2015
Arg Val Glu Met Leu Leu Ala Ala Asn Leu Gln Ser Ser Met Ala Gln
            2020                2025                2030
Leu Pro Met Glu Glu Leu Asn Arg Ile Gln Glu Tyr Leu Gln Ser Ser
        2035                2040                2045
Gly Leu Ala Gln Arg His Gln Arg Leu Tyr Ser Leu Leu Asp Arg Phe
        2050                2055                2060
Arg Leu Ser Thr Met Gln Asp Ser Leu Ser Pro Ser Pro Pro Val Ser
2065            2070                2075                2080
```

Ser His Pro Leu Asp Gly Asp Gly His Val Ser Leu Glu Thr Val Ser
               2085                2090                2095

Pro Asp Lys Asp Trp Tyr Val His Leu Val Lys Ser Gln Cys Trp Thr
            2100                2105                2110

Arg Ser Asp Ser Ala Leu Leu Glu Gly Ala Glu Leu Val Asn Arg Ile
            2115                2120                2125

Pro Ala Glu Asp Met Asn Ala Phe Met Met Asn Ser Glu Phe Asn Leu
            2130                2135                2140

Ser Leu Leu Ala Pro Cys Leu Ser Leu Gly Met Ser Glu Ile Ser Gly
2145            2150                2155                2160

Gly Gln Lys Ser Ala Leu Phe Glu Ala Ala Arg Glu Val Thr Leu Ala
                2165                2170                2175

Arg Val Ser Gly Thr Val Gln Gln Leu Pro Ala Val His His Val Phe
            2180                2185                2190

Gln Pro Glu Leu Pro Ala Glu Pro Ala Ala Tyr Trp Ser Lys Leu Asn
            2195                2200                2205

Asp Leu Phe Gly Asp Ala Ala Leu Tyr Gln Ser Leu Pro Thr Leu Ala
            2210                2215                2220

Arg Ala Leu Ala Gln Tyr Leu Val Val Val Ser Lys Leu Pro Ser His
2225            2230                2235                2240

Leu His Leu Pro Pro Glu Lys Glu Lys Asp Ile Val Lys Phe Val Val
                2245                2250                2255

Ala Thr Leu Glu Ala Leu Ser Trp His Leu Ile His Glu Gln Ile Pro
            2260                2265                2270

Leu Ser Leu Asp Leu Gln Ala Gly Leu Asp Cys Cys Cys Leu Ala Leu
            2275                2280                2285

Gln Leu Pro Gly Leu Trp Ser Val Val Ser Ser Thr Glu Phe Val Thr
            2290                2295                2300

His Ala Cys Ser Leu Ile Tyr Cys Val His Phe Ile Leu Glu Ala Val
2305            2310                2315                2320

Ala Val Gln Pro Gly Glu Gln Leu Leu Ser Pro Glu Arg Arg Thr Asn
                2325                2330                2335

Thr Pro Lys Ala Ile Ser Glu Glu Glu Glu Val Asp Pro Asn Thr
            2340                2345                2350

Gln Asn Pro Lys Tyr Ile Thr Ala Ala Cys Glu Met Val Ala Glu Met
            2355                2360                2365

Val Glu Ser Leu Gln Ser Val Leu Ala Leu Gly His Lys Arg Asn Ser
2370            2375                2380

Gly Val Pro Ala Phe Leu Thr Pro Leu Leu Arg Asn Ile Ile Ile Ser
2385            2390                2395                2400

Leu Ala Arg Leu Pro Leu Val Asn Ser Tyr Thr Arg Val Pro Pro Leu
            2405                2410                2415

Val Trp Lys Leu Gly Trp Ser Pro Lys Pro Gly Gly Asp Phe Gly Thr
            2420                2425                2430

Ala Phe Pro Glu Ile Pro Val Glu Phe Leu Gln Glu Lys Glu Val Phe
            2435                2440                2445

Lys Glu Phe Ile Tyr Arg Ile Asn Thr Leu Gly Trp Thr Ser Arg Thr
            2450                2455                2460

Gln Phe Glu Glu Thr Trp Ala Thr Leu Leu Gly Val Leu Val Thr Gln
2465            2470                2475                2480

Pro Leu Val Met Glu Gln Glu Glu Ser Pro Pro Glu Glu Asp Thr Glu
            2485                2490                2495

Arg Thr Gln Ile Asn Val Leu Ala Val Gln Ala Ile Thr Ser Leu Val

-continued

| | 2500 | | | | | 2505 | | | | | 2510 | | |
|---|---|---|---|---|---|---|---|---|---|---|---|---|---|
| Leu | Ser | Ala | Met | Thr | Val | Pro | Val | Ala | Gly | Asn | Pro | Ala | Val | Ser | Cys |
| | | 2515 | | | | 2520 | | | | 2525 | | | |
| Leu | Glu | Gln | Gln | Pro | Arg | Asn | Lys | Pro | Leu | Lys | Ala | Leu | Asp | Thr | Arg |
| | | 2530 | | | | 2535 | | | | 2540 | | | |
| Phe | Gly | Arg | Lys | Leu | Ser | Ile | Ile | Arg | Gly | Ile | Val | Glu | Gln | Glu | Ile |
| 2545 | | | | 2550 | | | | 2555 | | | | | | 2560 |
| Gln | Ala | Met | Val | Ser | Lys | Arg | Glu | Asn | Ile | Ala | Thr | His | His | Leu | Tyr |
| | | | | 2565 | | | | 2570 | | | | | 2575 |
| Gln | Ala | Trp | Asp | Pro | Val | Pro | Ser | Leu | Ser | Pro | Ala | Thr | Thr | Gly | Ala |
| | | | 2580 | | | | 2585 | | | | | 2590 |
| Leu | Ile | Ser | His | Glu | Lys | Leu | Leu | Leu | Gln | Ile | Asn | Pro | Glu | Arg | Glu |
| | | 2595 | | | | 2600 | | | | | 2605 |
| Leu | Gly | Ser | Met | Ser | Tyr | Lys | Leu | Gly | Gln | Val | Ser | Ile | His | Ser | Val |
| | 2610 | | | | | 2615 | | | | 2620 | | | |
| Trp | Leu | Gly | Asn | Ser | Ile | Thr | Pro | Leu | Arg | Glu | Glu | Glu | Trp | Asp | Glu |
| 2625 | | | | 2630 | | | | 2635 | | | | | | 2640 |
| Glu | Glu | Glu | Glu | Glu | Ala | Asp | Ala | Pro | Ala | Pro | Ser | Ser | Pro | Pro | Thr |
| | | | | 2645 | | | | 2650 | | | | | 2655 |
| Ser | Pro | Val | Asn | Ser | Arg | Lys | His | Arg | Ala | Gly | Val | Asp | Ile | His | Ser |
| | | | 2660 | | | | 2665 | | | | | 2670 |
| Cys | Ser | Gln | Phe | Leu | Leu | Glu | Leu | Tyr | Ser | Arg | Trp | Ile | Leu | Pro | Ser |
| | | 2675 | | | | 2680 | | | | | 2685 |
| Ser | Ser | Ala | Arg | Arg | Thr | Pro | Ala | Ile | Leu | Ile | Ser | Glu | Val | Val | Arg |
| | 2690 | | | | | 2695 | | | | 2700 | |
| Ser | Leu | Leu | Val | Val | Ser | Asp | Leu | Phe | Thr | Glu | Arg | Asn | Gln | Phe | Glu |
| 2705 | | | | 2710 | | | | 2715 | | | | | 2720 |
| Leu | Met | Tyr | Val | Thr | Leu | Thr | Glu | Leu | Arg | Arg | Val | His | Pro | Ser | Glu |
| | | | 2725 | | | | 2730 | | | | | 2735 |
| Asp | Glu | Ile | Leu | Ala | Gln | Tyr | Leu | Val | Pro | Ala | Thr | Cys | Lys | Ala | Ala |
| | | | 2740 | | | | 2745 | | | | 2750 | |
| Ala | Val | Leu | Gly | Met | Asp | Lys | Ala | Val | Ala | Glu | Pro | Val | Ser | Arg | Leu |
| | | 2755 | | | | 2760 | | | | 2765 | | |
| Leu | Glu | Ser | Thr | Leu | Arg | Ser | Ser | His | Leu | Pro | Ser | Arg | Val | Gly | Ala |
| | | 2770 | | | | 2775 | | | | | 2780 |
| Leu | His | Gly | Ile | Leu | Tyr | Val | Leu | Glu | Cys | Asp | Leu | Leu | Asp | Asp | Thr |
| 2785 | | | | 2790 | | | | 2795 | | | | | 2800 |
| Ala | Lys | Gln | Leu | Ile | Pro | Val | Ile | Ser | Asp | Tyr | Leu | Leu | Ser | Asn | Leu |
| | | | | 2805 | | | | 2810 | | | | | 2815 |
| Lys | Gly | Ile | Ala | His | Cys | Val | Asn | Ile | His | Ser | Gln | Gln | His | Val | Leu |
| | | | 2820 | | | | 2825 | | | | | 2830 |
| Val | Met | Cys | Ala | Thr | Ala | Phe | Tyr | Leu | Ile | Glu | Asn | Tyr | Pro | Leu | Asp |
| | 2835 | | | | | 2840 | | | | 2845 | | |
| Val | Gly | Pro | Glu | Phe | Ser | Ala | Ser | Ile | Ile | Gln | Met | Cys | Gly | Val | Met |
| | 2850 | | | | | 2855 | | | | | 2860 |
| Leu | Ser | Gly | Ser | Glu | Glu | Ser | Thr | Pro | Ser | Ile | Ile | Tyr | His | Cys | Ala |
| 2865 | | | | 2870 | | | | 2875 | | | | | 2880 |
| Leu | Arg | Gly | Leu | Glu | Arg | Leu | Leu | Leu | Ser | Glu | Gln | Leu | Ser | Arg | Leu |
| | | | 2885 | | | | 2890 | | | | | 2895 |
| Asp | Ala | Glu | Ser | Leu | Val | Lys | Leu | Ser | Val | Asp | Arg | Val | Asn | Val | His |
| | | | 2900 | | | | 2905 | | | | | 2910 |
| Ser | Pro | His | Arg | Ala | Met | Ala | Ala | Leu | Gly | Leu | Met | Leu | Thr | Cys | Met |
| | | 2915 | | | | 2920 | | | | | 2925 |

| Tyr | Thr | Gly | Lys | Glu | Lys | Val | Ser | Pro | Gly | Arg | Thr | Ser | Asp | Pro | Asn |
|---|---|---|---|---|---|---|---|---|---|---|---|---|---|---|---|
| | 2930 | | | | 2935 | | | | 2940 | | | | | | |

| Pro | Ala | Ala | Pro | Asp | Ser | Glu | Ser | Val | Ile | Val | Ala | Met | Glu | Arg | Val |
|---|---|---|---|---|---|---|---|---|---|---|---|---|---|---|---|
| 2945 | | | | | 2950 | | | | 2955 | | | | | | 2960 |

| Ser | Val | Leu | Phe | Asp | Arg | Ile | Arg | Lys | Gly | Phe | Pro | Cys | Glu | Ala | Arg |
|---|---|---|---|---|---|---|---|---|---|---|---|---|---|---|---|
| | | | | 2965 | | | | 2970 | | | | 2975 | | | |

| Val | Val | Ala | Arg | Ile | Leu | Pro | Gln | Phe | Leu | Asp | Asp | Phe | Phe | Pro | Pro |
|---|---|---|---|---|---|---|---|---|---|---|---|---|---|---|---|
| | | | 2980 | | | | | 2985 | | | | | 2990 | | |

| Gln | Asp | Ile | Met | Asn | Lys | Val | Ile | Gly | Glu | Phe | Leu | Ser | Asn | Gln | Gln |
|---|---|---|---|---|---|---|---|---|---|---|---|---|---|---|---|
| | | 2995 | | | | | 3000 | | | | | 3005 | | | |

| Pro | Tyr | Pro | Gln | Phe | Met | Ala | Thr | Val | Val | Tyr | Lys | Val | Phe | Gln | Thr |
|---|---|---|---|---|---|---|---|---|---|---|---|---|---|---|---|
| | | 3010 | | | | 3015 | | | | | 3020 | | | | |

| Leu | His | Ser | Thr | Gly | Gln | Ser | Ser | Met | Val | Arg | Asp | Trp | Val | Met | Leu |
|---|---|---|---|---|---|---|---|---|---|---|---|---|---|---|---|
| 3025 | | | | | 3030 | | | | | 3035 | | | | | 3040 |

| Ser | Leu | Ser | Asn | Phe | Thr | Gln | Arg | Ala | Pro | Val | Ala | Met | Ala | Thr | Trp |
|---|---|---|---|---|---|---|---|---|---|---|---|---|---|---|---|
| | | | | 3045 | | | | | 3050 | | | | | 3055 | |

| Ser | Leu | Ser | Cys | Phe | Phe | Val | Ser | Ala | Ser | Thr | Ser | Pro | Trp | Val | Ala |
|---|---|---|---|---|---|---|---|---|---|---|---|---|---|---|---|
| | | | 3060 | | | | | 3065 | | | | | 3070 | | |

| Ala | Ile | Leu | Pro | His | Val | Ile | Ser | Arg | Met | Gly | Lys | Leu | Glu | Gln | Val |
|---|---|---|---|---|---|---|---|---|---|---|---|---|---|---|---|
| | | 3075 | | | | | 3080 | | | | | 3085 | | | |

| Asp | Val | Asn | Leu | Phe | Cys | Leu | Val | Ala | Thr | Asp | Phe | Tyr | Arg | His | Gln |
|---|---|---|---|---|---|---|---|---|---|---|---|---|---|---|---|
| | 3090 | | | | | 3095 | | | | | 3100 | | | | |

| Ile | Glu | Glu | Glu | Leu | Asp | Arg | Arg | Ala | Phe | Gln | Ser | Val | Leu | Glu | Val |
|---|---|---|---|---|---|---|---|---|---|---|---|---|---|---|---|
| 3105 | | | | | 3110 | | | | | 3115 | | | | | 3120 |

| Val | Ala | Ala | Pro | Gly | Ser | Pro | Tyr | His | Arg | Leu | Leu | Thr | Cys | Leu | Arg |
|---|---|---|---|---|---|---|---|---|---|---|---|---|---|---|---|
| | | | | 3125 | | | | | 3130 | | | | | 3135 | |

| Asn | Val | His | Lys | Val | Thr | Thr | Cys |
|---|---|---|---|---|---|---|---|
| | | | | 3140 | | | |

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:7:

GAAAAGCTGA TGAAGGCT         18

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:8:

CTGCTGAAAC GACTTGAG         18

( 2 ) INFORMATION FOR SEQ ID NO:9:

( i ) SEQUENCE CHARACTERISTICS:
        ( A ) LENGTH: 18 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:9:

CACCGCCGCT GCCAGGTC         18

( 2 ) INFORMATION FOR SEQ ID NO:10:

( i ) SEQUENCE CHARACTERISTICS:
        ( A ) LENGTH: 18 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:10:

GGTCGGTGCA GCGGTTCC                                                                                      18

( 2 ) INFORMATION FOR SEQ ID NO:11:

( i ) SEQUENCE CHARACTERISTICS:
        ( A ) LENGTH: 30 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:11:

CTGATGAAGG CTTTCGAGTC GCTCAAGTCG                                         30

( 2 ) INFORMATION FOR SEQ ID NO:12:

( i ) SEQUENCE CHARACTERISTICS:
        ( A ) LENGTH: 30 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:12:

CCTTCTTTGG TCGGTGCAGC GGTTCCTCTG                                         30

( 2 ) INFORMATION FOR SEQ ID NO:13:

( i ) SEQUENCE CHARACTERISTICS:
        ( A ) LENGTH: 29 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:13:

AGUAGUAGUA GAUCAAGCTT ATCGATACC                                         29

( 2 ) INFORMATION FOR SEQ ID NO:14:

( i ) SEQUENCE CHARACTERISTICS:
        ( A ) LENGTH: 29 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:14:

AUGAUGAUGA UGAUCGAATT CCTGCAGCC                                         29

( 2 ) INFORMATION FOR SEQ ID NO:15:

( i ) SEQUENCE CHARACTERISTICS:
        ( A ) LENGTH: 9997 base pairs
        ( B ) TYPE: nucleic acid
        ( C ) STRANDEDNESS: both
        ( D ) TOPOLOGY: linear ( i x ) FEATURE:
        ( A ) NAME/KEY: CDS
        ( B ) LOCATION: 90..9446

( x i ) SEQUENCE DESCRIPTION: SEQ ID NO:15:

|  |  |  |  |  |  |  |  |  |  | CCCA | TTCATTGCCT | TGCTGCTAAG | TGGCGCCGCG | TAGTGCCAGT | 44 |
|---|---|---|---|---|---|---|---|---|---|---|---|---|---|---|---|

AGGCTCCAAG TCTTCAGGGT CTGTCCCATC GGGCAGGAAG CCGTC ATG GCA ACC      98
                                                 Met Ala Thr
                                                  1

CTG GAA AAG CTG ATG AAG GCT TTC GAG TCG CTC AAG TCG TTT CAG CAG    146
Leu Glu Lys Leu Met Lys Ala Phe Glu Ser Leu Lys Ser Phe Gln Gln
     5           10              15

CAA CAG CAG CAG CAG CCA CCG CCG CAG CCG CCG CCA CCG CCG CCG CCG    194
Gln Gln Gln Gln Gln Pro Pro Pro Gln Pro Pro Pro Pro Pro Pro Pro
 20              25              30                         35

CCT CCG CCT CAA CCC CCT CAG CCG CCG CCT CAG GGG CAG CCG CCG CCG    242
Pro Pro Pro Gln Pro Pro Gln Pro Pro Pro Gln Gly Gln Pro Pro Pro
             40              45                          50

CCA CCA CCG CCG CTG CCA GGT CCG GCA GAG GAA CCG CTG CAC CGA CCA    290
Pro Pro Pro Pro Leu Pro Gly Pro Ala Glu Glu Pro Leu His Arg Pro
             55              60                     65

AAG AAG GAA CTC TCA GCC ACC AAG AAA GAC CGT GTG AAT CAT TGT CTA    338
Lys Lys Glu Leu Ser Ala Thr Lys Lys Asp Arg Val Asn His Cys Leu
         70              75                      80

ACA ATA TGT GAA AAC ATT GTG GCA CAG TCT CTC AGA AAT TCT CCA GAA    386
Thr Ile Cys Glu Asn Ile Val Ala Gln Ser Leu Arg Asn Ser Pro Glu
     85              90                      95

TTT CAG AAA CTC TTG GGC ATC GCT ATG GAA CTG TTT CTG CTG TGC AGT    434
Phe Gln Lys Leu Leu Gly Ile Ala Met Glu Leu Phe Leu Leu Cys Ser
100              105             110                         115

GAC GAT GCG GAG TCA GAT GTC AGA ATG GTG GCT GAT GAG TGC CTC AAC    482
Asp Asp Ala Glu Ser Asp Val Arg Met Val Ala Asp Glu Cys Leu Asn
                 120             125                     130

AAA GTC ATC AAA GCT TTG ATG GAT TCT AAT CTT CCA AGG CTA CAG TTA    530
Lys Val Ile Lys Ala Leu Met Asp Ser Asn Leu Pro Arg Leu Gln Leu
             135             140                     145

GAA CTC TAT AAG GAA ATT AAA AAG AAT GGT GCT CCT CGA AGT TTG CGT    578
Glu Leu Tyr Lys Glu Ile Lys Lys Asn Gly Ala Pro Arg Ser Leu Arg
         150             155                     160

GCT GCC CTG TGG AGG TTT GCT GAG CTG GCT CAC CTG GTT CGA CCT CAG    626
Ala Ala Leu Trp Arg Phe Ala Glu Leu Ala His Leu Val Arg Pro Gln
165              170                     175

AAG TGC AGG CCT TAC CTG GTG AAT CTT CTT CCA TGC CTG ACC CGA ACA    674
Lys Cys Arg Pro Tyr Leu Val Asn Leu Leu Pro Cys Leu Thr Arg Thr
180              185                     190                 195

AGC AAA AGA CCG GAG GAA TCA GTT CAG GAG ACC TTG GCT GCA GCT GTT    722
Ser Lys Arg Pro Glu Glu Ser Val Gln Glu Thr Leu Ala Ala Ala Val
                 200             205                     210

CCT AAA ATT ATG GCT TCT TTT GGC AAT TTC GCA AAT GAC AAT GAA ATT    770
Pro Lys Ile Met Ala Ser Phe Gly Asn Phe Ala Asn Asp Asn Glu Ile
             215             220                     225

AAG GTT CTG TTG AAA GCT TTC ATA GCA AAT CTG AAG TCA AGC TCT CCC    818
Lys Val Leu Leu Lys Ala Phe Ile Ala Asn Leu Lys Ser Ser Ser Pro
             230             235                     240

ACC GTG CGG CGG ACA GCA GCC GGC TCA GCC GTG AGC ATC TGC CAA CAT    866
Thr Val Arg Arg Thr Ala Ala Gly Ser Ala Val Ser Ile Cys Gln His
     245             250                     255

TCT AGG AGG ACA CAG TAC TTC TAC AAC TGG CTC CTT AAT GTC CTC CTA    914
Ser Arg Arg Thr Gln Tyr Phe Tyr Asn Trp Leu Leu Asn Val Leu Leu
260              265                     270                 275

GGT CTG CTG GTT CCC ATG GAA GAA GAG CAC TCC ACT CTC CTG ATC CTC    962
Gly Leu Leu Val Pro Met Glu Glu Glu His Ser Thr Leu Leu Ile Leu
                 280             285                     290

GGT GTG TTG CTC ACA TTG AGG TGT CTA GTG CCC TTG CTC CAG CAG CAG    1010

| | | | | | | | | | | | | | | |
|---|---|---|---|---|---|---|---|---|---|---|---|---|---|---|
| Gly | Val | Leu | Leu 295 | Thr | Leu | Arg | Cys 300 | Leu | Val | Pro | Leu | Leu 305 | Gln | Gln | Gln |

| | | | | | | | | | | | | | | | |
|---|---|---|---|---|---|---|---|---|---|---|---|---|---|---|---|
| GTC | AAG | GAC | ACA | AGT | CTA | AAA | GGC | AGC | TTT | GGG | GTG | ACA | CGG | AAA | GAA |
| Val | Lys | Asp 310 | Thr | Ser | Leu | Lys 315 | Gly | Ser | Phe | Gly | Val 320 | Thr | Arg | Lys | Glu |

1058

| ATG | GAA | GTC | TCT | CCT | TCT | ACA | GAG | CAG | CTT | GTC | CAG | GTT | TAT | GAA | CTG |
|---|---|---|---|---|---|---|---|---|---|---|---|---|---|---|---|
| Met | Glu 325 | Val | Ser | Pro | Ser | Thr 330 | Glu | Gln | Leu | Val | Gln 335 | Val | Tyr | Glu | Leu |

1106

| ACT | TTG | CAT | CAT | ACT | CAG | CAC | CAA | GAC | CAC | AAT | GTG | GTG | ACA | GGG | GCA |
|---|---|---|---|---|---|---|---|---|---|---|---|---|---|---|---|
| Thr 340 | Leu | His | His | Thr 345 | Gln | His | Gln | Asp | His 350 | Asn | Val | Val | Thr | Gly 355 | Ala |

1154

| CTG | GAG | CTC | CTG | CAG | CAG | CTC | TTC | CGT | ACC | CCT | CCA | CCT | GAA | CTC | CTG |
|---|---|---|---|---|---|---|---|---|---|---|---|---|---|---|---|
| Leu | Glu | Leu | Leu | Gln 360 | Gln | Leu | Phe | Arg | Thr 365 | Pro | Pro | Pro | Glu | Leu 370 | Leu |

1202

| CAA | GCA | CTG | ACC | ACA | CCA | GGA | GGG | CTT | GGG | CAG | CTC | ACT | CTG | GTT | CAA |
|---|---|---|---|---|---|---|---|---|---|---|---|---|---|---|---|
| Gln | Ala | Leu | Thr 375 | Thr | Pro | Gly | Gly | Leu 380 | Gly | Gln | Leu | Thr | Leu 385 | Val | Gln |

1250

| GAA | GAG | GCC | CGG | GGC | CGA | GGC | CGC | AGC | GGG | AGC | ATC | GTG | GAG | CTT | TTA |
|---|---|---|---|---|---|---|---|---|---|---|---|---|---|---|---|
| Glu | Glu | Ala 390 | Arg | Gly | Arg | Gly | Arg 395 | Ser | Gly | Ser | Ile | Val 400 | Glu | Leu | Leu |

1298

| GCT | GGA | GGG | GGT | TCC | TCG | TGC | AGC | CCT | GTC | CTC | TCA | AGA | AAG | CAG | AAA |
|---|---|---|---|---|---|---|---|---|---|---|---|---|---|---|---|
| Ala | Gly 405 | Gly | Gly | Ser | Ser 410 | Cys | Ser | Pro | Val | Leu 415 | Ser | Arg | Lys | Gln | Lys |

1346

| GGC | AAA | GTG | CTC | TTA | GGA | GAG | GAA | GAA | GCC | TTG | GAA | GAT | GAC | TCG | GAG |
|---|---|---|---|---|---|---|---|---|---|---|---|---|---|---|---|
| Gly 420 | Lys | Val | Leu | Leu | Gly 425 | Glu | Glu | Glu | Ala | Leu 430 | Glu | Asp | Asp | Ser | Glu 435 |

1394

| TCC | AGA | TCA | GAT | GTC | AGC | AGC | TCA | GCC | TTT | GCA | GCC | TCT | GTG | AAG | AGT |
|---|---|---|---|---|---|---|---|---|---|---|---|---|---|---|---|
| Ser | Arg | Ser | Asp 440 | Val | Ser | Ser | Ser | Ala 445 | Phe | Ala | Ala | Ser | Val 450 | Lys | Ser |

1442

| GAG | ATT | GGT | GGA | GAG | CTC | GCT | GCT | TCT | TCA | GGT | GTT | TCC | ACT | CCT | GGT |
|---|---|---|---|---|---|---|---|---|---|---|---|---|---|---|---|
| Glu | Ile | Gly | Gly 455 | Glu | Leu | Ala | Ala | Ser 460 | Ser | Gly | Val | Ser | Thr 465 | Pro | Gly |

1490

| TCT | GTT | GGT | CAC | GAC | ATC | ATC | ACT | GAG | CAG | CCT | AGA | TCC | CAG | CAC | ACA |
|---|---|---|---|---|---|---|---|---|---|---|---|---|---|---|---|
| Ser | Val | Gly 470 | His | Asp | Ile | Ile | Thr 475 | Glu | Gln | Pro | Arg | Ser 480 | Gln | His | Thr |

1538

| CTT | CAA | GCA | GAC | TCT | GTG | GAT | TTG | TCC | GGC | TGT | GAC | CTG | ACC | AGT | GCT |
|---|---|---|---|---|---|---|---|---|---|---|---|---|---|---|---|
| Leu | Gln | Ala | Asp 485 | Ser | Val | Asp | Leu | Ser 490 | Gly | Cys | Asp | Leu | Thr 495 | Ser | Ala |

1586

| GCT | ACT | GAT | GGG | GAT | GAG | GAG | GAC | ATC | TTG | AGC | CAC | AGC | TCC | AGC | CAG |
|---|---|---|---|---|---|---|---|---|---|---|---|---|---|---|---|
| Ala 500 | Thr | Asp | Gly | Asp | Glu 505 | Glu | Asp | Ile | Leu | Ser 510 | His | Ser | Ser | Ser | Gln 515 |

1634

| TTC | AGT | GCT | GTC | CCA | TCC | GAC | CCT | GCC | ATG | GAC | CTG | AAT | GAT | GGG | ACC |
|---|---|---|---|---|---|---|---|---|---|---|---|---|---|---|---|
| Phe | Ser | Ala | Val | Pro 520 | Ser | Asp | Pro | Ala | Met 525 | Asp | Leu | Asn | Asp | Gly 530 | Thr |

1682

| CAG | GCC | TCC | TCA | CCC | ATC | AGT | GAC | AGT | TCT | CAG | ACC | ACC | ACT | GAA | GGA |
|---|---|---|---|---|---|---|---|---|---|---|---|---|---|---|---|
| Gln | Ala | Ser | Ser 535 | Pro | Ile | Ser | Asp | Ser 540 | Ser | Gln | Thr | Thr | Thr 545 | Glu | Gly |

1730

| CCT | GAT | TCA | GCT | GTG | ACT | CCT | TCG | GAC | AGT | TCT | GAA | ATT | GTG | TTA | GAT |
|---|---|---|---|---|---|---|---|---|---|---|---|---|---|---|---|
| Pro | Asp | Ser | Ala | Val 550 | Thr | Pro | Ser | Asp | Ser 555 | Ser | Glu | Ile | Val | Leu 560 | Asp |

1778

| GGT | GCC | GAT | AGC | CAG | TAT | TTA | GGC | ATG | CAG | ATA | GGA | CAG | CCA | CAG | GAG |
|---|---|---|---|---|---|---|---|---|---|---|---|---|---|---|---|
| Gly | Ala | Asp | Ser | Gln 565 | Tyr | Leu | Gly | Met | Gln 570 | Ile | Gly | Gln | Pro | Gln 575 | Glu |

1826

| GAC | GAT | GAG | GAG | GGA | GCT | GCA | GGT | GTT | CTT | TCT | GGT | GAA | GTC | TCA | GAT |
|---|---|---|---|---|---|---|---|---|---|---|---|---|---|---|---|
| Asp | Asp | Glu | Glu 580 | Gly | Ala | Ala | Gly | Val 585 | Leu | Ser | Gly | Glu | Val 590 | Ser | Asp 595 |

1874

| GTT | TTC | AGA | AAC | TCT | TCT | CTG | GCC | CTT | CAA | CAG | GCA | CAC | TTG | TTG | GAA |
|---|---|---|---|---|---|---|---|---|---|---|---|---|---|---|---|
| Val | Phe | Arg | Asn | Ser 600 | Ser | Leu | Ala | Leu | Gln 605 | Gln | Ala | His | Leu | Leu 610 | Glu |

1922

| AGA | ATG | GGC | CAT | AGC | AGG | CAG | CCT | TCC | GAC | AGC | AGT | ATA | GAT | AAG | TAT |
|---|---|---|---|---|---|---|---|---|---|---|---|---|---|---|---|

1970

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Arg | Met | Gly | His 615 | Ser | Arg | Gln | Pro | Ser 620 | Asp | Ser | Ser | Ile | Asp 625 | Lys | Tyr | |
| GTA | ACA | AGA | GAT | GAG | GTT | GCT | GAA | GCC | AGT | GAT | CCA | GAA | AGC | AAG | CCT | 2018 |
| Val | Thr | Arg 630 | Asp | Glu | Val | Ala | Glu 635 | Ala | Ser | Asp | Pro | Glu 640 | Ser | Lys | Pro | |
| TGC | CGA | ATC | AAA | GGT | GAC | ATA | GGA | CAG | CCT | AAT | GAT | GAT | GAT | TCT | GCT | 2066 |
| Cys | Arg 645 | Ile | Lys | Gly | Asp | Ile 650 | Gly | Gln | Pro | Asn | Asp 655 | Asp | Asp | Ser | Ala | |
| CCT | CTG | GTA | CAT | TGT | GTC | CGT | CTT | TTA | TCT | GCT | TCC | TTT | TTG | TTA | ACT | 2114 |
| Pro 660 | Leu | Val | His | Cys | Val 665 | Arg | Leu | Leu | Ser | Ala 670 | Ser | Phe | Leu | Leu | Thr 675 | |
| GGT | GAA | AAG | AAA | GCA | CTG | GTT | CCA | GAC | AGA | GAC | GTG | AGA | GTC | AGT | GTG | 2162 |
| Gly | Glu | Lys | Lys | Ala 680 | Leu | Val | Pro | Asp | Arg 685 | Asp | Val | Arg | Val | Ser 690 | Val | |
| AAG | GCC | CTG | GCC | CTC | AGC | TGC | ATT | GGT | GCG | GCT | GTG | GCC | CTT | CAT | CCA | 2210 |
| Lys | Ala | Leu | Ala 695 | Leu | Ser | Cys | Ile | Gly 700 | Ala | Ala | Val | Ala | Leu 705 | His | Pro | |
| GAG | TCG | TTC | TTC | AGC | AGA | CTG | TAC | AAA | GTA | CCT | CTT | AAT | ACC | ACG | GAA | 2258 |
| Glu | Ser | Phe 710 | Phe | Ser | Arg | Leu | Tyr 715 | Lys | Val | Pro | Leu | Asn 720 | Thr | Thr | Glu | |
| AGT | ACT | GAG | GAA | CAG | TAT | GTT | TCT | GAC | ATC | TTG | AAC | TAC | ATC | GAT | CAT | 2306 |
| Ser | Thr 725 | Glu | Glu | Gln | Tyr | Val 730 | Ser | Asp | Ile | Leu | Asn 735 | Tyr | Ile | Asp | His | |
| GGA | GAC | CCA | CAG | GTC | CGA | GGA | GCT | ACT | GCC | ATT | CTC | TGT | GGG | ACC | CTT | 2354 |
| Gly 740 | Asp | Pro | Gln | Val | Arg 745 | Gly | Ala | Thr | Ala | Ile 750 | Leu | Cys | Gly | Thr | Leu 755 | |
| GTC | TAC | TCC | ATC | CTC | AGT | AGG | TCC | CGT | CTC | CGT | GTT | GGT | GAG | TGG | CTG | 2402 |
| Val | Tyr | Ser | Ile | Leu 760 | Ser | Arg | Ser | Arg | Leu 765 | Arg | Val | Gly | Glu | Trp | Leu 770 | |
| GGC | AAC | ATC | AGA | ACC | CTG | ACA | GGA | AAT | ACA | TTT | TCT | CTG | GTG | GAC | TGC | 2450 |
| Gly | Asn | Ile | Arg 775 | Thr | Leu | Thr | Gly | Asn 780 | Thr | Phe | Ser | Leu | Val 785 | Asp | Cys | |
| ATT | CCT | TTA | CTG | CAG | AAA | ACG | TTG | AAG | GAT | GAA | TCT | TCT | GTT | ACT | TGC | 2498 |
| Ile | Pro | Leu 790 | Leu | Gln | Lys | Thr | Leu 795 | Lys | Asp | Glu | Ser | Ser 800 | Val | Thr | Cys | |
| AAG | TTG | GCT | TGT | ACA | GCT | GTG | AGG | CAC | TGT | GTC | CTG | AGT | CTT | TGC | AGC | 2546 |
| Lys | Leu | Ala 805 | Cys | Thr | Ala | Val 810 | Arg | His | Cys | Val | Leu 815 | Ser | Leu | Cys | Ser | |
| AGC | AGC | TAC | AGT | GAC | TTG | GGA | TTA | CAA | CTG | CTT | ATT | GAT | ATG | CTG | CCT | 2594 |
| Ser | Ser 820 | Tyr | Ser | Asp | Leu | Gly 825 | Leu | Gln | Leu | Leu | Ile 830 | Asp | Met | Leu | Pro 835 | |
| CTG | AAG | AAC | AGC | TCC | TAC | TGG | CTG | GTG | AGG | ACC | GAA | CTG | CTG | GAC | ACT | 2642 |
| Leu | Lys | Asn | Ser | Ser 840 | Tyr | Trp | Leu | Val | Arg 845 | Thr | Glu | Leu | Leu | Asp 850 | Thr | |
| CTG | GCA | GAG | ATT | GAC | TTC | AGG | CTC | GTG | AGT | TTT | GAG | GCA | AAA | GCA | | 2690 |
| Leu | Ala | Glu | Ile | Asp 855 | Phe | Arg | Leu | Val | Ser 860 | Phe | Leu | Glu | Ala | Lys 865 | Ala | |
| GAA | AGT | TTA | CAC | CGA | GGG | GCT | CAT | CAT | TAT | ACA | GGG | TTT | CTA | AAA | CTA | 2738 |
| Glu | Ser | Leu 870 | His | Arg | Gly | Ala | His 875 | His | Tyr | Thr | Gly | Phe 880 | Leu | Lys | Leu | |
| CAA | GAA | CGA | GTA | CTC | AAT | AAT | GTG | GTC | ATT | TAT | TTG | CTT | GGA | GAT | GAA | 2786 |
| Gln | Glu | Arg | Val 885 | Leu | Asn | Asn | Val | Val 890 | Ile | Tyr | Leu | Leu | Gly 895 | Asp | Glu | |
| GAC | CCC | AGG | GTT | CGA | CAT | GTT | GCT | GCA | ACA | TCA | TTA | ACA | AGG | CTT | GTC | 2834 |
| Asp 900 | Pro | Arg | Val | Arg | His 905 | Val | Ala | Ala | Thr | Ser 910 | Leu | Thr | Arg | Leu | Val 915 | |
| CCA | AAG | CTG | TTT | TAC | AAG | TGT | GAC | CAA | GGA | CAA | GCT | GAT | CCA | GTT | GTG | 2882 |
| Pro | Lys | Leu | Phe | Tyr 920 | Lys | Cys | Asp | Gln | Gly 925 | Gln | Ala | Asp | Pro | Val 930 | Val | |
| GCT | GTA | GCG | AGG | GAT | CAG | AGC | AGT | GTC | TAC | CTG | AAG | CTC | CTC | ATG | CAT | 2930 |

| | | | | | | | | | | | | | | | | |
|---|---|---|---|---|---|---|---|---|---|---|---|---|---|---|---|---|
| Ala | Val | Ala | Arg 935 | Asp | Gln | Ser | Ser | Val 940 | Tyr | Leu | Lys | Leu | Leu 945 | Met | His | |

| GAG | ACC | CAG | CCA | CCA | TCA | CAC | TTT | TCT | GTC | AGC | ACC | ATC | ACC | AGA | ATC | 2978 |
|---|---|---|---|---|---|---|---|---|---|---|---|---|---|---|---|---|
| Glu | Thr | Gln 950 | Pro | Pro | Ser | His | Phe 955 | Ser | Val | Ser | Thr | Ile 960 | Thr | Arg | Ile | |

| TAT | AGA | GGC | TAT | AGC | TTA | CTG | CCA | AGT | ATA | ACA | GAT | GTC | ACC | ATG | GAA | 3026 |
|---|---|---|---|---|---|---|---|---|---|---|---|---|---|---|---|---|
| Tyr | Arg 965 | Gly | Tyr | Ser | Leu | Leu 970 | Pro | Ser | Ile | Thr | Asp 975 | Val | Thr | Met | Glu | |

| AAC | AAT | CTC | TCA | AGA | GTT | GTT | GCC | GCA | GTT | TCT | CAT | GAA | CTC | ATT | ACG | 3074 |
|---|---|---|---|---|---|---|---|---|---|---|---|---|---|---|---|---|
| Asn | Asn 980 | Leu | Ser | Arg | Val 985 | Val | Ala | Ala | Val 990 | Ser | His | Glu | Leu | Ile 995 | Thr | |

| TCA | ACA | ACA | CGG | GCA | CTC | ACA | TTT | GGA | TGC | TGT | GAA | GCC | TTG | TGT | CTT | 3122 |
|---|---|---|---|---|---|---|---|---|---|---|---|---|---|---|---|---|
| Ser | Thr | Thr | Arg 1000 | Ala | Leu | Thr | Phe | Gly | Cys 1005 | Cys | Glu | Ala | Leu | Cys 1010 | Leu | |

| CTC | TCA | GCA | GCC | TTT | CCA | GTT | TGC | ACT | TGG | AGT | TTA | GGA | TGG | CAC | TGT | 3170 |
|---|---|---|---|---|---|---|---|---|---|---|---|---|---|---|---|---|
| Leu | Ser | Ala | Ala 1015 | Phe | Pro | Val | Cys | Thr 1020 | Trp | Ser | Leu | Gly | Trp 1025 | His | Cys | |

| GGA | GTG | CCC | CCA | CTG | AGT | GCC | TCT | GAT | GAG | TCC | AGG | AAG | AGC | TGC | ACT | 3218 |
|---|---|---|---|---|---|---|---|---|---|---|---|---|---|---|---|---|
| Gly | Val | Pro | Pro 1030 | Leu | Ser | Ala | Ser | Asp 1035 | Glu | Ser | Arg | Lys | Ser 1040 | Cys | Thr | |

| GTT | GGG | ATG | GCC | TCC | ATG | ATT | CTC | ACC | TTG | CTT | TCA | TCA | GCT | TGG | TTC | 3266 |
|---|---|---|---|---|---|---|---|---|---|---|---|---|---|---|---|---|
| Val | Gly | Met 1045 | Ala | Ser | Met | Ile | Leu 1050 | Thr | Leu | Leu | Ser | Ser 1055 | Ala | Trp | Phe | |

| CCA | CTG | GAT | CTC | TCA | GCC | CAT | CAG | GAT | GCC | TTG | ATT | TTG | GCT | GGA | AAC | 3314 |
|---|---|---|---|---|---|---|---|---|---|---|---|---|---|---|---|---|
| Pro | Leu 1060 | Asp | Leu | Ser | Ala | His 1065 | Gln | Asp | Ala | Leu | Ile 1070 | Leu | Ala | Gly | Asn 1075 | |

| TTG | CTA | GCA | GCG | AGT | GCC | CCC | AAG | TCT | CTG | AGA | AGT | TCA | TGG | ACC | TCT | 3362 |
|---|---|---|---|---|---|---|---|---|---|---|---|---|---|---|---|---|
| Leu | Leu | Ala | Ala | Ser 1080 | Ala | Pro | Lys | Ser | Leu 1085 | Arg | Ser | Ser | Trp | Thr 1090 | Ser | |

| GAA | GAA | GAA | GCC | AAC | TCA | GCA | GCC | ACC | AGA | CAG | GAG | GAA | ATC | TGG | CCT | 3410 |
|---|---|---|---|---|---|---|---|---|---|---|---|---|---|---|---|---|
| Glu | Glu | Glu | Ala | Asn 1095 | Ser | Ala | Ala | Thr | Arg 1100 | Gln | Glu | Glu | Ile | Trp 1105 | Pro | |

| GCT | CTG | GGG | GAT | CGG | ACT | CTA | GTG | CCC | TTG | GTG | GAG | CAG | CTT | TTC | TCC | 3458 |
|---|---|---|---|---|---|---|---|---|---|---|---|---|---|---|---|---|
| Ala | Leu | Gly | Asp | Arg 1110 | Thr | Leu | Val | Pro | Leu 1115 | Val | Glu | Gln | Leu | Phe 1120 | Ser | |

| CAC | CTG | CTG | AAG | GTG | ATC | AAT | ATC | TGT | GCT | CAT | GTC | TTG | GAC | GAT | GTG | 3506 |
|---|---|---|---|---|---|---|---|---|---|---|---|---|---|---|---|---|
| His | Leu | Leu | Lys | Val 1125 | Ile | Asn | Ile | Cys | Ala 1130 | His | Val | Leu | Asp | Asp 1135 | Val | |

| ACT | CCT | GGA | CCA | GCA | ATC | AAG | GCA | GCC | TTG | CCT | TCT | CTA | ACA | AAC | CCC | 3554 |
|---|---|---|---|---|---|---|---|---|---|---|---|---|---|---|---|---|
| Thr | Pro | Gly | Pro 1140 | Ala | Ile | Lys | Ala | Ala 1145 | Leu | Pro | Ser | Leu | Thr 1150 | Asn | Pro 1155 | |

| CCT | TCT | CTA | AGT | CCT | ATT | CGA | CGG | AAA | GGG | AAG | GAG | AAA | GAA | CCT | GGA | 3602 |
|---|---|---|---|---|---|---|---|---|---|---|---|---|---|---|---|---|
| Pro | Ser | Leu | Ser | Pro 1160 | Ile | Arg | Arg | Lys | Gly 1165 | Lys | Glu | Lys | Glu | Pro 1170 | Gly | |

| GAA | CAA | GCT | TCT | ACT | CCA | ATG | AGT | CCC | AAG | AAA | GTT | GGT | GAG | GCC | AGT | 3650 |
|---|---|---|---|---|---|---|---|---|---|---|---|---|---|---|---|---|
| Glu | Gln | Ala | Ser 1175 | Thr | Pro | Met | Ser | Pro 1180 | Lys | Lys | Val | Gly | Glu 1185 | Ala | Ser | |

| GCA | GCC | TCT | CGA | CAA | TCA | GAC | ACC | TCA | GGA | CCT | GTC | ACA | GCA | AGT | AAA | 3698 |
|---|---|---|---|---|---|---|---|---|---|---|---|---|---|---|---|---|
| Ala | Ala | Ser | Arg 1190 | Gln | Ser | Asp | Thr | Ser 1195 | Gly | Pro | Val | Thr | Ala 1200 | Ser | Lys | |

| TCA | TCC | TCA | CTG | GGG | AGT | TTC | TAC | CAT | CTC | CCC | TCC | TAC | CTC | AAA | CTG | 3746 |
|---|---|---|---|---|---|---|---|---|---|---|---|---|---|---|---|---|
| Ser | Ser | Ser 1205 | Leu | Gly | Ser | Phe | Tyr 1210 | His | Leu | Pro | Ser | Tyr 1215 | Leu | Lys | Leu | |

| CAT | GAT | GTC | CTG | AAA | GCC | ACT | CAC | GCC | AAC | TAT | AAG | GTC | ACC | TTA | GAT | 3794 |
|---|---|---|---|---|---|---|---|---|---|---|---|---|---|---|---|---|
| His | Asp 1220 | Val | Leu | Lys | Ala | Thr 1225 | His | Ala | Asn | Tyr | Lys 1230 | Val | Thr | Leu | Asp 1235 | |

| CTT | CAG | AAC | AGC | ACT | GAA | AAG | TTT | GGG | GGG | TTC | CTG | CGC | TCT | GCC | TTG | 3842 |
|---|---|---|---|---|---|---|---|---|---|---|---|---|---|---|---|---|
| Leu | Gln | Asn | Ser | Thr | Glu 1240 | Lys | Phe | Gly | Gly | Phe 1245 | Leu | Arg | Ser | Ala | Leu 1250 | |

| GAC | GTC | CTT | TCT | CAG | ATT | CTA | GAG | CTG | GCG | ACA | CTG | CAG | GAC | ATT | GGA | 3890 |
|---|---|---|---|---|---|---|---|---|---|---|---|---|---|---|---|---|

```
Asp Val Leu Ser Gln Ile Leu Glu Leu Ala Thr Leu Gln Asp Ile Gly
    1255             1260                 1265

AAG TGT GTT GAA GAG GTC CTT GGA TAC CTG AAA TCC TGC TTT AGT CGA    3938
Lys Cys Val Glu Glu Val Leu Gly Tyr Leu Lys Ser Cys Phe Ser Arg
        1270             1275             1280

GAA CCA ATG ATG GCA ACT GTC TGT GTG CAG CAG CTA TTG AAG ACT CTC    3986
Glu Pro Met Met Ala Thr Val Cys Val Gln Gln Leu Leu Lys Thr Leu
    1285             1290             1295

TTT GGG ACA AAC TTA GCC TCA CAG TTT GAT GGC TTA TCT TCC AAC CCC    4034
Phe Gly Thr Asn Leu Ala Ser Gln Phe Asp Gly Leu Ser Ser Asn Pro
1300             1305             1310             1315

AGC AAG TCT CAG TGC CGA GCT CAG CGC CTT GGC TCT TCA AGT GTG AGG    4082
Ser Lys Ser Gln Cys Arg Ala Gln Arg Leu Gly Ser Ser Ser Val Arg
            1320             1325             1330

CCC GGC TTA TAT CAC TAC TGC TTC ATG GCA CCA TAC ACG CAC TTC ACA    4130
Pro Gly Leu Tyr His Tyr Cys Phe Met Ala Pro Tyr Thr His Phe Thr
                1335             1340             1345

CAG GCC TTG GCT GAC GCA AGC CTG AGG AAC ATG GTG CAG GCG GAG CAG    4178
Gln Ala Leu Ala Asp Ala Ser Leu Arg Asn Met Val Gln Ala Glu Gln
    1350             1355             1360

GAG CGT GAT GCC TCG GGG TGG TTT GAT GTA CTC CAG AAA GTG TCT GCC    4226
Glu Arg Asp Ala Ser Gly Trp Phe Asp Val Leu Gln Lys Val Ser Ala
    1365             1370             1375

CAA TTG AAG ACG AAC CTA ACA AGC GTC ACA AAG AAC CGT GCA GAT AAG    4274
Gln Leu Lys Thr Asn Leu Thr Ser Val Thr Lys Asn Arg Ala Asp Lys
1380             1385             1390             1395

AAT GCT ATT CAT AAT CAC ATT AGG TTA TTT GAG CCT CTT GTT ATA AAA    4322
Asn Ala Ile His Asn His Ile Arg Leu Phe Glu Pro Leu Val Ile Lys
                1400             1405             1410

GCA TTG AAG CAG TAC ACC ACG ACA ACA TCT GTA CAA TTG CAG AAG CAG    4370
Ala Leu Lys Gln Tyr Thr Thr Thr Thr Ser Val Gln Leu Gln Lys Gln
    1415             1420             1425

GTT TTG GAT TTG CTG GCA CAG CTG GTT CAG CTA CGG GTC AAT TAC TGT    4418
Val Leu Asp Leu Leu Ala Gln Leu Val Gln Leu Arg Val Asn Tyr Cys
    1430             1435             1440

CTA CTG GAT TCA GAC CAG GTG TTC ATC GGG TTT GTG CTG AAG CAG TTT    4466
Leu Leu Asp Ser Asp Gln Val Phe Ile Gly Phe Val Leu Lys Gln Phe
    1445             1450             1455

GAG TAC ATT GAA GTG GGC CAG TTC AGG GAA TCA GAG GCA ATT ATT CCA    4514
Glu Tyr Ile Glu Val Gly Gln Phe Arg Glu Ser Glu Ala Ile Ile Pro
1460             1465             1470             1475

AAT ATA TTT TTC TTC CTG GTA TTA CTG TCT TAT GAG CGC TAC CAT TCA    4562
Asn Ile Phe Phe Phe Leu Val Leu Leu Ser Tyr Glu Arg Tyr His Ser
                1480             1485             1490

AAA CAG ATC ATT GGA ATT CCT AAA ATC ATC CAG CTG TGT GAT GGC ATC    4610
Lys Gln Ile Ile Gly Ile Pro Lys Ile Ile Gln Leu Cys Asp Gly Ile
            1495             1500             1505

ATG GCC AGT GGA AGG AAG GCC GTT ACA CAT GCT ATA CCT GCT CTG CAG    4658
Met Ala Ser Gly Arg Lys Ala Val Thr His Ala Ile Pro Ala Leu Gln
        1510             1515             1520

CCC ATT GTC CAT GAC CTC TTT GTG TTA CGA GGA ACA AAT AAA GCT GAT    4706
Pro Ile Val His Asp Leu Phe Val Leu Arg Gly Thr Asn Lys Ala Asp
    1525             1530             1535

GCA GGG AAA GAG CTT GAG ACA CAG AAG GAG GTG GTG GTC TCC ATG CTG    4754
Ala Gly Lys Glu Leu Glu Thr Gln Lys Glu Val Val Val Ser Met Leu
1540             1545             1550             1555

TTA CGA CTC ATC CAG TAC CAT CAG GTG CTG GAG ATG TTC ATC TTG GTC    4802
Leu Arg Leu Ile Gln Tyr His Gln Val Leu Glu Met Phe Ile Leu Val
            1560             1565             1570

CTG CAG CAG TGC CAC AAG GAG AAT GAG GAC AAG TGG AAA CGG CTC TCT    4850
```

```
Leu Gln Gln Cys His Lys Glu Asn Glu Asp Lys Trp Lys Arg Leu Ser
            1575                1580                1585

CGG CAG GTC GCA GAC ATC ATC CTG CCC ATG TTG GCC AAG CAG CAG ATG      4898
Arg Gln Val Ala Asp Ile Ile Leu Pro Met Leu Ala Lys Gln Gln Met
        1590                1595                1600

CAT ATT GAC TCT CAT GAA GCC CTT GGA GTG TTA AAT ACC TTG TTT GAG      4946
His Ile Asp Ser His Glu Ala Leu Gly Val Leu Asn Thr Leu Phe Glu
        1605                1610                1615

ATT TTG GCT CCT TCC TCC CTA CGT CCT GTG GAC ATG CTT TTG CGG AGT      4994
Ile Leu Ala Pro Ser Ser Leu Arg Pro Val Asp Met Leu Leu Arg Ser
1620                1625                1630                1635

ATG TTC ATC ACT CCA AGC ACA ATG GCA TCT GTA AGC ACT GTG CAG CTG      5042
Met Phe Ile Thr Pro Ser Thr Met Ala Ser Val Ser Thr Val Gln Leu
            1640                1645                1650

TGG ATA TCT GGA ATC CTC GCC ATT CTG AGG GTT CTC ATT TCC CAG TCA      5090
Trp Ile Ser Gly Ile Leu Ala Ile Leu Arg Val Leu Ile Ser Gln Ser
            1655                1660                1665

ACC GAG GAC ATT GTT CTT TGT CGT ATT CAG GAG CTC TCC TTC TCT CCA      5138
Thr Glu Asp Ile Val Leu Cys Arg Ile Gln Glu Leu Ser Phe Ser Pro
            1670                1675                1680

CAC TTG CTC TCC TGT CCA GTG ATT AAC AGG TTA AGG GGT GGA GGC GGT      5186
His Leu Leu Ser Cys Pro Val Ile Asn Arg Leu Arg Gly Gly Gly Gly
            1685                1690                1695

AAT GTA ACA CTA GGA GAA TGC AGC GAA GGG AAA CAA AAG AGT TTG CCA      5234
Asn Val Thr Leu Gly Glu Cys Ser Glu Gly Lys Gln Lys Ser Leu Pro
1700                1705                1710                1715

GAA GAT ACA TTC TCA AGG TTT CTT TTA CAG CTG GTT GGT ATT CTT CTA      5282
Glu Asp Thr Phe Ser Arg Phe Leu Leu Gln Leu Val Gly Ile Leu Leu
                1720                1725                1730

GAA GAC ATC GTT ACA AAA CAG CTC AAA GTG GAC ATG AGT GAA CAG CAG      5330
Glu Asp Ile Val Thr Lys Gln Leu Lys Val Asp Met Ser Glu Gln Gln
            1735                1740                1745

CAT ACG TTC TAC TGC CAA GAG CTA GGC ACA CTG CTC ATG TGT CTG ATC      5378
His Thr Phe Tyr Cys Gln Glu Leu Gly Thr Leu Leu Met Cys Leu Ile
            1750                1755                1760

CAC ATA TTC AAA TCT GGA ATG TTC CGG AGA ATC ACA GCA GCT GCC ACT      5426
His Ile Phe Lys Ser Gly Met Phe Arg Arg Ile Thr Ala Ala Ala Thr
            1765                1770                1775

AGA CTC TTC ACC AGT GAT GGC TGT GAA GGC AGC TTC TAT ACT CTA GAG      5474
Arg Leu Phe Thr Ser Asp Gly Cys Glu Gly Ser Phe Tyr Thr Leu Glu
1780                1785                1790                1795

AGC CTG AAT GCA CGG GTC CGA TCC ATG GTG CCC ACG CAC CCA GCC CTG      5522
Ser Leu Asn Ala Arg Val Arg Ser Met Val Pro Thr His Pro Ala Leu
                1800                1805                1810

GTA CTG CTC TGG TGT CAG ATC CTA CTT CTC ATC AAC CAC ACT GAC CAC      5570
Val Leu Leu Trp Cys Gln Ile Leu Leu Leu Ile Asn His Thr Asp His
            1815                1820                1825

CGG TGG TGG GCA GAG GTG CAG CAG ACA CCC AAG AGA CAC AGT CTG TCC      5618
Arg Trp Trp Ala Glu Val Gln Gln Thr Pro Lys Arg His Ser Leu Ser
            1830                1835                1840

TGC ACG AAG TCA CTT AAC CCC CAG AAG TCT GGC GAA GAG GAG GAT TCT      5666
Cys Thr Lys Ser Leu Asn Pro Gln Lys Ser Gly Glu Glu Glu Asp Ser
            1845                1850                1855

GGC TCG GCA GCT CAG CTG GGA ATG TGC AAT AGA GAA ATA GTG CGA AGA      5714
Gly Ser Ala Ala Gln Leu Gly Met Cys Asn Arg Glu Ile Val Arg Arg
1860                1865                1870                1875

GGG GCC CTT ATT CTC TTC TGT GAT TAT GTC TGT CAG AAT CTC CAT GAC      5762
Gly Ala Leu Ile Leu Phe Cys Asp Tyr Val Cys Gln Asn Leu His Asp
                1880                1885                1890

TCA GAA CAC TTA ACA TGG CTC ATT GTG AAT CAC ATT CAA GAT CTG ATC      5810
```

```
Ser Glu His Leu Thr Trp Leu Ile Val Asn His Ile Gln Asp Leu Ile
        1895                1900                1905

AGC TTG TCT CAT GAG CCT CCA GTA CAA GAC TTT ATT AGT GCC ATT CAT      5858
Ser Leu Ser His Glu Pro Pro Val Gln Asp Phe Ile Ser Ala Ile His
        1910                1915                1920

CGT AAT TCT GCA GCT AGT GGT CTT TTT ATC CAG GCA ATT CAG TCT CGC      5906
Arg Asn Ser Ala Ala Ser Gly Leu Phe Ile Gln Ala Ile Gln Ser Arg
        1925                1930                1935

TGT GAA AAT CTT TCA ACG CCA ACC ACT CTG AAG AAA ACA CTT CAG TGC      5954
Cys Glu Asn Leu Ser Thr Pro Thr Thr Leu Lys Lys Thr Leu Gln Cys
1940                1945                1950                1955

TTG GAA GGC ATC CAT CTC AGC CAG TCT GGT GCT GTG CTC ACA CTA TAT      6002
Leu Glu Gly Ile His Leu Ser Gln Ser Gly Ala Val Leu Thr Leu Tyr
                1960                1965                1970

GTG GAC AGG CTC CTG GGC ACC CCC TTC CGT GCG CTG GCT CGC ATG GTC      6050
Val Asp Arg Leu Leu Gly Thr Pro Phe Arg Ala Leu Ala Arg Met Val
        1975                1980                1985

GAC ACC CTG GCC TGT CGC CGG GTA GAA ATG CTT TTG GCT GCA AAT TTA      6098
Asp Thr Leu Ala Cys Arg Arg Val Glu Met Leu Leu Ala Ala Asn Leu
        1990                1995                2000

CAG AGC AGC ATG GCC CAG TTG CCA GAG GAG GAA CTA AAC AGA ATC CAA      6146
Gln Ser Ser Met Ala Gln Leu Pro Glu Glu Glu Leu Asn Arg Ile Gln
    2005                2010                2015

GAA CAC CTC CAG AAC AGT GGG CTT GCA CAA AGA CAC CAA AGG CTC TAT      6194
Glu His Leu Gln Asn Ser Gly Leu Ala Gln Arg His Gln Arg Leu Tyr
2020                2025                2030                2035

TCA CTG CTG GAC AGA TTC CGA CTC TCT ACT GTG CAG GAC TCA CTT AGC      6242
Ser Leu Leu Asp Arg Phe Arg Leu Ser Thr Val Gln Asp Ser Leu Ser
            2040                2045                2050

CCC TTG CCC CCA GTC ACT TCC CAC CCA CTG GAT GGG GAT GGG CAC ACA      6290
Pro Leu Pro Pro Val Thr Ser His Pro Leu Asp Gly Asp Gly His Thr
        2055                2060                2065

TCT CTG GAA ACA GTG AGT CCA GAC AAA GAC TGG TAC CTC CAG CTT GTC      6338
Ser Leu Glu Thr Val Ser Pro Asp Lys Asp Trp Tyr Leu Gln Leu Val
        2070                2075                2080

AGA TCC CAG TGT TGG ACC AGA TCA GAT TCT GCA CTG CTG GAA GGT GCA      6386
Arg Ser Gln Cys Trp Thr Arg Ser Asp Ser Ala Leu Leu Glu Gly Ala
        2085                2090                2095

GAG CTG GTC AAC CGT ATC CCT GCT GAA GAT ATG AAT GAC TTC ATG ATG      6434
Glu Leu Val Asn Arg Ile Pro Ala Glu Asp Met Asn Asp Phe Met Met
2100                2105                2110                2115

AGC TCG GAG TTC AAC CTA AGC CTT TTG GCT CCC TGT TTA AGC CTT GGC      6482
Ser Ser Glu Phe Asn Leu Ser Leu Leu Ala Pro Cys Leu Ser Leu Gly
            2120                2125                2130

ATG AGC GAG ATT GCT AAT GGC CAA AAG AGT CCC CTC TTT GAA GCA GCC      6530
Met Ser Glu Ile Ala Asn Gly Gln Lys Ser Pro Leu Phe Glu Ala Ala
        2135                2140                2145

CGT GGG GTG ATT CTG AAC CGG GTG ACC AGT GTT GTT CAG CAG CTT CCT      6578
Arg Gly Val Ile Leu Asn Arg Val Thr Ser Val Val Gln Gln Leu Pro
        2150                2155                2160

GCT GTC CAT CAA GTC TTC CAG CCC TTC CTG CCT ATA GAG CCC ACG GCC      6626
Ala Val His Gln Val Phe Gln Pro Phe Leu Pro Ile Glu Pro Thr Ala
        2165                2170                2175

TAC TGG AAC AAG TTG AAT GAT CTG CTT GGT GAT ACC ACA TCA TAC CAG      6674
Tyr Trp Asn Lys Leu Asn Asp Leu Leu Gly Asp Thr Thr Ser Tyr Gln
2180                2185                2190                2195

TCT CTG ACC ATA CTT GCC CGT GCC CTG GCA CAG TAC CTG GTG GTG CTC      6722
Ser Leu Thr Ile Leu Ala Arg Ala Leu Ala Gln Tyr Leu Val Val Leu
            2200                2205                2210

TCC AAA GTG CCT GCT CAT TTG CAC CTT CCT CCT GAG AAG GAG GGG GAC      6770
```

-continued

| | | | | | | | | | | | | | | | | |
|---|---|---|---|---|---|---|---|---|---|---|---|---|---|---|---|---|
| Ser | Lys | Val | Pro | Ala | His | Leu | His | Leu | Pro | Pro | Glu | Lys | Glu | Gly | Asp | |
| | | 2215 | | | | | 2220 | | | | | 2225 | | | | |

| ACG | GTG | AAG | TTT | GTG | GTA | ATG | ACA | GTT | GAG | GCC | CTG | TCA | TGG | CAT | TTG | 6818 |
|---|---|---|---|---|---|---|---|---|---|---|---|---|---|---|---|---|
| Thr | Val | Lys | Phe | Val | Val | Met | Thr | Val | Glu | Ala | Leu | Ser | Trp | His | Leu | |
| | | 2230 | | | | | 2235 | | | | | 2240 | | | | |

| ATC | CAT | GAG | CAG | ATC | CCA | CTG | AGT | CTG | GAC | CTC | CAA | GCC | GGG | CTA | GAC | 6866 |
|---|---|---|---|---|---|---|---|---|---|---|---|---|---|---|---|---|
| Ile | His | Glu | Gln | Ile | Pro | Leu | Ser | Leu | Asp | Leu | Gln | Ala | Gly | Leu | Asp | |
| | | 2245 | | | | | 2250 | | | | | 2255 | | | | |

| TGC | TGC | TGC | CTG | GCA | CTA | CAG | GTG | CCT | GGC | CTC | TGG | GGG | GTG | CTG | TCC | 6914 |
|---|---|---|---|---|---|---|---|---|---|---|---|---|---|---|---|---|
| Cys | Cys | Cys | Leu | Ala | Leu | Gln | Val | Pro | Gly | Leu | Trp | Gly | Val | Leu | Ser | |
| 2260 | | | | | 2265 | | | | | 2270 | | | | | 2275 | |

| TCC | CCA | GAG | TAC | GTG | ACT | CAT | GCC | TGC | TCC | CTC | ATC | CAT | TGT | GTG | CGA | 6962 |
|---|---|---|---|---|---|---|---|---|---|---|---|---|---|---|---|---|
| Ser | Pro | Glu | Tyr | Val | Thr | His | Ala | Cys | Ser | Leu | Ile | His | Cys | Val | Arg | |
| | | | 2280 | | | | | 2285 | | | | | 2290 | | | |

| TTC | ATC | CTG | GAA | GCC | ATT | GCA | GTA | CAA | CCT | GGA | GAC | CAG | CTT | CTC | GGT | 7010 |
|---|---|---|---|---|---|---|---|---|---|---|---|---|---|---|---|---|
| Phe | Ile | Leu | Glu | Ala | Ile | Ala | Val | Gln | Pro | Gly | Asp | Gln | Leu | Leu | Gly | |
| | | | 2295 | | | | | 2300 | | | | | 2305 | | | |

| CCT | GAA | AGC | AGG | TCA | CAT | ACT | CCA | AGA | GCT | GTC | AGA | AAG | GAG | GAA | GTA | 7058 |
|---|---|---|---|---|---|---|---|---|---|---|---|---|---|---|---|---|
| Pro | Glu | Ser | Arg | Ser | His | Thr | Pro | Arg | Ala | Val | Arg | Lys | Glu | Glu | Val | |
| | | | 2310 | | | | | 2315 | | | | | 2320 | | | |

| GAC | TCA | GAT | ATA | CAA | AAC | CTC | AGT | CAT | GTC | ACT | TCG | GCC | TGC | GAG | ATG | 7106 |
|---|---|---|---|---|---|---|---|---|---|---|---|---|---|---|---|---|
| Asp | Ser | Asp | Ile | Gln | Asn | Leu | Ser | His | Val | Thr | Ser | Ala | Cys | Glu | Met | |
| | | 2325 | | | | | 2330 | | | | | 2335 | | | | |

| GTG | GCA | GAC | ATG | GTG | GAA | TCC | CTG | CAG | TCA | GTG | CTG | GCC | TTG | GGC | CAC | 7154 |
|---|---|---|---|---|---|---|---|---|---|---|---|---|---|---|---|---|
| Val | Ala | Asp | Met | Val | Glu | Ser | Leu | Gln | Ser | Val | Leu | Ala | Leu | Gly | His | |
| 2340 | | | | | 2345 | | | | | 2350 | | | | | 2355 | |

| AAG | AGG | AAC | AGC | ACC | CTG | CCT | TCA | TTT | CTC | ACA | GCT | GTG | CTG | AAG | AAC | 7202 |
|---|---|---|---|---|---|---|---|---|---|---|---|---|---|---|---|---|
| Lys | Arg | Asn | Ser | Thr | Leu | Pro | Ser | Phe | Leu | Thr | Ala | Val | Leu | Lys | Asn | |
| | | | 2360 | | | | | 2365 | | | | | 2370 | | | |

| ATT | GTT | ATC | AGT | CTG | GCC | CGA | CTC | CCC | CTA | GTT | AAC | AGC | TAT | ACT | CGT | 7250 |
|---|---|---|---|---|---|---|---|---|---|---|---|---|---|---|---|---|
| Ile | Val | Ile | Ser | Leu | Ala | Arg | Leu | Pro | Leu | Val | Asn | Ser | Tyr | Thr | Arg | |
| | | | 2375 | | | | | 2380 | | | | | 2385 | | | |

| GTG | CCT | CCT | CTG | GTA | TGG | AAA | CTC | GGG | TGG | TCA | CCC | AAG | CCT | GGA | GGG | 7298 |
|---|---|---|---|---|---|---|---|---|---|---|---|---|---|---|---|---|
| Val | Pro | Pro | Leu | Val | Trp | Lys | Leu | Gly | Trp | Ser | Pro | Lys | Pro | Gly | Gly | |
| | | | 2390 | | | | | 2395 | | | | | 2400 | | | |

| GAT | TTT | GGC | ACA | GTG | TTT | CCT | GAG | ATC | CCT | GTA | GAG | TTC | CTC | CAG | GAG | 7346 |
|---|---|---|---|---|---|---|---|---|---|---|---|---|---|---|---|---|
| Asp | Phe | Gly | Thr | Val | Phe | Pro | Glu | Ile | Pro | Val | Glu | Phe | Leu | Gln | Glu | |
| | | | 2405 | | | | | 2410 | | | | | 2415 | | | |

| AAG | GAG | ATC | CTC | AAG | GAG | TTC | ATC | TAC | CGC | ATC | AAC | ACC | CTA | GGG | TGG | 7394 |
|---|---|---|---|---|---|---|---|---|---|---|---|---|---|---|---|---|
| Lys | Glu | Ile | Leu | Lys | Glu | Phe | Ile | Tyr | Arg | Ile | Asn | Thr | Leu | Gly | Trp | |
| 2420 | | | | | 2425 | | | | | 2430 | | | | | 2435 | |

| ACC | AAT | CGT | ACC | CAG | TTC | GAA | GAA | ACT | TGG | GCC | ACC | CTC | CTT | GGT | GTC | 7442 |
|---|---|---|---|---|---|---|---|---|---|---|---|---|---|---|---|---|
| Thr | Asn | Arg | Thr | Gln | Phe | Glu | Glu | Thr | Trp | Ala | Thr | Leu | Leu | Gly | Val | |
| | | | 2440 | | | | | 2445 | | | | | 2450 | | | |

| CTG | GTG | ACT | CAG | CCC | CTG | GTG | ATG | GAA | CAG | GAA | GAG | AGC | CCA | CCA | GAG | 7490 |
|---|---|---|---|---|---|---|---|---|---|---|---|---|---|---|---|---|
| Leu | Val | Thr | Gln | Pro | Leu | Val | Met | Glu | Gln | Glu | Glu | Ser | Pro | Pro | Glu | |
| | | | 2455 | | | | | 2460 | | | | | 2465 | | | |

| GAA | GAC | ACA | GAA | AGA | ACC | CAG | ATC | CAT | GTC | CTG | GCT | GTG | CAG | GCC | ATC | 7538 |
|---|---|---|---|---|---|---|---|---|---|---|---|---|---|---|---|---|
| Glu | Asp | Thr | Glu | Arg | Thr | Gln | Ile | His | Val | Leu | Ala | Val | Gln | Ala | Ile | |
| | | | 2470 | | | | | 2475 | | | | | 2480 | | | |

| ACC | TCT | CTA | GTG | CTC | AGT | GCA | ATG | ACC | GTG | CCT | GTG | GCT | GGC | AAT | CCA | 7586 |
|---|---|---|---|---|---|---|---|---|---|---|---|---|---|---|---|---|
| Thr | Ser | Leu | Val | Leu | Ser | Ala | Met | Thr | Val | Pro | Val | Ala | Gly | Asn | Pro | |
| | | 2485 | | | | | 2490 | | | | | 2495 | | | | |

| GCT | GTA | AGC | TGC | TTG | GAG | CAA | CAG | CCC | CGG | AAC | AAG | CCA | CTG | AAG | GCT | 7634 |
|---|---|---|---|---|---|---|---|---|---|---|---|---|---|---|---|---|
| Ala | Val | Ser | Cys | Leu | Glu | Gln | Gln | Pro | Arg | Asn | Lys | Pro | Leu | Lys | Ala | |
| 2500 | | | | | 2505 | | | | | 2510 | | | | | 2515 | |

| CTC | GAT | ACC | AGA | TTT | GGA | AGA | AAG | CTG | AGC | ATG | ATC | AGA | GGG | ATT | GTA | 7682 |
|---|---|---|---|---|---|---|---|---|---|---|---|---|---|---|---|---|
| Leu | Asp | Thr | Arg | Phe | Gly | Arg | Lys | Leu | Ser | Met | Ile | Arg | Gly | Ile | Val | |
| | | | 2520 | | | | | 2525 | | | | | 2530 | | | |

| GAA | CAA | GAA | ATC | CAA | GAG | ATG | GTT | TCC | CAG | AGA | GAG | AAT | ACT | GCC | ACT | 7730 |

-continued

| | | | | | | | | | | | | | | |
|---|---|---|---|---|---|---|---|---|---|---|---|---|---|---|
| Glu | Gln | Glu | Ile | Gln | Glu | Met | Val | Ser | Gln | Arg | Glu | Asn | Thr | Ala | Thr |
| | | | 2535 | | | | 2540 | | | | | | 2545 | | |

```
CAC CAT TCT CAC CAG GCG TGG GAT CCT GTC CCT TCT CTG TTA CCA GCT        7778
His His Ser His Gln Ala Trp Asp Pro Val Pro Ser Leu Leu Pro Ala
         2550            2555                2560

ACT ACA GGT GCT CTT ATC AGC CAT GAC AAG CTG CTG CTG CAG ATC AAC        7826
Thr Thr Gly Ala Leu Ile Ser His Asp Lys Leu Leu Leu Gln Ile Asn
         2565            2570                2575

CCA GAG CGG GAG CCA GGC AAC ATG AGC TAC AAG CTG GGC CAG GTG TCC        7874
Pro Glu Arg Glu Pro Gly Asn Met Ser Tyr Lys Leu Gly Gln Val Ser
2580            2585                2590                2595

ATA CAC TCC GTG TGG CTG GGA AAT AAC ATC ACA CCC CTG AGA GAG GAG        7922
Ile His Ser Val Trp Leu Gly Asn Asn Ile Thr Pro Leu Arg Glu Glu
         2600            2605                2610

GAA TGG GAT GAG GAA GAA GAG GAA GAA AGT GAT GTC CCT GCA CCA ACG        7970
Glu Trp Asp Glu Glu Glu Glu Glu Glu Ser Asp Val Pro Ala Pro Thr
         2615            2620                2625

TCA CCA CCT GTG TCT CCA GTC AAT TCC AGA AAA CAC CGT GCC GGG GTT        8018
Ser Pro Pro Val Ser Pro Val Asn Ser Arg Lys His Arg Ala Gly Val
         2630            2635                2640

GAT ATT CAC TCC TGT TCG CAG TTT CTG CTT GAA TTG TAC AGC CGA TGG        8066
Asp Ile His Ser Cys Ser Gln Phe Leu Leu Glu Leu Tyr Ser Arg Trp
         2645            2650                2655

ATC CTG CCA TCC AGT GCA GCC AGA AGG ACC CCC GTC ATC CTG ATC AGT        8114
Ile Leu Pro Ser Ser Ala Ala Arg Arg Thr Pro Val Ile Leu Ile Ser
2660            2665                2670                2675

GAA GTG GTT CGA TCT CTT CTT GTA GTG TCA GAC TTA TTC ACC GAA CGT        8162
Glu Val Val Arg Ser Leu Leu Val Val Ser Asp Leu Phe Thr Glu Arg
         2680            2685                2690

ACC CAG TTT GAA ATG ATG TAT CTG ACG CTG ACA GAA CTA CGG AGA GTG        8210
Thr Gln Phe Glu Met Met Tyr Leu Thr Leu Thr Glu Leu Arg Arg Val
         2695            2700                2705

CAC CCT TCA GAA GAT GAG ATC CTC ATT CAG TAC CTG GTG CCT GCC ACC        8258
His Pro Ser Glu Asp Glu Ile Leu Ile Gln Tyr Leu Val Pro Ala Thr
         2710            2715                2720

TGT AAG GCA GCT GCT GTC CTT GGA ATG GAC AAA ACT GTG GCA GAG CCA        8306
Cys Lys Ala Ala Ala Val Leu Gly Met Asp Lys Thr Val Ala Glu Pro
         2725            2730                2735

GTC AGC CGC CTA CTG GAG AGC ACA CTG AGG AGC AGC CAC CTG CCC AGC        8354
Val Ser Arg Leu Leu Glu Ser Thr Leu Arg Ser Ser His Leu Pro Ser
2740            2745                2750                2755

CAG ATC GGA GCC CTG CAC GGC ATC CTC TAT GTG TTG GAG TGT GAC CTC        8402
Gln Ile Gly Ala Leu His Gly Ile Leu Tyr Val Leu Glu Cys Asp Leu
         2760            2765                2770

TTG GAT GAC ACT GCA AAG CAG CTC ATT CCA GTT GTT AGT GAC TAT CTG        8450
Leu Asp Asp Thr Ala Lys Gln Leu Ile Pro Val Val Ser Asp Tyr Leu
         2775            2780                2785

CTG TCC AAC CTC AAA GGA ATA GCC CAC TGC GTG AAC ATT CAC AGC CAG        8498
Leu Ser Asn Leu Lys Gly Ile Ala His Cys Val Asn Ile His Ser Gln
         2790            2795                2800

CAG CAT GTG CTG GTA ATG TGT GCC ACT GCT TTC TAC CTG ATG GAA AAC        8546
Gln His Val Leu Val Met Cys Ala Thr Ala Phe Tyr Leu Met Glu Asn
         2805            2810                2815

TAC CCT CTG GAT GTG GGA CCA GAA TTT TCA GCA TCT GTG ATA CAG ATG        8594
Tyr Pro Leu Asp Val Gly Pro Glu Phe Ser Ala Ser Val Ile Gln Met
2820            2825                2830                2835

TGT GGA GTA ATG CTG TCT GGA AGT GAG GAG TCC ACC CCC TCC ATC ATT        8642
Cys Gly Val Met Leu Ser Gly Ser Glu Glu Ser Thr Pro Ser Ile Ile
         2840            2845                2850

TAC CAC TGT GCC CTC CGG GGT CTG GAG CGG CTC CTG CTG TCT GAG CAG        8690
```

5,686,288

-continued

| | | | | | | | | | | | | | | | | |
|---|---|---|---|---|---|---|---|---|---|---|---|---|---|---|---|---|
| Tyr | His | Cys | Ala | Leu | Arg | Gly | Leu | Glu | Arg | Leu | Leu | Leu | Ser | Glu | Gln | |
| | | | 2855 | | | | 2860 | | | | | 2865 | | | | |
| CTA | TCT | CGG | CTA | GAC | ACA | GAG | TCC | TTG | GTC | AAG | CTA | AGT | GTG | GAC | AGA | 8738 |
| Leu | Ser | Arg | Leu | Asp | Thr | Glu | Ser | Leu | Val | Lys | Leu | Ser | Val | Asp | Arg | |
| | | 2870 | | | | 2875 | | | | | 2880 | | | | | |
| GTG | AAT | GTA | CAA | AGC | CCA | CAC | AGG | GCC | ATG | GCA | GCC | CTA | GGC | CTG | ATG | 8786 |
| Val | Asn | Val | Gln | Ser | Pro | His | Arg | Ala | Met | Ala | Ala | Leu | Gly | Leu | Met | |
| | 2885 | | | | 2890 | | | | 2895 | | | | | | | |
| CTC | ACC | TGC | ATG | TAC | ACA | GGA | AAG | GAA | AAA | GCC | AGT | CCA | GGC | AGA | GCT | 8834 |
| Leu | Thr | Cys | Met | Tyr | Thr | Gly | Lys | Glu | Lys | Ala | Ser | Pro | Gly | Arg | Ala | |
| 2900 | | | | 2905 | | | | | 2910 | | | | | | 2915 | |
| TCT | GAC | CCC | AGC | CCT | GCT | ACA | CCT | GAC | AGC | GAG | TCT | GTG | ATT | GTA | GCT | 8882 |
| Ser | Asp | Pro | Ser | Pro | Ala | Thr | Pro | Asp | Ser | Glu | Ser | Val | Ile | Val | Ala | |
| | | | | 2920 | | | | | 2925 | | | | | 2930 | | |
| ATG | GAG | CGA | GTG | TCT | GTT | CTC | TTT | GAT | AGG | ATC | CGC | AAG | GGA | TTT | CCC | 8930 |
| Met | Glu | Arg | Val | Ser | Val | Leu | Phe | Asp | Arg | Ile | Arg | Lys | Gly | Phe | Pro | |
| | | | 2935 | | | | | 2940 | | | | | 2945 | | | |
| TGT | GAA | GCC | AGG | GTT | GTG | GCA | AGG | ATC | CTG | CCT | CAG | TTC | CTA | GAT | GAC | 8978 |
| Cys | Glu | Ala | Arg | Val | Val | Ala | Arg | Ile | Leu | Pro | Gln | Phe | Leu | Asp | Asp | |
| | | | 2950 | | | | | 2955 | | | | | 2960 | | | |
| TTC | TTT | CCA | CCT | CAA | GAT | GTC | ATG | AAC | AAA | GTC | ATT | GGA | GAG | TTC | CTG | 9026 |
| Phe | Phe | Pro | Pro | Gln | Asp | Val | Met | Asn | Lys | Val | Ile | Gly | Glu | Phe | Leu | |
| | | 2965 | | | | | 2970 | | | | | 2975 | | | | |
| TCC | AAT | CAG | CAG | CCA | TAC | CCA | CAG | TTC | ATG | GCC | ACT | GTA | GTT | TAC | AAG | 9074 |
| Ser | Asn | Gln | Gln | Pro | Tyr | Pro | Gln | Phe | Met | Ala | Thr | Val | Val | Tyr | Lys | |
| 2980 | | | | | 2985 | | | | 2990 | | | | | | 2995 | |
| GTT | TTT | CAG | ACT | CTG | CAC | AGT | GCT | GGG | CAG | TCA | TCC | ATG | GTC | CGG | GAC | 9122 |
| Val | Phe | Gln | Thr | Leu | His | Ser | Ala | Gly | Gln | Ser | Ser | Met | Val | Arg | Asp | |
| | | | | 3000 | | | | | 3005 | | | | | 3010 | | |
| TGG | GTC | ATG | CTG | TCC | CTG | TCC | AAC | TTC | ACA | CAA | AGA | ACT | CCA | GTT | GCC | 9170 |
| Trp | Val | Met | Leu | Ser | Leu | Ser | Asn | Phe | Thr | Gln | Arg | Thr | Pro | Val | Ala | |
| | | | 3015 | | | | | 3020 | | | | | 3025 | | | |
| ATG | GCC | ATG | TGG | AGC | CTC | TCC | TGC | TTC | CTT | GTT | AGC | GCA | TCT | ACC | AGC | 9218 |
| Met | Ala | Met | Trp | Ser | Leu | Ser | Cys | Phe | Leu | Val | Ser | Ala | Ser | Thr | Ser | |
| | | | 3030 | | | | | 3035 | | | | | 3040 | | | |
| CCA | TGG | GTT | TCT | GCG | ATC | CTT | CCA | CAT | GTC | ATC | AGC | AGG | ATG | GGC | AAA | 9266 |
| Pro | Trp | Val | Ser | Ala | Ile | Leu | Pro | His | Val | Ile | Ser | Arg | Met | Gly | Lys | |
| | | | 3045 | | | | | 3050 | | | | | 3055 | | | |
| CTG | GAA | CAG | GTG | GAT | GTG | AAC | CTT | TTC | TGC | CTG | GTT | GCC | ACA | GAC | TTC | 9314 |
| Leu | Glu | Gln | Val | Asp | Val | Asn | Leu | Phe | Cys | Leu | Val | Ala | Thr | Asp | Phe | |
| 3060 | | | | | 3065 | | | | | 3070 | | | | | 3075 | |
| TAC | AGA | CAC | CAG | ATA | GAG | GAG | GAA | TTC | GAC | CGC | AGG | GCT | TTC | CAG | TCT | 9362 |
| Tyr | Arg | His | Gln | Ile | Glu | Glu | Glu | Phe | Asp | Arg | Arg | Ala | Phe | Gln | Ser | |
| | | | | 3080 | | | | | 3085 | | | | | 3090 | | |
| GTG | TTT | GAG | GTG | GTG | GCT | GCA | CCA | GGA | AGT | CCA | TAC | CAC | AGG | CTG | CTT | 9410 |
| Val | Phe | Glu | Val | Val | Ala | Ala | Pro | Gly | Ser | Pro | Tyr | His | Arg | Leu | Leu | |
| | | | 3095 | | | | | 3100 | | | | | 3105 | | | |
| GCT | TGT | TTG | CAA | AAT | GTT | CAC | AAG | GTC | ACC | ACC | TGC | TGAGTAGTGC | | | | 9456 |
| Ala | Cys | Leu | Gln | Asn | Val | His | Lys | Val | Thr | Thr | Cys | | | | | |
| | | | 3110 | | | | | 3115 | | | | | | | | |

| | |
|---|---|
| CTGTGGGACA AAAGGCTGAA AGAAGGCAGC TGCTGGGGCC TGAGCCTCCA GGAGCCTGCT | 9516 |
| CCAAGCTTCT GCTGGGGCTG CCTTGGCCGT GCAGGCTTCA CTTGTGTCAA GTGGACAGCC | 9576 |
| AGGCAATGGC AGGAGTGCTT TGCAATGAGG GCTATGCAGG GAACATGCAC TATGTTGGGG | 9636 |
| TTGAGCCTGA GTCCTGGGTC CTGGCCTCGC TGCAGCTGGT GACAGTGCTA GGTTGACCAG | 9696 |
| GTGTTTGTCT TTTTCCTAGT GTTCCCTGG CCATAGTCGC CAGGTTGCAG CTGCCCTGGT | 9756 |
| ATGTGGATCA GAAGTCCTAG CTCCTGCCAG ATGGTTCTGA GCCGCCTGCT CCACTGGGCT | 9816 |
| GGAGAGCTCC CTCCCACATT TACCCAGTAG GCATACCTGC CACACCAGTG TCTGGACACA | 9876 |

-continued

```
AATGAATGGT GTGTGGGGCT GGGAACTGGG GCTGCCAGGT GTCCAGCACC ATTTTCCTTT      9936
CTGTGTTTTC TTCTCAGGAG TTAAAATTTA ATTATATCAG TAAAGAGATT AATTTTAATG      9996
T                                                                     9997
```

( 2 ) INFORMATION FOR SEQ ID NO:16:

( i ) SEQUENCE CHARACTERISTICS:
   ( A ) LENGTH: 3119 amino acids
   ( B ) TYPE: amino acid
   ( D ) TOPOLOGY: linear ( i i ) MOLECULE TYPE: protein ( x i ) SEQUENCE DESCRIPTION: SEQ ID NO:16:

| Met | Ala | Thr | Leu | Glu | Lys | Leu | Met | Lys | Ala | Phe | Glu | Ser | Leu | Lys | Ser |
|---|---|---|---|---|---|---|---|---|---|---|---|---|---|---|---|
| 1 | | | | 5 | | | | 10 | | | | | | 15 | |

| Phe | Gln | Gln | Gln | Gln | Gln | Gln | Gln | Pro | Pro | Gln | Pro | Pro | Pro | Pro | Pro |
| | | | | 20 | | | | 25 | | | | 30 | | | |

| Pro | Pro | Pro | Pro | Pro | Pro | Gln | Pro | Pro | Gln | Pro | Pro | Gln | Gly | Gln |
| | | 35 | | | | | 40 | | | | 45 | | | |

| Pro | Pro | Pro | Pro | Pro | Pro | Pro | Leu | Pro | Gly | Pro | Ala | Glu | Glu | Pro | Leu |
| | 50 | | | | | 55 | | | | 60 | | | | | |

| His | Arg | Pro | Lys | Lys | Glu | Leu | Ser | Ala | Thr | Lys | Lys | Asp | Arg | Val | Asn |
| 65 | | | | 70 | | | | | 75 | | | | | 80 | |

| His | Cys | Leu | Thr | Ile | Cys | Glu | Asn | Ile | Val | Ala | Gln | Ser | Leu | Arg | Asn |
| | | | | 85 | | | | 90 | | | | | 95 | | |

| Ser | Pro | Glu | Phe | Gln | Lys | Leu | Leu | Gly | Ile | Ala | Met | Glu | Leu | Phe | Leu |
| | | | 100 | | | | 105 | | | | 110 | | | | |

| Leu | Cys | Ser | Asp | Asp | Ala | Glu | Ser | Asp | Val | Arg | Met | Val | Ala | Asp | Glu |
| | | 115 | | | | 120 | | | | 125 | | | | | |

| Cys | Leu | Asn | Lys | Val | Ile | Lys | Ala | Leu | Met | Asp | Ser | Asn | Leu | Pro | Arg |
| | 130 | | | | 135 | | | | 140 | | | | | | |

| Leu | Gln | Leu | Glu | Leu | Tyr | Lys | Glu | Ile | Lys | Lys | Asn | Gly | Ala | Pro | Arg |
| 145 | | | | 150 | | | | 155 | | | | | 160 | |

| Ser | Leu | Arg | Ala | Ala | Leu | Trp | Arg | Phe | Ala | Glu | Leu | Ala | His | Leu | Val |
| | | | 165 | | | | 170 | | | | 175 | | | | |

| Arg | Pro | Gln | Lys | Cys | Arg | Pro | Tyr | Leu | Val | Asn | Leu | Leu | Pro | Cys | Leu |
| | | 180 | | | | 185 | | | | 190 | | | | | |

| Thr | Arg | Thr | Ser | Lys | Arg | Pro | Glu | Glu | Ser | Val | Gln | Glu | Thr | Leu | Ala |
| | | 195 | | | | 200 | | | | 205 | | | | | |

| Ala | Ala | Val | Pro | Lys | Ile | Met | Ala | Ser | Phe | Gly | Asn | Phe | Ala | Asn | Asp |
| | 210 | | | | 215 | | | | 220 | | | | | | |

| Asn | Glu | Ile | Lys | Val | Leu | Leu | Lys | Ala | Phe | Ile | Ala | Asn | Leu | Lys | Ser |
| 225 | | | | 230 | | | | 235 | | | | | 240 |

| Ser | Ser | Pro | Thr | Val | Arg | Arg | Thr | Ala | Ala | Gly | Ser | Ala | Val | Ser | Ile |
| | | | 245 | | | | 250 | | | | 255 | | | | |

| Cys | Gln | His | Ser | Arg | Arg | Thr | Gln | Tyr | Phe | Tyr | Asn | Trp | Leu | Leu | Asn |
| | | | 260 | | | | 265 | | | | 270 | | | | |

| Val | Leu | Leu | Gly | Leu | Leu | Val | Pro | Met | Glu | Glu | Glu | His | Ser | Thr | Leu |
| | | 275 | | | | 280 | | | | 285 | | | | | |

| Leu | Ile | Leu | Gly | Val | Leu | Leu | Thr | Leu | Arg | Cys | Leu | Val | Pro | Leu | Leu |
| | | 290 | | | | 295 | | | | 300 | | | | | |

| Gln | Gln | Gln | Val | Lys | Asp | Thr | Ser | Leu | Lys | Gly | Ser | Phe | Gly | Val | Thr |
| 305 | | | | 310 | | | | 315 | | | | | 320 |

| Arg | Lys | Glu | Met | Glu | Val | Ser | Pro | Ser | Thr | Glu | Gln | Leu | Val | Gln | Val |

-continued

|     |     |     | 325 |     |     |     | 330 |     |     |     | 335 |     |     |
|-----|-----|-----|-----|-----|-----|-----|-----|-----|-----|-----|-----|-----|-----|
| Tyr | Glu | Leu | Thr | Leu | His | His | Thr | Gln | His | Gln | Asp | His | Asn | Val | Val |

Thr Gly Ala Leu Glu Leu Leu Gln Gln Leu Phe Arg Thr Pro Pro Pro
340                     345                 350
                355                 360                 365

Glu Leu Leu Gln Ala Leu Thr Thr Pro Gly Gly Leu Gly Gln Leu Thr
370                 375                 380

Leu Val Gln Glu Glu Ala Arg Gly Arg Gly Arg Ser Gly Ser Ile Val
385                 390                 395                 400

Glu Leu Leu Ala Gly Gly Gly Ser Ser Cys Ser Pro Val Leu Ser Arg
                405                 410                 415

Lys Gln Lys Gly Lys Val Leu Leu Gly Glu Glu Ala Leu Glu Asp
                420                 425                 430

Asp Ser Glu Ser Arg Ser Asp Val Ser Ser Ser Ala Phe Ala Ala Ser
                435                 440                 445

Val Lys Ser Glu Ile Gly Gly Glu Leu Ala Ala Ser Ser Gly Val Ser
                450                 455                 460

Thr Pro Gly Ser Val Gly His Asp Ile Ile Thr Glu Gln Pro Arg Ser
465                 470                 475                 480

Gln His Thr Leu Gln Ala Asp Ser Val Asp Leu Ser Gly Cys Asp Leu
                485                 490                 495

Thr Ser Ala Ala Thr Asp Gly Asp Glu Asp Ile Leu Ser His Ser
                500                 505                 510

Ser Ser Gln Phe Ser Ala Val Pro Ser Asp Pro Ala Met Asp Leu Asn
                515                 520                 525

Asp Gly Thr Gln Ala Ser Ser Pro Ile Ser Asp Ser Ser Gln Thr Thr
                530                 535                 540

Thr Glu Gly Pro Asp Ser Ala Val Thr Pro Ser Asp Ser Ser Glu Ile
545                 550                 555                 560

Val Leu Asp Gly Ala Asp Ser Gln Tyr Leu Gly Met Gln Ile Gly Gln
                565                 570                 575

Pro Gln Glu Asp Asp Glu Glu Gly Ala Ala Gly Val Leu Ser Gly Glu
                580                 585                 590

Val Ser Asp Val Phe Arg Asn Ser Ser Leu Ala Leu Gln Gln Ala His
                595                 600                 605

Leu Leu Glu Arg Met Gly His Ser Arg Gln Pro Ser Asp Ser Ser Ile
610                 615                 620

Asp Lys Tyr Val Thr Arg Asp Glu Val Ala Glu Ala Ser Asp Pro Glu
625                 630                 635                 640

Ser Lys Pro Cys Arg Ile Lys Gly Asp Ile Gly Gln Pro Asn Asp Asp
                645                 650                 655

Asp Ser Ala Pro Leu Val His Cys Val Arg Leu Leu Ser Ala Ser Phe
                660                 665                 670

Leu Leu Thr Gly Glu Lys Lys Ala Leu Val Pro Asp Arg Asp Val Arg
                675                 680                 685

Val Ser Val Lys Ala Leu Ala Leu Ser Cys Ile Gly Ala Ala Val Ala
                690                 695                 700

Leu His Pro Glu Ser Phe Phe Ser Arg Leu Tyr Lys Val Pro Leu Asn
705                 710                 715                 720

Thr Thr Glu Ser Thr Glu Glu Gln Tyr Val Ser Asp Ile Leu Asn Tyr
                725                 730                 735

Ile Asp His Gly Asp Pro Gln Val Arg Gly Ala Thr Ala Ile Leu Cys
                740                 745                 750

| | | | | | | | | | | | | | |
|---|---|---|---|---|---|---|---|---|---|---|---|---|---|
|Gly|Thr|Leu 755|Val|Tyr|Ser|Ile 760|Leu|Ser|Arg|Ser 765|Arg|Leu|Arg|Val|Gly|
|Glu|Trp 770|Leu|Gly|Asn|Ile|Arg 775|Thr|Leu|Thr|Gly|Asn 780|Thr|Phe|Ser|Leu|
|Val 785|Asp|Cys|Ile|Pro|Leu 790|Leu|Gln|Lys|Thr|Leu 795|Lys|Asp|Glu|Ser|Ser 800|
|Val|Thr|Cys|Lys|Leu 805|Ala|Cys|Thr|Ala|Val|Arg 810|His|Cys|Val|Leu 815|Ser|
|Leu|Cys|Ser|Ser 820|Ser|Tyr|Ser|Asp|Leu 825|Gly|Leu|Gln|Leu|Leu 830|Ile|Asp|
|Met|Leu|Pro 835|Leu|Lys|Asn|Ser|Ser 840|Tyr|Trp|Leu|Val|Arg 845|Thr|Glu|Leu|
|Leu|Asp 850|Thr|Leu|Ala|Glu|Ile 855|Asp|Phe|Arg|Leu|Val 860|Ser|Phe|Leu|Glu|
|Ala 865|Lys|Ala|Glu|Ser|Leu 870|His|Arg|Gly|Ala|His 875|His|Tyr|Thr|Gly|Phe 880|
|Leu|Lys|Leu|Gln|Glu 885|Arg|Val|Leu|Asn|Asn 890|Val|Val|Ile|Tyr|Leu 895|Leu|
|Gly|Asp|Glu|Asp 900|Pro|Arg|Val|Arg|His 905|Val|Ala|Ala|Thr|Ser 910|Leu|Thr|
|Arg|Leu|Val 915|Pro|Lys|Leu|Phe|Tyr 920|Lys|Cys|Asp|Gln|Gly 925|Gln|Ala|Asp|
|Pro|Val 930|Val|Ala|Val|Ala|Arg 935|Asp|Gln|Ser|Ser|Val 940|Tyr|Leu|Lys|Leu|
|Leu 945|Met|His|Glu|Thr|Gln 950|Pro|Pro|Ser|His|Phe 955|Ser|Val|Ser|Thr|Ile 960|
|Thr|Arg|Ile|Tyr|Arg 965|Gly|Tyr|Ser|Leu|Leu 970|Pro|Ser|Ile|Thr|Asp 975|Val|
|Thr|Met|Glu|Asn 980|Asn|Leu|Ser|Arg|Val 985|Val|Ala|Ala|Val|Ser 990|His|Glu|
|Leu|Ile|Thr 995|Ser|Thr|Thr|Arg|Ala 1000|Leu|Thr|Phe|Gly|Cys 1005|Cys|Glu|Ala|
|Leu|Cys 1010|Leu|Leu|Ser|Ala|Ala 1015|Phe|Pro|Val|Cys|Thr 1020|Trp|Ser|Leu|Gly|
|Trp|His 1025|Cys|Gly|Val|Pro|Pro 1030|Leu|Ser|Ala|Ser 1035|Asp|Glu|Ser|Arg|Lys 1040|
|Ser|Cys|Thr|Val|Gly 1045|Met|Ala|Ser|Met|Ile 1050|Leu|Thr|Leu|Leu|Ser 1055|Ser|
|Ala|Trp|Phe|Pro 1060|Leu|Asp|Leu|Ser|Ala 1065|His|Gln|Asp|Ala|Leu 1070|Ile|Leu|
|Ala|Gly|Asn 1075|Leu|Leu|Ala|Ala|Ser 1080|Ala|Pro|Lys|Ser|Leu 1085|Arg|Ser|Ser|
|Trp|Thr 1090|Ser|Glu|Glu|Glu|Ala 1095|Asn|Ser|Ala|Ala|Thr 1100|Arg|Gln|Glu|Glu|
|Ile 1105|Trp|Pro|Ala|Leu|Gly 1110|Asp|Arg|Thr|Leu|Val 1115|Pro|Leu|Val|Glu|Gln 1120|
|Leu|Phe|Ser|His|Leu 1125|Leu|Lys|Val|Ile|Asn 1130|Ile|Cys|Ala|His|Val 1135|Leu|
|Asp|Asp|Val|Thr 1140|Pro|Gly|Pro|Ala|Ile 1145|Lys|Ala|Ala|Leu|Pro 1150|Ser|Leu|
|Thr|Asn|Pro 1155|Pro|Ser|Leu|Ser|Pro 1160|Ile|Arg|Arg|Lys|Gly 1165|Lys|Glu|Lys|
|Glu|Pro 1170|Gly|Glu|Gln|Ala|Ser 1175|Thr|Pro|Met|Ser|Pro 1180|Lys|Lys|Val|Gly|

```
Glu Ala Ser Ala Ala Ser Arg Gln Ser Asp Thr Ser Gly Pro Val Thr
1185                1190                1195                1200

Ala Ser Lys Ser Ser Ser Leu Gly Ser Phe Tyr His Leu Pro Ser Tyr
                1205                1210                1215

Leu Lys Leu His Asp Val Leu Lys Ala Thr His Ala Asn Tyr Lys Val
            1220                1225                1230

Thr Leu Asp Leu Gln Asn Ser Thr Glu Lys Phe Gly Gly Phe Leu Arg
        1235                1240                1245

Ser Ala Leu Asp Val Leu Ser Gln Ile Leu Glu Leu Ala Thr Leu Gln
    1250                1255                1260

Asp Ile Gly Lys Cys Val Glu Glu Val Leu Gly Tyr Leu Lys Ser Cys
1265                1270                1275                1280

Phe Ser Arg Glu Pro Met Met Ala Thr Val Cys Val Gln Gln Leu Leu
                1285                1290                1295

Lys Thr Leu Phe Gly Thr Asn Leu Ala Ser Gln Phe Asp Gly Leu Ser
            1300                1305                1310

Ser Asn Pro Ser Lys Ser Gln Cys Arg Ala Gln Arg Leu Gly Ser Ser
        1315                1320                1325

Ser Val Arg Pro Gly Leu Tyr His Tyr Cys Phe Met Ala Pro Tyr Thr
    1330                1335                1340

His Phe Thr Gln Ala Leu Ala Asp Ala Ser Leu Arg Asn Met Val Gln
1345                1350                1355                1360

Ala Glu Gln Glu Arg Asp Ala Ser Gly Trp Phe Asp Val Leu Gln Lys
                1365                1370                1375

Val Ser Ala Gln Leu Lys Thr Asn Leu Thr Ser Val Thr Lys Asn Arg
            1380                1385                1390

Ala Asp Lys Asn Ala Ile His Asn His Ile Arg Leu Phe Glu Pro Leu
        1395                1400                1405

Val Ile Lys Ala Leu Lys Gln Tyr Thr Thr Thr Thr Ser Val Gln Leu
    1410                1415                1420

Gln Lys Gln Val Leu Asp Leu Leu Ala Gln Leu Val Gln Leu Arg Val
1425                1430                1435                1440

Asn Tyr Cys Leu Leu Asp Ser Asp Gln Val Phe Ile Gly Phe Val Leu
                1445                1450                1455

Lys Gln Phe Glu Tyr Ile Glu Val Gly Gln Phe Arg Glu Ser Glu Ala
            1460                1465                1470

Ile Ile Pro Asn Ile Phe Phe Phe Leu Val Leu Leu Ser Tyr Glu Arg
        1475                1480                1485

Tyr His Ser Lys Gln Ile Ile Gly Ile Pro Lys Ile Ile Gln Leu Cys
    1490                1495                1500

Asp Gly Ile Met Ala Ser Gly Arg Lys Ala Val Thr His Ala Ile Pro
1505                1510                1515                1520

Ala Leu Gln Pro Ile Val His Asp Leu Phe Val Leu Arg Gly Thr Asn
                1525                1530                1535

Lys Ala Asp Ala Gly Lys Glu Leu Glu Thr Gln Lys Glu Val Val Val
            1540                1545                1550

Ser Met Leu Leu Arg Leu Ile Gln Tyr His Gln Val Leu Glu Met Phe
        1555                1560                1565

Ile Leu Val Leu Gln Gln Cys His Lys Glu Asn Glu Asp Lys Trp Lys
    1570                1575                1580

Arg Leu Ser Arg Gln Val Ala Asp Ile Ile Leu Pro Met Leu Ala Lys
1585                1590                1595                1600

Gln Gln Met His Ile Asp Ser His Glu Ala Leu Gly Val Leu Asn Thr
```

|   |   |   |
|---|---|---|
| 1605 | 1610 | 1615 |

Leu Phe Glu Ile Leu Ala Pro Ser Ser Leu Arg Pro Val Asp Met Leu
    1620                    1625                1630

Leu Arg Ser Met Phe Ile Thr Pro Ser Thr Met Ala Ser Val Ser Thr
    1635                    1640                1645

Val Gln Leu Trp Ile Ser Gly Ile Leu Ala Ile Leu Arg Val Leu Ile
    1650                    1655                1660

Ser Gln Ser Thr Glu Asp Ile Val Leu Cys Arg Ile Gln Glu Leu Ser
1665                1670                    1675                1680

Phe Ser Pro His Leu Leu Ser Cys Pro Val Ile Asn Arg Leu Arg Gly
                1685                    1690                1695

Gly Gly Gly Asn Val Thr Leu Gly Glu Cys Ser Glu Gly Lys Gln Lys
            1700                    1705                1710

Ser Leu Pro Glu Asp Thr Phe Ser Arg Phe Leu Leu Gln Leu Val Gly
        1715                    1720                1725

Ile Leu Leu Glu Asp Ile Val Thr Lys Gln Leu Lys Val Asp Met Ser
        1730                    1735                1740

Glu Gln Gln His Thr Phe Tyr Cys Gln Glu Leu Gly Thr Leu Leu Met
1745                1750                    1755                1760

Cys Leu Ile His Ile Phe Lys Ser Gly Met Phe Arg Arg Ile Thr Ala
                1765                    1770                1775

Ala Ala Thr Arg Leu Phe Thr Ser Asp Gly Cys Glu Gly Ser Phe Tyr
            1780                    1785                1790

Thr Leu Glu Ser Leu Asn Ala Arg Val Arg Ser Met Val Pro Thr His
        1795                    1800                1805

Pro Ala Leu Val Leu Leu Trp Cys Gln Ile Leu Leu Leu Ile Asn His
    1810                    1815                1820

Thr Asp His Arg Trp Trp Ala Glu Val Gln Gln Thr Pro Lys Arg His
1825                1830                    1835                1840

Ser Leu Ser Cys Thr Lys Ser Leu Asn Pro Gln Lys Ser Gly Glu Glu
                1845                    1850                1855

Glu Asp Ser Gly Ser Ala Ala Gln Leu Gly Met Cys Asn Arg Glu Ile
            1860                    1865                1870

Val Arg Arg Gly Ala Leu Ile Leu Phe Cys Asp Tyr Val Cys Gln Asn
        1875                    1880                1885

Leu His Asp Ser Glu His Leu Thr Trp Leu Ile Val Asn His Ile Gln
    1890                    1895                1900

Asp Leu Ile Ser Leu Ser His Glu Pro Pro Val Gln Asp Phe Ile Ser
1905                1910                    1915                1920

Ala Ile His Arg Asn Ser Ala Ala Ser Gly Leu Phe Ile Gln Ala Ile
                1925                    1930                1935

Gln Ser Arg Cys Glu Asn Leu Ser Thr Pro Thr Thr Leu Lys Lys Thr
            1940                    1945                1950

Leu Gln Cys Leu Glu Gly Ile His Leu Ser Gln Ser Gly Ala Val Leu
        1955                    1960                1965

Thr Leu Tyr Val Asp Arg Leu Leu Gly Thr Pro Phe Arg Ala Leu Ala
    1970                    1975                1980

Arg Met Val Asp Thr Leu Ala Cys Arg Arg Val Glu Met Leu Leu Ala
1985                1990                    1995                2000

Ala Asn Leu Gln Ser Ser Met Ala Gln Leu Pro Glu Glu Glu Leu Asn
                2005                    2010                2015

Arg Ile Gln Glu His Leu Gln Asn Ser Gly Leu Ala Gln Arg His Gln
            2020                    2025                2030

```
Arg Leu Tyr Ser Leu Leu Asp Arg Phe Arg Leu Ser Thr Val Gln Asp
    2035            2040            2045

Ser Leu Ser Pro Leu Pro Val Thr Ser His Pro Leu Asp Gly Asp
2050            2055            2060

Gly His Thr Ser Leu Glu Thr Val Ser Pro Asp Lys Asp Trp Tyr Leu
2065            2070            2075            2080

Gln Leu Val Arg Ser Gln Cys Trp Thr Arg Ser Asp Ser Ala Leu Leu
            2085            2090            2095

Glu Gly Ala Glu Leu Val Asn Arg Ile Pro Ala Glu Asp Met Asn Asp
        2100            2105            2110

Phe Met Met Ser Ser Glu Phe Asn Leu Ser Leu Leu Ala Pro Cys Leu
        2115            2120            2125

Ser Leu Gly Met Ser Glu Ile Ala Asn Gly Gln Lys Ser Pro Leu Phe
        2130            2135            2140

Glu Ala Ala Arg Gly Val Ile Leu Asn Arg Val Thr Ser Val Val Gln
2145            2150            2155            2160

Gln Leu Pro Ala Val His Gln Val Phe Gln Pro Phe Leu Pro Ile Glu
            2165            2170            2175

Pro Thr Ala Tyr Trp Asn Lys Leu Asn Asp Leu Leu Gly Asp Thr Thr
        2180            2185            2190

Ser Tyr Gln Ser Leu Thr Ile Leu Ala Arg Ala Leu Ala Gln Tyr Leu
        2195            2200            2205

Val Val Leu Ser Lys Val Pro Ala His Leu His Leu Pro Pro Glu Lys
        2210            2215            2220

Glu Gly Asp Thr Val Lys Phe Val Val Met Thr Val Glu Ala Leu Ser
2225            2230            2235            2240

Trp His Leu Ile His Glu Gln Ile Pro Leu Ser Leu Asp Leu Gln Ala
            2245            2250            2255

Gly Leu Asp Cys Cys Cys Leu Ala Leu Gln Val Pro Gly Leu Trp Gly
        2260            2265            2270

Val Leu Ser Ser Pro Glu Tyr Val Thr His Ala Cys Ser Leu Ile His
        2275            2280            2285

Cys Val Arg Phe Ile Leu Glu Ala Ile Ala Val Gln Pro Gly Asp Gln
        2290            2295            2300

Leu Leu Gly Pro Glu Ser Arg Ser His Thr Pro Arg Ala Val Arg Lys
2305            2310            2315            2320

Glu Glu Val Asp Ser Asp Ile Gln Asn Leu Ser His Val Thr Ser Ala
            2325            2330            2335

Cys Glu Met Val Ala Asp Met Val Glu Ser Leu Gln Ser Val Leu Ala
        2340            2345            2350

Leu Gly His Lys Arg Asn Ser Thr Leu Pro Ser Phe Leu Thr Ala Val
        2355            2360            2365

Leu Lys Asn Ile Val Ile Ser Leu Ala Arg Leu Pro Leu Val Asn Ser
        2370            2375            2380

Tyr Thr Arg Val Pro Pro Leu Val Trp Lys Leu Gly Trp Ser Pro Lys
2385            2390            2395            2400

Pro Gly Gly Asp Phe Gly Thr Val Phe Pro Glu Ile Pro Val Glu Phe
            2405            2410            2415

Leu Gln Glu Lys Glu Ile Leu Lys Glu Phe Ile Tyr Arg Ile Asn Thr
        2420            2425            2430

Leu Gly Trp Thr Asn Arg Thr Gln Phe Glu Glu Thr Trp Ala Thr Leu
        2435            2440            2445

Leu Gly Val Leu Val Thr Gln Pro Leu Val Met Glu Gln Glu Glu Ser
        2450            2455            2460
```

```
Pro Pro Glu Glu Asp Thr Glu Arg Thr Gln Ile His Val Leu Ala Val
2465                2470                2475                2480

Gln Ala Ile Thr Ser Leu Val Leu Ser Ala Met Thr Val Pro Val Ala
            2485                2490                2495

Gly Asn Pro Ala Val Ser Cys Leu Glu Gln Gln Pro Arg Asn Lys Pro
                2500                2505                2510

Leu Lys Ala Leu Asp Thr Arg Phe Gly Arg Lys Leu Ser Met Ile Arg
            2515                2520                2525

Gly Ile Val Glu Gln Glu Ile Gln Glu Met Val Ser Gln Arg Glu Asn
                2530                2535                2540

Thr Ala Thr His His Ser His Gln Ala Trp Asp Pro Val Pro Ser Leu
2545                2550                2555                2560

Leu Pro Ala Thr Thr Gly Ala Leu Ile Ser His Asp Lys Leu Leu Leu
                2565                2570                2575

Gln Ile Asn Pro Glu Arg Glu Pro Gly Asn Met Ser Tyr Lys Leu Gly
                2580                2585                2590

Gln Val Ser Ile His Ser Val Trp Leu Gly Asn Asn Ile Thr Pro Leu
            2595                2600                2605

Arg Glu Glu Glu Trp Asp Glu Glu Glu Glu Glu Ser Asp Val Pro
2610                2615                2620

Ala Pro Thr Ser Pro Pro Val Ser Pro Val Asn Ser Arg Lys His Arg
2625                2630                2635                2640

Ala Gly Val Asp Ile His Ser Cys Ser Gln Phe Leu Leu Glu Leu Tyr
                2645                2650                2655

Ser Arg Trp Ile Leu Pro Ser Ser Ala Ala Arg Arg Thr Pro Val Ile
            2660                2665                2670

Leu Ile Ser Glu Val Val Arg Ser Leu Leu Val Val Ser Asp Leu Phe
            2675                2680                2685

Thr Glu Arg Thr Gln Phe Glu Met Met Tyr Leu Thr Leu Thr Glu Leu
            2690                2695                2700

Arg Arg Val His Pro Ser Glu Asp Glu Ile Leu Ile Gln Tyr Leu Val
2705                2710                2715                2720

Pro Ala Thr Cys Lys Ala Ala Ala Val Leu Gly Met Asp Lys Thr Val
                2725                2730                2735

Ala Glu Pro Val Ser Arg Leu Leu Glu Ser Thr Leu Arg Ser Ser His
                2740                2745                2750

Leu Pro Ser Gln Ile Gly Ala Leu His Gly Ile Leu Tyr Val Leu Glu
            2755                2760                2765

Cys Asp Leu Leu Asp Asp Thr Ala Lys Gln Leu Ile Pro Val Val Ser
2770                2775                2780

Asp Tyr Leu Leu Ser Asn Leu Lys Gly Ile Ala His Cys Val Asn Ile
2785                2790                2795                2800

His Ser Gln Gln His Val Leu Val Met Cys Ala Thr Ala Phe Tyr Leu
                2805                2810                2815

Met Glu Asn Tyr Pro Leu Asp Val Gly Pro Glu Phe Ser Ala Ser Val
                2820                2825                2830

Ile Gln Met Cys Gly Val Met Leu Ser Gly Ser Glu Glu Ser Thr Pro
            2835                2840                2845

Ser Ile Ile Tyr His Cys Ala Leu Arg Gly Leu Glu Arg Leu Leu Leu
            2850                2855                2860

Ser Glu Gln Leu Ser Arg Leu Asp Thr Glu Ser Leu Val Lys Leu Ser
2865                2870                2875                2880

Val Asp Arg Val Asn Val Gln Ser Pro His Arg Ala Met Ala Ala Leu
```

-continued

```
                          2885                          2890                          2895
Gly  Leu  Met  Leu  Thr  Cys  Met  Tyr  Thr  Gly  Lys  Glu  Lys  Ala  Ser  Pro
                    2900                     2905                     2910
Gly  Arg  Ala  Ser  Asp  Pro  Ser  Pro  Ala  Thr  Pro  Asp  Ser  Glu  Ser  Val
                    2915                     2920                     2925
Ile  Val  Ala  Met  Glu  Arg  Val  Ser  Val  Leu  Phe  Asp  Arg  Ile  Arg  Lys
     2930                     2935                     2940
Gly  Phe  Pro  Cys  Glu  Ala  Arg  Val  Val  Ala  Arg  Ile  Leu  Pro  Gln  Phe
2945                          2950                     2955                     2960
Leu  Asp  Asp  Phe  Phe  Pro  Pro  Gln  Asp  Val  Met  Asn  Lys  Val  Ile  Gly
                    2965                     2970                     2975
Glu  Phe  Leu  Ser  Asn  Gln  Gln  Pro  Tyr  Pro  Gln  Phe  Met  Ala  Thr  Val
               2980                     2985                     2990
Val  Tyr  Lys  Val  Phe  Gln  Thr  Leu  His  Ser  Ala  Gly  Gln  Ser  Ser  Met
          2995                     3000                     3005
Val  Arg  Asp  Trp  Val  Met  Leu  Ser  Leu  Ser  Asn  Phe  Thr  Gln  Arg  Thr
     3010                     3015                     3020
Pro  Val  Ala  Met  Ala  Met  Trp  Ser  Leu  Ser  Cys  Phe  Leu  Val  Ser  Ala
3025                     3030                     3035                          3040
Ser  Thr  Ser  Pro  Trp  Val  Ser  Ala  Ile  Leu  Pro  His  Val  Ile  Ser  Arg
                    3045                     3050                          3055
Met  Gly  Lys  Leu  Glu  Gln  Val  Asp  Val  Asn  Leu  Phe  Cys  Leu  Val  Ala
                    3060                     3065                     3070
Thr  Asp  Phe  Tyr  Arg  His  Gln  Ile  Glu  Glu  Glu  Phe  Asp  Arg  Arg  Ala
               3075                     3080                     3085
Phe  Gln  Ser  Val  Phe  Glu  Val  Val  Ala  Ala  Pro  Gly  Ser  Pro  Tyr  His
     3090                     3095                     3100
Arg  Leu  Leu  Ala  Cys  Leu  Gln  Asn  Val  His  Lys  Val  Thr  Thr  Cys
3105                     3110                     3115
```

( 2 ) INFORMATION FOR SEQ ID NO:17:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

GGGAACAGCA TCACACCC 18

( 2 ) INFORMATION FOR SEQ ID NO:18:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

GTTGCGCTCG GTGAACA 17

( 2 ) INFORMATION FOR SEQ ID NO:19:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

```
GCTGGGGAAC AGCATCACAC CC                                                         22
```

( 2 ) INFORMATION FOR SEQ ID NO:20:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

```
CCTGGAGTTG ACTGGAGACG TG                                                         22
```

( 2 ) INFORMATION FOR SEQ ID NO:21:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

```
CAGGTACTGA GCGAGGAT                                                              18
```

( 2 ) INFORMATION FOR SEQ ID NO:22:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

```
GGAGAACACA GTCGTCTGTG                                                            20
```

( 2 ) INFORMATION FOR SEQ ID NO:23:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

```
CGTGTAAAGT ATGTGAATCG C                                                          21
```

( 2 ) INFORMATION FOR SEQ ID NO:24:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

```
CTTCAACGCT AGAAGAAC                                                              18
```

( 2 ) INFORMATION FOR SEQ ID NO:25:

(  i  ) SEQUENCE CHARACTERISTICS:
   ( A ) LENGTH: 20 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:25:

CAGACTTGAA GATGTGGATC 20